United States Patent [19]
Rorer

[11] Patent Number: 4,906,282
[45] Date of Patent: Mar. 6, 1990

[54] HERBICIDAL SULFONAMIDES

[75] Inventor: Morris P. Rorer, Newark, Del.

[73] Assignee: E. I. Du Pont de Nemours and Company, Wilmington, Del.

[21] Appl. No.: 204,556

[22] Filed: Jun. 15, 1988

Related U.S. Application Data

[63] Continuation-in-part of Ser. No. 78,191, Jul. 27, 1987, abandoned.

[51] Int. Cl.$^4$ .................. A01N 43/54; C07D 239/69; C07D 401/12; C07D 409/12
[52] U.S. Cl. ............................. 71/92; 71/90; 544/320; 544/321; 544/323; 544/324; 544/331; 544/332
[58] Field of Search ............ 71/90, 92; 544/320, 544/321, 323, 324, 331, 332

[56] References Cited
U.S. PATENT DOCUMENTS

| | | | |
|---|---|---|---|
| 4,370,480 | 1/1983 | Levitt et al. | 71/92 |
| 4,435,206 | 3/1984 | Levitt | 71/92 |
| 4,481,029 | 11/1984 | Levitt | 71/93 |
| 4,549,898 | 10/1985 | Böhner et al. | |
| 4,618,363 | 10/1986 | Gass et al. | 71/90 |
| 4,638,004 | 1/1987 | Stetter et al. | 71/92 |
| 4,659,366 | 4/1987 | Stetter et al. | 71/92 |
| 4,675,045 | 6/1987 | Petersen | 71/92 |
| 4,678,498 | 7/1987 | Artz | 71/87 |
| 4,743,290 | 5/1988 | Christensen et al. | 71/90 |
| 4,743,295 | 5/1988 | Petersen | 71/93 |
| 4,747,870 | 5/1988 | Wexler | 71/92 |

FOREIGN PATENT DOCUMENTS

| | | |
|---|---|---|
| 79772 | 5/1983 | European Pat. Off. . |
| 87780 | 7/1983 | European Pat. Off. . |
| 95925 | 7/1983 | European Pat. Off. . |
| 126711 | 11/1984 | European Pat. Off. . |
| 245058 | 11/1987 | European Pat. Off. . |
| 833850 | 11/1983 | South Africa . |
| 852603 | 10/1985 | South Africa . |

Primary Examiner—John M. Ford
Attorney, Agent, or Firm—James A. Costello

[57] ABSTRACT

Herbicidal sulfonamides having the general formula

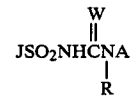

wherein J, W, R and A are more particularly described herein, such compounds and agricultural compositions containing them being useful as preemergent or postemergent herbicides or both, or as plant growth regulants, including the manner of their use.

23 Claims, No Drawings

HERBICIDAL SULFONAMIDES

CROSS-REFERENCE TO RELATED APPLICATION

This is a continuation-in-part of the application bearing U.S. Ser. No. 078,191 filed on July 27, 1987, now abandoned.

BACKGROUND OF THE INVENTION

The following publications disclose herbicidal sulfonylureas related to the sulfonamides of this invention in that substantially all disclosed compounds contain the characteristic sulfonylurea moiety. There are sufficient distinctions, however, to render these representative publications more useful as a backdrop against which to appreciate the instant invention rather than as suggestive of it.

| U.S. 4,370,480 | EP-A-79,772 |
| U.S. 4,435,206 | EP-A-87,780 |
| U.S. 4,481,029 | EP-A-95,925 |
| U.S. 4,549,898 | EP-A-126,711 |
| U.S. 4,618,363 | EP-A-203,825 |
| U.S. 4,638,004 | EP-A-245,058 |
| U.S. 4,659,366 | SA 85/2603 |
|  | SA 83/3850. |

SUMMARY OF THE INVENTION

This invention pertains to compounds of Formula I, including their agriculturally suitable salts, herbicidal compositions containing said compounds and use thereof as preemergent herbicides, postemergent herbicides and/or plant growth regulants. For the sake of brevity, the compounds will be described and claimed with respect to Formula I, it being understood that all salts are included as well. The compounds are:

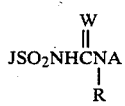

wherein
J is selected from

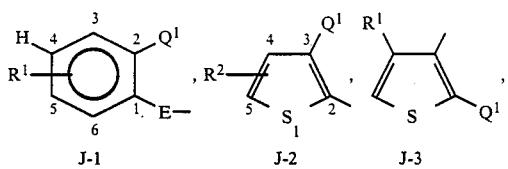

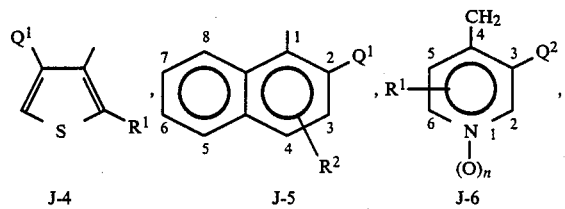

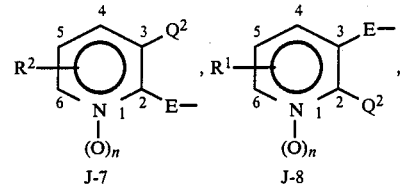

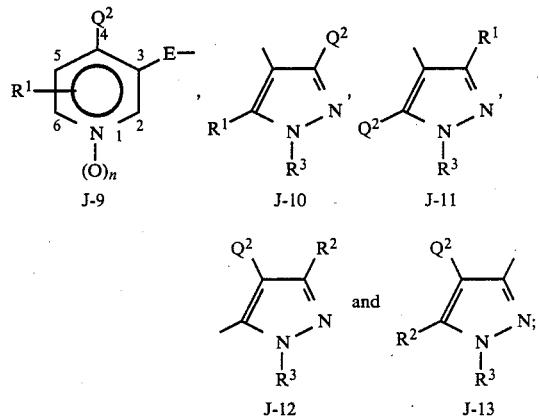

E is a single bond or —CH$_2$—;
Q$^1$ is —C(T$^1$)=N—O—Alk;
T$^1$ is selected from CN, F, Cl, Br, SCN, N$_3$, C$_1$ to C$_2$ alkoxy, C$_1$ to C$_2$ thioalkyl, NH(C$_1$ to C$_2$ alkyl), N(C$_1$ to C$_2$ alkyl)$_2$, N(OCH$_3$)CH$_3$ and N(CH$_2$)$_{3\ or\ 4}$;
Alk is selected from C$_1$ to C$_3$ alkyl, optionally substituted with CN, OCH$_3$, SCH$_3$ or halogen; and CH$_2$CH=CH$_2$;
Q$^2$ is —C(T$^2$)=N—O—Alk;
T$^2$ is selected from H; C$_1$ to C$_3$ alkyl optionally substituted with CN, OCH$_3$, SCH$_3$ or halogen; cyclopropyl; F; Cl; Br; CN; SCN; N$_3$; C$_1$ to C$_2$ alkoxy; C$_1$ to C$_2$ thioalkyl; NH(C$_1$ to C$_2$ alkyl); N(C$_1$ to C$_2$ alkyl)$_2$; N(OCH$_3$)CH$_3$ and N(CH$_2$)$_{3\ or\ 4}$;
R$^1$ is selected from H, C$_1$ to C$_3$ alkyl, C$_1$ to C$_3$ haloalkyl, halogen, CN, nitro, C$_1$ to C$_3$ alkoxy, C$_1$ to C$_3$ haloalkoxy, C$_1$ to C$_3$ alkylthio, C$_1$ to C$_3$ alkylsulfinyl, C$_1$ to C$_3$ alkylsulfonyl, SCF$_2$H, NH$_2$, NHCH$_3$, N(CH$_3$)$_2$ or C$_1$ to C$_2$ alkyl substituted with one C$_1$ to C$_2$ alkoxy, C$_1$ to C$_2$ haloalkoxy, SH, SCH$_3$, CN or OH;
R$^2$ is selected from H, F, Cl, Br, C$_1$ to C$_2$ alkyl, C$_1$ to C$_2$ haloalkyl or C$_1$ to C$_2$ alkoxy;
R$^3$ is selected from H, C$_1$ to C$_3$ alkyl, C$_1$ to C$_2$ haloalkyl, C$_3$ to C$_4$ alkenyl, C$_3$ to C$_4$ alkynyl, CH$_2$CN, phenyl and phenyl substituted by F, Cl, CH$_3$ or OCH$_3$;
n is 0 or 1;
R is H or CH$_3$;
W is O or S;
A is selected from

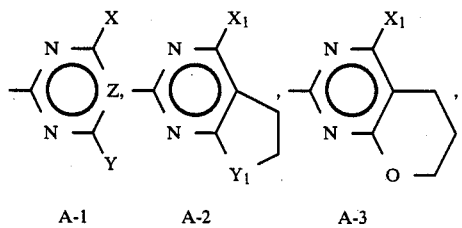

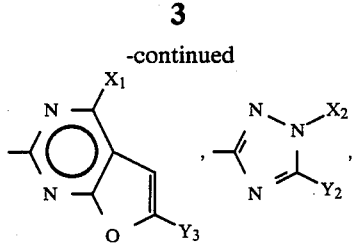

A-4   A-5

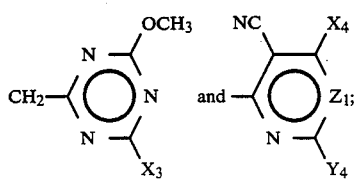

A-6   A-7

X is selected from H, $C_1$ to $C_4$ alkyl, $C_1$ to $C_4$ alkoxy, $C_1$ to $C_4$ haloalkoxy, $C_1$ to $C_4$ haloalkyl, $C_1$ to $C_4$ haloalkylthio, $C_1$ to $C_4$ alkylthio, halogen, $C_2$ to $C_5$ alkoxyalkyl, $C_2$ to $C_5$ alkoxyalkoxy, amino, $C_1$ to $C_3$ alkylamino, di($C_1$ to $C_3$ alkyl)amino or $C_3$ to $C_5$ cycloalkyl;

Y is selected from H, $C_1$ to $C_4$ alkyl, $C_1$ to $C_4$ alkoxy, $C_1$ to $C_4$ haloalkoxy, $C_1$ to $C_4$ haloalkylthio, $C_1$ to $C_4$ alkylthio, $C_2$ to $C_5$ alkoxyalkyl, $C_2$ to $C_5$ alkoxyalkoxy, amino, $C_1$ to $C_3$ alkylamino, di($C_1$ to $C_3$ alkyl)amino, $C_3$ to $C_4$ alkenyloxy, $C_3$ to $C_4$ alkynyloxy, $C_2$ to $C_5$ alkylthioalkyl, $C_1$ to $C_4$ haloalkyl, $C_2$ to $C_4$ alkynyl, azido, cyano, $C_2$ to $C_5$ alkylsulfinylalkyl, $C_2$ to $C_5$ alkylsulfonylalkyl,

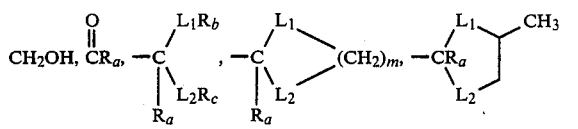

and $N(OCH_3)CH_3$;
m is 2 or 3;
$L_1$ and $L_2$ are independently O or S;
$R_a$ is H or $C_1$ to $C_3$ alkyl;
$R_b$ and $R_c$ are independently $C_1$ to $C_3$ alkyl;
Z is CH or N;
$Z_1$ is CH or N;
$Y_1$ is O or $CH_2$;
$X_1$ is $CH_3$, $OCH_3$, $OC_2H_5$ or $OCF_2H$;
$X_2$ is $CH_3$, $C_2H_5$ or $CH_2CF_3$;
$Y_2$ is $OCH_3$, $OC_2H_5$, $SCH_3$, $SC_2H_5$, $CH_3$ or $CH_2CH_3$;
$X_3$ is $CH_3$ or $OCH_3$;
$Y_3$ is H or $CH_3$;
$X_4$ is $CH_3$, $OCH_3$, $OC_2H_5$, $CH_2OCH_3$ or Cl; and
$Y_4$ is $CH_3$, $OCH_3$, $OC_2H_5$ or Cl; provided that
  (i) when X is Cl, F, Br or I, then Z is CH and Y is $OCH_3$, $OC_2H_5$, $N(OCH_3)CH_3$, $NHCH_3$, $N(CH_3)_2$ or $OCF_2H$;
  (ii) when X or Y is $C_1$ haloalkoxy, then Z is CH;
  (iii) $X_4$ and $Y_4$ are not simultaneously Cl;
  (iv) when W is S, then R is H, A is A-1 and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;

(v) when the total number of carbons of X and Y is greater than four, the number of carbon atoms of $Q_1$ or $Q_2$ is less than or equal to four;
  (vi) when J is J-6, J-7, J-8 or J-9, and A is A-7, then $Z_1$ is CH; and
  (vii) when J is J-6, J-7, J-8 or J-9, and A is A-1, and X and Y are haloalkoxy or haloalkylthio, then $T^2$ is F, Cl, Br, CN, SCN, $N_3$, $C_1$ to $C_2$ alkoxy, $C_1$ to $C_2$ thioalkyl, $NH(C_1$ to $C_2$ alkyl), $N(C_1$ to $C_2$ alkyl)$_2$, $N(OCH_3)CH_3$ or $N(CH_2)_3$ or 4.

In the above definitions, the term "alkyl", used either alone or in compound words such as "alkylthio" or "haloalkyl," denotes straight chain or branched alkyl, such as methyl, ethyl, n-propyl, isopropyl or the different butyl and pentyl isomers.

Alkoxy denotes methoxy, ethoxy, n-propyloxy, isopropyloxy and the different butyl isomers.

Alkenyl denotes straight chain or branched alkenes, such as 1-propenyl, 2-propenyl, 3-propenyl and the different butenyl and pentenyl isomers.

Alkynyl denotes straight chain or branched alkynes, such as ethynyl, 1-propynyl, 2-propynyl and the different butynyl and pentynyl isomers.

Alkylsulfonyl denotes methylsulfonyl, ethylsulfonyl and the different propylsulfonyl isomers.

Preferred Compounds A are compounds of Formula I wherein:
E is a single bond; and
W is O.

Preferred Compounds B are compounds of Formula I wherein:
E is $CH_2$ or J is J-6; and
W is O.

Preferred Compounds C are compounds A wherein:
$R^1$ is selected from H, F, Cl, Br, $CH_2CN$, $CH_3$, $OCH_3$, $SCH_3$ or $OCF_2H$;
$R^2$ is selected from H, F, Cl, Br or $CH_3$;
$R^3$ is selected from H, $C_1$ to $C_3$ alkyl, phenyl, $CH_2CF_3$ and $CH_2CH=CH_2$;
X is selected from $C_1$ to $C_2$ alkyl, $C_1$ to $C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ and $CH_2Br$;
Y is selected from H, $C_1$ to $C_2$ alkyl, $C_1$ to $C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

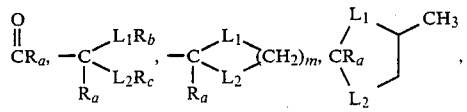

$OCF_2H$, $OCF_2Br$, $SCF_2H$, cyclopropyl, $C\equiv CH$ or $C\equiv CCH_3$; and
$R_b$ and $R_c$ are $C_1$ to $C_2$ alkyl.

Preferred Compounds D are compounds C wherein:
A is A-1;
n is O;
X is selected from $CH_3$, $OCH_3$, $OCH_2CH_3$, Cl or $OCF_2H$; and
Y is selected from $CH_3$, $OCH_3$, $C_2H_5$, $CH_2OCH_3$, $NHCH_3$, $CH(OCH_3)_2$ and cyclopropyl.

Preferred Compounds E are compounds D wherein:
R is H;
$T^1$ is selected from CN, Cl and $C_1$ to $C_2$ alkoxy; and $T^2$ is selected from H, $C_1$ to $C_3$ alkyl, cyclopropyl, Cl, CN and $C_1$ to $C_2$ alkoxy.

Other preferred compounds are Compounds E wherein:
J is J-1 to J-5 and J-7 to J-13.
Specifically preferred compounds are:
2-[[[[(4-chloro-6-methoxy-2-pyrimidinyl)amino]carbonyl]amino]sulfonyl]-N-methoxybenzenecarboximidoyl chloride, Compound 28,
2-[(cyano)(methoxyimino)methyl]-N-[[(4-methoxy-6-methyl-2-pyrimidinyl)amino]carbonyl]benzenesulfonamide, Compound 2, and
N-methoxy-2-[[[[(4-methoxy-6-methyl-1,3,5-triazin-2-yl)amino]carbonyl]amino]sulfonyl]benzenecarboximidoyl chloride, Compound 29.

DETAILS OF THE INVENTION

Compounds of Formula I are prepared by the methods shown below in Equations 1, 2, 3 and 4, wherein J, W, A and R are as previously defined. The method of choice for the individual compounds of Formula I will be readily apparent to those skilled in the art.

Equation 1 illustrates the reaction of sulfonamides II with the phenol ester of the appropriate carbamic acid or thiocarbamic acid of Formula III in the presence of a tertiary amine base such as 1,8-diazabicyclo[5.4.0]undec-7-ene (DBU). Similar coupling methods are described in EPA 70,804.

Equation 1

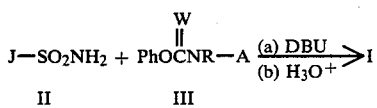

The reaction of Equation 1 is best carried out at about −5° to 25° C. is an inert solvent such as dioxane or acetonitrile for 1 to 24 hours, optionally under an inert atmosphere and in the presence of an equimolar quantity of DBU. The desired products of Formula I can be conveniently isolated by acidifying the reaction solution with aqueous hydrochloric acid or acetic acid and filtration. Alternatively, the aqueous layer can be extracted with a solvent such as methylene chloride. Drying and evaporating the solvent affords the desired product.

The phenylcarbamate and phenylthiocarbamate intermediates of Formula III can be prepared by methods, or obvious modifications thereof, described in South African Patent Application 82/5671 and South African Patent Application 82/5045.

Equation 2 illustrates the reaction of sulfonylisocyanates and sulfonylisothiocyanates of Formula IV with the appropriate heterocyclic amines of Formula V.

Equation 2

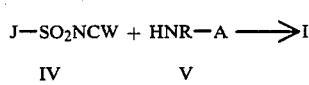

The reaction of Equation 2 is best carried out in an inert solvent such as methylene chloride, tetrahydrofuran, toluene or acetonitrile at a temperature between about 0° and 80° C. A catalytic amount of 1,4-diazabicyclo[2.2.2]octane (DABCO) can be used to accelerate the reaction. In cases where the products are insoluble in the reaction solvent, they can be isolated by simple filtration. Soluble products can be isolated by evaporation of the solvent and trituration of the residue with solvents such as 1-chlorobutane, diethyl ether or ethyl acetate, and filtration.

Sulfonyl isocyanates IV (W=O) can be prepared directly from the corresponding sulfonamides II according to the procedures described in Ulrich et al., *Newer Methods of Preparative Organic Chemistry*, Vol. VI, page 223 to 241, Academic Press, New York and London, W. Foerst Ed. By this two-step procedure, sulfonamides are converted to isolatable n-butylsulfonylureas which are reacted further with phosgene and a tertiary amine catalyst to form sulfonyl isocyanates. The analogous one-step procedure can be employed by using the method described in U.S. Pat. No. 4,238,621. Alternatively, sulfonamides can be reacted with thionyl chloride to form intermediate N-sulfinylsulfonamides, which upon exposure to phosgene in the presence of a catalytic amount of pyridine, provide sulfonyl isocyanates. For additional details, see Ulrich et al., *J. Org. Chem.*, 34, pages 3200 to 3202 (1969).

Sulfonyl isothiocyanates (iv, w=s) are prepared from the corresponding sulfonamides by reaction with carbon disulfide and potassium hydroxide followed by treatment of the resulting dipotassium salt with phosgene. Such a procedure is described in *Arch. Pharm.*, 299, 174 (1966).

Equation 3 illustrates the reaction of a sulfonyl carbamate or thiocarbamate of Formula VI with an appropriate heterocyclic amine V.

Equation 3

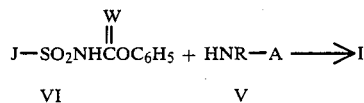

The reaction of Equation 3 is carried out at about 20° to 100° C. in an inert solvent such as p-dioxane for 0.5 to 24 hours. Additional details concerning the general coupling reaction to prepare sulfonylureas can be found in EPA 44,807. The product is isolated by evaporation of the reaction solvent and purified by trituration of the residue with solvents such as 1-chlorobutane or ethyl ether, and filtration, or by chromatography procedures on silica gel.

Phenylcarbamates and phenylthiocarbamates of Formula VI are prepared by methods described, or obvious modifications thereof, in U.S. Pat. No. 4,443,243, EPA 44,808 or South African Patent Application 82/5042.

Equation 4 illustrates the reaction of sulfonamides of Formula Ia with appropriate salts or amines to form corresponding sulfonamides of Formula Ib.

Equation 4

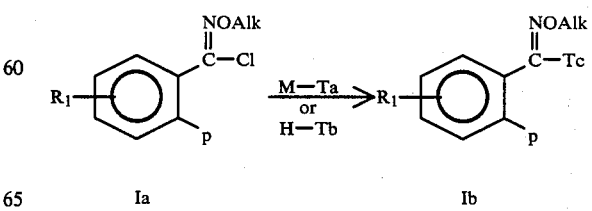

wherein
P is

A, Alk, R and $R_1$ are as previously defined;
M is $Na^+$ or $K^+$;
Ta is CN, SCN, $N_3$, $C_1$ to $C_3$ alkoxy, $C_1$ to $C_2$ thioalkyl, or F;
Tb is $NH(C_1$ to $C_2$ alkyl), $N(C_1$ to $C_2$ alkyl)$_2$, $N(OCH_3)CH_3$, or $\overset{\frown}{N(CH_2)}_3$ or 4; and
Tc is Ta or Tb.

The reaction of Equation 4 is effected by reacting Ia with at least one molar equivalent of salt M-Ta (at least two molar equivalents when Ta is an alkoxide or mercaptide) in an inert solvent such as acetone, methyl ethyl ketone, tetrahydrofuran, dioxane, methanol, dimethylformamide (DMF), dimethylsulfone or dimethylsulfoxide. The reaction is carried out at about 20° to 140° C. for 1 to 24 hours, and optionally in the presence of a phase transfer catalyst such as a crown ether. Products Ib (Tc is Ta) are isolated by addition of water, acidification if Ta is alkoxide or mercaptide, and filtration. Alternatively, the aqueous suspension is extracted with a solvent such as methylene chloride, dried and the solvent evaporated to yield crude Ib. Product Ib can be purified further by trituration with a solvent such as 1-chlorobutane, ethyl acetate or diethyl ether, and filtration, or by chromatography procedures on silica gel. Similarly, products Ib (Tc is Tb) can be prepared by reacting Ia with amines, H-Tb, preferably an excess of about 2 to 20 mole equivalents, in an inert solvent such as tetrahydrofuran, p-dioxane, methanol, methylene chloride or DMF. The reactions are carried out at about 0° C. to 100° C. for 1 to 24 hours. Work-up is as described above.

In analogous manner, other compounds of Formula I can be prepared using procedures described in Equation 4, from appropriate corresponding compounds of Formula I, wherein J is $J_2$ to $J_{13}$ and $Q^1$ or $Q^2$ is C(Cl)=NOAlk.

As illustrated in Equation 5, the intermediate sulfonamides of Formula II are conveniently prepared by amination of the corresponding sulfonyl chlorides with anhydrous ammonia or aqueous ammonium hydroxide by general methods known in the art, e.g., Crossley et al., *J. Am. Chem. Soc.*, 60, pages 2223 to 2224 (1938); Pailer, *Monatsh*, 92, pages 677 to 683 (1961); and U.S. Pat. No. 4,511,392.

Equation 5

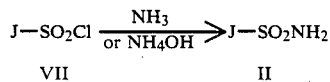

As illustrated in Equation 6, sulfonamides of Formula II can also be prepared by deprotection of t-butylsulfonamides of Formula VIII.

Equation 6

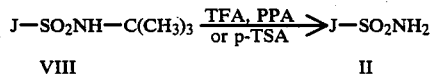

The reaction of Equation 6 is conveniently carried out in excess trifluoroacetic acid (TFA) according to the procedure of Catt et al., *J. Org. Chem.*, 39, pages 566 to 568 (1974), or with polyphosphoric acid (PPA) according to procedures of Lomardino, *J. Org. Chem.*, 36, pages 1843 to 1845 (1971). Alternatively, t-butylsulfonamide VIII can be treated with a catalytic amount of p-toluene sulfonic acid (p-TSA) in a solvent such as toluene or xylenes at reflux temperatures for 1 to 24 hours to yield II.

Intermediate sulfonyl chlorides of Formula VIIa are preferably prepared by oxidative-chlorination of an appropriate thioether of Formula IX, as shown below in Equation 7.

Equation 7

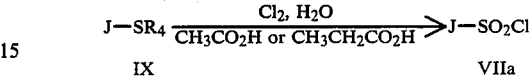

wherein J is as previously defined, E is a single bond, and $R_4$ is $C_2$ to $C_3$ alkyl or benzyl.

The reaction of Equation 7 is carried out by contacting a suspension of thioether IX in a solvent such as acetic or propionic acid in the presence of at least 2.5 equivalents of water and 3.0 equivalents of chlorine at about $-20°$ to 30° C. for 0.2 to 5 hours. The reaction mixture is poured into ice-water and the product is isolated by filtration or extraction with a solvent such as methylene chloride. The extraction product is optionally washed with aqueous sodium bicarbonate until neutral or slightly basic to litmus, then dried, and the solvent is evaporated to yield a product sufficiently pure to be carried directly on to the next step.

Alternatively, reaction of thioether IX, wherein $R_4$ is benzyl or hydrogen, with a hypochlorite solution, i.e., NaOCl, can provide sulfonyl chloride VIIa. For additional details, see analogous reactions in South African Patent Application No. 84/8845 and 84/8844. Mercaptans or thioethers can also be transformed to sulfonyl fluorides by reaction with chlorine and potassium hydrogen difluoride, which on further reaction with ammonia or ammonium hydroxide can provide sulfonamides; see, e.g., Brown et al., *J. Chem. Soc. Perkins Trans* I, pages 522 to 527 (1972).

Sulfonyl chlorides, VIIa, can also be prepared by diazotization reactions, as illustrated in Equation 8.

Equation 8

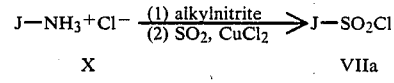

The amine hydrochloride salt is diazotized with an alkylnitrite in an organic solvent, such as acetonitrile or acetone, and the resulting diazonium salt is reacted with sulfur dioxide and cupric chloride to yield VIIa. Doyle, *J. Org. Chem.*, 42, pages 2426 to 2431 (1977) and ibid, pages 2431 to 2436, describe conditions for analogous reactions. Alternatively, sulfonyl chlorides VIIa can be prepared by aqueous diazotization; for additional details, see EPA 83,975 and 85,476. Aromatic amines of Formual X can be prepared from the corresponding nitro compounds by various known reduction procedures, e.g., *Preparative Organic Chemistry*, 4 Ed., pages 557 to 563, John Wiley and Sons, New York and London, Hilgetag et al., Eds., and EPA 207,894.

Sulfonyl chlorides of Formula VIIb can be prepared from compounds of Formula XI as shown in Equation 9 and described in U.S. Pat. No. 4,420,325.

Equation 9

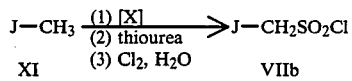

wherein J is as previously defined and [X] is a suitable halogenating agent, such as N-bromosuccinimide.

Thioethers of Formula IX are important intermediates for preparing compounds of this invention and can be prepared by a variety of general methods known in the art. Several such procedures are described below in Equations 10 through 15.

Equation 10 illustrates the preparation of thioethers of Formula IXa, containing an alpha-chlorooxime moiety, from carboxylic acids of Formula XII. Subsequent reaction of IXa with appropriate salts, M-Ta, or amines, H-Tb, provides thioethers of Formula IXb.

Equation 10

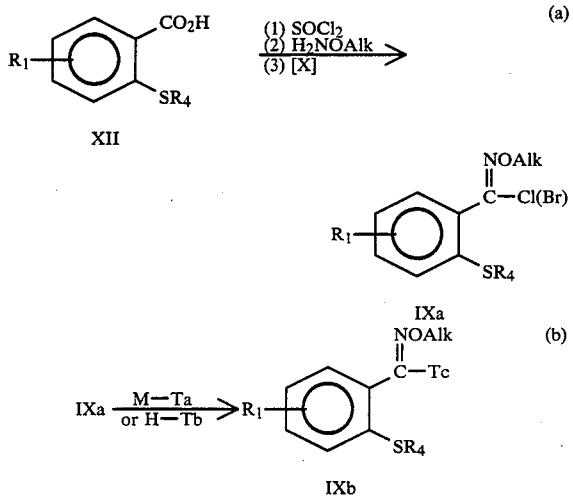

wherein $R_1$, $R_4$, Alk, M, Ta, Tb and Tc are as previously defined; and [X] is as defined below.

In Equation 10a, carboxylic acids XII are converted to acid chlorides which in turn are converted to isolatable N-alkoxyamides by known methods. Subsequent reaction of the amides with suitable halogenating agents, [X], provides compounds of Formula IXa. Suitable halogenating agents include phosphorous pentachloride or phosphorous pentabromide in an inert solvent such as benzene or chloroform at about 5° to 40° C. for 1 to 24 hours; or phosgene, preferably, or thionyl chloride and a catalytic amount of DMF in an inert solvent such as methylene chloride, benzene or chlorobenzene at about 10° to 130° C. for 0.5 to 24 hours; or more preferably equimolar amounts of triphenylphosphine and carbon tetrachloride (or carbon tetrabromide) in an inert solvent such as acetonitrile at about 0° C. to 80° C. for 1 to 24 hours. Compounds of Formula IXa are isolated by evaporation of reaction media under vacuum and can be purified by optionally treatment with water followed by chromatography procedures on silica gel.

The reactions of Equation 10b are carried out by the general procedures described in Equation 4.

Equation 11 illustrates the preparation of thioethers of Formula IXc, containing an alpha-cyanooxime moiety, from corresponding aldehydes of Formula XIII.

Equation 11

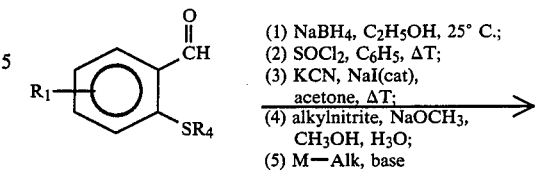

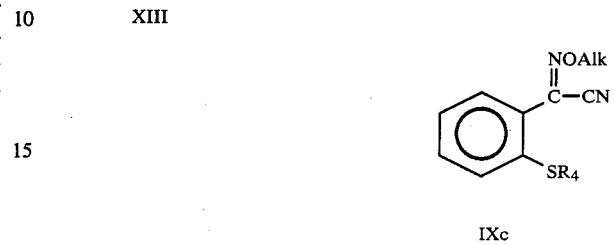

wherein $R_1$, $R_4$, M and Alk are as previously defined.

The reactions (1) to (4) of Equation 11 are carried out by generally known methods, to provide uncapped oximes of Formula IXc, wherein Alk is H. Subsequent reaction of the uncapped oximes by generally known methods with a suitable base and reagents, M-Alk, in an inert solvent provides capped oximes IXc. Suitable bases and solvents include potassium tert-butoxide in DMF or sodium methoxide in methanol. Reactions (4) and (5) of Equation 11 are further illustrated in Example 7.

In an analogous manner to reactions described in Equations 10 and 11, other thioethers of Formula IX can be prepared, wherein J is $J_2$ to $J_{13}$, by carrying out reactions on appropriate corresponding carboxylic acids or aldehydes.

Equation 12 illustrates the preparation of aldooximes and ketooximes of Formula IXd.

Equation 12

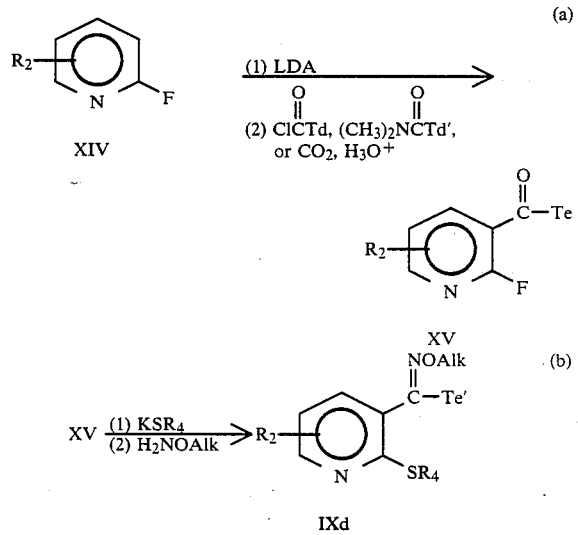

wherein:
$R_2$, $R_4$ and Alk are as previously defined;
$T_d$ is $C_1$ to $C_3$ alkyl, optionally substituted with $OCH_3$ or $SCH_3$; or cyclopropyl;
Td' is Td or $CF_3$, $CF_2CF_3$, $CF_2CF_2CF_3$, or H;
$T_e$ is $T_d'$ or $CO_2H$; and
$T_e'$ is $T_d'$.

In Equation 12a, 2-fluoropyridine XIV is metallated with lithium diisopropyl amide (LDA) according to the procedure of Gungor, et al., *J. Organomet. Chem.*, 215, pages 139 to 150 (1981), followed by treatment with an acid chloride or a N,N-dimethylamide (or carbon dioxide and H₃O) by known methods to yield corresponding ketones or aldehydes (or carboxylic acids). In Equation 12b, reaction of halopyridine XV with an appropriate mercaptide in a solvent such as DMF yields the corresponding thioethers, which on reaction with an alkoxyamine by known methods yields compounds of Formula IXd. U.S. Pat. No. 4,456,469 discloses analogous halopyridine-mercaptide reactions.

Also, by known methods, aldo or keto-thioethers in Equation 12b can be reacted with hydroxylamine followed by a suitable base and an alkylating reagent, M-Alk, to provide capped oximes Ixd. Suitable bases and solvents are described in Equation 11. For details on the reaction of trifluoromethyl ketones with hydroxylamine see, for example, Rosenfeld, U.S. Pat. No. 3,748,361 and R. L. Salvador et al., *J. Med. Chem.*, 15, pages 646 to 650 (1972).

Oximes of Formula IXd, wherein Te' is $CH_2CN$, can be prepared in a two-step procedure from an appropriate 2-benzylthio-3-pyridyl-carboxylate ester using generally known methods. Thus, reaction of the ester with a suitable base such as sodium hydride and acetonitrile in an inert solvent such as tetrahydrofuran can provide the corresponding 3-ketoacetonitrile, which on subsequent reaction with an appropriate alkoxyamine, or more preferably, its hydrochloride salt, in an inert solvent such as methanol or DMF can provide IXd (Te' is $CH_2CN$).

Pyridyl alkyl ketones described in Equations 12a and 12b can also be prepared by reaction of appropriate pyridyl acid chlorides with alkyl Grignard reagents. For details see, for example, Japanese Patent Application 60-253,531.

Marsais, et al., *J. Orgmet. Chem.*, 216, pages 139 to 147 (1981) describes the preparation of 3,4 and 2,3-disubstituted pyridines by reacting 3-chloropyridine with, respectively, lithium dialkylamides in tetrahydrofuran or butyl lithium in diethyl ether. By reacting such lithium intermediates with reagents described in Equation 12a followed by Equation 12b, the corresponding 3,4- and 2,3-isomers of IXd can be obtained.

For further details pertaining to the synthesis of pyridines, see Beritmaier, et al., *Tetrahedron*, 26, 5907 (1970); Blank, et al., *J. Med. Chem.*, 17, pages 1065 to 1071 (1974); Mallet, et al., *Tetrahedron*, 41, 3433 (1985); and Delarge, et al., *Annales Pharm. France*, 36, 369 (1978); and R. L. Salvador et al., *Tetrahedron*, 27, pages 1221 to 1226 (1971). The N-oxidation of pyridine sulfonamides of Formula II, wherein J is J-6 to J-9, is carried out according to known methods for the oxidation of pyridine compounds.

Equations 13 and 14 illustrate the preparation of thiophene carboxylic acids of Formula IXe and IXf. The acids can be used as intermediates for preparing compounds analogous to those described in Equation 10. Also, reduction of the acids or their esters can provide methyl alcohols for analogous reactions described in Equation 11.

Equation 13

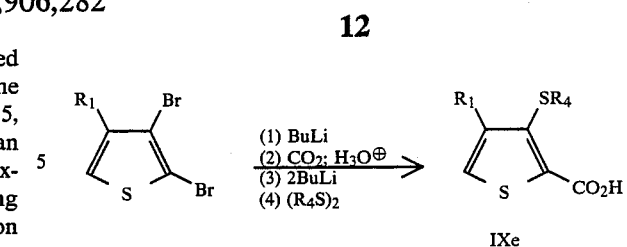

Equation 14

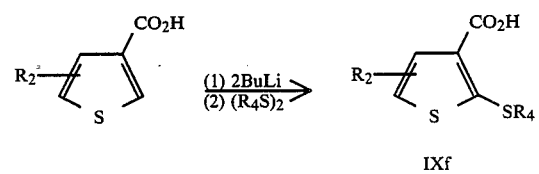

In Equations 13 and 14, metal-halogen exchange or metallation with carbon dioxide or a disulfide by known methods provides carboxylic acids IXe and IXf. Starting with 3,4-dibromo-thiophene, and carrying out the reactions of Equation 13, can provide the 3,4-substituted isomer of acid IXe. Further details pertaining to the preparation and functional group manipulation of thiophenes are found in U.S. Pat. No. 4,481,029 and Knight, et al., *J. Chem. Soc. Perkin Trans I*, pages 791 to 794, (1983).

Equation 15 illustrates the preparation of some pyrazolethioethers of Formula IXg, which can undergo further reactions analogous to those described in Equations 10, 11 and 12.

Equation 15

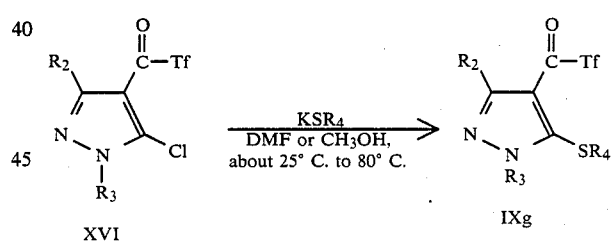

wherein Tf is H, $C_1$ to $C_3$ alkyl, optionally substituted with $OCH_3$, $SCH_3$ or halogen; cyclopropyl, OH or $OCH_3$, and $R_2$, $R_3$ and $R_4$ are as previously defined.

The compounds of Formula XVI in Equation 15 are known or can be prepared by known methods; see, for example, Kviko et al., *Zhurnal Org. Khimi*, 5, pages 1685 to 1692 (1969); Koshelev et al., Ibid, 8, pages 1750 to 1754 (1972); and Japanese Patent Application 57-228261.

The t-butylsulfonamides of Formulas XIX, XXI and XXIII are useful intermediates for preparing compounds of this invention and they can be prepared by known methods or simple modifications thereof. Several such methods are illustrated in Equations 16, 17 and 18.

Equation 16

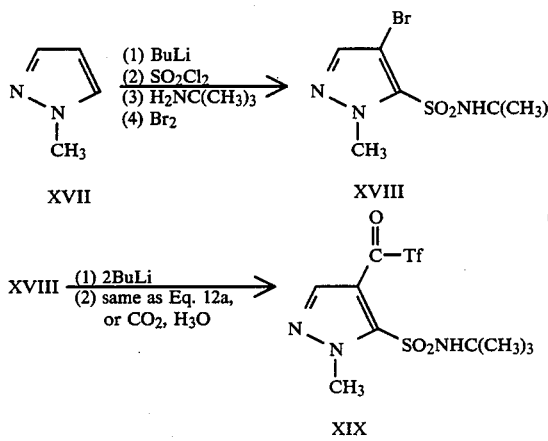

wherein Tf is as previously defined.

Preparation of intermediates such as bromide XVIII can be found in EPA 95,925. Exposure of bromide XVIII to BuL; followed by treatment with an appropriate acid chloride, DMF or carbon dioxide yields XIX.

Equation 17

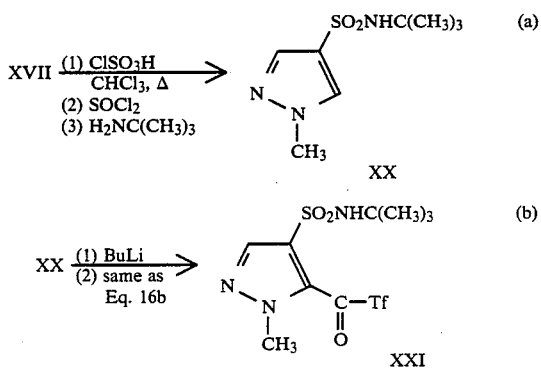

In Equation 17, the isomeric 5-keto-4-sulfonamide is prepared as outlined, while in Equation 18, the isomeric 4-keto-3-sulfonamide XXIII is prepared as outlined.

Equation 18

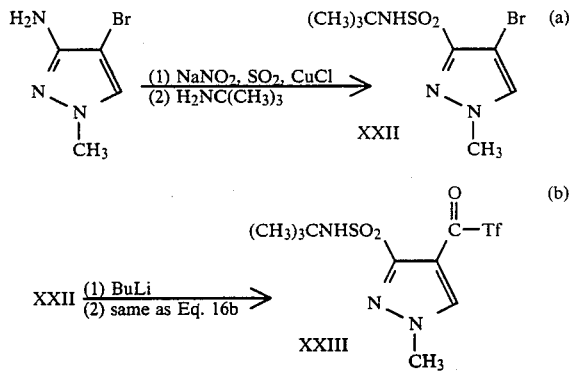

Intermediate compounds of Formula XIX, XXI and XXIII in Equations 16, 17 and 18 can undergo further reactions analogous to those described in Equations 10, 11 and 12.

For further details pertaining to the synthesis of pyrazoles see, for example, EPA 87,780; South African Patent Application 833,350, EPA 95,925; and Jacobs, "Heterocycloc Compounds", Elderfield ed., Vol. 5, pages 45 to 161, Wiley, New York, 1957.

Chemical compatibility of the wide variety of reactions, reactants and reaction conditions described throughout this disclosure with respect to J, $R_1$ to $R_3$, $Q_1$ and $Q_2$ must be evaluated and judicious choices made; one skilled in the art, having this disclosure before him, will be able to readily make such evaluations and choices without undue difficulty. In addition, incompatibility can readily be avoided in certain instances by suitable selection of a protecting group as will be obvious to one skilled in the art. For a compilation of references describing the wide variety of such protecting groups available, see Greene et al., "Protective Groups in Organic Synthesis", John Wiley and Sons, Inc., New York, 1981.

The heterocyclic amines of Formula V in Equation 2 above can be prepared by methods known in the literature, or simple modifications thereof, by those skilled in the art. For instance, EPA 84,224 and Braker et al., J. Chem. Soc., 69, 3072 (1947), describe methods for preparing aminopyridines and triazines substituted by acetal groups such as dialkoxymethyl or 1,3-dioxolan-2-yl, among other groups. Also, South African Patent Application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, and $OCF_2H$. South African Patent Application 83/7434 describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2,3-d]pyrimidine-2-amines, the cyclopenta[d]pyrimidines-2-amines (V, A is A-2) and the 6,7-dihydro-5H-pyrano[2,3-d]pyrimidin-2-amines (V, A is A-3) can be prepared as described in EPA 15,683. The furo[2,3-d]pyrimidine-2-amines (V, A is A-4) are described in EPA 46,677. Compounds of Formula V, where A is A-7, are described in EPA 125,864.

Compounds of Formula V, where A is A-5, are described in EPA 73,562. Compounds of Formula V where A is A-6, are described in EPA 94,260.

In addition, general methods for preparing aminopyrimidines and triazines have been reviewed in the following publications: "The Chemistry of Heterocyclic Compounds", a series published by Interscience Publ., New York and London; "Pyrimidines", Vol. 16 of the same series by Brown; "s-Triazines and Derivatives", Vol. 13 of the same series of Smolin et al.,; U.S. Pat. No. 3,154,547; and Huffman et al., J. Org. Chem., 28, pages 1812 to 1816 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange can also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees Celsius.

EXAMPLE 1

N-Methoxy-2-[(phenylmethyl)thio]benzamide

A suspension of 100 g of 2-[(phenylmethyl)thio]benzoic acid and 97.6 g of thionyl chloride in 800 ml of benzene was refluxed for about three hours then evaporated to dryness under vacuum. The residue was triturated with hexane to yield 101.2 g of 2-[(phenylmethyl)thio]benzoyl chloride, m.p. 113° to 116° C.

To a suspension of 80.2 g of potassium carbonate in 500 ml of water and 200 ml of methylene chloride, cooled at less than 5° C. with external cooling, was added, portionwise, 48.2 of methoxyamine hydrochloride followed, after about 10 minutes, by the dropwise addition of 101 g of the above acid chloride dissolved in 700 ml of methylene chloride. After the suspension was stirred at 0° C. for one hour, then two hours without external cooling, the organic layer was separated, dried (MgSO$_4$), and evaporated to dryness under vacuum. The residue was recrystallized from 1-chlorobutane to yield 79 g of the subject compound, m.p. 100° to 105° C.

EXAMPLE 2

N-Methoxy-2-[(phenylmethyl)thio]benzene carboximidoyl chloride

To a suspension of 79 g of the product of Example 1 in 1500 ml of benzene under a N$_2$ atmosphere, cooled at 20° to 30° C. with external cooling, was added, portionwise, 60.2 g of phosphorous pentachloride. After stirring at 25° C. for about 24 hours, the suspension was warmed at 40° C. for about four hours, then cooled to 25° C. and filtered. The filtrate was evaporated at less than 40° C. under vacuum, and residue was chromatographed on silica gel with methylene chloride at eluant to yield 47 g of the subject compound as a crude yellow oil.

NMR(CDCl$_3$): ppm 4.15 (m, 3H, OCH$_3$) 4.6 (s, 2H, CH$_2$) 7.4 (m, 9H, Ar).

EXAMPLE 3

2-(Chlorosulfonyl)-N-methoxybenzenecarboximidoyl chloride

To a solution of 10 g of the product of Example 2 and 1.9 g of water in 125 ml of glacial acetic acid, cooled at about 13° C. with external cooling, was added, dropwise, 8.6 ml of chlorine. After stirring at 10° to 15° C. for one hour, the suspension was poured into excess ice-water, and the mixture was extracted with 1-chlorobutane. The extraction was washed with water, twice with saturated aqueous sodium bicarbonate, then again with water, then dried (MgSO$_4$) and evaporated at less than 40° C. under vacuum to yield the subject compound as a crude oil.

EXAMPLE 4

2-(Aminosulfonyl)-N-methoxybenzenecarboximidoyl chloride

To a solution of the oil prepared in Example 3 in 100 ml of tetrahydrofuran, cooled at −30° C. with external cooling, was added dropwise 1.7 ml of ammonia. After stirring at −30° C. for about 15 minutes, the suspension was purged with N$_2$ to remove excess ammonia, then evaporated at less than 30° C. under vacuum. After adding ice-water to the residue, the suspension was extracted with methylene chloride, dried (MgSO$_4$) and evaporated under vacuum. The residue was triturated with hexane to yield 2.5 g of the subject compound as a crude solid, m.p. 155° to 158° C., NMR(CDCl$_3$+DMSO):

ppm 4.2 (s, 3H, OCH$_3$) 6.6 (bs, 2H, NH$_2$) 7.8 (m, 4H, Ar).

EXAMPLE 5

2-[[(4-Methoxy-6-methyl-2-pyrimidinyl)aminocarbonyl]aminosulfonyl]-N-methoxybenzenecarboximidoyl chloride To a suspension of 0.4 g of the product of Example 4 and 0.46 g of phenyl(4-methoxy-6-methylpyrimidin-2-yl)carbamate in 10 ml of dry acetonitrile was added 0.25 g of DBU. The suspension was stirred for about two hours at room temperature, then diluted with excess water and filtered. The filtrate was acidified with concentrated hydrochloric acid to yield a precipitate. After filtration, the residue was washed with excess water and suction-dried to yield 0.35 g of the subject compound, m.p. 178° to 179° C.;

IR(Nujol): 1700 cm$^{-1}$ (C=O);
NMR(CDCl$_3$): PPM 2.4 (s, 3H, CH$_3$), 3.9 (s, 3H, OCH$_3$), 3.95 (s, 3H, NOCH$_3$), 6.3 (s, 1H, py-H), 7.3 (m, 1H, NH), 7.5 (m, 1H, Ar), 7.7 (m, 2H, Ar), 8.4 (m, 1H, Ar), 13.2 (bs, 1H, NH).

EXAMPLE 6

N-Methoxy-2-[[[[(4-methoxy-6-methyl-1,3,5-triazin-2-yl)amino]carbonyl]amino]sulfonyl]benzenecarboximidoyl chloride By the procedure of Example 5, 0.4 g of the product of Example 4 was reacted with 0.46 g of phenyl(4-methoxy-6-methyl-1,3,5-triazin-2-yl)carbamate and 0.25 g of DBU. The resulting suspension was acidified, without prior filtration, with concentrated hydrochloric acid and filtered. The residue was washed with excess water and suction-dried to yield 0.45 g of the subject compound, m.p. 182° to 184° C.

IR(Nujol): 1700 cm$^{-1}$ (C=O)
NMR(CDCl$_3$): ppm 2.6 (s, 3H, CH$_3$), 3.95 (s, 3H, NOCH$_3$), 4.1 (s, 3H, OCH$_3$), 7.4 (bs, 1H, NH), 7.5 (m, 1H, Ar), 7.7 (m, 2H, Ar), 8.4 (m, 1H, Ar), 12.4 (bs, 1H, NH).

EXAMPLE 7

Alpha-(Methoxyimino)-2-[(phenylmethyl)thio]benzeneacetonitrile

A suspension of 41 g of 2-[(phenylmethyl)thio]benzeneacetonitrile and 9.4 g of sodium methoxide in 350 ml of methanol, under a $N_2$ atmosphere, was stirred at 25° C. for one hour, then refluxed one hour and cooled to 10° C. Then, n-butyl nitrite (17.7 g) was added dropwise and the suspension was stirred at about 25° C. for 16 hours, then evaporated under vacuum. Excess water was added to the residue and the emulsion was washed with methylene chloride to yield a 3-phase water-oil-methylene chloride mixture. The oil layer was separated and acidified in water with concentrated hydrochloric acid. The suspension was extracted with methylene chloride, dried ($MgSO_4$), and evaporated under vacuum to yield 26.9 g of crude alpha-(hydroxyimino)-2-[(phenylmethyl)thio]benzeneacetonitrile as an oil.

To 15 g of the above oil in 125 ml of DMF, under $N_2$, was added 6.6 of potassium tert-butoxide. After stirring for one hour, the suspension was heated at 50° C. for one hour, then 7.1 g of dimethyl sulfate was added dropwise at 40° C. The suspension was stirred at 25° C. overnight, diluted with excess water, extracted with diethyl ether, and the extracts dried ($MgSO_4$) and evaporated under vacuum. The residue was chromatographed on silica gel with methylene chloride to yield 13 g of the subject compound as an oil.

NMR($CDCl_3$): ppm 4.0–4.2 (m, 5H, $OCH_3$, $CH_2$) 7.4 (m, 9H, Ar).

EXAMPLE 8

2-[Cyano(methoxyimino)methyl]benzenesulfonamide

By the procedure of Example 3, 11 g of the product of Example 7 was reacted with 2.2 g of water and 9.9 ml of chlorine in 125 ml of glacial acetic acid. After work-up, 2-[cyano(methoxyimino)methyl]benzenesulfonyl chloride was obtained as a crude oil.

By the procedure of Example 4, all of the above oil was reacted with 1.7 ml of ammonia in 100 ml of tetrahydrofuran. Following work-up, the residue was triturated with hexane and recrystallized from 1-chlorobutane to yield 2 g of the subject compound; m.p. 82° to 90° C.;

NMR($CDCl_3$): ppm 4.3 (s, 3H, $OCH_3$), 5.4 (bs, 2H, $NH_2$), 7.7 (m, 3H, Ar), 8.2 (m, 1H, Ar).

EXAMPLE 9

2-[(Cyano)(methoxyimino)methyl]-N-[[4,6-dimethoxy-1,3,5-triazin-2-yl)amino]carbonyl]benzenesulfonamide By the procedure of Example 5, 0.4 g of the product of Example 8 was reacted with 0.51 g of phenyl(4,6-dimethoxy-1,3,5-triazin-2-yl)carbamate and 0.28 g of DBU in 10 ml of dry acetonitrile to yield 0.6 g of the subject compound; m.p. 191° to 194° C.

IR(Nujol): 1710 $cm^{-1}$ (C=O).

NMR($CDCl_3$): ppm 4.1 (s, 6H, $OCH_3$), 4.2 (s, 3H, $NOCH_3$), 7.4 (bs, 1H, NH), 7.6 (m, 1H, Ar), 7.8 (m, 2H, Ar), 8.5 (m, 1H, Ar), 12.3 (bs, 1H, NH).

Using the techniques described in Equations 1 through 18 and Examples 5, 6 and 9, or simple modifications thereof, the following compounds in Tables 1 through 9 can be made.

| General Formulas for Tables 1 to 9 |
|---|
| General Formula 1 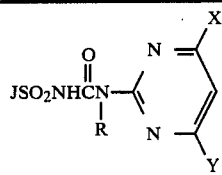 |
| General Formula 2 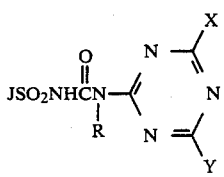 |
| General Formula 3 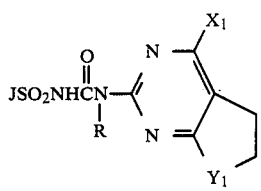 |
| General Formula 4 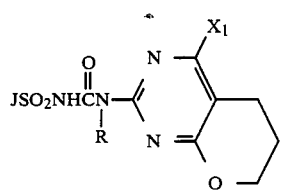 |
| General Formula 5 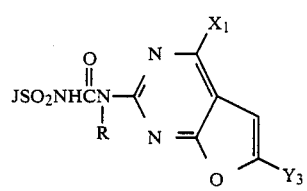 |
| General Formula 6 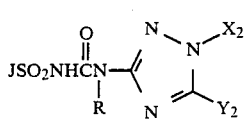 |
| General Formula 7 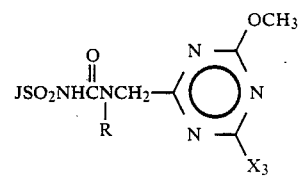 |
| General Formula 8 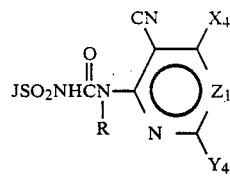 |
| General Formula 9 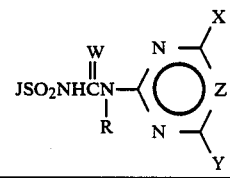 |

TABLE 1

General Formula 1

| J | E | R | R$^1$/R$^2$ | T$^1$/T$^2$ | Alk | X | Y |
|---|---|---|---|---|---|---|---|
| J-1 | — | H | H | Cl | CH$_3$ | OCH$_3$ | OCH$_3$ |
| J-1 | — | H | H | Cl | CH$_3$ | CH$_3$ | OCH$_3$ |
| J-1 | — | H | H | Cl | CH$_3$ | CH$_3$ | CH$_3$ |
| J-1 | — | H | H | Cl | CH$_3$ | Cl | OCH$_3$ |
| J-1 | — | H | H | Cl | CH$_3$ | Br | OCH$_3$ |
| J-1 | — | H | H | Cl | CH$_3$ | H | CH$_3$ |
| J-1 | — | H | H | Cl | CH$_3$ | OCH$_3$ | H |
| J-1 | — | H | H | Cl | CH$_3$ | OCH$_3$ | CH$_2$OC$_2$H$_5$ |
| J-1 | — | H | H | Cl | CH$_3$ | OCF$_2$H | OCH$_3$ |
| J-1 | — | H | H | Cl | CH$_3$ | OCH$_3$ | CH(OCH$_3$)$_2$ |
| J-1 | — | H | H | Cl | CH$_3$ | CH$_3$ | OC$_2$H$_5$ |
| J-1 | — | H | H | Cl | CH$_3$ | CH$_3$ | CH$_2$OCH$_3$ |
| J-1 | — | H | H | Cl | CH$_3$ | OCH$_3$ | CH$_2$OCH$_3$ |
| J-1 | — | H | H | Cl | CH$_3$ | C$_2$H$_5$ | OCH$_3$ |
| J-1 | — | H | H | Cl | CH$_3$ | OC$_2$H$_5$ | OCH$_3$ |
| J-1 | — | H | H | Cl | CH$_3$ | OCH$_2$CF$_3$ | OCH$_3$ |
| J-1 | — | H | H | Cl | CH$_3$ | CF$_3$ | OCH$_3$ |
| J-1 | — | H | H | Cl | CH$_3$ | CH$_2$F | OCH$_3$ |
| J-1 | — | H | H | Cl | CH$_3$ | CH$_2$Cl | OCH$_3$ |
| J-1 | — | H | H | Cl | CH$_3$ | CH$_2$Br | OCH$_3$ |
| J-1 | — | H | H | Cl | CH$_3$ | F | OCH$_3$ |
| J-1 | — | H | H | Cl | CH$_3$ | I | OCH$_3$ |
| J-1 | — | H | H | Cl | CH$_3$ | OCH$_2$CH$_2$F | OCH$_3$ |
| J-1 | — | H | H | Cl | CH$_3$ | OCH$_2$CH$_2$CF$_3$ | OCH$_3$ |
| J-1 | — | H | H | Cl | CH$_3$ | OCH$_2$CHF$_2$ | CH$_3$ |
| J-1 | — | H | H | Cl | CH$_3$ | OCH$_2$CF$_3$ | CH$_3$ |
| J-1 | — | H | H | Cl | CH$_3$ | Cl | OC$_2$H$_5$ |
| J-1 | — | H | H | Cl | CH$_3$ | OC$_2$H$_5$ | NCH$_3$ |
| J-1 | — | H | H | Cl | CH$_3$ | OCH$_3$ | CH$_2$SCH$_3$ |
| J-1 | — | H | H | Cl | CH$_3$ | OCF$_2$H | CH$_3$ |
| J-1 | — | H | H | Cl | CH$_3$ | Cl | OCF$_2$H |
| J-1 | CH$_2$ | H | H | Cl | CH$_3$ | OCH$_3$ | OCH$_3$ |
| J-1 | CH$_2$ | H | H | CN | CH$_3$ | OCH$_3$ | OCH$_3$ |
| J-1 | — | H | H | Cl | C$_2$H$_5$ | OCH$_3$ | OCH$_3$ |
| J-1 | — | H | H | Cl | C$_2$H$_5$ | CH$_3$ | OCH$_3$ |
| J-1 | — | H | H | Cl | C$_2$H$_5$ | CH$_3$ | CH$_3$ |
| J-1 | — | H | H | Cl | C$_2$H$_5$ | Cl | OCH$_3$ |
| J-1 | — | H | H | Cl | C$_2$H$_5$ | Br | OCH$_3$ |
| J-1 | — | H | H | Cl | C$_2$H$_5$ | CH$_3$ | H |
| J-1 | — | H | H | Cl | C$_2$H$_5$ | OCH$_3$ | H |
| J-1 | — | H | H | Cl | C$_2$H$_5$ | OCH$_3$ | CH$_2$OC$_2$H$_5$ |
| J-1 | — | H | H | Cl | C$_2$H$_5$ | OCF$_2$H | OCH$_3$ |
| J-1 | — | H | H | Cl | C$_2$H$_5$ | OCH$_3$ | CH(OCH$_3$)$_2$ |
| J-1 | — | H | H | Cl | C$_2$H$_5$ | CH$_3$ | OC$_2$H$_5$ |
| J-1 | — | H | H | Cl | C$_2$H$_5$ | CH$_3$ | CH$_2$OCH$_3$ |
| J-1 | — | H | H | Cl | C$_2$H$_5$ | OCH$_3$ | CH$_2$OCH$_3$ |
| J-1 | — | H | H | Cl | C$_2$H$_5$ | OCH$_3$ | C$_2$H$_5$ |
| J-1 | — | H | H | Cl | C$_2$H$_5$ | OC$_2$5 | OCH$_3$ |
| J-1 | — | H | H | Cl | C$_2$H$_5$ | OCH$_2$CF$_3$ | OCH$_3$ |
| J-1 | — | H | H | Cl | C$_2$H$_5$ | CF$_3$ | OCH$_3$ |
| J-1 | — | H | H | Cl | C$_2$H$_5$ | CH$_2$F | OCH$_3$ |
| J-1 | — | H | H | Cl | C$_2$H$_5$ | CH$_2$Cl | OCH$_3$ |
| J-1 | — | H | H | Cl | C$_2$H$_5$ | CH$_2$Br | OCH$_3$ |
| J-1 | — | H | H | Cl | C$_2$H$_5$ | F | OCH$_3$ |
| J-1 | — | H | H | Cl | C$_2$H$_5$ | I | OCH$_3$ |
| J-1 | — | H | H | Cl | C$_2$H$_5$ | OCH$_2$CH$_2$F | OCH$_3$ |
| J-1 | — | H | H | Cl | C$_2$H$_5$ | OCH$_2$CH$_2$CF$_3$ | OCH$_3$ |
| J-1 | — | H | H | Cl | C$_2$H$_5$ | OCH$_2$CHF$_2$ | CH$_3$ |
| J-1 | — | H | H | Cl | C$_2$H$_5$ | OCH$_2$CF$_3$ | CH$_3$ |
| J-1 | — | H | H | Cl | C$_2$H$_5$ | Cl | OC$_2$H$_5$ |
| J-1 | — | H | H | Cl | C$_2$H$_5$ | OC$_2$H$_5$ | NHCH$_3$ |
| J-1 | — | H | H | Cl | C$_2$H$_5$ | OCH$_3$ | CH$_2$SCH$_3$ |
| J-1 | — | H | H | Cl | C$_2$H$_5$ | OCF$_2$H | CH$_3$ |
| J-1 | — | H | H | Cl | C$_2$H$_5$ | Cl | OCF$_2$H |
| J-1 | — | H | H | Cl | n-C$_3$H$_7$ | OCH$_3$ | OCH$_3$ |
| J-1 | — | H | H | Cl | n-C$_3$H$_7$ | CH$_3$ | OCH$_3$ |
| J-1 | — | H | H | Cl | n-C$_3$H$_7$ | CH$_3$ | CH$_3$ |
| J-1 | — | H | H | Cl | n-C$_3$H$_7$ | Cl | OCH$_3$ |
| J-1 | — | H | H | Cl | n-C$_3$H$_7$ | Br | OCH$_3$ |
| J-1 | — | H | H | Cl | n-C$_3$H$_7$ | CH$_3$ | H |
| J-1 | — | H | H | Cl | n-C$_3$H$_7$ | OCH$_3$ | H |
| J-1 | — | H | H | Cl | n-C$_3$H$_7$ | OCH$_3$ | CH$_2$OC$_2$H$_5$ |
| J-1 | — | H | H | Cl | n-C$_3$H$_7$ | OCF$_2$H | OCH$_3$ |
| J-1 | — | H | H | Cl | n-C$_3$H$_7$ | OCH$_3$ | CH(OCH$_3$)$_2$ |
| J-1 | — | H | H | Cl | n-C$_3$H$_7$ | CH$_3$ | OC$_2$H$_5$ |
| J-1 | — | H | H | Cl | n-C$_3$H$_7$ | CH$_3$ | CH$_2$OCH$_3$ |
| J-1 | — | H | H | Cl | n-C$_3$H$_7$ | OCH$_3$ | CH$_2$OCH$_3$ |
| J-1 | — | H | H | Cl | n-C$_3$H$_7$ | OCH$_3$ | C$_2$H$_5$ |
| J-1 | — | H | H | Cl | n-C$_3$H$_7$ | OC$_2$H$_5$ | OCH$_3$ |
| J-1 | — | H | H | Cl | n-C$_3$H$_7$ | OCH$_2$CF$_3$ | OCH$_3$ |

TABLE 1-continued

General Formula 1

| J | E | R | R¹/R² | T¹/T² | Alk | X | Y |
|---|---|---|---|---|---|---|---|
| J-1 | — | H | H | Cl | n-C$_3$H$_7$ | CF$_3$ | OCH$_3$ |
| J-1 | — | H | H | Cl | n-C$_3$H$_7$ | CH$_2$F | OCH$_3$ |
| J-1 | — | H | H | Cl | n-C$_3$H$_7$ | CH$_2$Cl | OCH$_3$ |
| J-1 | — | H | H | Cl | n-C$_3$H$_7$ | CH$_2$Br | OCH$_3$ |
| J-1 | — | H | H | Cl | n-C$_3$H$_7$ | F | OCH$_3$ |
| J-1 | — | H | H | Cl | n-C$_3$H$_7$ | I | OCH$_3$ |
| J-1 | — | H | H | Cl | n-C$_3$H$_7$ | OCH$_2$CH$_2$F | OCH$_3$ |
| J-1 | — | H | H | Cl | n-C$_3$H$_7$ | OCH$_2$CH$_2$CF$_3$ | OCH$_3$ |
| J-1 | — | H | H | Cl | n-C$_3$H$_7$ | OCH$_2$CHF$_2$ | CH$_3$ |
| J-1 | — | H | H | Cl | n-C$_3$H$_7$ | OCH$_2$CF$_3$ | CH$_3$ |
| J-1 | — | H | H | Cl | n-C$_3$H$_7$ | Cl | OC$_2$H$_5$ |
| J-1 | — | H | H | Cl | n-C$_3$H$_7$ | OC$_2$H$_5$ | NHCH$_3$ |
| J-1 | — | H | H | Cl | n-C$_3$H$_7$ | OCH$_3$ | CH$_2$SCH$_3$ |
| J-1 | — | H | H | Cl | n-C$_3$H$_7$ | OCF$_2$H | CH$_3$ |
| J-1 | — | H | H | Cl | n-C$_3$H$_7$ | Cl | OCF$_2$H |
| J-1 | — | H | H | Cl | CH(CH$_3$)$_2$ | OCH$_3$ | OCH$_3$ |
| J-1 | — | H | H | Cl | CH(CH$_3$)$_2$ | CH$_3$ | OCH$_3$ |
| J-1 | — | H | H | Cl | CH(CH$_3$)$_2$ | CH$_3$ | CH$_3$ |
| J-1 | — | H | H | Cl | CH(CH$_3$)$_2$ | Cl | OCH$_3$ |
| J-1 | — | H | H | Cl | CH(CH$_3$)$_2$ | Br | OCH$_3$ |
| J-1 | — | H | H | Cl | CH(CH$_3$)$_2$ | CH$_3$ | H |
| J-1 | — | H | H | Cl | CH(CH$_3$)$_2$ | OCH$_3$ | H |
| J-1 | — | H | H | Cl | CH(CH$_3$)$_2$ | OCH$_3$ | CH$_2$OC$_2$H$_5$ |
| J-1 | — | H | H | Cl | CH(CH$_3$)$_2$ | OCF$_2$H | OCH$_3$ |
| J-1 | — | H | H | Cl | CH(CH$_3$)$_2$ | OCH$_3$ | CH(OCH$_3$)$_2$ |
| J-1 | — | H | H | Cl | CH(CH$_3$)$_2$ | CH$_3$ | OC$_2$H$_5$ |
| J-1 | — | H | H | Cl | CH(CH$_3$)$_2$ | CH$_3$ | CH$_2$OCH$_3$ |
| J-1 | — | H | H | Cl | CH(CH$_3$)$_2$ | OCH$_3$ | CH$_2$OCH$_3$ |
| J-1 | — | H | H | Cl | CH(CH$_3$)$_2$ | OCH$_3$ | C$_2$H$_5$ |
| J-1 | — | H | H | Cl | CH(CH$_3$)$_2$ | OC$_2$H$_5$ | OCH$_3$ |
| J-1 | — | H | H | Cl | CH(CH$_3$)$_2$ | OCH$_2$CF$_3$ | OCH$_3$ |
| J-1 | — | H | H | Cl | CH(CH$_3$)$_2$ | CF$_3$ | OCH$_3$ |
| J-1 | — | H | H | Cl | CH(CH$_3$)$_2$ | CH$_2$F | OCH$_3$ |
| J-1 | — | H | H | Cl | CH(CH$_3$)$_2$ | CH$_2$Cl | OCH$_3$ |
| J-1 | — | H | H | Cl | CH(CH$_3$)$_2$ | CH$_2$Br | OCH$_3$ |
| J-1 | — | H | H | Cl | CH(CH$_3$)$_2$ | F | OCH$_3$ |
| J-1 | — | H | H | Cl | CH(CH$_3$)$_2$ | I | OCH$_3$ |
| J-1 | — | H | H | Cl | CH(CH$_3$)$_2$ | OCH$_2$CH$_2$F | OCH$_3$ |
| J-1 | — | H | H | Cl | CH(CH$_3$)$_2$ | OCH$_2$CH$_2$CF$_3$ | OCH$_3$ |
| J-1 | — | H | H | Cl | CH(CH$_3$)$_2$ | OCH$_2$CHF$_2$ | CH$_3$ |
| J-1 | — | H | H | Cl | CH(CH$_3$)$_2$ | OCH$_2$CF$_3$ | CH$_3$ |
| J-1 | — | H | H | Cl | CH(CH$_3$)$_2$ | Cl | OC$_2$H$_5$ |
| J-1 | — | H | H | Cl | CH(CH$_3$)$_2$ | OC$_2$H$_5$ | NHCH$_3$ |
| J-1 | — | H | H | Cl | CH(CH$_3$)$_2$ | OCH$_3$ | CH$_2$SCH$_3$ |
| J-1 | — | H | H | Cl | CH(CH$_3$)$_2$ | OCF$_2$ | CH$_3$ |
| J-1 | — | H | H | Cl | CH(CH$_3$)$_2$ | Cl | OCF$_2$H |
| J-1 | — | H | H | CN | CH$_3$ | OCH$_3$ | OCH$_3$ |
| J-1 | — | H | H | CN | CH$_3$ | CH$_3$ | OCH$_3$ |
| J-1 | — | H | H | CN | CH$_3$ | CH$_3$ | CH$_3$ |
| J-1 | — | H | H | CN | CH$_3$ | Cl | OCH$_3$ |
| J-1 | — | H | H | CN | CH$_3$ | Br | OCH$_3$ |
| J-1 | — | H | H | CN | CH$_3$ | CH$_3$ | H |
| J-1 | — | H | H | CN | CH$_3$ | OCH$_3$ | H |
| J-1 | — | H | H | CN | CH$_3$ | OCH$_3$ | CH$_2$OC$_2$H$_5$ |
| J-1 | — | H | H | CN | CH$_3$ | OCF$_2$H | OCH$_3$ |
| J-1 | — | H | H | CN | CH$_3$ | OCH$_3$ | CH(OCH$_2$)$_2$ |
| J-1 | — | H | H | CN | CH$_3$ | CH$_3$ | OC$_2$H$_5$ |
| J-1 | — | H | H | CN | CH$_3$ | CH$_3$ | CH$_2$OCH$_3$ |
| J-1 | — | H | H | CN | CH$_3$ | OCH$_3$ | CH$_2$OCH$_3$ |
| J-1 | — | H | H | CN | CH$_3$ | OCH$_3$ | C$_2$H$_5$ |
| J-1 | — | H | H | CN | CH$_3$ | OC$_2$H$_5$ | OCH$_3$ |
| J-1 | — | H | H | CN | CH$_3$ | OCH$_2$CF$_3$ | OCH$_3$ |
| J-1 | — | H | H | CN | CH$_3$ | CF$_3$ | OCH$_3$ |
| J-1 | — | H | H | CN | CH$_3$ | CH$_2$F | OCH$_3$ |
| J-1 | — | H | H | CN | CH$_3$ | CH$_2$Cl | OCH$_3$ |
| J-1 | — | H | H | CN | CH$_3$ | CH$_2$Br | OCH$_3$ |
| J-1 | — | H | H | CN | CH$_3$ | F | OCH$_3$ |
| J-1 | — | H | H | CN | CH$_3$ | I | OCH$_3$ |
| J-1 | — | H | H | CN | CH$_3$ | OCH$_2$CH$_2$F | OCH$_3$ |
| J-1 | — | H | H | CN | CH$_3$ | OCH$_2$CH$_2$CF$_3$ | OCH$_3$ |
| J-1 | — | H | H | CN | CH$_3$ | OCH$_2$CHF$_2$ | CH$_3$ |
| J-1 | — | H | H | CN | CH$_3$ | OCH$_2$CF$_3$ | CH$_3$ |
| J-1 | — | H | H | CN | CH$_3$ | Cl | OC$_2$H$_5$ |
| J-1 | — | H | H | CN | CH$_3$ | OC$_2$H$_5$ | NHCH$_3$ |
| J-1 | — | H | H | CN | CH$_3$ | OCH$_3$ | CH$_2$SCH$_3$ |
| J-1 | — | H | H | CN | CH$_3$ | OCF$_2$ | CH$_3$ |
| J-1 | — | H | H | CN | CH$_3$ | Cl | OCF$_2$H |
| J-1 | — | H | H | OCH$_3$ | CH$_3$ | OCH$_3$ | OCH$_3$ |
| J-1 | — | H | H | OCH$_3$ | CH$_3$ | CH$_3$ | OCH$_3$ |
| J-1 | — | H | H | OCH$_3$ | CH$_3$ | CH$_3$ | CH$_3$ |

TABLE 1-continued

General Formula 1

| J | E | R | R¹/R² | T¹/T² | Alk | X | Y |
|---|---|---|---|---|---|---|---|
| J-1 | — | H | H | OCH$_3$ | CH$_3$ | Cl | OCH$_3$ |
| J-1 | — | H | H | OCH$_3$ | CH$_3$ | Br | OCH$_3$ |
| J-1 | — | H | H | OCH$_3$ | CH$_3$ | CH$_3$ | H |
| J-1 | — | H | H | OCH$_3$ | CH$_3$ | OCH$_3$ | H |
| J-1 | — | H | H | OCH$_3$ | CH$_3$ | OCH$_3$ | CH$_2$OC$_2$H$_5$ |
| J-1 | — | H | H | OCH$_3$ | CH$_3$ | OCF$_2$H | OCH$_3$ |
| J-1 | — | H | H | OCH$_3$ | CH$_3$ | OCH$_3$ | CH(OCH$_2$)$_2$ |
| J-1 | — | H | H | OCH$_3$ | CH$_3$ | CH$_3$ | OC$_2$H$_5$ |
| J-1 | — | H | H | OCH$_3$ | CH$_3$ | CH$_3$ | CH$_2$OCH$_3$ |
| J-1 | — | H | H | OCH$_3$ | CH$_3$ | OCH$_3$ | CH$_2$OCH$_3$ |
| J-1 | — | H | H | OCH$_3$ | CH$_3$ | OCH$_3$ | C$_2$H$_5$ |
| J-1 | — | H | H | OCH$_3$ | CH$_3$ | OC$_2$H$_5$ | OCH$_3$ |
| J-1 | — | H | H | OCH$_3$ | CH$_3$ | OCH$_2$CF$_3$ | OCH$_3$ |
| J-1 | — | H | H | OCH$_3$ | CH$_3$ | CF$_3$ | OCH$_3$ |
| J-1 | — | H | H | OCH$_3$ | CH$_3$ | CH$_2$F | OCH$_3$ |
| J-1 | — | H | H | OCH$_3$ | CH$_3$ | CH$_2$Cl | OCH$_3$ |
| J-1 | — | H | H | OCH$_3$ | CH$_3$ | CH$_2$Br | OCH$_3$ |
| J-1 | — | H | H | OCH$_3$ | CH$_3$ | F | OCH$_3$ |
| J-1 | — | H | H | OCH$_3$ | CH$_3$ | I | OCH$_3$ |
| J-1 | — | H | H | OCH$_3$ | CH$_3$ | OCH$_2$CH$_2$F | OCH$_3$ |
| J-1 | — | H | H | OCH$_3$ | CH$_3$ | OCH$_2$CH$_2$CF$_3$ | OCH$_3$ |
| J-1 | — | H | H | OCH$_3$ | CH$_3$ | OCH$_2$CHF$_2$ | CH$_3$ |
| J-1 | — | H | H | OCH$_3$ | CH$_3$ | OCH$_2$CF$_3$ | CH$_3$ |
| J-1 | — | H | H | OCH$_3$ | CH$_3$ | Cl | OC$_2$H$_5$ |
| J-1 | — | H | H | OCH$_3$ | CH$_3$ | OC$_2$H$_5$ | NHCH$_3$ |
| J-1 | — | H | H | OCH$_3$ | CH$_3$ | OCH$_3$ | CH$_2$SCH$_3$ |
| J-1 | — | H | H | OCH$_3$ | CH$_3$ | OCF$_2$H | CH$_3$ |
| J-1 | — | H | H | OCH$_3$ | CH$_3$ | Cl | OCF$_2$H |
| J-1 | — | H | H | N(CH$_3$)$_2$ | CH$_3$ | OCH$_3$ | OCH$_3$ |
| J-1 | — | H | H | N(CH$_3$)$_2$ | CH$_3$ | CH$_3$ | OCH$_3$ |
| J-1 | — | H | H | N(CH$_3$)$_2$ | CH$_3$ | CH$_3$ | CH$_3$ |
| J-1 | — | H | H | N(CH$_3$)$_2$ | CH$_3$ | Cl | OCH$_3$ |
| J-1 | — | H | H | N(CH$_3$)$_2$ | CH$_3$ | Br | OCH$_3$ |
| J-1 | — | H | H | N(CH$_3$)$_2$ | CH$_3$ | CH$_3$ | H |
| J-1 | — | H | H | N(CH$_3$)$_2$ | CH$_3$ | OCH$_3$ | H |
| J-1 | — | H | H | N(CH$_3$)$_2$ | CH$_3$ | OCH$_3$ | CH$_2$OC$_2$H$_5$ |
| J-1 | — | H | H | N(CH$_3$)$_2$ | CH$_3$ | OCF$_2$H | OCH$_3$ |
| J-1 | — | H | H | N(CH$_3$)$_2$ | CH$_3$ | OCH$_3$ | CH(OCH$_2$)$_2$ |
| J-1 | — | H | H | N(CH$_3$)$_2$ | CH$_3$ | CH$_3$ | OC$_2$H$_5$ |
| J-1 | — | H | H | N(CH$_3$)$_2$ | CH$_3$ | CH$_3$ | CH$_2$OCH$_3$ |
| J-1 | — | H | H | N(CH$_3$)$_2$ | CH$_3$ | OCH$_3$ | CH$_2$OCH$_3$ |
| J-1 | — | H | H | N(CH$_3$)$_2$ | CH$_3$ | OCH$_3$ | C$_2$H$_5$ |
| J-1 | — | H | H | N(CH$_3$)$_2$ | CH$_3$ | OC$_2$H$_5$ | OCH$_3$ |
| J-1 | — | H | H | N(CH$_3$)$_2$ | CH$_3$ | OCH$_2$CF$_3$ | OCH$_3$ |
| J-1 | — | H | H | N(CH$_3$)$_2$ | CH$_3$ | CF$_3$ | OCH$_3$ |
| J-1 | — | H | H | N(CH$_3$)$_2$ | CH$_3$ | CH$_2$F | OCH$_3$ |
| J-1 | — | H | H | N(CH$_3$)$_2$ | CH$_3$ | CH$_2$Cl | OCH$_3$ |
| J-1 | — | H | H | N(CH$_3$)$_2$ | CH$_3$ | CH$_2$Br | OCH$_3$ |
| J-1 | — | H | H | N(CH$_3$)$_2$ | CH$_3$ | F | OCH$_3$ |
| J-1 | — | H | H | N(CH$_3$)$_2$ | CH$_3$ | I | OCH$_3$ |
| J-1 | — | H | H | N(CH$_3$)$_2$ | CH$_3$ | OCH$_2$CH$_2$F | OCH$_3$ |
| J-1 | — | H | H | N(CH$_3$)$_2$ | CH$_3$ | OCH$_2$CH$_2$CF$_3$ | OCH$_3$ |
| J-1 | — | H | H | N(CH$_3$)$_2$ | CH$_3$ | OCH$_2$CHF$_2$ | CH$_3$ |
| J-1 | — | H | H | N(CH$_3$)$_2$ | CH$_3$ | OCH$_2$CF$_3$ | CH$_3$ |
| J-1 | — | H | H | N(CH$_3$)$_2$ | CH$_3$ | Cl | OC$_2$H$_5$ |
| J-1 | — | H | H | N(CH$_3$)$_2$ | CH$_3$ | OC$_2$H$_5$ | NHCH$_3$ |
| J-1 | — | H | H | N(CH$_3$)$_2$ | CH$_3$ | OCH$_3$ | CH$_2$SCH$_3$ |
| J-1 | — | H | H | N(CH$_3$)$_2$ | CH$_3$ | OCF$_2$ | CH$_3$ |
| J-1 | — | H | H | N(CH$_3$)$_2$ | CH$_3$ | Cl | OCF$_2$H |
| J-1 | — | H | H | CN | C$_2$H$_5$ | OCH$_3$ | OCH$_3$ |
| J-1 | — | H | H | CN | C$_2$H$_5$ | CH$_3$ | OCH$_3$ |
| J-1 | — | H | H | CN | C$_2$H$_5$ | CH$_3$ | CH$_3$ |
| J-1 | — | H | H | CN | C$_2$H$_5$ | Cl | OCH$_3$ |
| J-1 | — | H | H | CN | n-C$_3$H$_7$ | OCH$_3$ | OCH$_3$ |
| J-1 | — | H | H | CN | n-C$_3$H$_7$ | CH$_3$ | OCH$_3$ |
| J-1 | — | H | H | CN | n-C$_3$H$_7$ | CH$_3$ | CH$_3$ |
| J-1 | — | H | H | CN | n-C$_3$H$_7$ | Cl | OCH$_3$ |
| J-1 | — | H | H | CN | CH(CH$_3$)$_2$ | OCH$_3$ | OCH$_3$ |
| J-1 | — | H | H | CN | CH(CH$_3$)$_2$ | CH$_3$ | OCH$_3$ |
| J-1 | — | H | H | CN | CH(CH$_3$)$_2$ | CH$_3$ | CH$_3$ |
| J-1 | — | H | H | CN | CH(CH$_3$)$_2$ | Cl | OCH$_3$ |
| J-1 | — | H | H | OCH$_3$ | C$_2$H$_5$ | OCH$_3$ | OCH$_3$ |
| J-1 | — | H | H | OCH$_3$ | C$_2$H$_5$ | CH$_3$ | OCH$_3$ |
| J-1 | — | H | H | OCH$_3$ | C$_2$H$_5$ | CH$_3$ | CH$_3$ |
| J-1 | — | H | H | OCH$_3$ | C$_2$H$_5$ | Cl | OCH$_3$ |
| J-1 | — | H | H | OCH$_3$ | n-C$_3$H$_7$ | OCH$_3$ | OCH$_3$ |
| J-1 | — | H | H | OCH$_3$ | n-C$_3$H$_7$ | CH$_3$ | OCH$_3$ |
| J-1 | — | H | H | OCH$_3$ | n-C$_3$H$_7$ | CH$_3$ | CH$_3$ |
| J-1 | — | H | H | OCH$_3$ | n-C$_3$H$_7$ | Cl | OCH$_3$ |
| J-1 | — | H | H | OCH$_3$ | CH(CH$_3$)$_2$ | OCH$_3$ | OCH$_3$ |

TABLE 1-continued

General Formula 1

| J | E | R | $R^1/R^2$ | $T^1/T^2$ | Alk | X | Y |
|---|---|---|---|---|---|---|---|
| J-1 | — | H | H | $OCH_3$ | $CH(CH_3)_2$ | $CH_3$ | $OCH_3$ |
| J-1 | — | H | H | $OCH_3$ | $CH(CH_3)_2$ | $CH_3$ | $CH_3$ |
| J-1 | — | H | H | $OCH_3$ | $CH(CH_3)_2$ | Cl | $OCH_3$ |
| J-1 | — | H | H | $OC_2H_5$ | $CH_3$ | $OCH_3$ | $OCH_3$ |
| J-1 | — | H | H | $OC_2H_5$ | $CH_3$ | $CH_3$ | $OCH_3$ |
| J-1 | — | H | H | $OC_2H_5$ | $CH_3$ | $CH_3$ | $CH_3$ |
| J-1 | — | H | H | $OC_2H_5$ | $CH_3$ | Cl | $OCH_3$ |
| J-1 | — | H | H | $OC_2H_5$ | $C_2H_5$ | $OCH_3$ | $OCH_3$ |
| J-1 | — | H | H | $OC_2H_5$ | $C_2H_5$ | $CH_3$ | $OCH_3$ |
| J-1 | — | H | H | $OC_2H_5$ | $C_2H_5$ | $CH_3$ | $CH_3$ |
| J-1 | — | H | H | $OC_2H_5$ | $n$-$C_3H_7$ | Cl | $OCH_3$ |
| J-1 | — | H | H | $OC_2H_5$ | $n$-$C_3H_7$ | $OCH_3$ | $OCH_3$ |
| J-1 | — | H | H | $OC_3H_5$ | $n$-$C_3H_7$ | $CH_3$ | $OCH_3$ |
| J-1 | — | H | H | $OCH_3$ | $n$-$C_3H_7$ | $CH_3$ | $CH_3$ |
| J-1 | — | H | H | $OC_2H_5$ | $CH(CH_3)_2$ | Cl | $OCH_3$ |
| J-1 | — | H | H | $OC_2H_5$ | $CH(CH_3)_2$ | $OCH_3$ | $OCH_3$ |
| J-1 | — | H | H | $OC_2H_5$ | $CH(CH_3)_2$ | $CH_3$ | $OCH_3$ |
| J-1 | — | H | H | $OC_2H_5$ | $CH(CH_3)_2$ | $CH_3$ | $CH_3$ |
| J-1 | — | H | H | $OC_2H_5$ | $CH(CH_3)_2$ | Cl | $OCH_3$ |
| J-1 | — | H | H | $SCH_3$ | $CH_3$ | $OCH_3$ | $OCH_3$ |
| J-1 | — | H | H | $SCH_3$ | $CH_3$ | $CH_3$ | $OCH_3$ |
| J-1 | — | H | H | $SCH_3$ | $CH_3$ | $CH_3$ | $CH_3$ |
| J-1 | — | H | H | $SCH_3$ | $CH_3$ | Cl | $OCH_3$ |
| J-1 | — | H | H | $SC_2H_5$ | $CH_3$ | $OCH_3$ | $OCH_3$ |
| J-1 | — | H | H | $SC_2H_5$ | $CH_3$ | $CH_3$ | $OCH_3$ |
| J-1 | — | H | H | $SC_2H_5$ | $CH_3$ | $CH_3$ | $CH_3$ |
| J-1 | — | H | H | $SC_2H_5$ | $CH_3$ | Cl | $OCH_3$ |
| J-1 | — | H | H | SCN | $CH_3$ | $OCH_3$ | $OCH_3$ |
| J-1 | — | H | H | Br | $CH_3$ | $OCH_3$ | $OCH_3$ |
| J-1 | — | H | H | $N_3$ | $CH_3$ | $OCH_3$ | $OCH_3$ |
| J-1 | — | H | H | $NHCH_3$ | $CH_3$ | $OCH_3$ | $OCH_3$ |
| J-1 | — | H | H | $NHC_2H_5$ | $CH_3$ | $OCH_3$ | $OCH_3$ |
| J-1 | — | H | H | $N(CH_3)C_2H_5$ | $CH_3$ | $OCH_3$ | $OCH_3$ |
| J-1 | — | H | H | $N(C_2H_5)_2$ | $CH_3$ | $OCH_3$ | $OCH_3$ |
| J-1 | — | H | H | $N(OCH_3)CH_3$ | $CH_3$ | $OCH_3$ | $OCH_3$ |
| J-1 | — | H | H | $N(OCH_3)CH_3$ | $CH_3$ | $CH_3$ | $OCH_3$ |
| J-1 | — | H | H | $N(OCH_3)CH_3$ | $CH_3$ | $CH_3$ | $CH_3$ |
| J-1 | — | H | H | $N(OCH_3)CH_3$ | $CH_3$ | Cl | $OCH_3$ |
| J-1 | — | H | H | $N(CH_2)_3$ | $CH_3$ | $OCH_3$ | $OCH_3$ |
| J-1 | — | H | H | $N(CH_2)_4$ | $CH_3$ | $OCH_3$ | $OCH_3$ |
| J-7 (n=0) | — | H | H | H | $CH_3$ | $OCH_3$ | $OCH_3$ |
| J-7 (n=0) | — | H | H | H | $CH_3$ | $CH_3$ | $OCH_3$ |
| J-7 (n=0) | — | H | H | H | $CH_3$ | $CH_3$ | $CH_3$ |
| J-7 (n=0) | — | H | H | H | $CH_3$ | Cl | $OCH_3$ |
| J-7 (n=0) | — | H | H | H | $C_2H_5$ | $OCH_3$ | $OCH_3$ |
| J-7 (n=0) | — | H | H | H | $C_2H_5$ | $CH_3$ | $OCH_3$ |
| J-7 (n=0) | — | H | H | H | $C_2H_5$ | $CH_3$ | $CH_3$ |
| J-7 (n=0) | — | H | H | H | $C_2H_5$ | Cl | $OCH_3$ |
| J-7 (n=0) | — | H | H | H | $n$-$C_3H_7$ | $OCH_3$ | $OCH_3$ |
| J-7 (n=0) | — | H | H | H | $CH(CH_3)_2$ | $OCH_3$ | $OCH_3$ |
| J-7 (n=0) | — | H | H | $CH_3$ | $CH_3$ | $OCH_3$ | $OCH_3$ |
| J-7 (n=0) | — | H | H | $C_2H_5$ | $CH_3$ | $OCH_3$ | $OCH_3$ |
| J-7 (n=0) | — | H | H | $n$-$C_3H_7$ | $CH_3$ | $OCH_3$ | $OCH_3$ |
| J-7 (n=0) | — | H | H | $CH(CH_3)_2$ | $CH_3$ | $OCH_3$ | $OCH_3$ |
| J-7 (n=0) | — | H | H | cyclopropyl | $CH_3$ | $OCH_3$ | $OCH_3$ |
| J-7 (n=0) | — | H | H | cyclopropyl | $CH_3$ | $CH_3$ | $OCH_3$ |
| J-7 (n=0) | — | H | H | cyclopropyl | $CH_3$ | $CH_3$ | $CH_3$ |
| J-7 (n=0) | — | H | H | cyclopropyl | $CH_3$ | Cl | $OCH_3$ |
| J-7 (n=0) | — | H | H | Cl | $CH_3$ | $OCH_3$ | $OCH_3$ |
| J-7 (n=0) | — | H | H | Cl | $CH_3$ | $CH_3$ | $OCH_3$ |

TABLE 1-continued

General Formula 1

| J | E | R | R¹/R² | T¹/T² | Alk | X | Y |
|---|---|---|---|---|---|---|---|
| J-7 (n=0) | — | H | H | Cl | $CH_3$ | $CH_3$ | $CH_3$ |
| J-7 (n=0) | — | H | H | Cl | $CH_3$ | Cl | $OCH_3$ |
| J-7 (n=0) | — | H | H | CN | $CH_3$ | $OCH_3$ | $OCH_3$ |
| J-7 (n=0) | — | H | H | CN | $CH_3$ | $CH_3$ | $OCH_3$ |
| J-7 (n=0) | — | H | H | CN | $CH_3$ | $CH_3$ | $CH_3$ |
| J-7 (n=0) | — | H | H | CN | $CH_3$ | Cl | $OCH_3$ |
| J-7 (n=0) | — | H | H | $OCH_3$ | $CH_3$ | $OCH_3$ | $OCH_3$ |
| J-7 (n=0) | — | H | H | $OCH_3$ | $CH_3$ | $CH_3$ | $OCH_3$ |
| J-7 (n=0) | — | H | H | $OCH_3$ | $CH_3$ | $CH_3$ | $CH_3$ |
| J-7 (n=0) | — | H | H | $OCH_3$ | $CH_3$ | Cl | $OCH_3$ |
| J-7 (n=0) | — | H | H | $N(CH_3)_2$ | $CH_3$ | $OCH_3$ | $OCH_3$ |
| J-7 (n=0) | — | H | H | $N(CH_3)_2$ | $CH_3$ | $CH_3$ | $OCH_3$ |
| J-7 (n=0) | — | H | H | $N(CH_3)_2$ | $CH_3$ | $CH_3$ | $CH_3$ |
| J-7 (n=0) | — | H | H | $N(CH_3)_2$ | $CH_3$ | Cl | $OCH_3$ |
| J-7 (n=1) | — | H | H | Cl | $CH_3$ | $OCH_3$ | $OCH_3$ |
| J-7 (n=1) | — | H | H | H | $CH_3$ | $OCH_3$ | $OCH_3$ |
| J-2 | — | H | H | Cl | $CH_3$ | $OCH_3$ | $OCH_3$ |
| J-2 | — | H | H | Cl | $CH_3$ | $CH_3$ | $OCH_3$ |
| J-2 | — | H | H | Cl | $CH_3$ | $CH_3$ | $CH_3$ |
| J-2 | — | H | H | Cl | $CH_3$ | Cl | $OCH_3$ |
| J-2 | — | H | H | CN | $CH_3$ | $OCH_3$ | $OCH_3$ |
| J-2 | — | H | H | CN | $CH_3$ | $CH_3$ | $OCH_3$ |
| J-2 | — | H | H | CN | $CH_3$ | $CH_3$ | $CH_3$ |
| J-2 | — | H | H | CN | $CH_3$ | Cl | $OCH_3$ |
| J-2 | — | H | H | $OCH_3$ | $CH_3$ | $OCH_3$ | $OCH_3$ |
| J-2 | — | H | H | $OCH_3$ | $CH_3$ | $CH_3$ | $OCH_3$ |
| J-2 | — | H | H | $OCH_3$ | $CH_3$ | $CH_3$ | $CH_3$ |
| J-2 | — | H | H | $OCH_3$ | $CH_3$ | Cl | $OCH_3$ |
| J-2 | — | H | H | $N(CH_3)_2$ | $CH_3$ | $OCH_3$ | $OCH_3$ |
| J-2 | — | H | H | $N(CH_3)_2$ | $CH_3$ | $CH_3$ | $OCH_3$ |
| J-2 | — | H | H | $N(CH_3)_2$ | $CH_3$ | $CH_3$ | $CH_3$ |
| J-2 | — | H | H | $N(CH_3)_2$ | $CH_3$ | Cl | $OCH_3$ |
| J-3 | — | H | H | Cl | $CH_3$ | $OCH_3$ | $OCH_3$ |
| J-3 | — | H | H | Cl | $CH_3$ | $CH_3$ | $OCH_3$ |
| J-3 | — | H | H | Cl | $CH_3$ | $CH_3$ | $CH_3$ |
| J-3 | — | H | H | Cl | $CH_3$ | Cl | $OCH_3$ |
| J-3 | — | H | H | CN | $CH_3$ | $OCH_3$ | $OCH_3$ |
| J-3 | — | H | H | CN | $CH_3$ | $CH_3$ | $OCH_3$ |
| J-3 | — | H | H | CN | $CH_3$ | $CH_3$ | $CH_3$ |
| J-3 | — | H | H | CN | $CH_3$ | Cl | $OCH_3$ |
| J-3 | — | H | H | $OCH_3$ | $CH_3$ | $OCH_3$ | $OCH_3$ |
| J-3 | — | H | H | $OCH_3$ | $CH_3$ | $CH_3$ | $OCH_3$ |
| J-3 | — | H | H | $OCH_3$ | $CH_3$ | $CH_3$ | $CH_3$ |
| J-3 | — | H | H | $OCH_3$ | $CH_3$ | Cl | $OCH_3$ |
| J-3 | — | H | H | $N(CH_3)_2$ | $CH_3$ | $OCH_3$ | $OCH_3$ |
| J-3 | — | H | H | $N(CH_3)_2$ | $CH_3$ | $CH_3$ | $OCH_3$ |
| J-3 | — | H | H | $N(CH_3)_2$ | $CH_3$ | $CH_3$ | $CH_3$ |
| J-3 | — | H | H | $N(CH_3)_2$ | $CH_3$ | Cl | $OCH_3$ |
| J-4 | — | H | H | Cl | $CH_3$ | $OCH_3$ | $OCH_3$ |
| J-4 | — | H | H | CN | $CH_3$ | $OCH_3$ | $OCH_3$ |
| J-4 | — | H | H | $OCH_3$ | $CH_3$ | $OCH_3$ | $OCH_3$ |
| J-4 | — | H | H | $N(CH_3)_2$ | $CH_3$ | $OCH_3$ | $OCH_3$ |
| J-5 | — | H | H | Cl | $CH_3$ | $OCH_3$ | $OCH_3$ |
| J-5 | — | H | H | Cl | $CH_3$ | $CH_3$ | $OCH_3$ |
| J-5 | — | H | H | Cl | $CH_3$ | $CH_3$ | $CH_3$ |
| J-5 | — | H | H | Cl | $CH_3$ | Cl | $OCH_3$ |
| J-5 | — | H | H | CN | $CH_3$ | $OCH_3$ | $OCH_3$ |
| J-5 | — | H | H | CN | $CH_3$ | $CH_3$ | $OCH_3$ |
| J-5 | — | H | H | CN | $CH_3$ | $CH_3$ | $CH_3$ |
| J-5 | — | H | H | CN | $CH_3$ | Cl | $OCH_3$ |
| J-5 | — | H | H | $OCH_3$ | $CH_3$ | $OCH_3$ | $OCH_3$ |
| J-5 | — | H | H | $N(CH_3)_2$ | $CH_3$ | $OCH_3$ | $OCH_3$ |
| J-6 (n=0) | — | H | H | H | $CH_3$ | $OCH_3$ | $OCH_3$ |

TABLE 1-continued

General Formula 1

| J | E | R | R$^1$/R$^2$ | T$^1$/T$^2$ | Alk | X | Y |
|---|---|---|---|---|---|---|---|
| J-6 (n=1) | — | H | H | H | CH$_3$ | OCH$_3$ | OCH$_3$ |
| J-8 (n=0) | — | H | H | H | CH$_3$ | OCH$_3$ | OCH$_3$ |
| J-8 (n=1) | — | H | H | H | CH$_3$ | OCH$_3$ | OCH$_3$ |
| J-9 (n=0) | — | H | H | H | CH$_3$ | OCH$_3$ | OCH$_3$ |
| J-10 (R$_3$=CH$_3$) | — | H | H | Cl | CH$_3$ | OCH$_3$ | OCH$_3$ |
| J-10 (R$_3$=CH$_3$) | — | H | H | CN | CH$_3$ | OCH$_3$ | OCH$_3$ |
| J-10 (R$_3$=CH$_3$) | — | H | H | H | CH$_3$ | OCH$_3$ | OCH$_3$ |
| J-11 (R$_3$=CH$_3$) | — | H | H | Cl | CH$_3$ | OCH$_3$ | OCH$_3$ |
| J-11 (R$_3$=CH$_3$) | — | H | H | CN | CH$_3$ | OCH$_3$ | OCH$_3$ |
| J-11 (R$_3$=CH$_3$) | — | H | H | H | CH$_3$ | OCH$_3$ | OCH$_3$ |
| J-12 (R$_3$=CH$_3$) | — | H | H | Cl | CH$_3$ | OCH$_3$ | OCH$_3$ |
| J-12 (R$_3$=CH$_3$) | — | H | H | CN | CH$_3$ | OCH$_3$ | OCH$_3$ |
| J-12 (R$_3$=CH$_3$) | — | H | H | H | CH$_3$ | OCH$_3$ | OCH$_3$ |
| J-13 (R$_3$=CH$_3$) | — | H | H | Cl | CH$_3$ | OCH$_3$ | OCH$_3$ |
| J-13 (R$_3$=CH$_3$) | — | H | H | CN | CH$_3$ | OCH$_3$ | OCH$_3$ |
| J-13 (R$_3$=CH$_3$) | — | H | H | H | CH$_3$ | OCH$_3$ | OCH$_3$ |
| J-12 (R$_3$=C$_2$H$_5$) | — | H | CH$_3$ | H | CH$_3$ | OCH$_3$ | OCH$_3$ |
| J-11 (R$_3$=CH(CH$_3$)$_2$) | — | H | H | H | CH$_3$ | OCH$_3$ | OCH$_3$ |
| J-10 (R$_3$=n-C$_3$H$_7$) | — | H | H | cyclopropyl | CH$_3$ | OCH$_3$ | OCH$_3$ |
| J-12 (R$_3$=C$_6$H$_5$) | — | H | CH$_3$ | H | CH$_3$ | OCH$_3$ | OCH$_3$ |
| J-11 (R$_3$=CH$_2$CF$_3$) | — | H | H | CH$_3$ | CH$_3$ | OCH$_3$ | OCH$_3$ |
| J-12 (R$_3$=CH$_2$CH=CH$_2$) | — | H | H | H | CH$_3$ | OCH$_3$ | OCH$_3$ |
| J-1 | — | H | H | Cl | CH$_3$ | NH$_2$ | OCH$_3$ |
| J-1 | — | H | H | Cl | CH$_3$ | n-C$_3$H$_7$ | OCH$_3$ |
| J-1 | — | H | H | Cl | CH$_3$ | NHCH$_3$ | OCH$_3$ |
| J-1 | — | H | H | CN | CH$_3$ | OCH$_3$ | SCH$_3$ |
| J-1 | — | H | H | Cl | CH$_3$ | OCH$_3$ | SCF$_2$H |
| J-1 | — | H | H | Cl | CH$_3$ | OCH$_3$ | OCH$_2$C≡CH |
| J-1 | — | H | H | Cl | CH$_3$ | OCH$_3$ | OCH$_2$CH=CH$_2$ |
| J-1 | — | H | H | Cl | CH$_3$ | OCH$_3$ | C≡CH |
| J-1 | — | H | H | Cl | CH$_3$ | OCH$_3$ | N(CH$_3$)$_2$ |
| J-7 (n=0) | — | H | H | Cl | CH$_3$ | OCH$_3$ | cyclopropyl |
| J-1 | — | H | H | Cl | CH$_3$ | OCH$_3$ | NH$_2$ |
| J-1 | — | H | H | Cl | CH$_3$ | OCH$_3$ | CF$_3$ |
| J-1 | — | H | H | Cl | CH$_3$ | OCH$_3$ | OCH$_2$CH$_2$OCH$_3$ |
| J-1 | — | H | H | Cl | CH$_3$ | OCH$_3$ | CH$_2$SCH$_3$ |
| J-1 | — | H | H | Cl | CH$_3$ | OCH$_3$ | CHO |
| J-1 | — | H | H | CN | CH$_3$ | OCH$_3$ | COCH$_3$ |
| J-1 | — | H | H | Cl | CH$_3$ | OCH$_3$ | CH(SCH$_3$)OC$_2$H$_5$ |
| J-1 | — | H | H | Cl | CH$_3$ | OCH$_3$ | C(CH$_3$)SCH$_3$)$_2$ |
| J-1 | — | H | H | Cl | CH$_3$ | OCH$_3$ | C(SC$_2$H$_5$)$_2$ |
| J-1 | — | H | H | Cl | CH$_3$ | OCH$_3$ | 1,3-dioxolan-2-yl |
| J-1 | — | H | H | Cl | CH$_3$ | OCH$_3$ | 2-methyl-1,3-oxathiolan-2-yl |
| J-1 | — | H | H | Cl | CH$_3$ | OCH$_3$ | 1,3-oxathian-2-yl |
| J-1 | — | H | H | Cl | CH$_3$ | OCH$_3$ | 2-methyl-1,3-dithian-2-yl |
| J-1 | — | H | H | Cl | CH$_3$ | OCH$_3$ | 4-methyl-1,3-dioxolan-2-yl |
| J-1 | — | H | H | Cl | CH$_3$ | OCH$_3$ | 2-4-dimethyl-1,3-dithiolan-2-yl |
| J-1 | — | H | H | Cl | CH$_3$ | OCH$_3$ | N(OCH$_3$)(CH$_3$) |
| J-1 | — | H | H | CN | CH$_3$ | OCH$_3$ | C≡CCH$_3$ |
| J-1 | — | H | H | Cl | CH$_3$ | OCH$_3$ | C$_2$H$_5$ |
| J-1 | — | H | H | Cl | CH$_3$ | OCH$_3$ | OCF$_2$Br |
| J-7 (n=0) | — | H | 6-F | H | CH$_3$ | OCH$_3$ | OCH$_3$ |

TABLE 1-continued

| | | | | General Formula 1 | | | |
|---|---|---|---|---|---|---|---|
| J | E | R | R¹/R² | T¹/T² | Alk | X | Y |
| J-1 | — | H | 5-F | Cl | $CH_3$ | $OCH_3$ | $OCH_3$ |
| J-1 | — | H | 6-Cl | Cl | $CH_3$ | $OCH_3$ | $OCH_3$ |
| J-2 | — | H | 4-Cl | Cl | $CH_3$ | $OCH_3$ | $OCH_3$ |
| J-7 (n=0) | — | H | 6-Br | H | $CH_3$ | $OCH_3$ | $OCH_3$ |
| J-1 | — | H | 5-Br | Cl | $CH_3$ | $OCH_3$ | $OCH_3$ |
| J-3 | — | H | 4-$CH_3$ | H | $CH_3$ | $OCH_3$ | $OCH_3$ |
| J-12 ($R_3=CH_3$) | — | H | 3-$CH_3$ | H | $CH_3$ | $OCH_3$ | $OCH_3$ |
| J-1 | — | H | 5-$CH_2CN$ | Cl | $CH_3$ | $OCH_3$ | $OCH_3$ |
| J-1 | — | H | 5-$OCH_3$ | Cl | $CH_3$ | $OCH_3$ | $OCH_3$ |
| J-1 | — | H | 5-$SCH_3$ | Cl | $CH_3$ | $OCH_3$ | $OCH_3$ |
| J-12 ($R_3=CH_3$) | — | H | 3-$CH_3$ | H | $CH_3$ | $CH_3$ | $OCH_3$ |
| J-12 ($R_3=CH_3$) | — | H | 3-$CH_3$ | H | $CH_3$ | $CH_3$ | $CH_3$ |
| J-12 ($R_3=CH_3$) | — | H | 3-$CH_3$ | H | $CH_3$ | Cl | $OCH_3$ |
| J-1 | — | H | 5-$OCF_2H$ | Cl | $CH_3$ | $OCH_3$ | $OCH_3$ |
| J-7 (n=0) | $CH_2$ | H | H | H | $CH_3$ | $OCH_3$ | $OCH_3$ |
| J-1 | — | $CH_3$ | H | Cl | $CH_3$ | $OCH_3$ | $OCH_3$ |
| J-1 | — | $CH_3$ | H | Cl | $CH_3$ | $CH_3$ | $OCH_3$ |
| J-1 | — | $CH_3$ | H | CN | $CH_3$ | $OCH_3$ | $OCH_3$ |
| J-1 | — | $CH_3$ | H | CN | $CH_3$ | $CH_3$ | $OCH_3$ |
| J-2 | — | $CH_3$ | H | Cl | $CH_3$ | $OCH_3$ | $OCH_3$ |
| J-3 | — | $CH_3$ | H | Cl | $CH_3$ | $OCH_3$ | $OCH_3$ |
| J-7 (n=0) | — | $CH_3$ | H | H | $CH_3$ | $OCH_3$ | $OCH_3$ |
| J-1 | — | H | 6-Cl | CN | $CH_3$ | $OCH_3$ | $OCH_3$ |
| J-1 | — | H | 6-Cl | CN | $CH_3$ | $CH_3$ | $OCH_3$ |
| J-1 | — | H | 6-Cl | CN | $CH_3$ | $CH_3$ | $CH_3$ |
| J-1 | — | H | 6-Cl | CN | $CH_3$ | Cl | $OCH_3$ |
| J-7 (n=0) | — | H | H | $CF_3$ | $CH_3$ | $OCH_3$ | $OCH_3$ |
| J-7 (n=0) | — | H | H | $CF_3$ | $CH_3$ | $CH_3$ | $OCH_3$ |
| J-7 (n=0) | — | H | H | $CF_3$ | $CH_3$ | $CH_3$ | $CH_3$ |
| J-7 (n=0) | — | H | H | $CF_3$ | $CH_3$ | Cl | $OCH_3$ |
| J-7 (n=0) | — | H | H | $CF_3$ | $CH_2CH_3$ | $OCH_3$ | $OCH_3$ |
| J-7 (n=0) | — | H | H | $CF_3$ | $CH_2CH_3$ | $CH_3$ | $OCH_3$ |
| J-7 (n=0) | — | H | H | $CF_3$ | $CH_2CH_3$ | $CH_3$ | $CH_3$ |
| J-7 (n=0) | — | H | H | $CF_3$ | $CH_2CH_3$ | Cl | $OCH_3$ |
| J-7 (n=0) | — | H | H | $CF_3$ | n-$C_3H_7$ | $OCH_3$ | $OCH_3$ |
| J-7 (n=0) | — | H | H | $CF_3$ | n-$C_3H_7$ | $CH_3$ | $OCH_3$ |
| J-7 (n=0) | — | H | H | $CF_3$ | n-$C_3H_7$ | $CH_3$ | $CH_3$ |
| J-7 (n=0) | — | H | H | $CF_3$ | n-$C_3H_7$ | Cl | $OCH_3$ |
| J-7 (n=0) | — | H | H | $CF_3$ | $CH(CH_3)_2$ | $OCH_3$ | $OCH_3$ |
| J-7 (n=0) | — | H | H | $CF_3$ | $CH(CH_3)_2$ | $CH_3$ | $OCH_3$ |
| J-7 (n=0) | — | H | H | $CF_3$ | $CH(CH_3)_2$ | $CH_3$ | $CH_3$ |
| J-7 (n=0) | — | H | H | $CF_3$ | $CH(CH_3)_2$ | Cl | $OCH_3$ |
| J-7 (n=0) | — | H | H | $CF_3$ | $CH_2CN$ | $OCH_3$ | $OCH_3$ |
| J-7 (n=0) | — | H | H | $CF_3$ | $CH_2CN$ | $CH_3$ | $OCH_3$ |
| J-7 (n=0) | — | H | H | $CF_3$ | $CH_2CN$ | $CH_3$ | $CH_3$ |
| J-7 (n=0) | — | H | H | $CF_3$ | $CH_2CN$ | Cl | $OCH_3$ |
| J-7 (n=0) | — | H | H | $CF_3$ | $CH_2OCH_3$ | $OCH_3$ | $OCH_3$ |
| J-7 (n=0) | — | H | H | $CF_3$ | $CH_2OCH_3$ | $CH_3$ | $OCH_3$ |
| J-7 (n=0) | — | H | H | $CF_3$ | $CH_2OCH_3$ | $CH_3$ | $CH_3$ |
| J-7 | — | H | H | $CF_3$ | $CH_2OCH_3$ | Cl | $OCH_3$ |

TABLE 1-continued

General Formula 1

| J | E | R | R¹/R² | T¹/T² | Alk | X | Y |
|---|---|---|---|---|---|---|---|
| J-7 (n=0) | — | CH₃ | H | CF₃ | CH₃ | OCH₃ | OCH₃ |
| J-7 (n=0) | — | CH₃ | H | CF₃ | CH₃ | CH₃ | OCH₃ |
| J-7 (n=0) | — | CH₃ | H | CF₃ | CH₃ | CH₃ | CH₃ |
| J-7 (n=0) | — | CH₃ | H | CF₃ | CH₃ | Cl | OCH₃ |
| J-7 (n=0) | — | H | H | CH₂CN | CH₃ | OCH₃ | OCH₃ |
| J-7 (n=0) | — | H | H | CH₂OCH₃ | CH₃ | OCH₃ | OCH₃ |
| J-7 (n=0) | — | H | H | CH₂OCH₃ | CH₃ | CH₃ | OCH₃ |
| J-7 (n=0) | — | H | H | CH₂OCH₃ | CH₃ | CH₃ | CH₃ |
| J-7 (n=0) | — | H | H | CH₂OCH₃ | CH₃ | Cl | OCH₃ |
| J-12 (R₃=CH₃) | — | H | H | CH₂SCH₃ | CH₃ | OCH₃ | OCH₃ |
| J-11 (R₃=CH₃) | — | H | H | CH₃ | CH₂SCH₃ | OCH₃ | OCH₃ |
| J-7 (n=0) | — | H | H | F | CH₃ | OCH₃ | OCH₃ |
| J-7 (n=0) | — | H | H | F | CH₃ | CH₃ | OCH₃ |
| J-7 (n=0) | — | H | H | F | CH₃ | CH₃ | CH₃ |
| J-7 (n=0) | — | H | H | F | CH₃ | Cl | OCH₃ |
| J-7 (n=0) | — | H | H | CH₃ | CH₃ | CH₃ | OCH₃ |
| J-7 (n=0) | — | H | H | CH₃ | CH₃ | CH₃ | CH₃ |
| J-7 (n=0) | — | H | H | CH₃ | CH₃ | Cl | OCH₃ |
| J-7 (n=0) | — | H | H | CH₃ | C₂H₅ | CH₃ | OCH₃ |
| J-7 (n=0) | — | H | H | CH₃ | C₂H₅ | CH₃ | CH₃ |
| J-7 (n=0) | — | H | H | CH₃ | C₂H₅ | Cl | OCH₃ |
| J-7 (n=0) | — | H | H | CH₃ | C₂H₅ | Cl | OCH₃ |
| J-7 (n=0) | — | H | H | CH₃ | n-C₃H₇ | OCH₃ | OCH₃ |
| J-7 (n=0) | — | H | H | CH₃ | n-C₃H₇ | CH₃ | OCH₃ |
| J-7 (n=0) | — | H | H | CH₃ | n-C₃H₇ | CH₃ | CH₃ |
| J-7 (n=0) | — | H | H | CH₃ | n-C₃H₇ | Cl | OCH₃ |
| J-7 (n=0) | — | H | H | CH₃ | CH(CH₃)₂ | OCH₃ | OCH₃ |
| J-7 (n=0) | — | H | H | CH₃ | CH(CH₃)₂ | CH₃ | OCH₃ |
| J-7 (n=0) | — | H | H | CH₃ | CH(CH₃)₂ | CH₃ | CH₃ |
| J-7 (n=0) | — | H | H | CH₃ | CH(CH₃)₂ | Cl | OCH₃ |
| J-7 (n=0) | — | H | H | CH₃ | CH₂CF₃ | OCH₃ | OCH₃ |
| J-1 | — | H | H | F | CH₃ | OCH₃ | OCH₃ |
| J-1 | — | H | H | F | CH₃ | CH₃ | OCH₃ |
| J-1 | — | H | H | F | CH₃ | CH₃ | CH₃ |
| J-1 | — | H | H | F | CH₃ | Cl | OCH₃ |
| J-1 | — | H | H | CN | CH₂CN | OCH₃ | OCH₃ |
| J-1 | — | H | H | CN | CH₂OCH₃ | OCH₃ | OCH₃ |
| J-7 (n=0) | — | H | H | CH₃ | CH₂CH₂CN | OCH₃ | OCH₃ |
| J-7 (n=0) | — | H | H | CH₃ | CH₂CH₂OCH₃ | OCH₃ | OCH₃ |
| J-7 (n=0) | — | H | H | CH₃ | CH₂(CH₂)₂CN | OCH₃ | OCH₃ |
| J-7 (n=0) | — | H | H | CH₂(CH₂)₂OCH₃ | CH₃ | OCH₃ | OCH₃ |
| J-7 (n=0) | — | H | H | CH₂CH₂OCH₃ | CH₃ | OCH₃ | OCH₃ |
| J-7 (n=0) | — | H | H | CH₂CH₂OCH₃ | CH₃ | OCH₃ | OCH₃ |

TABLE 1-continued

General Formula 1

| J | E | R | R¹/R² | T¹/T² | Alk | X | Y |
|---|---|---|---|---|---|---|---|
| J-7 (n=0) | — | $CH_3$ | H | $CH_3$ | $CH_3$ | $OCH_3$ | $OCH_3$ |
| J-7 (n=0) | — | $CH_3$ | H | $CH_3$ | $CH_3$ | $CH_3$ | $OCH_3$ |
| J-7 (n=0) | — | $CH_3$ | H | $CH_3$ | $CH_3$ | $CH_3$ | $CH_3$ |
| J-7 (n=0) | — | $CH_3$ | H | $CH_3$ | $CH_3$ | Cl | $OCH_3$ |
| J-7 (n=0) | — | H | H | $CH_2CN$ | $CH_3$ | $CH_3$ | $OCH_3$ |
| J-7 (n=0) | — | H | H | $CH_2CN$ | $CH_3$ | $CH_3$ | $CH_3$ |
| J-7 (n=0) | — | H | H | $CH_2CN$ | $CH_3$ | Cl | $OCH_3$ |

TABLE 2

General Formula 2

| J | E | R | R¹/R² | T¹/T² | Alk | X | Y |
|---|---|---|---|---|---|---|---|
| J-1 | — | H | H | Cl | $CH_3$ | $CH_3$ | $OCH_3$ |
| J-1 | — | H | H | Cl | $CH_3$ | $OCH_3$ | $OCH_3$ |
| J-1 | — | H | H | Cl | $CH_3$ | $OC_2H_5$ | $NHCH_3$ |
| J-1 | — | H | H | Cl | $CH_3$ | $OCH_3$ | $N(OCH_3)(CH_3)$ |
| J-1 | — | H | H | Cl | $CH_3$ | $OCH_3$ | $N(CH_3)_2$ |
| J-1 | — | H | H | Cl | $C_2H_5$ | $CH_3$ | $OCH_3$ |
| J-1 | — | H | H | Cl | $C_2H_5$ | $OCH_3$ | $OCH_3$ |
| J-1 | — | H | H | Cl | $C_2H_5$ | $OC_2H_5$ | $NHCH_3$ |
| J-1 | — | H | H | Cl | $C_2H_5$ | $OCH_3$ | $N(OCH_3)(CH_3)$ |
| J-1 | — | H | H | Cl | $C_2H_5$ | $OCH_3$ | $N(CH_3)_2$ |
| J-1 | — | H | H | Cl | $n-C_3H_7$ | $CH_3$ | $OCH_3$ |
| J-1 | — | H | H | Cl | $n-C_3H_7$ | $OCH_3$ | $OCH_3$ |
| J-1 | — | H | H | Cl | $n-C_3H_7$ | $OC_2H_5$ | $NHCH_3$ |
| J-1 | — | H | H | Cl | $n-C_3H_7$ | $OCH_3$ | $N(OCH_3)(CH_3)$ |
| J-1 | — | H | H | Cl | $n-C_3H_7$ | $OCH_3$ | $N(CH_3)_2$ |
| J-1 | — | H | H | Cl | $CH(CH_3)_2$ | $CH_3$ | $OCH_3$ |
| J-1 | — | H | H | Cl | $CH(CH_3)_2$ | $OCH_3$ | $OCH_3$ |
| J-1 | — | H | H | Cl | $CH(CH_3)_2$ | $OC_2H_5$ | $NHCH_3$ |
| J-1 | — | H | H | Cl | $CH(CH_3)_2$ | $OCH_3$ | $N(OCH_3)(CH_3)$ |
| J-1 | — | H | H | Cl | $CH(CH_3)_2$ | $OCH_3$ | $N(CH_3)_2$ |
| J-1 | $CH_2$ | H | H | Cl | $CH_3$ | $OCH_3$ | $CH_3$ |
| J-1 | — | $CH_3$ | H | Cl | $CH_3$ | $OCH_3$ | $OCH_3$ |
| J-1 | — | $CH_3$ | H | Cl | $CH_3$ | $OCH_3$ | $OCH_3$ |
| J-1 | — | H | H | CN | $CH_3$ | $CH_3$ | $OCH_3$ |
| J-1 | — | H | H | CN | $CH_3$ | $OCH_3$ | $OCH_3$ |
| J-1 | — | H | H | CN | $CH_3$ | $OC_2H_5$ | $NHCH_3$ |
| J-1 | — | H | H | CN | $CH_3$ | $OCH_3$ | $N(OCH_3)(CH_3)$ |
| J-1 | — | H | H | CN | $CH_3$ | $OCH_3$ | $N(CH_3)_2$ |
| J-1 | — | H | H | CN | $C_2H_5$ | $CH_3$ | $OCH_3$ |
| J-1 | — | H | H | CN | $C_2H_5$ | $OCH_3$ | $OCH_3$ |
| J-1 | — | H | H | CN | $C_2H_5$ | $OC_2H_5$ | $NHCH_3$ |
| J-1 | — | H | H | CN | $C_2H_5$ | $OCH_3$ | $N(OCH_3)(CH_3)$ |
| J-1 | — | H | H | CN | $C_2H_5$ | $OCH_3$ | $N(CH_3)_2$ |
| J-1 | — | H | H | CN | $n-C_3H_7$ | $CH_3$ | $OCH_3$ |
| J-1 | — | H | H | CN | $n-C_3H_7$ | $OCH_3$ | $OCH_3$ |
| J-1 | — | H | H | CN | $n-C_3H_7$ | $OC_2H_5$ | $NHCH_3$ |
| J-1 | — | H | H | CN | $n-C_3H_7$ | $OCH_3$ | $N(OCH_3)(CH_3)$ |
| J-1 | — | H | H | CN | $n-C_3H_7$ | $OCH_3$ | $N(CH_3)_2$ |
| J-1 | — | H | H | CN | $CH(CH_3)_2$ | $CH_3$ | $OCH_3$ |
| J-1 | — | H | H | CN | $CH(CH_3)_2$ | $OCH_3$ | $OCH_3$ |
| J-1 | — | H | H | CN | $CH(CH_3)_2$ | $OC_2H_5$ | $NHCH_3$ |
| J-1 | — | H | H | CN | $CH(CH_3)_2$ | $OCH_3$ | $N(OCH_3)(CH_3)$ |
| J-1 | — | H | H | CN | $CH(CH_3)_2$ | $OCH_3$ | $N(CH_3)_2$ |
| J-1 | $CH_2$ | H | H | CN | $CH_3$ | $OCH_3$ | $CH_3$ |
| J-1 | — | $CH_3$ | H | CN | $CH_3$ | $OCH_3$ | $OCH_3$ |
| J-1 | — | $CH_3$ | H | CN | $CH_3$ | $OCH_3$ | $CH_3$ |
| J-1 | — | H | H | $N(CH_3)_2$ | $CH_3$ | $CH_3$ | $OCH_3$ |
| J-1 | — | H | H | $N(CH_3)_2$ | $CH_3$ | $OCH_3$ | $OCH_3$ |
| J-1 | — | H | H | $N(CH_3)_2$ | $CH_3$ | $OC_2H_5$ | $NHCH_3$ |
| J-1 | — | H | H | $N(CH_3)_2$ | $CH_3$ | $OCH_3$ | $N(OCH_3)(CH_3)$ |
| J-1 | — | H | H | $N(CH_3)_2$ | $CH_3$ | $OCH_3$ | $N(CH_3)_2$ |
| J-1 | — | H | H | $N(CH_3)_2$ | $C_2H_5$ | $CH_3$ | $OCH_3$ |
| J-1 | — | H | H | $N(CH_3)_2$ | $C_2H_5$ | $OCH_3$ | $OCH_3$ |
| J-1 | — | H | H | $N(CH_3)_2$ | $C_2H_5$ | $OC_2H_5$ | $NHCH_3$ |
| J-1 | — | H | H | $N(CH_3)_2$ | $C_2H_5$ | $OCH_3$ | $N(OCH_3)(CH_3)$ |
| J-1 | — | H | H | $N(CH_3)_2$ | $C_2H_5$ | $OCH_3$ | $N(CH_3)_2$ |
| J-1 | — | H | H | $N(CH_3)_2$ | $n-C_3H_7$ | $CH_3$ | $OCH_3$ |
| J-1 | — | H | H | $N(CH_3)_2$ | $n-C_3H_7$ | $OCH_3$ | $OCH_3$ |

TABLE 2-continued

General Formula 2

| J | E | R | R¹/R² | T¹/T² | Alk | X | Y |
|---|---|---|---|---|---|---|---|
| J-1 | — | H | H | N(CH$_3$)$_2$ | n-C$_3$H$_7$ | OC$_2$H$_5$ | NHCH$_3$ |
| J-1 | — | H | H | N(CH$_3$)$_2$ | n-C$_3$H$_7$ | OCH$_3$ | N(OCH$_3$)(CH$_3$) |
| J-1 | — | H | H | N(CH$_3$)$_2$ | n-C$_3$H$_7$ | OCH$_3$ | N(CH$_3$)$_2$ |
| J-1 | — | H | H | N(CH$_3$)$_2$ | CH(CH$_3$)$_2$ | CH$_3$ | OCH$_3$ |
| J-1 | — | H | H | N(CH$_3$)$_2$ | CH(CH$_3$)$_2$ | OCH$_3$ | OCH$_3$ |
| J-1 | — | H | H | N(CH$_3$)$_2$ | CH(CH$_3$)$_2$ | OC$_2$H$_5$ | NHCH$_3$ |
| J-1 | — | H | H | N(CH$_3$)$_2$ | CH(CH$_3$)$_2$ | OCH$_3$ | N(OCH$_3$)(CH$_3$) |
| J-1 | — | H | H | N(CH$_3$)$_2$ | CH(CH$_3$)$_2$ | OCH$_3$ | N(CH$_3$)$_2$ |
| J-1 | CH$_2$ | H | H | N(CH$_3$)$_2$ | CH$_3$ | OCH$_3$ | CH$_3$ |
| J-1 | — | CH$_3$ | H | N(CH$_3$)$_2$ | CH$_3$ | OCH$_3$ | OCH$_3$ |
| J-1 | — | CH$_3$ | H | N(CH$_3$)$_2$ | CH$_3$ | OCH$_3$ | CH$_3$ |
| J-1 | — | H | H | OCH$_3$ | CH$_3$ | CH$_3$ | OCH$_3$ |
| J-1 | — | H | H | OCH$_3$ | CH$_3$ | OCH$_3$ | OCH$_3$ |
| J-1 | — | H | H | OCH$_3$ | CH$_3$ | OC$_2$H$_5$ | NHCH$_3$ |
| J-1 | — | H | H | OCH$_3$ | CH$_3$ | OCH$_3$ | N(OCH$_3$)(CH$_3$) |
| J-1 | — | H | H | OCH$_3$ | CH$_3$ | OCH$_3$ | N(CH$_3$)$_2$ |
| J-1 | — | H | H | OCH$_3$ | C$_2$H$_5$ | CH$_3$ | OCH$_3$ |
| J-1 | — | H | H | OCH$_3$ | C$_2$H$_5$ | OCH$_3$ | OCH$_3$ |
| J-1 | — | H | H | OCH$_3$ | C$_2$H$_5$ | OC$_2$H$_5$ | NHCH$_3$ |
| J-1 | — | H | H | OCH$_3$ | C$_2$H$_5$ | OCH$_3$ | N(OCH$_3$)(CH$_3$) |
| J-1 | — | H | H | OCH$_3$ | C$_2$H$_5$ | OCH$_3$ | NCH$_3$ |
| J-1 | — | H | H | OCH$_3$ | n-C$_3$H$_7$ | CH$_3$ | OCH$_3$ |
| J-1 | — | H | H | OCH$_3$ | n-C$_3$H$_7$ | OCH$_3$ | OCH$_3$ |
| J-1 | — | H | H | OCH$_3$ | n-C$_3$H$_7$ | OC$_2$H$_5$ | NHCH$_3$ |
| J-1 | — | H | H | OCH$_3$ | n-C$_3$H$_7$ | OCH$_3$ | N(OCH$_3$)(CH$_3$) |
| J-1 | — | H | H | OCH$_3$ | n-C$_3$H$_7$ | OCH$_3$ | N(CH$_3$)$_2$ |
| J-1 | — | H | H | OCH$_3$ | CH(CH$_3$)$_2$ | CH$_3$ | OCH$_3$ |
| J-1 | — | H | H | OCH$_3$ | CH(CH$_3$)$_2$ | OCH$_3$ | OCH$_3$ |
| J-1 | — | H | H | OCH$_3$ | CH(CH$_3$)$_2$ | OC$_2$H$_5$ | NHCH$_3$ |
| J-1 | — | H | H | OCH$_3$ | CH(CH$_3$)$_2$ | OCH$_3$ | N(OCH$_3$)(CH$_3$) |
| J-1 | — | H | H | OCH$_3$ | CH(CH$_3$)$_2$ | OCH$_3$ | N(CH$_3$)$_2$ |
| J-1 | CH$_2$ | H | H | OCH$_3$ | CH$_3$ | OCH$_3$ | CH$_3$ |
| J-1 | — | CH$_3$ | H | OCH$_3$ | CH$_3$ | OCH$_3$ | OCH$_3$ |
| J-1 | — | CH$_3$ | H | OCH$_3$ | CH$_3$ | OCH$_3$ | CH$_3$ |
| J-1 | — | H | H | OC$_2$H$_5$ | CH$_3$ | OCH$_3$ | CH$_3$ |
| J-1 | — | H | H | OC$_2$H$_5$ | CH$_3$ | OCH$_3$ | OCH$_3$ |
| J-1 | — | H | H | OC$_2$H$_5$ | C$_2$H$_5$ | OCH$_3$ | OCH$_3$ |
| J-1 | — | H | H | OC$_2$H$_5$ | C$_2$H$_5$ | OCH$_3$ | CH$_3$ |
| J-1 | — | H | H | Br | CH$_3$ | CH$_3$ | OCH$_3$ |
| J-1 | — | H | H | SCN | CH$_3$ | CH$_3$ | OCH$_3$ |
| J-1 | — | H | H | SCH$_3$ | CH$_3$ | CH$_3$ | OCH$_3$ |
| J-1 | — | H | H | SCH$_3$ | CH$_3$ | OCH$_3$ | CH$_3$ |
| J-1 | — | H | H | SC$_2$H$_5$ | CH$_3$ | OCH$_3$ | CH$_3$ |
| J-1 | — | H | H | NHCH$_3$ | CH$_3$ | OCH$_3$ | CH$_3$ |
| J-1 | — | H | H | NHC$_2$H$_5$ | CH$_3$ | OCH$_3$ | CH$_3$ |
| J-1 | — | H | H | N(CH$_3$)C$_2$H$_5$ | CH$_3$ | OCH$_3$ | CH$_3$ |
| J-1 | — | H | H | N(C$_2$H$_5$)$_2$ | CH$_3$ | OCH$_3$ | CH$_3$ |
| J-1 | — | H | H | N(OCH$_3$)(CH$_3$) | CH$_3$ | OCH$_3$ | CH$_3$ |
| J-1 | — | H | H | N(OCH$_3$)(CH$_3$) | CH$_3$ | OCH$_3$ | OCH$_3$ |
| J-1 | — | H | H | N(CH$_2$)$_3$ | CH$_3$ | CH$_3$ | OCH$_3$ |
| J-1 | — | H | H | N(CH$_2$)$_4$ | CH$_3$ | CH$_3$ | OCH$_3$ |
| J-1 | — | H | H | N$_3$ | CH$_3$ | OCH$_3$ | CH$_3$ |
| J-7 (n = 0) | — | H | H | H | CH$_3$ | OCH$_3$ | CH$_3$ |
| J-7 (n = 0) | — | H | H | H | CH$_3$ | OCH$_3$ | CH$_3$ |
| J-7 (n = 0) | — | H | H | H | CH$_3$ | OC$_2$H$_5$ | NHCH$_3$ |
| J-7 (n = 0) | — | H | H | CH$_3$ | CH$_3$ | OCH$_3$ | CH$_3$ |
| J-7 (n = 0) | — | H | H | C$_2$H$_5$ | CH$_3$ | OCH$_3$ | OCH$_3$ |
| J-7 (n = 0) | — | H | H | n-C$_3$H$_7$ | CH$_3$ | OCH$_3$ | CH$_3$ |
| J-7 (n = 0) | — | H | H | CH(CH$_3$)$_2$ | CH$_3$ | OCH$_3$ | CH$_3$ |
| J-7 (n = 0) | — | H | H | cyclopropyl | CH$_3$ | OCH$_3$ | CH$_3$ |
| J-2 | — | H | H | Cl | CH$_3$ | OCH$_3$ | CH$_3$ |
| J-2 | — | H | H | Cl | CH$_3$ | OCH$_3$ | OCH$_3$ |
| J-2 | — | H | H | CN | CH$_3$ | OCH$_3$ | OCH$_3$ |
| J-2 | — | H | H | CN | CH$_3$ | OCH$_3$ | CH$_3$ |
| J-2 | — | H | H | OCH$_3$ | CH$_3$ | OCH$_3$ | CH$_3$ |
| J-2 | — | H | H | OCH$_3$ | CH$_3$ | OCH$_3$ | OCH$_3$ |
| J-2 | — | H | H | N(CH$_3$)$_2$ | CH$_3$ | OCH$_3$ | CH$_3$ |
| J-2 | — | H | H | N(CH$_3$)$_2$ | CH$_3$ | OCH$_3$ | OCH$_3$ |
| J-3 | — | H | H | Cl | CH$_3$ | OCH$_3$ | CH$_3$ |
| J-3 | — | H | H | Cl | CH$_3$ | OCH$_3$ | OCH$_3$ |
| J-3 | — | H | H | CN | CH$_3$ | OCH$_3$ | OCH$_3$ |
| J-3 | — | H | H | CN | CH$_3$ | OCH$_3$ | CH$_3$ |

TABLE 2-continued

General Formula 2

| J | E | R | R¹/R² | T¹/T² | Alk | X | Y |
|---|---|---|---|---|---|---|---|
| J-3 | — | H | H | OCH$_3$ | CH$_3$ | OCH$_3$ | CH$_3$ |
| J-3 | — | H | H | OCH$_3$ | CH$_3$ | OCH$_3$ | OCH$_3$ |
| J-3 | — | H | H | N(CH$_3$)$_2$ | CH$_3$ | OCH$_3$ | CH$_3$ |
| J-3 | — | H | H | N(CH$_3$)$_2$ | CH$_3$ | OCH$_3$ | OCH$_3$ |
| J-4 | — | H | H | Cl | CH$_3$ | OCH$_3$ | CH$_3$ |
| J-4 | — | H | H | Cl | CH$_3$ | OCH$_3$ | OCH$_3$ |
| J-4 | — | H | H | CN | CH$_3$ | OCH$_3$ | OCH$_3$ |
| J-4 | — | H | H | CN | CH$_3$ | OCH$_3$ | CH$_3$ |
| J-4 | — | H | H | OCH$_3$ | CH$_3$ | OCH$_3$ | CH$_3$ |
| J-4 | — | H | H | OCH$_3$ | CH$_3$ | OCH$_3$ | OCH$_3$ |
| J-4 | — | H | H | N(CH$_3$)$_2$ | CH$_3$ | OCH$_3$ | CH$_3$ |
| J-4 | — | H | H | N(CH$_3$)$_2$ | CH$_3$ | OCH$_3$ | OCH$_3$ |
| J-5 | — | H | H | Cl | CH$_3$ | OCH$_3$ | CH$_3$ |
| J-5 | — | H | H | Cl | CH$_3$ | OCH$_3$ | OCH$_3$ |
| J-5 | — | H | H | CN | CH$_3$ | OCH$_3$ | OCH$_3$ |
| J-5 | — | H | H | CN | CH$_3$ | OCH$_3$ | CH$_3$ |
| J-5 | — | H | H | OCH$_3$ | CH$_3$ | OCH$_3$ | CH$_3$ |
| J-5 | — | H | H | OCH$_3$ | CH$_3$ | OCH$_3$ | OCH$_3$ |
| J-5 | — | H | H | N(CH$_3$)$_2$ | CH$_3$ | OCH$_3$ | CH$_3$ |
| J-5 | — | H | H | N(CH$_3$)$_2$ | CH$_3$ | OCH$_3$ | OCH$_3$ |
| J-7 (n = 1) | — | H | H | H | CH$_3$ | CH$_3$ | OCH$_3$ |
| J-7 (n = 1) | CH$_2$ | H | H | H | CH$_3$ | OCH$_3$ | CH$_3$ |
| J-7 (n = 0) | — | H | H | CN | CH$_3$ | OCH$_3$ | CH$_3$ |
| J-7 (n = 0) | — | H | H | CN | CH$_3$ | OCH$_3$ | OCH$_3$ |
| J-8 (n = 0) | — | H | H | H | CH$_3$ | OCH$_3$ | CH$_3$ |
| J-8 (n = 1) | — | H | H | H | CH$_3$ | OCH$_3$ | CH$_3$ |
| J-9 (n = 0) | — | H | H | H | CH$_3$ | OCH$_3$ | CH$_3$ |
| J-10 (R$_3$ = CH$_3$) | — | H | H | Cl | CH$_3$ | CH$_3$ | OCH$_3$ |
| J-10 (R$_3$ = CH$_3$) | — | H | H | CN | CH$_3$ | CH$_3$ | OCH$_3$ |
| J-11 (R$_3$ = CH$_3$) | — | H | H | Cl | CH$_3$ | CH$_3$ | OCH$_3$ |
| J-12 (R$_3$ = CH$_3$) | — | H | 3-CH$_3$ | H | CH$_3$ | CH$_3$ | OCH$_3$ |
| J-12 (R$_3$ = CH$_3$) | — | H | 3-CH$_3$ | H | CH$_3$ | OCH$_3$ | OCH$_3$ |
| J-12 (R$_3$ = CH$_3$) | — | H | H | Cl | CH$_3$ | CH$_3$ | OCH$_3$ |
| J-12 (R$_3$ = CH$_3$) | — | H | H | Cl | CH$_3$ | OCH$_3$ | OCH$_3$ |
| J-13 (R$_3$ = CH$_3$) | — | H | H | H | CH$_3$ | OCH$_3$ | CH$_3$ |
| J-12 (R$_3$ = C$_6$H$_5$) | — | H | H | H | CH$_3$ | CH$_3$ | OCH$_3$ |
| J-12 (R$_3$ = C$_2$H$_5$) | — | H | 3-CH$_3$ | H | CH$_3$ | CH$_3$ | OCH$_3$ |
| J-11 (R$_3$ = CH(CH$_3$)$_2$) | — | H | H | H | CH$_3$ | CH$_3$ | OCH$_3$ |
| J-10 (R$_3$ = n-C$_3$H$_7$) | — | H | H | cyclopropyl | CH$_3$ | OCH$_3$ | CH$_3$ |
| J-11 (R$_3$ = CH$_2$CF$_3$) | — | H | H | CH$_3$ | CH$_3$ | OCH$_3$ | CH$_3$ |
| J-12 (R$_3$ = CH$_2$CH=CH$_2$) | — | H | H | H | CH$_3$ | CH$_3$ | OCH$_3$ |
| J-7 (n = 0) | — | H | 6-F | H | CH$_3$ | CH$_3$ | OCH$_3$ |
| J-1 | — | H | 5-F | Cl | CH$_3$ | CH$_3$ | OCH$_3$ |
| J-1 | — | H | 6-Cl | Cl | CH$_3$ | OCH$_3$ | CH$_3$ |
| J-2 | — | H | 4-Cl | Cl | CH$_3$ | OCH$_3$ | OCH$_3$ |
| J-7 (n = 0) | — | H | 6-Br | H | CH$_3$ | OCH$_3$ | OCH$_3$ |
| J-1 | — | H | 5-Br | Cl | CH$_3$ | CH$_3$ | OCH$_3$ |
| J-3 | — | H | 4-CH$_3$ | Cl | CH$_3$ | CH$_3$ | OCH$_3$ |
| J-1 | — | H | 5-CH$_2$CN | Cl | CH$_3$ | OCH$_3$ | OCH$_3$ |
| J-1 | — | H | 5-OCH$_3$ | Cl | CH$_3$ | CH$_3$ | OCH$_3$ |
| J-1 | — | H | 5-SCH$_3$ | Cl | CH$_3$ | CH$_3$ | OCH$_3$ |
| J-1 | — | H | 5-OCF$_2$H | Cl | CH$_3$ | CH$_3$ | OCH$_3$ |
| J-1 | — | H | 6-Cl | CN | CH$_3$ | CH$_3$ | OCH$_3$ |
| J-1 | — | H | 6-Cl | CN | CH$_3$ | OCH$_3$ | OCH$_3$ |
| J-1 | — | H | 6-Cl | CN | CH$_3$ | OC$_2$H$_5$ | NHCH$_3$ |
| J-1 | — | H | H | Cl | CH$_3$ | OCH$_2$CH$_2$F | CH$_3$ |
| J-1 | — | H | H | Cl | CH$_3$ | OCH$_2$CH$_2$F | OCH$_3$ |

TABLE 2-continued

General Formula 2

| J | E | R | R¹/R² | T¹/T² | Alk | X | Y |
|---|---|---|---|---|---|---|---|
| J-1 | — | H | H | Cl | $CH_3$ | $OCH_2CF_3$ | $NHCH_3$ |
| J-1 | — | H | H | Cl | $CH_3$ | $OCH_2CF_3$ | $OCH_3$ |
| J-1 | — | H | H | Cl | $CH_3$ | $OCH_2CH_2Cl$ | $CH_3$ |
| J-1 | — | H | H | Cl | $CH_3$ | $CH_2Cl$ | $OCH_3$ |
| J-1 | — | H | H | CN | $CH_3$ | $CH_2Br$ | $OCH_3$ |
| J-1 | — | H | H | Cl | $CH_3$ | $OCH_3$ | H |
| J-1⁻ | — | H | H | Cl | $CH_3$ | $OCH_3$ | $SCH_3$ |
| J-1 | — | H | H | Cl | $CH_3$ | $OCH_2CHF_2$ | $CH_3$ |
| J-1 | — | H | H | Cl | $CH_3$ | $OCH_3$ | $C≡CH$ |
| J-1 | — | H | H | Cl | $CH_3$ | $OCH_3$ | $C_2H_5$ |
| J-1 | — | H | H | Cl | $CH_3$ | $OCH_3$ | $CH_2OCH_3$ |
| J-1 | — | H | H | Cl | $CH_3$ | $OCH_3$ | $CH_2(OCH_3)_2$ |
| J-1 | — | H | H | Cl | $CH_3$ | $OCH_3$ | cyclopropyl |
| J-1 | — | H | H | CN | $CH_3$ | $C_2H_5$ | $OCH_3$ |
| J-1 | — | H | H | Cl | $CH_3$ | $CH_2F$ | $OCH_3$ |
| J-1 | — | H | H | Cl | $CH_3$ | $CF_3$ | $OCH_3$ |
| J-1 | — | H | H | Cl | $CH_3$ | $OC_2F_5$ | $CH_3$ |
| J-1 | — | H | H | CN | $CH_3$ | $CH_3$ | $OC_2H_5$ |
| J-1 | — | H | H | CN | $CH_3$ | $OCH_3$ | $CF_3$ |
| J-1 | — | H | H | CN | $CH_3$ | $CH_3$ | $OCH_2CH=CH_2$ |
| J-1 | — | H | H | Cl | $CH_3$ | $CH_3$ | $OCH_2C≡CH$ |
| J-1 | — | H | H | Cl | $CH_3$ | $OCH_3$ | $C≡CCH_3$ |
| J-1 | — | H | H | Cl | $CH_3$ | $OCH_3$ | $CH_2OCH_2CH_3$ |
| J-1 | — | H | H | Cl | $CH_3$ | $CH_3$ | $OCH_2CH_2OCH_3$ |
| J-7 (n = 0) | — | H | H | $CF_3$ | $CH_3$ | $OCH_3$ | $OCH_3$ |
| J-7 (n = 0) | — | H | H | $CF_3$ | $CH_3$ | $CH_3$ | $OCH_3$ |
| J-7 (n = 0) | — | H | H | $CF_3$ | $CH_3$ | $OC_2H_5$ | $NHCH_3$ |
| J-7 (n = 0) | — | H | H | $CF_3$ | $CH_3$ | $OCH_2CF_3$ | $N(CH_3)_2$ |
| J-7 (n = 0) | — | H | H | $CF_3$ | $C_2H_5$ | $OCH_3$ | $OCH_3$ |
| J-7 (n = 0) | — | H | H | $CF_3$ | $C_2H_5$ | $CH_3$ | $OCH_3$ |
| J-7 (n = 0) | — | H | H | $CF_3$ | $n-C_3H_7$ | $OCH_3$ | $OCH_3$ |
| J-7 (n = 0) | — | H | H | $CF_3$ | $n-C_3H_7$ | $CH_3$ | $OCH_3$ |
| J-7 (n = 0) | — | H | H | $CF_3$ | $CH_2CN$ | $OCH_3$ | $OCH_3$ |
| J-7 (n = 0) | — | H | H | $CF_3$ | $CN_2CN$ | $CH_3$ | $OCH_3$ |
| J-7 (n = 0) | — 3 | H | H | $CF_3$ | $CH_2CN$ | $OC_2H_5$ | $NHCH_3$ |
| J-7 (n = 0) | — | H | H | $CF_3$ | $CH_2CN$ | $OCH_3CF_3$ | $N(CH_3)_2$ |
| J-7 (n = 0) | — | H | H | $CF_3$ | $CH_2OCH$ | $OCH_3$ | $OCH_3$ |
| J-7 (n = 0) | — | H | H | $CF_3$ | $CH_2OCH$ | $CH_3$ | $OCH_3$ |
| J-7 (n = 0) | — | H | H | $CH_2OCH_3$ | $CH_3$ | $OCH_3$ | $OCH_3$ |
| J-7 (n = 0) | — | H | H | $CH_2OCH_3$ | $CH_3$ | $CH_3$ | $OCH_3$ |
| J-7 (n = 0) | — | H | H | F | $CH_3$ | $OCH_3$ | $OCH_3$ |
| J-7 (n = 0) | — | H | H | F | $CH_3$ | $CH_3$ | $OCH_3$ |
| J-7 (n = 0) | — | H | H | $CH_3$ | $CH_3$ | $CH_3$ | $OCH_3$ |
| J-7 (n = n) | — | H | H | $CH_3$ | $CH_3$ | $OC_2H_5$ | $NHCH_3$ |
| J-7 (n = 0) | — | H | H | $CH_3$ | $CH_3$ | $OCH_3CF_3$ | $N(CH_3)_2$ |
| J-11 (R₃ = $CH_3$) | — | H | H | $CH_2SCH_3$ | $CH_3$ | $OCH_3$ | $CH_3$ |
| J-1 | — | H | H | F | $CH_3$ | $OCH_3$ | $OCH_3$ |
| J-7 (n =0) | — | H | H | $CH_2CN$ | $CH_3$ | $CH_3$ | $OCH_3$ |
| J-11 (R₃ = $CH_3$) | — | H | H | $CH_3$ | $CH_2SCH_3$ | $CH_3$ | $OCH_3$ |

TABLE 3

General Formula 3

| J | E | R | R¹/R² | T¹/T² | Alk | $X_1$ | $Y_1$ |
|---|---|---|---|---|---|---|---|
| J-1 | — | H | H | Cl | $CH_3$ | $CH_3$ | O |
| J-1 | — | H | H | Cl | $CH_3$ | $OCH_3$ | O |
| J-1 | — | H | H | Cl | $CH_3$ | $OC_2H_5$ | O |
| J-1 | — | H | H | Cl | $CH_3$ | $OCF_2H$ | O |
| J-1 | — | H | H | Cl | $CH_3$ | $OCH_3$ | $CH_2$ |
| J-1 | — | H | H | CN | $CH_3$ | $CH_3$ | O |
| J-1 | — | H | H | CN | $CH_3$ | $OCH_3$ | O |
| J-1 | — | H | H | $OCH_3$ | $CH_3$ | $CH_3$ | O |
| J-2 | — | H | H | Cl | $CH_3$ | $CH_3$ | O |
| J-3 | — | H | H | Cl | $CH_3$ | $CH_3$ | O |
| J-12 ($R_3 = CH_3$) | — | H | 3-$CH_3$ | Cl | $CH_3$ | $CH_3$ | O |
| J-7 (n = 0) | — | H | H | H | $CH_3$ | $CH_3$ | O |
| J-7 (n = 0) | — | H | 6-F | H | $CH_3$ | $CH_3$ | O |
| J-1 | — | H | 5-$OCH_3$ | Cl | $CH_3$ | $CH_3$ | O |
| J-1 | — | H | 6-Cl | CN | $CH_3$ | $CH_3$ | O |
| J-12 ($R_3 = CH_3$) | — | H | 3-$CH_3$ | H | $CH_3$ | $CH_3$ | O |
| J-1 | $CH_2$ | H | H | CN | $CH_3$ | $CH_3$ | O |
| J-1 | — | $CH_3$ | H | Cl | $CH_3$ | $CH_3$ | O |
| J-1 | — | H | H | F | $CH_3$ | $CH_3$ | O |
| J-7 (n = 0) | — | H | H | F | $CH_3$ | $CH_3$ | O |
| J-7 (n = 0) | — | H | H | CF | $CH_3$ | $CH_3$ | O |
| J-7 (n = 0) | — | H | H | $CH_3$ | $CH_2CN$ | $OCH_3$ | O |
| J-7 (n = 0) | — | H | H | $CH_3$ | $CH_2OCH_3$ | $OCH_3$ | O |

TABLE 4

General Formula 4

| J | E | R | R¹/R² | T¹/T² | Alk | $X_1$ |
|---|---|---|---|---|---|---|
| J-1 | — | H | H | Cl | $CH_3$ | $CH_3$ |
| J-1 | — | H | H | Cl | $CH_3$ | $OCH_3$ |
| J-1 | — | H | H | Cl | $CH_3$ | $OC_2H_5$ |
| J-1 | — | H | H | Cl | $CH_3$ | $OCF_2H$ |
| J-1 | — | H | H | CN | $CH_3$ | $CH_3$ |
| J-1 | — | H | H | CN | $CH_3$ | $OCH_3$ |
| J-1 | — | H | H | $OCH_3$ | $CH_3$ | $CH_3$ |
| J-2 | — | H | H | Cl | $CH_3$ | $CH_3$ |
| J-3 | — | H | H | Cl | $CH_3$ | $OCH_3$ |
| J-12 ($R_3 = CH_3$) | — | H | 3-$CH_3$ | Cl | $CH_3$ | $CH_3$ |
| J-7 (n = 0) | — | H | H | H | $CH_3$ | $OCH_3$ |
| J-7 (n = 0) | — | H | 6-F | H | $CH_3$ | $CH_3$ |
| J-1 | — | H | 5-$OCH_3$ | Cl | $CH_3$ | $CH_3$ |
| J-1 | — | H | 6-Cl | CN | $CH_3$ | $CH_3$ |
| J-12 ($R_3 = CH_3$) | — | H | 3-$CH_3$ | H | $CH_3$ | $CH_3$ |
| J-1 | $CH_2$ | H | H | CN | $CH_3$ | $CH_3$ |
| J-1 | — | $CH_3$ | H | Cl | $CH_3$ | $CH_3$ |
| J-1 | — | H | H | F | $CH_3$ | $CH_3$ |
| J-7 (n = 0) | — | H | H | F | $CH_3$ | $OCH_3$ |
| J-7 (n = 0) | — | H | H | $CF_3$ | $CH_3$ | $OCH_3$ |
| J-7 (n = 0) | — | H | H | $CH_3$ | $CH_2CN$ | $OCH_3$ |

TABLE 5

General Formula 5

| J | E | R | R¹/R² | T¹/T² | Alk | $X_1$ | $Y_3$ |
|---|---|---|---|---|---|---|---|
| J-1 | — | H | H | Cl | $CH_3$ | $CH_3$ | $CH_3$ |
| J-1 | — | H | H | Cl | $CH_3$ | $OCH_3$ | $CH_3$ |
| J-1 | — | H | H | Cl | $CH_3$ | $OC_2H_5$ | $CH_3$ |
| J-1 | — | H | H | Cl | $CH_3$ | $OCF_2H$ | $CH_3$ |
| J-1 | — | H | H | Cl | $CH_3$ | $OCH_3$ | H |
| J-1 | — | H | H | Cl | $CH_3$ | $CH_3$ | H |
| J-1 | — | H | H | CN | $CH_3$ | $CH_3$ | $CH_3$ |
| J-2 | — | H | H | Cl | $CH_3$ | $CH_3$ | $CH_3$ |
| J-3 | — | H | H | Cl | $CH_3$ | $OCH_3$ | $CH_3$ |
| J-12 ($R_3 = CH_3$) | — | H | 3-$CH_3$ | Cl | $CH_3$ | $CH_3$ | $CH_3$ |
| J-7 (n = 0) | — | H | H | H | $CH_3$ | $OCH_3$ | $CH_3$ |
| J-7 (n = 0) | — | H | 6-F | H | $CH_3$ | $CH_3$ | $CH_3$ |
| J-1 | — | H | 5-$OCH_3$ | Cl | $CH_3$ | $OCH_3$ | $CH_3$ |
| J-1 | — | H | 6-Cl | CN | $CH_3$ | $OCH_3$ | $CH_3$ |
| J-12 ($R_3 = CH_3$) | — | H | 3-$CH_3$ | H | $CH_3$ | $CH_3$ | $CH_3$ |
| J-1 | $CH_2$ | H | H | CN | $CH_3$ | $OCH_3$ | $CH_3$ |
| J-1 | — | $CH_3$ | H | Cl | $CH_3$ | $OCH_3$ | $CH_3$ |

TABLE 5-continued

General Formula 5

| J | E | R | R¹/R² | T¹/T² | Alk | $X_1$ | $Y_3$ |
|---|---|---|---|---|---|---|---|
| J-1 | — | H | H | OCH₃ | CH₃ | OCH₃ | CH₃ |
| J-1 | — | H | H | F | CH₃ | OCH₃ | CH₃ |
| J-7 (n = 0) | — | H | H | F | CH₃ | OCH₃ | CH₃ |
| J-7 (n = 0) | — | H | H | CF₃ | CH₃ | OCH₃ | CH₃ |
| J-7 (n = 0) | — | H | H | CH₃ | CH₂CN | OCH₃ | CH₃ |

TABLE 6

General Formula 6

| J | E | R | R¹/R² | T¹/T² | Alk | $X_2$ | $Y_2$ |
|---|---|---|---|---|---|---|---|
| J-1 | — | H | H | Cl | CH₃ | CH₃ | OCH₃ |
| J-1 | — | H | H | Cl | CH₃ | CH₃ | OC₂H₅ |
| J-1 | — | H | H | Cl | CH₃ | CH₃ | SCH₃ |
| J-1 | — | H | H | Cl | CH₃ | CH₃ | SC₂H₅ |
| J-1 | — | H | H | Cl | CH₃ | CH₃ | CH₃ |
| J-1 | — | H | H | Cl | CH₃ | CH₃ | C₂H₅ |
| J-1 | — | H | H | Cl | CH₃ | C₂H₅ | OCH₃ |
| J-1 | — | H | H | Cl | CH₃ | CH₂CF₃ | OCH₃ |
| J-1 | — | H | H | CN | CH₃ | CH₃ | OCH₃ |
| J-1 | — | H | H | OCH₃ | CH₃ | CH₃ | OCH₃ |
| J-1 (n = 0) | — | H | H | H | CH₃ | CH₃ | OCH₃ |
| J-1 | — | CH₃ | H | Cl | CH₃ | CH₃ | OCH₃ |
| J-1 | CH₂ | H | H | CN | CH₃ | CH₃ | OCH₃ |
| J-2 | — | H | H | Cl | CH₃ | CH₃ | OCH₃ |
| J-3 | — | H | H | Cl | CH₃ | CH₃ | OCH₃ |
| J-12 (R₃ = CH₃) | — | H | 3-CH₃ | H | CH₃ | CH₃ | OCH₃ |
| J-12 (R₃ = CH₃) | — | H | H | Cl | CH₃ | CH₃ | OCH₃ |
| J-1 | — | H | 5-OCH₃ | Cl | CH₃ | CH₃ | OCH₃ |
| J-1 | — | H | 6-Cl | CN | CH₃ | CH₃ | OCH₃ |
| J-7 (n = 0) | — | H | 6-F | H | CH₃ | CH₃ | OCH₃ |
| J-7 (n = 0) | — | H | H | CH₃ | CH₃ | CH₃ | OCH₃ |
| J-7 (n = 0) | — | H | H | CH₃ | CH₂CN | CH₃ | OCH₃ |

TABLE 7

General Formula 7

| J | E | R | R¹/R² | T¹/T² | Alk | $X_3$ |
|---|---|---|---|---|---|---|
| J-1 | — | H | H | Cl | CH₃ | CH₃ |
| J-1 | — | H | H | Cl | CH₃ | OCH₃ |
| J-1 | — | H | H | CN | CH₃ | CH₃ |
| J-1 | — | H | H | CN | CH₃ | OCH₃ |
| J-1 | — | H | H | OCH₃ | CH₃ | OCH₃ |
| J-2 | — | H | H | Cl | CH₃ | CH₃ |
| J-3 | — | H | H | Cl | CH₃ | CH₃ |
| J-4 | — | H | H | Cl | CH₃ | OCH₃ |
| J-5 | — | H | H | H | CH₃ | CH₃ |
| J-7 (n = 0) | — | H | H | H | CH₃ | OCH₃ |
| J-12 (R₃ = CH₃) | — | H | H | H | CH₃ | OCH₃ |
| J-7 (n = 0) | — | H | 6-F | H | CH₃ | OCH₃ |
| J-1 | — | H | 6-Cl | CN | CH₃ | OCH₃ |
| J-12 (R₃ = CH₃) | — | H | 3-CH₃ | H | CH₃ | CH₃ |
| J-1 | — | H | 5-OCH₃ | Cl | CH₃ | CH₃ |
| J-1 | CH₂ | H | H | CN | CH₃ | CH₃ |
| J-1 | — | CH₃ | H | Cl | CH₃ | CH₃ |
| J-7 (n = 0) | — | H | H | CH₃ | CH₃ | CH₃ |
| J-7 (n = 0) | — | H | H | CF₃ | CH₃ | CH₃ |
| J-7 | — | H | H | CH₃ | CH₂CN | CH₃ |

TABLE 8

General Formula 8

| J | E | R | R¹/R² | T¹/T² | Alk | $X_4$ | $Y_4$ | $Z_1$ |
|---|---|---|---|---|---|---|---|---|
| J-1 | — | H | H | CN | CH₃ | CH₃ | CH₃ | CH |
| J-1 | — | H | H | Cl | CH₃ | CH₃ | CH₃ | N |
| J-1 | — | H | H | Cl | CH₃ | OCH₃ | CH₃ | CH |
| J-1 | — | H | H | CN | CH₃ | OCH₃ | CH₃ | N |
| J-1 | — | H | H | Cl | CH₃ | OCH₃ | OCH₃ | CH |
| J-1 | — | H | H | Cl | CH₃ | OCH₃ | OCH₃ | N |
| J-1 | — | H | H | Cl | CH₃ | Cl | CH₃ | CH |
| J-1 | — | H | H | Cl | CH₃ | OCH₃ | Cl | CH |
| J-1 | — | H | H | Cl | CH₃ | OC₂H₅ | CH₃ | CH |
| J-1 | — | H | H | Cl | CH₃ | CH₂OCH₃ | CH₃ | N |

TABLE 8-continued

General Formula 8

| J | E | R | $R^1/R^2$ | $T^1/T^2$ | Alk | $X_4$ | $Y_4$ | $Z_1$ |
|---|---|---|---|---|---|---|---|---|
| J-1 | — | H | H | Cl | $CH_3$ | $CH_2OCH_3$ | $OCH_3$ | CH |
| J-1 | — | H | H | Cl | $CH_3$ | $OC_2H_5$ | $OC_2H_5$ | N |
| J-1 | $CH_2$ | H | H | CN | $CH_3$ | $OCH_3$ | $CH_3$ | CH |
| J-1 | — | $CH_3$ | H | Cl | $CH_3$ | $OCH_3$ | $CH_3$ | CH |
| J-2 | — | H | H | Cl | $CH_3$ | $OCH_3$ | $CH_3$ | CH |
| J-3 | — | H | H | Cl | $CH_3$ | $OCH_3$ | $CH_3$ | CH |
| J-4 | — | H | H | Cl | $CH_3$ | $OCH_3$ | $CH_3$ | CH |
| J-5 | — | H | H | H | $CH_3$ | $OCH_3$ | $CH_3$ | CH |
| J-7 (n = 0) | — | H | H | H | $CH_3$ | $OCH_3$ | $CH_3$ | CH |
| J-12 ($R_3 = CH_3$) | — | H | H | H | $CH_3$ | $OCH_3$ | $CH_3$ | CH |
| J-7 (n = 0) | — | H | 6-F | H | $CH_3$ | $OCH_3$ | $CH_3$ | CH |
| J-12 ($R_3 = CH_3$) | — | H | 3-$CH_3$ | H | $CH_3$ | $OCH_3$ | $CH_3$ | CH |
| J-1 | — | H | 5-$OCH_3$ | Cl | $CH_3$ | $OCH_3$ | $CH_3$ | CH |
| J-1 | — | H | 6-Cl | CN | $CH_3$ | $OCH_3$ | $CH_3$ | CH |
| J-1 | — | H | H | F | $CH_3$ | $OCH_3$ | $CH_3$ | CH |
| J-7 (n = 0) | — | H | H | F | $CH_3$ | $OCH_3$ | $CH_3$ | CH |
| J-7 (n = 0) | — | H | H | $CH_3$ | $CH_3$ | $OCH_3$ | $CH_3$ | CH |
| J-7 (n = 0) | — | H | H | $CH_3$ | $CH_2CN$ | $OCH_3$ | $CH_3$ | CH |
| J-7 (n = 0) | — | H | H | $CF_3$ | $CH_3$ | $OCH_3$ | $CH_3$ | CH |

TABLE 9

| J | E | R | $R^1/R^2$ | $T^1/T^2$ | Alk | W | $X_4$ | $Y_4$ | $Z_1$ |
|---|---|---|---|---|---|---|---|---|---|
| J-1 | — | H | H | Cl | $CH_3$ | S | $OCH_3$ | $OCH_3$ | CH |
| J-1 | — | H | H | Cl | $CH_3$ | S | $CH_3$ | $OCH_3$ | N |
| J-1 | — | H | H | Cl | $CH_3$ | S | $OCH_3$ | $OCH_3$ | N |
| J-1 | — | H | H | CN | $CH_3$ | S | $OCH_3$ | $OCH_3$ | CH |
| J-1 | — | $CH_3$ | H | Cl | $CH_3$ | S | $OCH_3$ | $OCH_3$ | CH |
| J-1 | $CH_2$ | H | H | CN | $CH_3$ | S | $OCH_3$ | $OCH_3$ | CH |
| J-2 | — | H | H | Cl | $CH_3$ | S | $OCH_3$ | $OCH_3$ | CH |
| J-3 | — | H | H | Cl | $CH_3$ | S | $OCH_3$ | $OCH_3$ | CH |
| J-4 | — | H | H | Cl | $CH_3$ | S | $OCH_3$ | $OCH_3$ | CH |
| J-1 | — | H | 5-$OCH_3$ | Cl | $CH_3$ | S | $OCH_3$ | $OCH_3$ | CH |
| J-1 | — | H | 6-Cl | CN | $CH_3$ | S | $OCH_3$ | $OCH_3$ | CH |
| J-7 (n = 0) | — | H | H | $CH_3$ | $CH_3$ | S | $OCH_3$ | $OCH_3$ | CH |
| J-7 (n = 0) | — | H | H | $CF_3$ | $CH_3$ | S | $OCH_3$ | $OCH_3$ | CH |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used as spray volumes of from a few liters to several hundred liters per hectare. High strength compositions are primarily used as intermediates for further formulation. The formulations, broadly, contain about 0.1% to 99% by weight of active ingredient(s) and at least one of these carriers: (a) about 0.1% to 20% surfactant(s) and (b) about 1% to 99.9% solid or liquid inert diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutios are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pages 147ff. and "Perry's Chemical Engineer's Handbook", 5th Ed., McGraw-Hill, New York, 1963, pages 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138 to 140, 162 to 164, 166, 167 and 169 to 182;

H. Gysin and E. Knusli, U.S. Pat. No. 2,891,855, June 23, 1959, Col. 3, line 66 through Col. 5, line 17 and Examples 1 to 4;

G. C. Klingman, "Weed Control as a Science", John Wiley and Sons, Inc., New York, 1961, pages 81 to 96; and J. D. Fryer and S. A. Evans, "Weed Control Handbook", 5th Ed., Blackwell Scientific Publications, Oxford, 1968, pages 101 to 103.

In the following examples, all parts are by weight unless otherwise indicated.

EXAMPLE 10

High Strength Concentrate

| | |
|---|---|
| 2-[[[[(4-chloro-6-methoxy-2-pyrimidinyl)-amino]carbonyl]amino]sulfonyl]-N—methoxybenzenecarboximidoyl chloride | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE 11

Wettable Powder

| | |
|---|---|
| 2-[(cyano)(methoxyimino)methyl]-N—[[(4-methoxy-6-methyl-2-pyrimidinyl)-amino]carbonyl]benzenesulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 12

Aqueous Suspension

| | |
|---|---|
| N—methoxy-2-[[[[(4-methoxy-6-methyl-1,3,5-triazin-2-yl)amino]carbonyl]-amino]sulfonyl]benzenecarboximidoyl chloride | 50.0% |
| polyacrylic acid thickener | 0.3% |
| dodecylphenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 13

Oil Suspension

| | |
|---|---|
| 2-[[[[(4-chloro-6-methoxy-2-pyrimidinyl)-amino]carbonyl]amino]sulfonyl]-N—methoxybenzenecarboximidoyl chloride | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 14

Oil Suspension

| | |
|---|---|
| 2-[(cyano)(methoxyimino)methyl]-N—[[(4-methoxy-6-methyl-2-pyrimidinyl)-amino]carbonyl]benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 15

Aqueous Suspension

| | |
|---|---|
| N—methoxy-2-[[[[(4-methoxy-6-methyl-1,3,5-triazin-2-yl)amino]carbonyl]-amino]sulfonyl]benzenecarboximidoyl chloride | 25.0% |
| hydrated attapulgite | 3.0% |
| crude calcium ligninsulfonate | 20.0% |

| | |
|---|---|
| sodium dihydrogen phosphate | 0.5% |
| water | 61.5% |

The ingredients are ground together in a ball or roller mill until the solid particles have been reduced to diameters under 10 microns.

EXAMPLE 16

Wettable Powder

| | |
|---|---|
| 2-[[[[(4-chloro-6-methoxy-2-pyrimidinyl)-amino]carbonyl]amino]sulfonyl]-N—methoxybenzenecarboximidoyl chloride | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 17

Granule

| | |
|---|---|
| wettable powder of Example 16 | 15% |
| gypsum | 69% |
| potassium sulfate | 16% |

The ingredients are blended in a rotating mixer and water sprayed on to accomplish granulation. When most of the material has reached the desired range of 1.0 to 0.42 cm (U.S.S. No. 18 to 40 sieves), the granules are removed, dried, and screened. Oversized material is crushed to produce additional material in the desired range. These granules contain % active ingredient.

EXAMPLE 18

Wettable Powder

| | |
|---|---|
| 2-[(cyano)(methoxyimino)methyl]-N—[[(4-methoxy-6-methyl-2-pyrimidinyl)-amino]carbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air milled to produce particles of active essentially all below 10 microns in diameter. The product is reblended before packaging.

EXAMPLE 19

Extruded Pellet

| | |
|---|---|
| N—methoxy-2-[[[[(4-methoxy-6-methyl-1,3,5-triazin-2-yl)amino]carbonyl]-amino-9 sulfonyl]benzenecarboximidoyl chloride | 25% |
| anhydrous sodium sulfate | 10% |
| crude calcium ligninsulfonate | 5% |
| sodium alkylnaphthalenesulfonate | 1% |

| | |
|---|---|
| calcium magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 20

Wettable Powder

| | |
|---|---|
| 2-[[[[(4-chloro-6-methoxy-2-pyrimidinyl)-amino]carbonyl]amino]sulfonyl]-N—methoxybenzenecarboximidoyl chloride | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammer-mill to produce particles with an average particle size less than 25 microns in diameter. The material is reblended and sifted through a U.S.S. No. 50 sieve (0.3 mm opening) before being packaged.

EXAMPLE 21

High Strength Concentrate

| | |
|---|---|
| 2-[(cyano)(methoxyimino)methyl]-N—[[(4-methoxy-6-methyl-2-pyrimidinyl)-amino]carbonyl]benzenesulfonamide | 98.5% |
| silica aerogel | 0.5% |
| synthetic amorphous fine silica | 1.0% |

The ingredients are blended and ground in a hammer-mill to produce a high strength concentrate essentially all passing a U.S.S. No. 50 sieve (0.3 mm opening). This material may then be formulated in a variety of ways.

Utility

Test results indicate that the compounds of the present invention are highly active preemergent or postemergent herbicides or plant growth regulants. Many of them have utility for broad-spectrum pre-and/or post-emergence weed control in areas where complete control of all vegetation is desired, such as around storage tanks, industrial storage areas, parking lots, drive-in theaters, around billboards, highway and railroad structures. Some of the compounds have utility for selective weed control in crops such as rice, wheat, barley, corn, sorghum, soybeans and cotton. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.001 to 20 kg/ha, the lower rates being suggested for use on lighter soils and/or those having a low organic matter content, for plant growth modication or for situations where only shortterm persistence is required, such as a herbicide for fallow land.

The compounds of the invention may be used in combination with any other commercial herbicide, representative examples of which are those of the sulfonylurea, triazine, triazole, uracil, urea, amide, diphenyl ether, carbamate, imidazolinone, cineole and bipyridylium types. A partial listing follows:

| Common Name | Chemical Name |
| --- | --- |
| acetochlor | 2-chloro-N—(ethoxymethyl)-N—(2-ethyl-6-methylphenyl)acetamide |
| acifluorfen | 5-[2-chloro-4-(trifluoromethyl)phenoxy]-2-nitrobenzoic acid |
| acrolein | 2-propenal |
| alachlor | 2-chloro-N—(2,6-diethylphenyl)-N—(methoxymethyl)acetamide |
| ametryn | N—ethyl-N'—(1-methylethyl)-6-(methylthio)-1,3,5-triazine-2,4-diamine |
| amitrole | 1H—1,2,4-triazol-3-amine |
| AMS | ammonium sulfamate |
| asulam | methyl [(4-aminophenyl)sulfonyl]carbamate |
| atrazine | 6-chloro-N—ethyl-N'—(1-methylethyl)-1,3,5-triazine-2,4-diamine |
| barban | 4-chloro-2-butynyl 3-chlorocarbamate |
| benefin methy | N—butyl-N—ethyl-2,6-dinitro-4-(trifluoromethyl)benzenamine |
| bensulfuron | 2-[[[[(4,6-dimethoxy-2-pyrimidinyl)amino]carbonyl]amino]sulfonyl]methyl]benzoic acid, methyl ester |
| bensulide | O,O—bis(1-methylethyl) S—[2-[(phenylsulfonyl)amino]ethyl] phosphorodithioate |
| bentazon | 3-(1-methylethyl)-(1H)-2,1,3-benzothiadiazin-4(3H)-one, 2,2-dioxide |
| benzofluor | N—[4-(ethylthio)-2-(trifluoromethyl)phenyl]methanesulfonamide |
| benzoylprop | N—benzoyl-N—(3,4-dichlorophenyl)-DL-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidinedione |
| bromoxynil | 3,5-dibromo-4-hydroxybenzonitrile |
| butachlor | N—(butoxymethyl)-2-chloro-N—(2,6-diethylphenyl)acetamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N—(1-methylpropyl)-2,6-dinitrobenzenamine |
| butylate | S—ethyl bis(2-methylpropyl)carbamothioate |
| cacodylic acid | dimethyl arsinic oxide |
| CDAA | 2-chloro-N,N—di-2-propenylacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)amino]carbonyl]amino]sulfonyl]benzoic acid, ethyl ester |
| chloroxuron | N'—[4-(4-chlorophenoxy)phenyl]-N,N—dimethylurea |
| chlorpropham | 1-methylethyl 3-chlorophenylcarbamate |
| chlorsulfuron | 2-chloro-N—[[(4-methoxy-6-methyl-1,3,5-triazin-2-yl)amino]carbonyl]benzenesulfonamide |
| chlortoluron | N'—(3-chloro-4-methylphenyl)-N,N—dimethylurea |
| cinmethylin | exo-1-methyl-4-(1-methylethyl)-2-[(2-methylphenyl)methoxy]-7-oxabicyclo[2.2.1]heptane |
| clethodim | (E,E)-(±)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy]imino]butyl]-5-[2-(ethylthio)propyl]-3-hydroxy-2-cyclohexen-1-one |
| clopyralid | 3,6-dichloro-2-pyridinecarboxylic acid |

-continued

| Common Name | Chemical Name |
| --- | --- |
| CMA | calcium salt of MAA |
| cyanazine | 2-[[4-chloro-6-(ethylamino-1,3,5-triazin-2-yl]amino]-2-methylpropanenitrile |
| cycloate | S—ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N—[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmediphan | ethyl [3-[[(phenylamino)carbonyl]oxy]phenyl]carbamate |
| desmetryn | 2-(isopropylamino)-4-(methylamino)-6-(methylthio)-s-triazine |
| diallate | S—(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)propanoic acid |
| dichlofop | (±)-2-[4-(2,4-dichlbrophenoxy)phenoxy]propanoic acid |
| diethatyl | N—(chloroacetyl)-N—(2,6-diethylphenyl)-glycine |
| difenzoquat | 1,2-dimethyl-3,5-diphenyl-1H—pyrazolium |
| dinitramine | $N^3,N^3$-diethyl-2,4-dinitro-6-(trifluoromethyl)-1,3-benzenediamine |
| dinoseb | 2-(1-methylpropyl)-4,6-dinitrophenol |
| diphenamid | N,N—dimethyl-α-phenylbenzeneacetamide |
| dipropetryn | 6-(ethylthio)-N,N'—bis(1-methylethyl)-1,3,5-triazine-2,4-diamine |
| diquat | 6,7-dihydrodipyrido[1,2-a:2',1'-c]-pyrazinedium ion |
| diuron | N'—(3,4-dichlorophenyl)-N,N—dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| endothall | 7-oxabicyclo[2.2.1]heptane-2,3-dicarboxylic acid |
| EPTC | S—ethyl dipropylcarbamothioate |
| ethalfluralin | N—ethyl-N—(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| Express ® | 2-[[[[N—(4-methoxy-6-methyl-1,3,5-triazine-2-yl)-N—methylamino]carbonyl]amino]sulfonyl]benzoic acid, methyl eter |
| fenac | 2,3,6-trichlorobenzeneacetic acid |
| fenoxaprop | (±)-2-[4-[(6-chloro-2-benzoxazolyl)oxy]phenoxy]propanoic acid |
| fenuron | N,N—dimethyl-N'—phenylurea |
| fenuron TCA | Salt of fenuron and TCA |
| flamprop | N—benzoyl-N—(3-chloro-4-fluorophenyl)-DL-alanine |
| fluazifop | (±)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N—(2-chloroethyl)-2,6-dinitro-N—propyl-4-(trifluoromethyl)benzenamine |
| fluometuron | N,N—dimethyl-N'—[3-(trifluoromethyl)phenyl]urea |
| fluorochloridone | 3-chloro-4-(chloromethyl)-1-[3-(trifluoromethyl)phenyl]-2-pyrrolidinone |
| fluorodifen | p-nitrophenyl α,α,α-trifluoro-2-nitro-p-tolyl ether |
| fluoroglycofen | carboxymethyl 5-[2-chloro-4-(trifluoromethyl)phenoxy]-2-nitrobenzoate |
| fluridone | 1-methyl-3-phsnyl-5-[3-(trifluoromethyl)phenyl]-4(1H)-pyridinone |

-continued

| Common Name | Chemical Name |
|---|---|
| fomesafen | 5-[2-chloro-4-(trifluoromethyl)phenoxy]-N—(methylsulfonyl)-2-nitrobenzamide |
| fosamine | ethyl hydrogen (aminocarbonyl)phosphate |
| glyphosate | N—(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1-methylethyl)-5-oxo-1H—imidazol-2-yl]-3-pyridinecarboxylic acid |
| imazaquin | 2-[4,5-dihydro-4-methyl-4-(1-methylethyl)-5-oxo-1H—imidazol-2-yl]-3-quinolinecarboxylic acid |
| imazethapyr | (±)-2-[4,5-dihydro-4-methyl-4-(1-methylethyl)-5-oxo-1H—imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N—dipropylbenzenamine |
| isoproturon | N—(4-isopropylphenyl)-N',N'—dimethylurea |
| isouron | N'—[5-(1,1-dimethylethyl)-3-isoxazolyl]-N,N—dimethylurea |
| isoxaben | N—[3-(1-ethyl-1-methylpropyl)-5-isoxazolyl]-2,6-dimethoxybenzamide |
| karbutilate | 3-[[(dimethylamino)carbonyl]amino]phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H—cyclopentapyrimidine-2,4(3H,5H)-dione |
| linuron | N'—(3,4-dichlorophenyl)-N—methoxy-N—methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| mecoprop | (±)-2-(4-chloro-2-methylphenoxy)propanoic acid |
| mefluidide | N—[2,4-dimethyl-5-[[(trifluoromethyl)sulfonyl]amino]phenyl]acetamide |
| methalpropalin | N—(2-methyl-2-propenyl)-2,6-dinitro-N—propyl-4-(trifluoromethyl)benzenamide |
| methabenzthiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'—(3-chloro-4-methoxyphenyl)-N,N—dimethylurea |
| metolachlor | 2-chloro-N—(2-ethyl-6-methylphenyl)-N—(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]amino]sulfonyl]benzoic acid, methyl ester |
| MH | 1,2-dihydro-3,6-pyridazinedione |
| molinate | S—ethyl hexahydro-1H—azepine-1-carbothioate |
| monolinuron | 3-(p-chlorophenyl)-1-methoxy-1-methylurea |
| monuron | N'—(4-chlorophenyl)-N,N—dimethylurea |
| monuron TCA | Salt of monuron and TCA |
| MSMA | monosodium salt of MAA |
| napropamide | N,N—diethyl-2-(1-naphthalenyloxy)propanamide |
| naptalam | 2-[(1-naphthalenylamino)carbonyl]benzoic acid |
| neburon | 1-butyl-3-(3,4-dichlorophenyl)-1-methylurea |
| nitralin | 4-(methylsulfonyl)-2,6-dinitro-N,N—dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N—dimethyl-N'—(octahydro-4,7-methano-1H—inden-5-yl)urea 3aα,-4α,5α,7α,7aα-isomer |
| norflurazon | 4-chloro-5-(methylamino)-2-[3-(trifluoromethyl)phenyl]-3(2H)-pyridazinone |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S—propyl butylethylcarbamothioate |
| pendimethalin | N—(1-ethylpropyl)-3,4-dimethyl-2,6-dinitrobenzenamine |
| perfluidone | 1,1,1-trifluoro-N—[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridinecarboxylic acid |
| PPG-1013 | 5-[2-chloro-4-(trifluoromethyl)phenoxy]-2-nitroacetophenone oxime-O—acetic acid, methyl ester |
| procyazine | 2-[[4-chloro-6-(cyclopropylamino)-1,3,5-triazine-2-yl]amino]-2-methylpropanenitrile |
| profluralin | N—(cyclopropylmethyl)-2,6-dinitro-N—propyl-4-(trifluoromethyl)benzenamine |
| prometon | 6-methoxy-N,N'—bis(1-methylethyl)-1,3,5-triazine-2,4-diamine |
| prometryn | N,N'—bis(1-methylethyl)-6-(methylthio)-1,3,5-triazine-2,4-diamine |
| pronamide | 3,5-dichloro-N—(1,1-dimethyl-2-propynyl)benzamide |
| propachlor | 2-chloro-N—(1-methylethyl)-N—phenylacetamide |
| propanil | N—(3,4-dichlorophenyl)propanamide |
| propazine | 6-chloro-N,N'—bis(1-methylethyl)-1,3,5-triazine-2,4-diamine |
| propham | 1-methylethyl phenylcarbamate |
| prosulfalin | N—[[(dipropylamino)-3,5-dinitrophenyl]sulfonyl]-S,S—dimethylsulfilimine |
| prynachlor | 2-chloro-N—(1-methyl-2-propynyl)acetanilide |
| pyrazon | 5-amino-4-chloro-2-phenyl-3(2H)-pyridazinone |
| quizalofop ethyl | (±)-2-[4-[(6-chloro-2-quinoxalinyl)oxy]phenoxy]propanoic acid, ethyl ester |
| secbumeton | N—ethyl-6-methoxy-N'—(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N—(2-methylcyclohexyl)-N'—phenylurea |
| simazine | 6-chloro-N,N'—diethyl-1,3,5-triazine-2,4-diamine |
| sulfometuron methyl | 2-[[[[(4,6-dimethyl-2-pyrimidinyl)amino]carbonyl]amino]sulfonyl]benzoic acid, methyl ester |
| TCA | trichloroacetic acid |
| tebuthiuron | N—[5-(1,1-dimethylethyl)-1,3,4-thiadiazol-2-yl]-N,N'—dimethylurea |
| terbacil | 5-chloro-3-(1,1-dimethylethyl)-6-methyl-2,4(1H,3H)-pyrimidinedione |
| terbuchlor | N—(butoxymethyl)-2-chloro-N—[2-(1,1-dimethylethyl)-6-methylphenyl]acetamide |
| terbuthylazine | 2-(tert-butylamino)-4-chloro-6-(ethylamino-s-triazine |
| terbutol | 2,6-di-tert-butyl-p-tolyl methylcarbamate |
| terbutryn | N—(1,1-dimethylethyl)-N'—ethyl-6- |

-continued

| Common Name | Chemical Name |
|---|---|
|  | (methylthio)-1,3,5-triazine-2,4-diamine |
| thiameturon methyl | 3-[[[[(4-methoxy-6-methyl-1,3,5-triazin-2-yl)amino]carbonyl]amino]sulfonyl]-2-thiophenecarboxylic acid, methyl ester |
| thiobencarb | S—[(4-chlorophenyl)methyl]diethylcarbamothioate |
| triallate | S—(2,3,3-trichloro-2-propenyl) bis(1-methylethyl)carbamothioate |
| triclopyr | [(3,5,6-trichloro-2-pyridinyl)oxy]acetic acid |
| tridiphane | 2-(3,5-dichlorophenyl)-2-(2,2,2-trichloroethyl)oxirane |
| trifluralin | 2,6-dinitro-N,N—dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S—propyl dipropylcarbamothioate |
| xylachlor | 2-chloro-N—(2,3-dimethylphenyl)-N—(1-methylethyl)acetamide |

The herbicidal properties of the subject compounds were discovered in a number of greenhouse tests. The test procedures and results follow.

COMPOUND TABLES

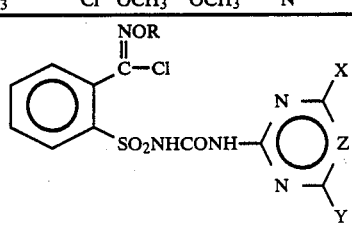

| CMPD | R | R¹ | X | Y | Z | m.p. (°C.) |
|---|---|---|---|---|---|---|
| 1 | $CH_3$ | H | $OCH_3$ | $OCH_3$ | CH | 203 to 210 |
| 2 | $CH_3$ | H | $CH_3$ | $OCH_3$ | CH | 190 to 192 |
| 3 | $CH_3$ | H | $CH_3$ | $CH_3$ | CH | 201 to 203 dec. |
| 4 | $CH_3$ | H | Cl | $OCH_3$ | CH | 195 to 200 |
| 5 | $CH_3$ | H | $OCH_3$ | $CH_3$ | N | 189 to 191 |
| 6 | $CH_3$ | H | $OCH_3$ | $OCH_3$ | N | 191 to 194 |
| 7 | $CH_3$ | H | $OC_2H_5$ | $NHCH_3$ | N | 180 to 186 |
| 8 | $CH_2CH_3$ | H | $OCH_3$ | $OCH_3$ | CH | 203 to 207 |
| 9 | $CH_2CH_3$ | H | $CH_3$ | $OCH_3$ | CH | 182 to 186 |
| 10 | $CH_2CH_3$ | H | $CH_3$ | $CH_3$ | CH | 191 to 196 |
| 11 | $CH_2CH_3$ | H | Cl | $OCH_3$ | CH | 165 to 170 |
| 12 | $CH_2CH_3$ | H | $CH_3$ | $OCH_3$ | N | 188 to 192 |
| 13 | $CH_2CH_3$ | H | $OCH_3$ | $OCH_3$ | N | 178 to 182 |
| 14 | $CH(CH_3)_2$ | H | $OCH_3$ | $OCH_3$ | CH | 190 to 193 |
| 15 | $CH(CH_3)_2$ | H | $CH_3$ | $OCH_3$ | CH | 190 to 192 |
| 16 | $CH(CH_3)_2$ | H | $CH_3$ | $CH_3$ | CH | 172 to 176 |
| 17 | $CH(CH_3)_2$ | H | Cl | $OCH_3$ | CH | 155 to 160 |
| 18 | $CH(CH_3)_2$ | H | $CH_3$ | $OCH_3$ | N | 176 to 180 |
| 19 | $CH(CH_3)_2$ | H | $OCH_3$ | $OCH_3$ | N | 178 to 183 |
| 20 | $CH_3$ | Cl | $OCH_3$ | $OCH_3$ | CH | 197 to 200 |
| 21 | $CH_3$ | Cl | $CH_3$ | $CH_3$ | CH | 153 to 160 |
| 22 | $CH_3$ | Cl | Cl | $OCH_3$ | CH | 175 to 183 |
| 23 | $CH_3$ | Cl | $OCH_3$ | $CH_3$ | N | 182 to 184 dec. |
| 24 | $CH_3$ | Cl | $OCH_3$ | $OCH_3$ | N | 183 to 187 |

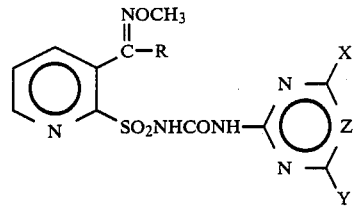

| CMPD | R | X | Y | Z | m.p. (°C.) |
|---|---|---|---|---|---|
| 25 | $CH_3$ | $OCH_3$ | $OCH_3$ | CH | 195 to 200 |
| 26 | $CH_3$ | $CH_3$ | $OCH_3$ | CH | 178 to 179 |
| 27 | $CH_3$ | $CH_3$ | $CH_3$ | CH | 179 to 180 |
| 28 | $CH_3$ | Cl | $OCH_3$ | CH | 185 to 222 |
| 29 | $CH_3$ | $CH_3$ | $OCH_3$ | N | 182 to 184 |
| 30 | $CH_3$ | $OCH_3$ | $OCH_3$ | N | 186 to 188 |
| 31 | $CH_2CH_3$ | $OCH_3$ | $OCH_3$ | CH | 163 to 167 |
| 32 | $CH_2CH_3$ | $CH_3$ | $OCH_3$ | CH | 168 to 170 |
| 33 | $CH_2CH_3$ | $CH_3$ | $CH_3$ | CH | 161 to 163 |
| 34 | $CH_2CH_3$ | Cl | $OCH_3$ | CH | 160 to 163 |
| 35 | $CH_2CH_3$ | $CH_3$ | $OCH_3$ | N | 180 to 182 |
| 36 | $CH_2CH_3$ | $OCH_3$ | $OCH_3$ | N | 110 to 120 dec. |

| CMPD | R | X | Y | Z | m.p. (°C.) |
|---|---|---|---|---|---|
| 37 | Cl | $OCH_3$ | $OCH_3$ | CH | 175 to 178 |
| 38 | Cl | $CH_3$ | $OCH_3$ | CH | 165 to 170 |
| 39 | Cl | $CH_3$ | $CH_3$ | CH | 140 to.148 |
| 40 | Cl | Cl | $OCH_3$ | CH | 160 to 164 |
| 41 | Cl | $CH_3$ | $OCH_3$ | N | 138 to 147 |
| 42 | Cl | $OCH_3$ | $OCH_3$ | N | 165 to 169 |
| 43 | $OCH_3$ | $OCH_3$ | $OCH_3$ | CH | 182 to 185 |
| 44 | $OCH_3$ | $CH_3$ | $OCH_3$ | CH | 158 to 161 |
| 45 | $OCH_3$ | $CH_3$ | $CH_3$ | CH | 184 to 188 |
| 46 | $OCH_3$ | Cl | $OCH_3$ | CH | 170 to 173 |
| 47 | $OCH_3$ | $CH_3$ | $OCH_3$ | N | 143 to 147 |
| 48 | $OCH_3$ | $OCH_3$ | $OCH_3$ | N | 160 to 164 |
| 49 | CN | $OCH_3$ | $OCH_3$ | CH | 175 to 178 |
| 50 | CN | $CH_3$ | $OCH_3$ | CH | 169 to 170 |
| 51 | CN | $CH_3$ | $CH_3$ | CH | 175 to 178 |
| 52 | CN | Cl | $OCH_3$ | CH | 158 to 160 |
| 53 | CN | $CH_3$ | $OCH_3$ | N | 159 to 161 |
| 54 | CN | $OCH_3$ | $OCH_3$ | N | 168 to 170 |
| 55 | H | $OCH_3$ | $OCH_3$ | CH | 167 to 170 dec. |
| 56 | H | $OCH_3$ | $CH_3$ | CH | 177 to 178 dec. |
| 57 | H | $CH_3$ | $CH_3$ | CH | 170 to 171 dec. |
| 58 | H | Cl | $OCH_3$ | CH | 166 to 168 dec. |
| 59 | H | $CH_3$ | $OCH_3$ | N | 164 to 165 dec. |
| 60 | H | $OCH_3$ | $OCH_3$ | N | 167 to 169 dec. |

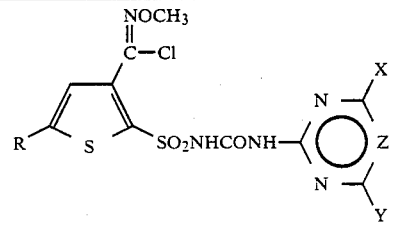

| CMPD | R | X | Y | Z | m.p. (°C.) |
|---|---|---|---|---|---|
| 61 | H | $OCH_3$ | $OCH_3$ | CH | 184 to 192 |
| 62 | H | $CH_3$ | $OCH_3$ | CH | 196 to 200 |
| 63 | H | $CH_3$ | $CH_3$ | CH | 187 to 190 |
| 64 | H | Cl | $OCH_3$ | CH | 175 to 179 |
| 65 | H | $CH_3$ | $OCH_3$ | N | 166 to 170 |
| 66 | H | $OCH_3$ | $OCH_3$ | N | 180 to 185 |
| 67 | Cl | $OCH_3$ | $OCH_3$ | CH | 169 to 175 |
| 68 | Cl | $CH_3$ | $OCH_3$ | CH | 202 to 204 |
| 69 | Cl | $CH_3$ | $CH_3$ | CH | 180 to 184 |
| 70 | Cl | Cl | $OCH_3$ | CH | 180 to 193 |
| 71 | Cl | $CH_3$ | $OCH_3$ | N | 168 to 172 |
| 72 | Cl | $OCH_3$ | $OCH_3$ | N | 182 to 186 |

COMPOUND TABLES
-continued

Structure:
CH₃ group and CH=NOCH₃ group on pyrazole ring (N-N with CH₃), connected via SO₂NHCONH to a ring with X, Y, Z substituents (N positions shown).

| CMPD | X | Y | Z | m.p. (°C) |
|------|------|------|----|-----------|
| 73 | OCH₃ | OCH₃ | CH | 206 to 208 |
| 74 | CH₃ | OCH₃ | CH | 204 to 206 |
| 75 | CH₃ | CH₃ | CH | 179 to 182 |
| 76 | Cl | OCH₃ | CH | 197 to 201 |
| 77 | CH₃ | OCH₃ | N | 190 to 194 |
| 78 | OCH₃ | OCH₃ | N | 198 to 201 |

Structure: Pyridine with C(=NOCH₃)CH₃ group, SO₂NHCONH linker to ring with X, Y, Z.

| CMPD | X | Y | Z | m.p. (°C) |
|------|------|------|----|-----------|
| 79 | OCH₃ | OCH₃ | CH | 179 to 181 dec. |
| 80 | CH₃ | OCH₃ | CH | 148 to 163 dec. |
| 81 | CH₃ | CH₃ | CH | 145 to 160 dec. |
| 82 | Cl | OCH₃ | CH | 140 to 151 dec. |
| 83 | CH₃ | OCH₃ | N | 140 to 150 dec. |
| 84 | OCH₃ | OCH₃ | N | 156 to 164 dec. |

COMPOUND TABLES
-continued

Structure: Pyridine with C(=NOCH₃)CF₃ group, SO₂NHCONH linker to ring with X, Y, Z.

| CMPD | X | Y | Z | m.p. (°C) |
|------|------|------|----|-----------|
| 85 | OCH₃ | OCH₃ | CH | 179 to 182 |
| 86 | CH₃ | OCH₃ | CH | 176 to 179 |
| 87 | CH₃ | CH₃ | CH | 194 to 197 |
| 88 | Cl | OCH₃ | CH | 167 to 170 |
| 89 | CH₃ | OCH₃ | N | 157 to 160 |
| 90 | OCH₃ | OCH₃ | N | 173 to 177 |

Test A

Seeds of crabgrass (Digitaria spp.), barnyardgrass (Echinochloa crus-galli), giant foxtail (Setaria faberi), wild oats (Avena fatua), cheatgrass (Bromus secalinus) or downy brome (Bromus tectorum), velvetleaf (Abutilon theophrasti), morningglory (Ipomoea spp.), cocklebur (Xanthium pensylvanicum), sorghum, corn, soybean, sugarbeet, cotton, rice, wheat, barley and purple nutsedge (Cyperus rotundus) tubers were planted and treated preemergence with the test chemicals dissolved in a non-phytotoxic solvent. At the same time, these crop and weed species were treated with a soil/foliage application. At the same time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:
C=chlorosis/necrosis
B=burn
D=defoliation
E=emergence inhibition
G=growth refardation
H=formative effect
U=unusual pigmentation
X=auxillary stimulation
S=albinism
6Y=abscised buds or flowers.

TABLE A

POSTEMERGENCE

| RATE=KG/HA | CMPD 1 | | CMPD 2 | | CMPD 3 | | CMPD 4 | | CMPD 5 | | CMPD 6 | | CMPD 7 | | CMPD 8 | | CMPD 9 | | CMPD 10 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 9C | 9C | 9C | 5C,9G | 5C,9G | 5C,9G | 9C | 4C,9H | 4C,96 | 9C | 5C,9G | 5C,9G | 4C,9G | 4C,9G | 5C,9G | 9C | 5C,9G | 6G | 4C,9G | 2G |
| MORNINGGLORY | 10C | 10C | 10C | 10C | 2C,7G | 10C | 10C | 10C | 5C,9G | 10C | 5C,9G | 5C,9G | 5C,9G | 9C | 10C | 2C,6G | 10C | 10C | 3C,6G | 1C,1H |
| COCKLEBUR | 9C | 9C | 10C | 3C,8G | 10C | 10C | 10C | 10C | 10C | 10C | 3H,6G | 0 | 1H | 10C | 10C | 4C,9G | 5C,9G | 9C | 9C | 4C,9G |
| NUTSEDGE | 9C | 9C | 9C | 0 | 9C | 4C,9G | 9C | 5C,9G | 8G | 0 | 0 | 0 | 3C,5G | 4C,9G | 5C,9G | 4C,9H | 4C,9G | 2C,2G | 4C,9G | 2C,5G |
| CRABGRASS | 0 | 0 | 3G | 3H | 5G | 5G | 4C,9G | 6H | 0 | 0 | 0 | 0 | 3G | 3G | 0 | 0 | 0 | 3G | 3G | 0 |
| BARNYARDGRASS | 9C | 9C | 9C | 3C,9H | 5C,9H | 5C,9H | 3C,9H | 0 | 0 | 0 | 0 | 0 | 3C,8H | 0 | 9C | 3C,9H | 9C | 3C,7G | 0 | 0 |
| WILD OATS | 6G | 2G | 5C,9G | 6G | 4C,9G | 4C,9G | 6G | 0 | 0 | 0 | 0 | 0 | 3G | 0 | 4G | 2G | 4G | 2C,3G | 2C,2G | 0 |
| WHEAT | 7G | 6G | 5C,9G | 7G | 5C,9G | 9G | 5G | 0 | 0 | 0 | 0 | 0 | 2G | 0 | 2G | 0 | 2G | 3G | 3C,5G | 0 |
| CORN | 9G | 2C,9G | 5U,9G | 3C,9G | 8U,9G | 4U,9G | 8H | 3H,4G | 3H | 0 | 0 | 0 | 3C,8H | 3C,9H | 3C,6H | 2C,4G | 3C,8H | 3C,6G | 3C,7G | 3C,6G |
| SOYBEANS | 9C | 9C | 9C | 9C | 9C | 9C | 5C,9G | 3C,5G | 5C,9G | 5C,9G | 0 | 5C,9G | 4C,9G | 4C,9G | 4C,9G | 3C,5G | 10C | 4C,9G | 4C,9G | 4C,9G |
| RICE | 5C,9G | 2C,6G | 5C,9G | 3C,7G | 6C,9G | 6C,9G | 3C,5G | 5G | 10C | 3H | 0 | 0 | 3C,7G | 4C,9G | 3C,7G | 3C,9G | 10C | 7G | 3C,7G | 2C,4G |
| SORGHUM | 6G | 5G | 4C,9G | 4C,9G | 6C,9G | 6C,9G | 8H | 2C,8G | 2G | 0 | 0 | 0 | 10C | 6G | 2C,4G | 2C,4G | 3C,9G | 3C,7G | 2C,4G |
| CHEATGRASS | 9G | 7G | 9C | 5C,9G | 5C,9G | 5C,9G | 9G | 5G | 10C | 2G | 9C | 9C | 10C | 2C,2G | 10C | 10C | 9C | 4C,9G | 4C,9G | 9C |
| SUGARBEETS | — | 9C | 10C | 10C | 10C | 10C | 10C | 9C | — | 10C | 5C,9H | 0 | 5C,9G | 10C | 9C | 10C | 9C | 9C | 3C,7G |
| VELVETLEAF | 10C | 9C | 10C | 5C,9G | 5C,9G | 5C,9G | 5G | 9C | 5C,9H | 9C | 9C | 0 | 3G | 4C,8H | 2G | 3C,7G | 3C,7G | 2G | 2C,5G | 2C,4G |
| GIANT FOXTAIL | 2C,7G | 3G | 5C,9G | 7G | 5G | 5G | 5G | 6G | 0 | 0 | 5C,9H | 0 | 2C,2G | 0 | 3G | 2G | 2C,5G | 3C,5G | 3C,5G | 2C,4G |
| BARLEY | 8G | 6G | 4C,9H | 2C,7G | 5C,9G | 9G | 6G | 2G | 0 | 0 | 0 | 0 | 0 | 0 | 3C,8G | 3G | 4C,8H | 3C,4G | 3C,7G | 2C,4G |

PREEMERGENCE

| RATE=KG/HA | CMPD 1 | | CMPD 2 | | CMPD 3 | | CMPD 4 | | CMPD 5 | | CMPD 6 | | CMPD 7 | | CMPD 8 | | CMPD 9 | | CMPD 10 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 9G | 3C,8G | 0 | 9G | 5H | 3C,7G | 8H | 4G | 3C,7G | 2G | 5G | 3G | 7G | 1C | 0 | 7G | 2G | 0 |
| MORNINGGLORY | 9H | 3C,8G | 0 | 9G | 9G | 9G | 9G | 8G | — | 9G | 3C,7G | 2G | 9G | 9C | 2C,5H | 7G | 9G | 3C,3H | 7G | 2G |
| COCKLEBUR | 2C,7G | 3C,4H | — | 9G | 3C,5H | 3C,6H | 3C,8G | 8H | 3G | 0 | 5G | 3G | 3C,8H | 9H | 3C,7H | 3C,7H | 3C,7H | 3C,5H |
| NUTSEDGE | 9G | 9G | 5G | 9G | 5G | 10E | 10E | 0 | 0 | 0 | 0 | 10E | 10E | 10E | 0 | 0 |
| CRABGRASS | 0 | 5G | 9G | 5G | 0 | 0 | 3G | 0 | 0 | 2C,3G | 0 | 2C,3G | 0 | 2C,3G | 3C,3G | 2C,3G | 0 |
| BARNYARDGRASS | 6H | 9H | 3H | 9H | 2C | 3C,7H | 0 | 0 | 0 | 0 | 3C,7G | 0 | 3C,4G | 3C,4G | 3C,7H | 0 |
| WILD OATS | 3G | 3C,5G | 2C,3G | 2C,3G | 3C,7G | 2C,3G | 0 | 0 | 0 | 0 | 0 | 3G | 2C,5G | 2C,5G | 2C,5G | 0 | 2G |
| WHEAT | 5G | 3C,8G | 5G | 9G | 2C,8G | 3C,8G | 2G | 0 | 0 | 0 | 0 | 2G | 3G | 3G | 3G | 3G |
| CORN | 2C,6G | 2C,6G | 2C,3G | 9G | 3C,6H | 9G | 2C,2G | 7G | 2G | 2G | 9G | 3C,6G | 3C,9H | 3C,9H | 3C,9G | 3C,5G | 3C,5H |
| SOYBEANS | 8G | 4H | 5G | 9H | 3C,6H | 3C,6G | 0 | 4C,8H | 8G | 3C,5H | 3C,7H | 7H | 3C,7H | 8H | 8H | 3C,7G | 3C,6H |
| RICE | 3C,9H | 6G | 3C,6H | 9G | 3C,7H | 3C,4G | 2C,2G | 2G | 0 | 0 | 5G | 2G | 2C,4G | 8H | 5G | 5G | 3G |
| SORGHUM | 9G | 0 | 2G | 9H | 9H | 9G | 7G | 7G | 3C,5G | 0 | 3C,5G | 0 | 8H | 2C,2G | 8H | 3C,9H | 2C,3G |
| CHEATGRASS | 3C,8H | 3C,8G | 7H | 10E | 3C,9H | 3C,9G | 2C,7G | 0 | 0 | 2G | 0 | 3G | 5C,9G | 7G | 5C,9G | 8G | 9H | 9G |
| SUGARBEETS | 3C,8G | 3C,8G | 5G | 9H | 9H | 7G | 7G | 7G | 5C,9G | 5G | 5C,9G | 8G | 2G | 3C,8G | 8H | 8H | 3C,6G | 0 |
| VELVETLEAF | 9G | 9G | 9G | 3H | 9H | 8H | 9G | 6G | 0 | 0 | 0 | 2C,8G | 2C,4G | 4G | 4G | 2G | 3H |
| GIANT FOXTAIL | 9G | 4C,9G | 3H | 9G | 9G | 3H | 8H | 9G | 0 | 0 | 0 | 0 | 9H | 0 | 0 | 3C,7G | 3C,8G | 0 |
| BARLEY | 8G | 9H | 3G | 9H | 9H | 3G | 2G | 0 | 0 | 9C | 0 | 1C | 0 | 0 | 3C,8G | 3G | 3G | 3G |
| DOWNY BROME | 8G | 8G | 2C,7G | 5C,9G | 5C,9G | 9G | 2G | 6G | 5C,9H | 0 | 0 | 2G | 9H | 2C,5G | 9H | 2C,5G | 5G | 2C,5G | 2C,4G |

POSTEMERGENCE

| RATE=KG/HA | CMPD 11 | | CMPD 12 | | CMPD 13 | | CMPD 14 | | CMPD 15 | | CMPD 16 | | CMPD 17 | | CMPD 18 | | CMPD 19 | | CMPD 20 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 9H | 3C,86 | 5C,9G | 5C,9G | 5C,9G | 4C,9G | 7G | 7G | 9H | 7G | 6G | 5G | 4G | 4C,8G | 3C,7H | 3G | 3G | 4C,8G | 5C,9G |
| MORNINGGLORY | 10C | 9C | 10C | 10C | 10C | 10C | 3C,8G. | 5C,9G | 10C | 5C,9G | 3C,8H | 2C,5G | 2H | 9C | 3C,9H | 4C,9G | 4C,8H | 9C | 10C |

TABLE A-continued

| | CMPD 21 | | CMPD 22 | | CMPD 23 | | CMPD 24 | | CMPD 25 | | CMPD 26 | | CMPD 27 | | CMPD 28 | | CMPD 29 | | CMPD 30 | |
|---|---|---|---|---|---|---|---|---|---|---|---|---|---|---|---|---|---|---|---|---|
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COCKLEBUR | 9C | 9C | 10C | 10C | 10C | 5C,9G | 4C,9H | 4C,9H | 5C,9G | 5C,9G | 3C,9H | 3C,6H | 4C,9H | 3C,8H | 9C | 0 | 3C,9H | 5C,9G | 10C | 9C |
| NUTSEDGE | 10C | 5C,9G | 3C,7G | 4C,9G | 9C | 0 | 4C,9G | 4C,9G | 8G | 0 | 0 | 0 | 2G | 0 | 0 | 0 | 0 | 0 | 5G | 0 |
| CRABGRASS | 3G | 0 | 0 | 9G | 0 | 0 | 3G | 0 | 7G | 0 | 0 | 0 | 4G | 0 | 0 | 0 | 0 | 0 | 9C | 3C,9G |
| BARNYARDGRASS | 2C,5G | 2H | 0 | 8H | 0 | 0 | 0 | 0 | 6G | 0 | 0 | 0 | 3G | 0 | 0 | 0 | 0 | 0 | 5G | 2G |
| WILD OATS | 0 | 0 | 0 | 0 | 0 | 0 | 0 | 0 | 3G | 0 | 0 | 0 | 0 | 0 | 0 | 0 | 0 | 0 | 8G | 0 |
| WHEAT | 0 | 0 | 0 | 0 | 2C,3G | 0 | 0 | 0 | 0 | 0 | 1C | 0 | 0 | 0 | 0 | 0 | 0 | 0 | 2G | 0 |
| CORN | 3C,4G | 2G | 3C,6G | 4C,9G | 5C,9G | 4C,9G | 3G | 4G | 3C,7G | 3C,3G | 2C,3H | 0 | 0 | 0 | 0 | 0 | 0 | 0 | 4U,9G | 3C,8G |
| SOYBEANS | 4G | 1H | 9C | 9C | 1C | 2G | 0 | 3C,6H | 5C,9G | 3C,5G | 0 | 1H | 0 | 0 | 0 | 0 | 0 | 0 | 9C | 9C |
| RICE | 2C,5G | 1C | 0 | 0 | 0 | 2G | 0 | 2G | 3C,5G | 3C,5G | 0 | 0 | 0 | 2G | 0 | 5H | 0 | 0 | 3C,8G | 5G |
| SORGHUM | 3C,7G | 2C,4G | 2G | 4C,9G | 0 | 3G | 0 | 3G | 3G | 3G | 0 | 0 | 0 | 0 | 0 | 0 | 2G | 0 | 9C | 3C,9G |
| SUGARBEETS | 10C | 3C,8G | 10C | 9C | 9C | 2G | 3C,7H | 3C,4G | 3C,4G | 2G | 4C,9H | 0 | 4C,9H | 5C,9G | 4C,9G | 4C,9H | 3C,8H | 10C | 10C |
| VELVETLEAF | 10C | 5C,9H | 9C | 5C,9G | 3C,8G | 2C,8G | 2G | 3C,4G | 3C,5G | 5G | 4C,9H | 8G | 8G | 4C,9H | 3C,8H | 10C | 10C |
| GIANT FOXTAIL | 2G | 0 | 0 | 0 | 3C,7G | 0 | 0 | 2H | 4C,9G | 2H | 3C,7G | 0 | 7G | 0 | 0 | 3C,7H | 3C,6G | 2G |
| BARLEY | 0 | 0 | 0 | 0 | 0 | 0 | 0 | 0 | 3G | 0 | 0 | 0 | 0 | 0 | 0 | 0 | 0 | 0 | 3C,6G | 2G |
| DOWNY BROME | 3C,7G | 0 | 0 | 0 | 2G | 0 | 0 | 0 | 0 | 4G | 0 | 0 | 0 | 0 | 0 | 0 | 0 | 0 | 3G | 0 |
| CHEATGRASS | 0 | 0 | 0 | 0 | 0 | 0 | 0 | 0 | 5G | 0 | 0 | 0 | 0 | 0 | 0 | 0 | 0 | 0 | 2C,7G | 0 |

PREEMERGENCE

| | CMPD 21 | | CMPD 22 | | CMPD 23 | | CMPD 24 | | CMPD 25 | | CMPD 26 | | CMPD 27 | | CMPD 28 | | CMPD 29 | | CMPD 30 | |
|---|---|---|---|---|---|---|---|---|---|---|---|---|---|---|---|---|---|---|---|---|
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 3G | 3G | 6G | 7H | 2C,5G | 0 | 0 | 0 | 0 | 0 | 0 | 0 | 0 | 0 | 0 | 0 | 0 | 0 | 3G | 5C,9G |
| MORNINGGLORY | 5G | 4G | — | 9G | 3C,3G | 0 | 0 | 0 | 8H | 1H | 0 | 0 | 0 | 0 | 0 | 0 | 0 | 2G | 9G | 2G |
| COCKLEBUR | 3C,4H | 3C,5H | 3C,5H | 7H | 3C,3G | 2H | 0 | 0 | 7H | 1H | 0 | 0 | 0 | 0 | 0 | 0 | 2C,2H | 3C,8H | 5G |
| NUTSEDGE | 10E | 0 | 0 | 0 | 0 | 0 | 0 | 0 | 0 | 0 | 0 | 0 | 0 | 0 | 0 | 0 | 0 | 0 | 9G | 8G |
| CRABGRASS | 0 | 2C,5G | 1C | 0 | 0 | 0 | 0 | 0 | 2G | 2C,3H | 0 | 0 | 0 | 0 | 0 | 0 | 0 | 0 | 3G | 0 |
| BARNYARDGRASS | 0 | 0 | 0 | 0 | 0 | 0 | 0 | 0 | 2G | 8G | 0 | 0 | 0 | 0 | 0 | 0 | 0 | 0 | 0 | 0 |
| WILD OATS | 2G | 0 | 0 | 0 | 0 | 0 | 0 | 0 | 4G | 0 | 0 | 0 | 2G | 0 | 0 | 0 | 0 | 0 | 0 | 0 |
| WHEAT | 0 | 0 | 0 | 0 | 0 | 0 | 0 | 0 | 3G | 0 | 0 | 0 | 0 | 0 | 0 | 0 | 0 | 0 | 0 | 0 |
| CORN | 2C,5G | 0 | 0 | 3C,7G | 2C,5G | 4C,8H | 0 | 3C,7G | 3C,7G | 2C,3G | 0 | 0 | 2C,5G | 2C,5G | 0 | 3C,3H | 0 | 3C,9G | 3C,5G | 2C,5G |
| SOYBEANS | 0 | 0 | 0 | 9H | 4C,8G | 3C,8H | 3C,8G | 2G | 3C,7H | 0 | 0 | 2G | 0 | 3C,7G | 0 | 0 | 2C,2H | 3C,4H | 3C,8G | 0 |
| RICE | 7G | 4G | 3C,8G | 0 | 0 | 0 | 0 | 0 | 6G | 5G | 0 | 0 | 2G | 0 | 0 | 0 | 0 | 0 | 3C,8G | 0 |
| SORGHUM | 7G | 0 | 0 | 5C,9G | 5C,9G | 4G | 0 | 0 | 6G | 2G | 0 | 0 | 0 | 0 | 0 | 0 | 0 | 0 | 3C,8G | 0 |
| SUGARBEETS | 9G | 8G | 5C,9G | 8G | 3G | 0 | 0 | 0 | 2C,5G | 3G | 0 | 2G | 5G | 8G | 0 | 7G | 5H | 9G | 9G | 2G |
| VELVETLEAF | 5H | 3C,5H | 7H | 0 | 2C,3G | 3G | 0 | 4G | 4H | 4G | 0 | 0 | 5G | 3G | 0 | 2C,2H | 0 | 5C,9G | 5C,9G | 7G |
| GIANT FOXTAIL | 2G | 2G | 0 | 0 | 0 | 0 | 0 | 0 | 2G | 4G | 0 | 0 | 0 | 0 | 0 | 0 | 0 | 0 | 2G | 3H |
| BARLEY | 0 | 0 | 1C | 0 | 0 | 0 | 0 | 0 | 0 | 0 | 0 | 0 | 0 | 0 | 0 | 0 | 0 | 0 | 0 | 0 |
| DOWNY BROME | 3G | 2G | 3G | 0 | 0 | 0 | 0 | 0 | 6G | 4G | 0 | 0 | 0 | 0 | 0 | 0 | 0 | 0 | 2G | 2C |
| CHEATGRASS | 0 | 0 | 0 | 0 | 0 | 0 | — | 0 | 7G | 3G | 0 | 0 | 0 | 0 | 0 | 0 | 0 | 0 | 7G | 0 |

POSTEMERGENCE

| | CMPD 21 | | CMPD 22 | | CMPD 23 | | CMPD 24 | | CMPD 25 | | CMPD 26 | | CMPD 27 | | CMPD 28 | | CMPD 29 | | CMPD 30 | |
|---|---|---|---|---|---|---|---|---|---|---|---|---|---|---|---|---|---|---|---|---|
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 10C | 3C,6G | 9C | 5G | 4C,9G | 5C,9G | 0 | 10C | 10C | 3C,7G | 6G | 2C,7G | 9C | 5C,9G | 5C,9G | 9C | 5C,9G |
| MORNINGGLORY | 10C | 3C,7H | 10C | 3C,8G | 5C,9H | 5C,9H | 3C,4G | 10C | 10C | 4C,8G | 3C,7G | 9C | 10C | 5C,9G | 5C,9G | 9C | 5C,9G |
| COCKLEBUR | 10C | 3C,8H | 10C | 2C,9G | 3C,9H | 2C,7G | 1C,3G | 9C | 9C | 5C,9G | 4C,9G | 10C | 10C | 9C | 10C | 10C | 5C,9G |
| NUTSEDGE | 5C,9G | 9G | 8G | 3G | 3G | 3G | 3C,4G | 9C | 3C,8G | 2C,9G | 4C,9G | 3C,8G | 3C,8G | 2C,6G | 0 | 0 | 4C,7G |
| CRABGRASS | 4G | 0 | 0 | 0 | 0 | 2G | 3G | 2G | 2G | 2G | 4G | 0 | 6G | 2H | 0 | 0 |
| BARNYARDGRASS | 5C,9G | 1C,5H | 9C | 9C | 4C,8H | 3C,9H | 3C,7H | 5C,9H | 5C,9G | 4C,9H | 4G | 3C,8G | 3C,9G | 0 | 2H | 3C,8H |
| WILD OATS | 2C,7G | 3G | 8G | 8G | 2C,3G | 2C,6G | 2G | 9G | 6G | 2C,9G | 9C | 6G | 0 | 0 | 5C,9G |
| WHEAT | 9G | 0 | 5G | 5G | 3G | 2G | 3C,4G | 9G | 4C,9G | 8G | 4C,9H | 5G | 5U,9H | 6H | 0 | 0 |
| CORN | 3C,9G | 2C,7H | 2C,7H | 3C,8G | 3C,7H | 2C,8G | 3C,4G | 9G | 4C,9G | 2C,8G | 2C,9G | 4C,8H | 5C,9G | 5C,9G | 4C,9G | 3C,8H |
| SOYBEANS | 9C | 9C | 6C,9G | 6C,9G | 4C,9G | 4C,9G | 4C,8G | 9C | 5C,9G | 5C,9G | 9C | 4C,8H | 9C | 5C,9G | 5C,9G |

TABLE A-continued

|  | CMPD 31 | | CMPD 32 | | CMPD 33 | | CMPD 34 | | CMPD 35 | | CMPD 36 | | CMPD 37 | | CMPD 38 | | CMPD 39 | | CMPD 40 | |
|---|---|---|---|---|---|---|---|---|---|---|---|---|---|---|---|---|---|---|---|---|
| RICE | 8G | 2G | 2G | 4G | 2G | 0 | 0 | 9C | 9C | 3C,8G | 5C,9G | 9C | 5C,9G | 2C,2G | 0 | 5C,9G |
| SORGHUM | 5C,9G | 9G | 2C,8H | 6C,9G | 3C,8G | 8G | 2C,7H | 4C,9G | 4C,9G | 2C,9G | 4C,9G | 3C,8G | 4C,9G | 0 | 0 |
| CHEATGRASS | 4C,9G | 6G | 6G | 5C,9G | 8G | 8G | 6C,9G | 9C | 5C,9G | 4C,9G | 5C,9G | 8G | 6G | 4G | 0 | 9C |
| SUGARBEETS | 5C,9G | 9C | 3C,7G | 3C,6G | 3C,6G | 5C,9G | 10C | 9C | 9C | 9C | 8G | 10C | 9C | 9C | 10C |
| VELVETLEAF | 10C | 9C | 2C,7G | 3C,8G | — | — | 10C | 10C | 9C | 3C,8G | 10C | 7G | — | 9C | 10C |
| GIANT FOXTAIL | 8G | 2G | 0 | 6G | 3G | 3G | 4C,8G | 5C,9G | 5C,9G | 4C,9G | 0 | 5G | 0 | 4C,9G |
| BARLEY | 9G | 4G | 0 | 0 | 0 | 0 | 3G | 3G | 3C,9G | 2C,9G | 2G | 0 | 0 |

PREEMERGENCE

|  | CMPD 31 | | CMPD 32 | | CMPD 33 | | CMPD 34 | | CMPD 35 | | CMPD 36 | | CMPD 37 | | CMPD 38 | | CMPD 39 | | CMPD 40 | |
|---|---|---|---|---|---|---|---|---|---|---|---|---|---|---|---|---|---|---|---|---|
| COTTON | 1C | 6G | 0 | 8G | 0 | 0 | 0 | 9G | 9H | 2C,7G | 9G | 7G | 9G | 5G | 3C,8G | 5G |
| MORNINGGLORY | 5G | 9G | 4G | 9G | 2C,6G | 1C,5G | 2C,4G | 9G | 9H | 8G | 5G | 5G | 9H | 9G | 5G |
| COCKLEBUR | 3C,7H | 8G | 6G | 9G | 6G | 5G | 2C,6G | 7G | 9H | 3C,7H | 7G | 9H | 8H | 7H | 1C |
| NUTSEDGE | 10E | 10E | — | 8G | 0 | 2G | 5G | 5G | 10E | — | 9G | 8H | 4G | 0 | 0 |
| CRABGRASS | 3G | 0 | 0 | 4G | 2G | — | 3G | 5G | 4G | 9H | 5G | 0 | 0 | 0 | 0 |
| BARNYARDGRASS | 2G | 0 | 0 | 4G | 0 | 0 | 0 | 5G | 9H | 9H | 8H | 0 | 7H | 2G | 0 |
| WILD OATS | 4G | 0 | 0 | 0 | 0 | 0 | 0 | 8H | 2C,8G | 3C,8G | 3C,5G | 0 | 0 | 0 | 0 |
| WHEAT | 2C,5G | 0 | 0 | 2G | 0 | 0 | 0 | 3G | 3C,9H | 3C,5G | 7G | 0 | 0 | 0 | 0 |
| CORN | 3C,9G | 2G | 0 | 0 | 1C | 0 | 0 | 6G | 8G | 2C,5G | 2C,9G | 2G | 8G | 0 | 3C,8H |
| SOYBEANS | 9H | 2C,8G | 4C,8H | 4C,7H | 2C,2G | 0 | 0 | 8H | 3G | 3C,7H | 8H | 7G | 9H | 3C,6G | 9H |
| RICE | 5C,8H | 1C,4G | 0 | 4C,8H | 0 | 0 | 0 | 9H | 4C,8H | 3C,4H | 9H | 8H | 9H | 2C,7G | 3G |
| SORGHUM | 9H | 0 | 4C,9G | 5C,9G | 3C,7H | 3C,5G | 3C,5G | 8G | 3C,9G | 8G | 10H | 3C,8H | 2C,8G | 0 | 3G |
| CHEATGRASS | 2C,7H | 3G | 2C,8G | 4C,8H | 3C,8G | 0 | 0 | 8G | 2C,9G | 3C,9G | 8H | 7H | 3G | 0 | 0 |
| SUGARBEETS | 2G | 2G | 0 | 4G | 0 | — | 4G | 9G | 9H | 8G | 9C | 9C | 0 | 2G | 0 |
| VELVETLEAF | 9G | 3C,9G | 3C,9G | 5C,9G | 3C,8G | 5C,9G | 2G | 9G | 3H | 9G | 8H | 4C,9G | 4C,9G | 8H | 4C,9G |
| GIANT FOXTAIL | 3G | 0 | 8G | 2C,4G | 0 | 2C,3G | 3G | 3G | 9H | 3C,8H | 8G | 2G | 5C,9G | 7H | 5C,9G |
| BARLEY | 7G | 6G | 5G | 3C,8H | 2G | 3G | 2G | 7G | 9H | 8H | 9H | 2C,6G | 0 | 0 | 0 |
| | 9G | 4G | 1C,5G | 2C,4G | 2G | 4G | 0 | 9G | 8G | 2C,8G | 8G | 3G | 3C | 2C | 0 |
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |

POSTEMERGENCE

|  | CMPD 31 | | CMPD 32 | | CMPD 33 | | CMPD 34 | | CMPD 35 | | CMPD 36 | | CMPD 37 | | CMPD 38 | | CMPD 39 | | CMPD 40 | |
|---|---|---|---|---|---|---|---|---|---|---|---|---|---|---|---|---|---|---|---|---|
| COTTON | 9C | 3C,9G | 3C,9G | 3C,9G | 2C,9G | 2C,9G | 5C,9G | 5C,9G | 4C,9G | 4C,9G | 5C,9G | 9C | 5C,9G | 5C,9G | 9C | 5C,9G |
| MORNINGGLORY | 10C | 3C,8G | 10C | 10C | 4C,9G | 3C,8G | 9C | 10C | 9C | 9C | 10C | 10C | 10C | 4C,9G | 10C | 9C |
| COCKLEBUR | 10C | 4C,9G | 9C | 9C | 3C,9H | 4C,9G | 9C | 9C | 9C | 9C | 10C | 3C,8G | 9C | 4C,9G | 9C | 9C |
| NUTSEDGE | 9C | 9C | 4C,9G | 9C | 9C | 3C,8G | 9C | — | 9C | 2C,9G | 9C | 2C,9G | 2C,9G | 9G | 9G | 9G |
| CRABGRASS | 5G | 2G | 5G | 3C,7G | 3C,7G | — | — | 4G | 2C,9G | 4G | 4G | 5C,9G | 4G | 9G | 5C,9G |
| BARNYARDGRASS | 4C,9H | 4C,9H | 8H | 9H | 7H | 3C,7G | 3C,7H | 4G | 9C | 9C | 5C,9G | 9C | 5C,9G | 5C,9G | 9C | 5C,9G |
| WILD OATS | 0 | 3C,5G | 3C,7G | 3C,7G | 2C | 3C,8H | 3C,8H | 9H | 5C,9G | 5C,9G | 5C,9G | 5C,9G | 3G | 9G | 2C,9G | 3C,7G |
| WHEAT | 2G | 0 | 3G | 3G | 4G | 2C,3G | 2C,3G | 5H | 5C,9G | 5C,9G | 4U,9G | 5C,9G | 5G | 9G | 9G | 8G |
| CORN | 3C,8G | 3G | 3C,9H | 3C,9G | 3C,7G | 3G | 3G | 3C,8G | 3C,9G | 3C,7G | 9C | 4C,8G | 3C,6G | 3C,8H | 3C,8H | 3C,7H |
| SOYBEANS | 4C,9G | 3C,8G | 3C,9H | 3C,9G | 8H | 2H | 2H | 3C,9G | 3C,9G | 3C,9H | 4U,9G | 5G | 4C,9G | 2G | 5C,9G | 2C,7G |
| RICE | 3C,9G | 7G | 9G | 5C,9G | 8G | 7G | 7G | 6C,9G | 4C,8H | 3C,9G | 9C | 7G | 3C,7G | 4C,9G | 4C,9G | 2C,7G |
| SORGHUM | 4C,9G | 3C,7G | 3C,9G | 2C,9G | 3C,8G | 2G | 2C,4G | 3C,9G | 4C,9G | 3C,9G | 6C,9G | 6C,9G | 3C,9G | 9G | 5C,9G | 4C,9G |
| CHEATGRASS | 4C,9G | 7G | 5G | 5C,9G | 8G | 2G | 2G | 3C,9G | 5C,9G | 2C,9G | 3C,9G | 3C,9G | 4C,8G | 4C,9G | 5C,9G | 9C |
| SUGARBEETS | 10C | 2C,8G | 3C,9G | 10C | 10C | 8G | 7G | 9C | 10C | 9C | 6C,9G | 4C,9H | 4C,9G | 9G | 5C,9G | 9C |
| VELVETLEAF | 9C | 5C,9G | 9C | 9C | 9C | 3C,9G | 3C,9G | 9C | 10C | 9C | 10C | 9C | 4C,9G | 4C,9G | 9C | 10C |
| GIANT FOXTAIL | 3C,6G | 3C,7G | 0 | 2C,9G | 3C,8G | 3C,7G | 3C,7G | 4C,9G | 9C | 3C,8H | 4C,9G | 4C,8G | 3C,9G | 9C | 4C,9G | 4C,8H |
| BARLEY | 2C,2G | 0 | 9G | 2C,9G | 8G | 7G | 0 | 3C,9G | 9C | 3C,9G | 3C,5G | 3C,8G | 7G | 3C,8G | 7G | 4G |
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |

| | CMPD 31 | | CMPD 32 | | CMPD 33 | | CMPD 34 | | CMPD 35 | | CMPD 36 | | CMPD 37 | | CMPD 38 | | CMPD 39 | | CMPD 40 | |
|---|---|---|---|---|---|---|---|---|---|---|---|---|---|---|---|---|---|---|---|---|
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| PREEMERGENCE | | | | | | | | | | | | | | | | | | | | |
| COTTON | 2G | 1C | 8G | 7G | 7G | 0 | 2G | 0 | 2C,9G | 3G | 9G | 3G | 9G | 8G | 0 | 0 | 9G | 7G | 4C,9G | 9G |
| MORNINGGLORY | 2C,3H | 0 | 8H | 3C,5G | 2C,2G | 1H | 7H | 1H | 9H | 3H | 9G | 0 | 9G | 4G | 0 | 0 | 9G | 8H | 9G | 9G |
| COCKLEBUR | 8H | 2C,3H | 9H | 3C,7H | — | 2C,2H | 8H | 2C,5G | 9H | 3C,5G | 8H | 3C,6H | 8H | 10E | 0 | 1C | 9H | 3C,5H | 9H | 3C,6H |
| NUTSEDGE | 10E | 0 | 10E | 0 | 8G | 4G | 10E | 0 | 10E | 0 | 9G | 0 | 10E | 0 | 0 | 0 | 9G | 10E | 9G | 9G |
| CRABGRASS | 0 | 0 | 2C,5G | 0 | 2C,4G | 3C,5G | 0 | 0 | 0 | 0 | 4G | 0 | 4G | 4G | 0 | 0 | 6G | 2G | 10E | 9G |
| BARNYARDGRASS | 0 | 0 | 9H | 6G | 9H | 1C | 2G | 0 | 0 | 0 | 9H | 0 | 9H | 2G | 0 | 0 | 9H | 3C,5G | 9G | 3G |
| WILD OATS | 3H | 0 | 3C,8G | 3G | 7G | 2G | 0 | 0 | 0 | 0 | 3C,8G | 2G | 3C,6G | 3G | 0 | 0 | 4C,8H | 7G | 3C,6G | 3G |
| WHEAT | 0 | 0 | 8H | 3G | 8G | 3C,6G | 0 | 0 | 0 | 0 | 4C,9H | 2C,2G | 6G | 3G | 0 | 0 | 3C,9H | 5G | 8H | 8G |
| CORN | 4G | 0 | 9H | 3C,6G | 2C,9H | 3C,4G | 2G | 0 | 2C,5G | 3C,5G | 3C,9H | 2C,3G | 3C,9H | 2C,5G | 0 | 0 | 2C,6G | 7G | 3C,8G | 5G |
| SOYBEANS | 3C,7H | 2C,3G | 3C,7H | 3C,7H | 2C,9H | 3C,6G | 0 | 0 | 0 | 3C,5G | 4C,9H | 3C,7G | 3C,7G | 2G | 0 | 0 | 9H | 5G | 8H | 3C,7G |
| RICE | 3C,8H | 6G | 8G | 3C,7G | 3C,6G | 0 | 5G | 5G | 0 | 0 | 3C,7H | 2G | 9H | 3C,7G | 0 | 0 | 9H | 9H | 9H | 9H |
| SORGHUM | 9H | 2C,5G | 9H | 3C,9G | 7G | 2C,8H | 8H | 4G | 0 | 0 | 10H | 2G | 10H | 9H | 0 | 0 | 3C,9H | 4C,9H | 3C,9H | 3C,9H |
| CHEATGRASS | 7G | 3G | 7G | 9H | 2C,8H | 3C,7G | 2C,5G | 4G | 5G | 4G | 4C,9H | 2G | 2C,8G | 2C,8G | 0 | 0 | 8H | 5G | 3C,8H | 4G |
| SUGARBEETS | 3H | 8G | 8G | 7G | 3C,9H | 3H | 5G | 3H | 3C,9G | 4C,9G | 5C,9G | 3C,8G | 4C,9G | 3G | 0 | 0 | 4C,9G | 7G | 5C,9G | 8G |
| VELVETLEAF | 3G | 0 | 7H | 3H | 8G | 1H | 8G | 1H | 5C,9G | 5C,9G | 2H | 2G | 4C,9G | 7G | 0 | 0 | 4C,8H | 3C,7H | 4C,8H | 3G |
| GIANT FOXTAIL | 0 | 0 | 2C,4G | 0 | 0 | 0 | 0 | 0 | 0 | 0 | 0 | 0 | 3C,7G | 0 | 0 | 0 | 3C,8H | 3C,7G | 3C,6G | 3C,7G |
| BARLEY | 5G | 0 | 9G | 8G | 2G | 0 | 3G | 0 | 1C | 4G | 9G | 0 | 8G | 3G | 0 | 0 | 9H | 8G | 8G | 9H |

| | CMPD 41 | | CMPD 42 | | CMPD 43 | | CMPD 44 | | CMPD 45 | | CMPD 46 | | CMPD 47 | | CMPD 48 | | CMPD 49 | | CMPD 50 | |
|---|---|---|---|---|---|---|---|---|---|---|---|---|---|---|---|---|---|---|---|---|
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| POSTEMERGENCE | | | | | | | | | | | | | | | | | | | | |
| COTTON | 4C,9G | 3C,5G | 4C,9G | 3C,8H | 5C,9G | 5C,9G | 4C,9G | 4C,9G | 9G | 9G | 9C | 9G | 6G | 0 | 6G | 0 | 9C | 10C | 3C,9G | 3C,9G |
| MORNINGGLORY | 5C,9G | 3C,9G | 10C | 4C,9G | 9C | 10C | 10C | 9C | 5C,9G | 5C,9G | 5C,9G | 5C,9G | 4C,8H | 2C,2G | 4C,8H | 0 | 10C | 10C | 9C | 9C |
| COCKLEBUR | 4C,9G | 2C,7G | 4C,9G | 3C,7G | 4C,8H | 4C,9G | 4C,9G | 4C,9G | 4C,9G | 4C,9G | 3C,7G | 3C,9G | 2C,3H | — | 2C,3H | 1C | 10C | 3C,7H | 2C,4H | 2C,4H |
| NUTSEDGE | 5G | 4G | 3C,8G | 0 | 5G | — | 9G | 9G | 9C | 9G | 9G | 9G | 4G | — | 4G | 2G | 4C,9G | — | 7G | 7G |
| CRABGRASS | 4G | 2G | 3C,5G | 3C,5G | 9C | 5G | 2G | 2G | 3G | 3G | 3G | 9H | 2G | 3C,4H | 2C,4G | 2G | 5G | 5C,9G | 2G | 2G |
| BARNYARDGRASS | 5C,9G | 5C,9G | 4C,9G | 4C,9G | 5G | 9C | 2C,6G | 3C,7G | 4C,8H | 4C,8H | 3G | 9H | 2G | 3C,6H | 3C,6H | 8G | 9C | 5G | 9G | 3C,5H |
| WILD OATS | 4C,9G | 2C,8G | 4C,9G | 4C,9G | 9C | 4C,9G | 5C,9G | 3C,9G | 7G | 4C,8H | 9H | 6G | 4C,6H | 3G | 2C,6G | 2G | 9G | 5G | 2G | 2G |
| WHEAT | 3C,7G | 8G | 5C,9G | 4C,9G | 2C,9G | 0 | 3C,9G | 3C,7G | 8G | 7G | 6G | 0 | 4C,9H | 3G | 2C,6G | 8G | 9G | 5G | 4G | 7G |
| CORN | 4C,9G | 3C,9G | 5C,9G | 5C,9G | 4C,9G | 4C,9G | 9G | 9G | 0 | 8G | 0 | 0 | 4C,9H | 0 | 9G | 2C,4G | 5C,9G | 4C,9G | 3C,5H | 3C,5H |
| SOYBEANS | 5C,9G | 3C,9G | 5C,9G | 3C,8G | 9C | 4C,9H | 3C,6H | 3C,6H | 2C,3H | 2C,3H | 4H | 4C,9G | 3C,9G | 3G | 3C,9G | 2C,9G | 9C | 5G | 2G | 2G |
| RICE | 4C,9G | 3C,9G | 9C | 3C,8G | 4C,9H | — | 9C | 9C | 9C | 2C,6G | 6G | 3C,9G | 0 | 3C,9G | 1C | 9G | 4C,9G | 5G | 7G | 7G |
| SORGHUM | 5C,9G | 3C,8H | 4C,9G | 4C,9G | 6C,9G | 6C,9G | 4C,9G | 4C,9G | 2G | 2C,6G | 0 | 4C,9G | 3C,9G | 3C,9G | 4C,9G | 3C,9G | 5C,9G | 5C,9G | 5H | 5H |
| CHEATGRASS | 5C,9G | 4C,9G | 4C,9G | 4C,9G | 9C | 9C | 4C,9G | 4C,9G | 4C,9G | 4C,9G | 4C,9G | 3C,7G | 4C,9G | 3C,7G | 3C,7G | 2G | 4C,9G | 5C,9G | 2C,3G | 2C,3G |
| SUGARBEETS | 5C,9G | 3C,9G | 5C,9G | 4C,9G | 4C,9G | 4C,9G | 4C,9G | 4C,9G | 4C,8H | 4C,9G | 3C,9G | 3C,9G | 4C,9G | 6G | 9G | 7G | 5C,9G | 4C,9G | 4G | 4G |
| VELVETLEAF | 9C | 3C,7G | 9C | 5C,9G | 4C,9G | 5G | 5C,9H | 5C,9H | 5C,9H | 5C,9H | 5C,9G | 9C | 3C,6H | 3H | 3C,6H | 3H | 9C | 5C,9G | 7G | 7G |
| GIANT FOXTAIL | 3C,7H | 2G | 4C,8H | 4G | 10C | 9C | 3C,7H | 3C,6H | 9G | 3C,6G | 2C,6G | 4C,8H | 2G | 2G | C | 0 | 10C | 10C | 3C,8H | 3C,8H |
| BARLEY | 5C,9G | 4C,9G | 9C | 9C | 9C | 5C,9G | 5C,9G | 5C,9G | 9G | 3C,6G | 9G | 4G | 9G | 3C,8G | 3C,8G | 3C,7G | 4C,9G | 3C,7G | 3C,7G | 3C,7G |
| | 8G | 7G | 4C,9G | 8G | 3C,9G | 9C | 0 | 0 | | | | | 2G | 9G | 9G | | 0 | 2C,5G | 2C,5G | 0 |

| | CMPD 41 | | CMPD 42 | | CMPD 43 | | CMPD 44 | | CMPD 45 | | CMPD 46 | | CMPD 47 | | CMPD 48 | | CMPD 49 | | CMPD 50 | |
|---|---|---|---|---|---|---|---|---|---|---|---|---|---|---|---|---|---|---|---|---|
| PREEMERGENCE | | | | | | | | | | | | | | | | | | | | |
| COTTON | 6G | 2G | 3C,7G | 2G | 9G | 5G | 2G | 0 | 0 | 0 | 2G | 5G | 0 | 0 | 0 | 0 | 5C,9G | 7G | 0 | 0 |
| MORNINGGLORY | 9G | 0 | 9G | 2C | 9H | 9G | 5G | 3G | 3G | 3G | 8H | 9G | 0 | 0 | 0 | 4G | 9G | 8G | 4G | 0 |
| COCKLEBUR | 2G | 0 | 2C,7G | 2G | 8H | 9H | 3C,6H | 2C,7H | 2C,7H | 2C,2G | 8H | 9H | 0 | 0 | 0 | 2G | 9H | 1C,1H | 0 | 0 |
| NUTSEDGE | 0 | 0 | 5G | 0 | 10E | 8H | 0 | 9G | 9G | 9G | 10E | 10E | 0 | 0 | 0 | 0 | 10E | 10E | 0 | 0 |

-continued

| | | | | | | | | | | | | | | | | | | |
|---|---|---|---|---|---|---|---|---|---|---|---|---|---|---|---|---|---|---|
| CRABGRASS | 2G | 0 | 5G | 0 | 7G | 3G | 2G | 0 | 2G | 3C,7H | 0 | 0 | 4G | 0 | 2G | 0 | 5G | 0 | 0 |
| BARNYARDGRASS | 2C,7G | 0 | 4C,8H | 4G | 9H | 9H | 4C,7H | 4H | 3C,7H | 2C,3G | 2H | 0 | 0 | 0 | 0 | 0 | 9H | 0 | 0 |
| WILD OATS | 3C,7G | 2C,2G | 3C,7H | 2C,2G | 4C,8G | 3C,7G | 3C,6G | 0 | 2C,3G | 0 | 2G | 2C,5G | 0 | 0 | 0 | 0 | 3C,6G | 2G | 0 |
| WHEAT | 2C,9G | 6G | 9H | 5G | 9H | 9H | 9H | 7H | 5G | 0 | 3G | 8H | 0 | 0 | 0 | 0 | 7G | 0 | 0 |
| CORN | 9G | 3C,7G | 9H | 4C,6G | 10H | 3C,7G | 4C,9H | 3C,7G | 3C,7G | 0 | 4G | 4C,7G | 3C,6G | 2C,6G | 1C,2G | 4C,9G | 3C,7G | 3G |
| SOYBEANS | 9H | 2C,2H | 3C,7H | 2C | 9H | 8H | 9H | 4C,7H | 2C,5G | 0 | 00 | 4C,8H | 0 | 0 | 9H | 3C,7G | 0 |
| RICE | 10E | 6G | 10H | 9H | 10H | 9H | 10H | 3C,6H | 4C,8H | 0 | 2C,5G | 2C,5G | 0 | 4G | 2G | 9H | 6G | 2G |
| SORGHUM | 4C,9H | 3C,8H | 3C,9H | 3C,3G | 9H | 4C,9H | 5C,9H | 3C,8H | 3C,9H | 3C,3G | 2C,3G | 3C,8H | 0 | 0 | 0 | 3C,9G | 2C,5G | 3G |
| CHEATGRASS | 4G | 0 | 3C,6G | 6G | 10E | 9H | 9H | 8H | 8H | 0 | 0 | 6G | 0 | 0 | 0 | 4C,8G | 0 | 2G |
| SUGARBEETS | 7G | 2H | 3C,9G | 4G | 10E | 9G | 3C,9G | 3C,6H | 9G | 8G | 2G | 8G | 2G | 0 | 0 | 5C,9G | 7G | 3G |
| VELVETLEAF | 2G | 0 | 3G | 1H | 9G | 4C,9G | 4C,8H | 3C,6H | 4C,7H | 2C,4H | 5G | 2C,5H | 2G | 0 | 0 | 4C,9G | 2H | 1C |
| GIANT FOXTAIL | 3C,7G | 5G | 4C,8H | 3G | 4C,9G | 3C,8G | 3C,8H | 5H | 5H | 6H | 4G | 7H | 3C,7H | 3G | 4C,9H | 3G | 2G |
| BARLEY | 9H | 3C,8G | 9H | 2C,4G | 3C,9G | 9G | 9G | 8H | 3C,8H | 0 | 0 | 9G | 0 | 0 | 0 | 2C,8G | 3C,7G | 0 |

| | CMPD 51 | | CMPD 52 | | CMPD 53 | | CMPD 54 | | CMPD 55 | | CMPD 56 | | CMPD 57 | | CMPD 58 | | CMPD 59 | | CMPD 60 | |
|---|---|---|---|---|---|---|---|---|---|---|---|---|---|---|---|---|---|---|---|---|
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |

POSTEMERGENCE

| | | | | | | | | | | | | | | | | | | | | |
|---|---|---|---|---|---|---|---|---|---|---|---|---|---|---|---|---|---|---|---|---|
| COTTON | 5C,9G | 3C,9G | 4C,9G | 3C,4G | 2C,3G | 2C,3G | 3C | 3C | 5C,9G | 5C,9G | 10C | 9C | 3C,9H | 3C,7H | 4C,8G | 6G | 2C,3G | 0 | 5G | 0 |
| MORNINGGLORY | 9C | 4C,9G | 10C | 3C,3G | 1C,2G | 1C,2G | 1C,1H | 1C,1H | 10C | 2C,7G | 2C,4G | 2C,4G | 2C,2G | 0 | 10C | 3C,7H | 3C,8G | 1H | 3C,8H | 1C,1H |
| COCKLEBUR | 5C,9G | 4C,9G | 9C | 9H | 1H | 1H | 0 | 0 | 9C | 9C | 5C,9G | 5C,9G | 9C | 1C,3H | 3C,7H | 4H | 3C,8H | 2G | 3C,8H | 2H |
| NUTSEDGE | 9G | 2C,9G | 4C,9G | 3C,5G | 0 | 0 | 0 | 0 | 10C | 9C | 3C,8G | 3C,8G | 3G | 3G | 5C,9G | 0 | 0 | 0 | 3G | 4G |
| CRABGRASS | 2C,2G | 0 | 0 | 0 | 0 | 0 | 4G | 6G | 10C | 4G | 2G | 2G | 3G | 3G | 2G | 0 | 0 | 0 | 2G | 0 |
| BARNYARDGRASS | 4C,9G | 3C,8H | 4C,9G | 4C,9G | 2C,3H | 2C,3H | 3G | 2G | 4C,9G | 3G | 3C,9H | 3C,9H | 3C,7H | 3C,4H | 3C,8H | 2H | 3C,8H | 2H | 4C,8H | 2C,4H |
| WILD OATS | 9G | 8G | 5C,9G | 0 | 0 | 0 | 0 | 0 | 9C | 9H | 9H | 9H | 3G | 5G | 0 | 0 | 9G | 5G | 8G | 0 |
| WHEAT | 9G | 2C,9G | 2C,7G | 0 | 6C | 6C | 0 | 0 | 8G | 9G | 9G | 9G | 3G | 4G | 0 | 0 | 4G | 0 | 5G | 0 |
| CORN | 2C,9H | 6G | 8G | 3G | 2G | 2G | 6G | 6G | 8G | 3G | 8G | 8G | 3G | 3G | 3G | 0 | 3C,9H | 3C,6H | 5C,9G | 4G |
| SOYBEANS | 5C,9G | 4C,9G | 4C,9H | 3C,8G | 0 | 0 | 2G | 2G | 5C,9G | 5C,9G | 5C,9G | 5C,9G | 3G | 3G | 3C,7H | 2C,5G | 4C,9H | 4H | 3C,8G | 0 |
| RICE | 5C,9G | 4C,9G | 5C,9G | 3C,7H | 0 | 0 | 2H | 2H | 9C | 9C | 9C | 9C | 4C,9H | 4H | 3C,7H | 4H | 9C | 5C,9G | 5C,9G | 4G |
| SORGHUM | 5C,9G | 3C,6G | 5C,9G | 2C,4G | 0 | 0 | 2G | 2G | 3C,8G | 3C,8G | 5C,9G | 5C,9G | 3C,8G | 2G | 2C,7G | 2G | 3C,6G | 3C,6G | 5C,9G | 4H |
| CHEATGRASS | 4C,9G | 4C,8G | 5C,9G | 4C,9G | 3C,5G | 3C,5G | 2G | 2G | 3C,8G | 2C,5G | 9C | 9C | 3C,9H | 3C,8H | 4C,9G | 0 | 9C | 3C,6G | 5C,9G | 3C,7H |
| SUGARBEETS | 5C,9G | 8G | 7G | 9G | 5G | 5G | 3G | 3G | 2C,8G | 3C,7G | 4C,9G | 4C,9G | 4C,9G | 4C,9G | 4G | 0 | 2C,7G | 6G | 4G | 6G |
| VELVETLEAF | 9C | 4C,9G | 9C | 4C,9G | 4C,9G | 4C,9G | 1H | 1H | 10C | 9C | 9C | 9C | 5C,9G | 5C,9G | 9C | 5C,9G | 9C | 3C,5G | 5C,9H | 2C,4H |
| GIANT FOXTAIL | 9C | 3C,8H | 10C | 3C,8H | 0 | 0 | 2G | 2G | 9C | 3C,8G | 3C,9G | 3C,9G | 3C,8H | 1C,2H | 3C,9G | 0 | 2C,5G | 0 | 2C,7G | 0 |
| BARLEY | 4C,9G | 3C,9G | 3C,7G | 2C,3G | 2C,6G | 2C,6G | 2G | 2G | 3C,7G | 3C,7G | 9C | 9C | 3C,8G | 3C,8G | 2C,6G | 3C,7G | 3G | 0 | 3G | 0 |
| | 8G | 6G | 6G | 2C,3G | 6G | 3G | 2C,5G | 2C,5G | 5G | 0 | 5G | 0 | 2G | 0 | 0 | 0 | 0 | 0 | 0 | 0 |

PREEMERGENCE

| | | | | | | | | | | | | | | | | | | | | |
|---|---|---|---|---|---|---|---|---|---|---|---|---|---|---|---|---|---|---|---|---|
| COTTON | 9G | 3C,7G | 3C,7G | 3C,4G | 2C,2H | 2C,2H | 0 | 0 | 8G | 3G | 0 | 0 | 5G | 2G | 8G | 3G | 0 | 0 | 0 | 0 |
| MORNINGGLORY | 9G | 2H | 9C | 3C,3G | 2C,2H | 2C,2H | 0 | 0 | 9G | 0 | 1C,1H | 1C | 0 | 3G | 2C,6G | 0 | 0 | 0 | 0 | 0 |
| COCKLEBUR | 7H | 2C | 9H | 0 | 1H | 1H | 0 | 0 | 3C,7H | 0 | 2C | 2C | 1C | 0 | 0 | 0 | 0 | 0 | 0 | 0 |
| NUTSEDGE | 10E | 3C,5G | 10E | 3G | 0 | 0 | 0 | 0 | 10E | 4G | 9G | 9G | 9G | 0 | 8G | 0 | 10E | 0 | 0 | 0 |
| CRABGRASS | 2C | 0 | 0 | 0 | 0 | 0 | 0 | 0 | 5G | 2G | 3G | 3G | 0 | 0 | 0 | 0 | 0 | 0 | 0 | 0 |
| BARNYARDGRASS | 3C,8G | 3C,4G | 3C,8H | 3G | 0 | 0 | 0 | 0 | 2C,8H | 3C,8H | 3C,5G | 2C,4H | 3G | 0 | 0 | 0 | 0 | 0 | 0 | 0 |
| WILD OATS | 3C,7G | 3C,4G | 2C,3G | 0 | 0 | 0 | 0 | 0 | 3C,6G | 3C,5G | 6G | 1C | 2C,7G | 0 | 7G | 0 | 0 | 0 | 0 | 0 |
| WHEAT | 3C,8H | 7G | 5G | 0 | 0 | 0 | 0 | 0 | 5G | 5G | 5G | 1C | 5G | 0 | 0 | 0 | 0 | 0 | 0 | 0 |
| CORN | 3C,9H | 3C,8G | 4C,9H | 2G | 0 | 0 | 0 | 0 | 5C,9G | 3C,7H | 2C,3G | 1C | 3G | 0 | 2C,3G | 0 | 1C | 0 | 2C,2G | 0 |
| SOYBEANS | 9H | 4C,8G | 4C,8H | 3C,6G | 0 | 0 | 0 | 0 | 3C,8H | 2C,3H | 2C,4H | 1C | 0 | 0 | 1C | 0 | 3C,6G | 0 | 1C | 0 |
| RICE | 9H | 3C,4G | 4C,9G | 2C,7G | 0 | 0 | 2G | 2G | 9H | 6G | 9H | 2G | 6G | 0 | 5G | 0 | 3G | 0 | 5G | 0 |
| SORGHUM | 3C,9H | 3C,7G | 5C,9G | 4C,8G | 0 | 0 | 0 | 0 | 9H | 6G | 2C,7G | 3G | 4G | 0 | 3C,7G | 0 | 0 | 0 | 2C,5G | 0 |
| CHEATGRASS | 9G | 8G | 3C,8H | 6G | 0 | 0 | 0 | 0 | 8G | 3G | 4C,9G | 8G | 2C,6G | 0 | 2C,6G | 0 | 3G | 0 | 2H | 0 |
| SUGARBEETS | 3C,9G | 3C,6H | 4C,9G | 3C,7G | 2G | 2G | 2G | 2G | 9G | 5H | 3C,5H | 0 | 9G | 7G | 9G | 7G | 7G | 2G | 0 | 0 |
| VELVETLEAF | 3C,5H | 2C,3G | 3C,8H | 2C,2H | 3H | 3H | 0 | 0 | 9H | 3G | 7G | 0 | 3C,5H | 0 | 2C,3G | 0 | 0 | 0 | 0 | 0 |
| GIANT FOXTAIL | 3C,7G | 2C,5G | — | 2C,3G | 0 | 0 | 0 | 0 | 3G | 0 | 3G | 0 | 3G | 0 | 2G | 0 | 0 | 0 | 0 | 0 |
| BARLEY | 9G | 2G | 4C,8G | 0 | 0 | 0 | 0 | 0 | 6G | 0 | 2G | 0 | 2G | 0 | 0 | 0 | 0 | 0 | 0 | 0 |

| | CMPD 61 | | CMPD 62 | | CMPD 63 | | CMPD 64 | | CMPD 65 | | CMPD 66 | | CMPD 67 | | CMPD 68 | | CMPD 69 | | CMPD 70 | |
|---|---|---|---|---|---|---|---|---|---|---|---|---|---|---|---|---|---|---|---|---|---|
| RATE=KG/HA | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |

POSTEMERGENCE

| | | | | | | | | | | | | | | | | | | | | |
|---|---|---|---|---|---|---|---|---|---|---|---|---|---|---|---|---|---|---|---|---|
| COTTON | 10C | 10C | 10C | 9C | 10C | 10C | 10C | 5C,9G | 10C | 5C,9G | 5C,9G | 5C,9G | 5C,9G | 2C,8G | 5C,9G | 3C,8G | 5C,9G | 3C,8G | 7G | 5G |
| MORNINGGLORY | 9C | 10C | 10C | 10C | 10C | 10C | 10C | 10C | 9C | 9C | 10C | 10C | 5C,9H | 3G | 3C,7G | 3C,3H | 1C | 3C,8G | 10C | 3C,7G |
| COCKLEBUR | 10C | 10C | 10C | 10C | 10C | 10C | 10C | 10C | 9C | 9C | 10C | 10C | 10C | 9C | 10C | 5C,9G | 10C | 5C,9G | 9C | 3C,7G |
| NUTSEDGE | 10C | 10C | 10C | 10C | 9C | 9C | 10C | 10C | 5C,9G | 5C,9G | 3G | 5C,8G | 6C,9G | 9C | 9C | 9C | 3C,8G | 5C,9G | 5C,9G | 4C,8G |

-continued

| | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| CRABGRASS | 4C,8G | 2C,5G | 5C,9G | 3G | 4C,8G | 5C,9G | 0 | 4G | 4C,8G | 0 | 0 | 3C,5H | 0 | 0 | 0 | 0 | 0 | 0 | 0 | 0 |
| BARNYARDGRASS | 9H | 4C,8H | 9C | 5C,9H | 9C | 9C | 4G | 0 | 3C,6G | 5C,9G | 0 | 0 | 3H | 0 | 0 | 0 | 0 | 0 | 0 | 0 |
| WILD OATS | 0 | 0 | 6G | 2G | 3C,8G | 5G | 0 | 0 | 0 | 3G | 0 | 0 | 0 | 0 | 0 | 0 | 0 | 0 | 0 | 0 |
| WHEAT | 0 | 0 | 6G | 2G | 8G | 9G | 0 | 0 | 2G | 2C,7G | 0 | 0 | 0 | 0 | 0 | 0 | 0 | 0 | 0 | 0 |
| CORN | 3C,6G | 3G | 5C,9G | 3C,9H | 10C | 9G | 0 | 0 | 3C,7H | 9C | 9C | 0 | 0 | 0 | 3G | 3C,8G | 0 | 0 | 0 | 0 |
| SOYBEANS | 4C,9G | 5C,9G | 9C | 5C,9G | 5C,9G | 5C,9G | 2C,7G | 2C,3H | 9C | 9C | 3C,5H | 5C,9G | 4C,9G | 4C,9G | 3C,8G | 3C,8G | 2C,8G | 2C,3H | 0 | 0 |
| RICE | 3C,8G | 3G | 4C,9G | 4C,9G | 5C,9G | 4C,9G | 0 | 0 | 5C,9G | 3G | 0 | 0 | 0 | 0 | 3C,6G | 3C,8G | 2G | 0 | 0 | 0 |
| SORGHUM | 3C,7G | 6G | 4C,9G | 4C,9G | 9C | 3C,7G | 0 | 5G | 4,9G | 5C,9G | 9C | 0 | 3G | 0 | 9C | 3C,7G | 2G | 0 | 0 | 0 |
| CHEATGRASS | 3C,7G | 5G | 9C | 8G | 5C,9G | 5G | 0 | 0 | 0 | 2G | 0 | 0 | 3G | 0 | 0 | 0 | 2G | 0 | 0 | 0 |
| SUGARBEETS | 10C | 10C | 10C | 10C | 10C | 9C | 10C | 3C,8G | 10C | 10C | 9C | 0 | 9C | 10C | 9C | 4C,9G | 3C,6G | 3C,7G | 7G | 3C,8G |
| VELVETLEAF | 10C | 10C | 10C | 10C | 10C | 9C | 3C,8G | 0 | 10C | 9C | 9C | 0 | 5C,9G | 3C,7G | 9C | 3C,8G | 3C,6G | 4C,8G | 5G | 4C,8G |
| GIANT FOXTAIL | 3C,6G | 2G | 5C,9G | 6G | 4C,8G | 5G | 5G | 0 | 3G | 2G | 0 | 0 | 2G | 0 | 3G | 0 | 2C,5G | 0 | 7G | 0 |
| BARLEY | 2C,4G | 0 | 8G | 7G | 9G | 9G | 0 | 0 | 5G | 0 | 2G | 0 | 0 | 0 | 3G | 0 | 0 | 0 | 5G | 0 |

PREEMERGENCE

| | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 9G | 6G | 9G | 8G | 9G | 9G | 9G | 5G | 9G | 9G | 8G | 2G | 2G | 0 | 2G | 0 | 0 | 0 | 0 | 0 |
| MORNINGGLORY | 9G | 5G | 9H | 6G | 9G | 9G | 9G | 2C,3H | 9G | 9G | 9G | 0 | 0 | 0 | 2G | 3G | 0 | 0 | 0 | 0 |
| COCKLEBUR | 7H | 2C,2G | 9H | 3C,6H | 9H | 9H | 7G | 3C,9G | 8H | 9H | 7H | 0 | 3C,5H | 0 | 3C,5H | 3C,5G | 0 | 1C | 0 | 0 |
| NUTSEDGE | 10E | 8G | 10E | 3G | 10E | 10C | 9G | 10C | 3G | 3G | 0 | 0 | 10E | 0 | 10C | 0 | 0 | 5G | 0 | 0 |
| CRABGRASS | 3C,8G | 0 | 3C,8G | 3C,6G | 8G | 3C,8G | 9G | 3C,8G | 10E | 2G | 0 | 0 | 0 | 2C | 0 | 0 | 0 | 0 | 0 | 0 |
| BARNYARDGRASS | 8H | 1C | 9H | 7H | 10H | 9H | 2G | 0 | 3C,8G | 5G | 0 | 0 | 0 | 0 | 0 | 0 | 0 | 0 | 0 | 0 |
| WILD OATS | 2G | 0 | 3C,7G | 2C,3G | 9H | 3C,7G | 3G | 0 | 5G | 3G | 3G | 0 | 0 | 0 | 0 | 0 | 0 | 0 | 0 | 0 |
| WHEAT | 2G | 0 | 8G | 8G | 3H | 0 | 0 | 0 | 0 | 2G | 0 | 0 | 0 | 0 | 0 | 0 | 0 | 0 | 0 | 0 |
| CORN | 3C,6G | 0 | 3C,9H | 3C,7G | 9G | 3C,9G | 0 | 0 | 3C,7G | 3C,7G | 3C,7G | 2G | 3C,6G | 3C,6G | 3C,6G | 2G | 0 | 2G | 0 | 0 |
| SOYBEANS | 4C,9H | 5G | 3C,9H | 3C,8G | 9H | 3C,8H | 3G | 5H | 9G | 9H | 3C,7H | 0 | 3C,3H | 3C,3H | 3C,3H | 3C,4H | 0 | 3C,4H | 0 | 2H |
| RICE | 8H | 0 | 8G | 3C,7G | 9G | 2C,6G | 4C,9H | 0 | 9G | 9H | 5G | 2C | 5G | 5G | 5G | 4G | 0 | 4G | 0 | 0 |
| SORGHUM | 8G | 0 | 3C,9H | 3C,8G | 10H | 3C,9H | 5H | 0 | 8G | 3C,4G | 3C,4G | 0 | 3C,5H | 0 | 3C,6G | 7G | 0 | 0 | 0 | 0 |
| CHEATGRASS | 4C,9G | 2G | 5C,8G | 8G | 9H | 9G | 3G | 4G | 0 | 55G | 3C,4G | 0 | 10E | 0 | 3C,6G | 0 | 0 | 3H | 5G | 1C |
| SUGARBEETS | 9G | 8G | 5C,9G | 4C,9G | 9G | 9G | 9C | 4G | 9G | 5C,9G | 5C,9G | 0 | 8G | 5G | 5G | 3H | 0 | 0 | 0 | 5G |
| VELVETLEAF | 4C,8G | 3G | 3C,8G | 7G | 5G | 8G | 9G | 5G | 5G | 5G | 4G | 0 | 4H | 4H | 4H | 0' | 0 | 0 | 0 | 0 |
| GIANT FOXTAIL | 3G | 0 | 3C,8G | 5G | 9G | 5G | 0 | 0 | 3C,5G | 4C,8G | 4C,8G | 2G | 0 | 0 | 2G | 0 | 0 | 2G | 3G | 0 |
| BARLEY | 3C,7G | 0 | 3C,9G | 3C,7G | 9G | 3C,8G | 3C,7G | 6G | 2G | 3G | 3G | 0 | 2G | 0 | 0 | 2G | 0 | 2G | 0 | 0 |

RATE=KG/HA

POSTEMERGENCE

| | CMPD 71 | | CMPD 72 | | CMPD 73 | | CMPD 74 | | CMPD 75 | | CMPD 76 | | CMPD 77 | | CMPD 78 | | CMPD 79 | | CMPD 80 | |
|---|---|---|---|---|---|---|---|---|---|---|---|---|---|---|---|---|---|---|---|---|
| | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| COTTON | 4C,9G | 4C,9G | 4C,9G | 5G | 9C | 3C,7G | 5G | 3C,7G | 0 | 0 | 0 | 0 | 0 | 0 | 7G | 0 | 0 | 0 | 9C | 9C |
| MORNINGGLORY | 5C,9G | 3C,7G | 4C,9G | 4C,8G | 5C,9G | 7G | 2C,3H | 4C,9H | 0 | 0 | 0 | 0 | 2G | 0 | 2C,3H | 0 | 10C | 10C | 5C,9G | 5C,9G |
| COCKLEBUR | 10C | 9C | 9C | 2C,6G | 9C | 10C | 3C,9G | 10C | 0 | 0 | 2C,5G | 0 | 3C,8H | 0 | 4C,8H | 0 | 10C | 10C | 5C,9G | 5C,9G |
| NUTSEDGE | 4C,8G | 0 | 9C | 0 | 4C,9G | 3C,8G | 10C | 10C | 0 | 0 | 0 | 0 | 0 | 0 | 0 | 0 | — | 0 | 8G | 1C |
| CRABGRASS | 0 | 0 | 0 | 0 | 3G | 0 | 3G | 3C,8G | 0 | 0 | 0 | 0 | 0 | 0 | 0 | 0 | 5C,9G | 3C,8G | 3C,8G | 3C,8G |
| BARNYARDGRASS | 0 | 0 | 0 | 0 | 3H | 0 | 3C,7G | 0 | 0 | 0 | 0 | 0 | 0 | 0 | 0 | 0 | 9C | 9C | 9C | 1C |
| WILD OATS | 0 | 0 | 0 | 0 | 0 | 0 | 0 | 0 | 0 | 0 | 0 | 0 | 0 | 0 | 0 | 0 | 3C,9G | 3C,9H | 3C,9H | 3C,9H |
| WHEAT | 2G | 0 | 0 | 0 | 0 | 0 | 0 | 0 | 0 | 0 | 0 | 0 | 0 | 0 | 0 | 0 | 5C,9G | 3C,8G | 3C,8G | 3C,8G |
| CORN | 4C,9G | 4C,9G | 5C,9G | 9G | 4C,9G | 7H | 3G | 4C,9H | 0 | 0 | 0 | 0 | 0 | 0 | 3H | 3G | 9C | 9C | 3C,7G | 9G |
| SOYBEANS | 0 | 0 | 0 | 0 | 4G | 3C,8H | 5H | 5H | 1H | 0 | 0 | 0 | 1H | 0 | 4G | 3C,4H | 4U,9G | 5C,9H | 5C,9H | 5G |
| RICE | 0 | 0 | 9C | 0 | 4G | 7H | 0 | 0 | 0 | 0 | 0 | 0 | 3G | 0 | 2C | 0 | 9C | 9C | 5C,9H | 3C,8G |
| SORGHUM | 0 | 0 | 4G | 0 | 4G | 3C,6G | 3G | 0 | 0 | 0 | 0 | 0 | 0 | 0 | 0 | 3H | 4C,9G | 10C | 10C | 9G |
| CHEATGRASS | 0 | 0 | 9C | 0 | 4G | 3C,7H | 3C,6G | 0 | 0 | 0 | 0 | 0 | 0 | 0 | 3C,7H | 6C,9G | 5C,9G | 10C | 2C,9G | 3C,8G |
| SUGARBEETS | 5C,9G | 5C,9G | 9C | 4C,8G | 10C | 3C,7H | 3C,9G | 3C,7G | 0 | 0 | 0 | 0 | 5H | 2G | 3C,7H | 0 | 9C | 10C | 5C,9G | 5C,9G |

| | 5C,9G | 3C,5G | 3C,8G | 7G | 9C 2C,4G | 3C,7G | 3C,7G | | | | | | | | | | | 9C 10C 9C | 10C 9C 5C,9G | 9C 9C 2C,9G | 4C,8H 4C,8G 7G |
|---|---|---|---|---|---|---|---|---|---|---|---|---|---|---|---|---|---|---|---|---|---|
| VELVETLEAF | 5C,9G | 0 | 0 | 0 | 9C | 0 | 0 | 0 | 0 | 0 | 0 | 0 | 0 | 0 | 0 | 0 | 0 | 9C | 10C | 9C | 4C,8H |
| GIANT FOXTAIL | 0 | 0 | 0 | 0 | 2C,4G | 0 | 0 | 0 | 0 | 0 | 0 | 0 | 0 | 0 | 0 | 0 | 0 | 10C | 9C | 9C | 4C,8G |
| BARLEY | 0 | 0 | 0 | 0 | 0 | 0 | 0 | 0 | 0 | 0 | 0 | 0 | 0 | 0 | 0 | 0 | 0 | 9C | 5C,9G | 2C,9G | 7G |

PREEMERGENCE

| | | | | | | | | | | | | | | | | | | | | | |
|---|---|---|---|---|---|---|---|---|---|---|---|---|---|---|---|---|---|---|---|---|---|
| COTTON | 6G | 0 | 0 | 0 | 0 | 0 | 0 | 0 | 0 | 0 | 0 | 0 | 0 | 0 | 0 | 0 | — | 9C | 3C,9G | 3C,8H | 8G |
| MORNINGGLORY | 3G | 0 | 0 | 2G | 3H | 0 | 0 | 0 | 0 | 0 | 0 | 0 | 0 | 0 | 0 | 0 | 0 | 10C | 9H | 5C,9G | 2C,5H |
| COCKLEBUR | 3C,5G | 3H | 6G | 0 | 5H | 1H | 0 | 0 | 0 | 0 | 0 | 0 | 0 | 0 | 0 | 0 | — | 9H | 8H | 9H | 2C,2H |
| NUTSEDGE | 0 | 0 | 2C | 0 | 5G | 0 | 0 | 0 | 0 | 0 | 0 | 0 | 0 | 0 | 0 | 0 | 0 | 10E | 10E | 9G | 0 |
| CRABGRASS | 0 | 0 | 0 | 0 | 0 | 0 | 0 | 0 | 0 | 0 | 0 | 0 | 0 | 0 | 0 | 0 | 0 | 3C,7G | 3C,7G | 8H | 3C,7G |
| BARNYARDGRASS | 0 | 0 | 0 | 0 | 2H | 0 | 0 | 0 | 0 | 0 | 0 | 0 | 0 | 0 | 0 | 0 | 0 | 9H | 3C,7G | 3C,7G | 2C,2G |
| WILD OATS | 0 | 0 | 0 | 0 | 2G | 0 | 0 | 0 | 0 | 0 | 0 | 0 | 0 | 0 | 0 | 0 | 0 | 4C,8G | 3C,7G | 3C,7G | 6G |
| WHEAT | 0 | 0 | 0 | 0 | 2G | 0 | 0 | 0 | 0 | 0 | 0 | 0 | 0 | 0 | 0 | 0 | 0 | 10H | 2C,8G | 2C,9G | 3G |
| CORN | 2G | 0 | 0 | 0 | 2C,7G | 0 | 0 | 0 | 0 | 0 | 0 | 0 | 0 | 0 | 0 | 0 | 0 | 10H | 2C,9G | 3C,7H | 3C,6H |
| SOYBEANS | 3C,6G | 3C,3H | 3C,7H | 0 | 3C,6H | 1C | 0 | 0 | 0 | 0 | 0 | 0 | 0 | 0 | 0 | 0 | 0 | 9H | 9H | 9H | 3G |
| RICE | 0 | 0 | 0 | 0 | 6G | 0 | 0 | 0 | 0 | 0 | 0 | 0 | 0 | 0 | 0 | 0 | 0 | 10E | 9G | 10H | 4G |
| SORGHUM | 0 | 0 | 0 | 0 | 3G | 2C | 0 | 0 | 0 | 0 | 0 | 0 | 0 | 0 | 0 | 0 | 0 | 5C,9G | 3C,9G | 5C,9G | 3C,7H |
| CHEATGRASS | 0 | 0 | 0 | 0 | 7G | 0 | 0 | 0 | 0 | 0 | 0 | 0 | 0 | 0 | 0 | 0 | 0 | 9H | 8G | 3C,8G | 7G |
| SUGARBEETS | 5C,9G | 4C,9G | 3C,8G | 3C,5H | 9G | 7G | 0 | 0 | 0 | 0 | 0 | 0 | 0 | 0 | 0 | 5G | 2H | 9G | 4C,9G | 5C,9G | 1C |
| VELVETLEAF | 2G | 0 | 0 | 0 | 7H | 1H | 0 | 0 | 0 | 0 | 0 | 0 | 0 | 0 | 0 | 0 | 0 | 4C,9G | 4C,9G | 3C,9H | 3G |
| GIANT FOXTAIL | 0 | 0 | 0 | 0 | 0 | 0 | 0 | 0 | 0 | 0 | 0 | 0 | 0 | 0 | 0 | 0 | 0 | 9H | 9H | 3C,7G | 3G |
| BARLEY | 0 | 0 | 0 | 0 | 2G | 0 | 0 | 0 | 0 | 0 | 0 | 0 | 0 | 0 | 0 | 0 | 0 | 9H | 9G | 3C,9G | 2C,5G |

| | CMPD 81 | | CMPD 82 | | CMPD 83 | | CMPD 84 | |
|---|---|---|---|---|---|---|---|---|
| RATE=KG/HA | 0.05 | 0.01 | 0.05 | 0.01 | 0.05 | 0.01 | 0.05 | 0.01 |

POSTEMERGENCE

| | | | | | | | | |
|---|---|---|---|---|---|---|---|---|
| COTTON | 5C,9G | 5C,9G | 5C,9G | 8H | 3C,9H | 4C,9G | 2C,3H | |
| MORNINGGLORY | 10C | 10C | 10C | 3C,8H | 10C | 4C,9G | 5C,9G | |
| COCKLEBUR | 5C,9H | 4C,9G | 9C | 3C,8H | 5C,9G | 4C,9G | 3C,7H | |
| NUTSEDGE | 6C,9G | 2C,9G | 10C | 0 | 2G | 0 | 4G | |
| CRABGRASS | 3C,7G | 3C,6G | 5C,8G | 3G | 5C,9G | 5C,9G | 2C,3G | |
| BARNYARDGRASS | 9C | 4C,9H | 3C,7G | 4C,8H | 3C,9G | 9C | 4C,9G | |
| WILD OATS | 6C,9G | 2C,8G | 4C,9G | 3G | 4C,9G | 5C,9G | 2C,3G | |
| WHEAT | 9G | 9G | 6G | 2C,9G | 3C,9G | 9C | 3C,7G | |
| CORN | 0 | 0 | 9G | 4U,9G | 3U,9G | 5C,9H | 9G | |
| SOYBEANS | 9C | 5C,9G | 0 | 5C,9G | 5C,9G | 9C | 4U,9G | |
| RICE | 9C | 5C,9G | 2C,7H | 9C | 3C,8H | 5C,9H | 4C,8G | |
| SORGHUM | 5C,9G | 3C,7G | 5C,9G | 8G | 5C,9G | 9C | 9C | |
| CHEATGRASS | 4C,9G | 4C,9H | 8G | 6C,9G | 4C,9G | 9C | 4C,9G | |
| SUGARBEETS | 9C | 10C | 4C,9H | 9C | 7G | 10C | 9C | |
| VELVETLEAF | 9C | 4C,9G | 2C,8G | 3C,7H | 3C,4H | 5C,9G | 2H | |
| GIANT FOXTAIL | 5C,9G | 3C,8G | 5C,9G | 3C,4H | 3C,8G | 6C,9G | 3C,8G | |
| BARLEY | 8G | 6G | 8G | 9G | 9G | 5C,9G | 8G | |

PREEMERGENCE

| | | | | | | | | |
|---|---|---|---|---|---|---|---|---|
| COTTON | 9G | 9G | 9G | 3G | 2C,3G | 0 | 0 | |
| MORNINGGLORY | 9H | 3C,4H | 2C,8H | 9G | 2C,6H | 0 | 4G | |
| COCKLEBUR | 9H | 3C,7H | 8H | 3C,3H | 2C,2H | 1C | 0 | |

-continued

| | | | | | | | | | |
|---|---|---|---|---|---|---|---|---|---|
| NUTSEDGE | 10E | 9G | 10E | 9G | 0 | 0 | 0 | 0 | |
| CRABGRASS | 9H | 5G | 8H | 0 | 3G | 3G | 3G | | |
| BARNYARDGRASS | 3C,8H | 1C | 9H | 2C,3G | 3C,7H | 3C,5G | 3C,5G | | |
| WILD OATS | 4C,7G | 3C,5G | 3C,5G | 1C | 7G | 0 | 3C,4G | | |
| WHEAT | 2C,9H | 6G | 8G | 0 | 7G | 0 | 0 | | |
| CORN | 2C,3G | 0 | 3G | 0 | 3C,9G | 2C,5G | 2C,9G | 2G | |
| SOYBEANS | 9H | 4C,7H | 4C,8H | 3C,6H | 4C,8H | 2C,5G | 3C,7H | 3G | |
| RICE | 10E | 3C,7G | 10E | 9H | 10E | 6G | 10H | | |
| SORGHUM | 5C,9G | 3C,8G | 4C,9G | 4C,9G | 3C,9G | 3C,8G | 4C,9G | 3C,9G | |
| CHEATGRASS | 9H | 3C,8H | 9H | 8G | 8G | 0 | 8G | 0 | |
| SUGARBEETS | 4C,9G | 3C,7H | 9G | 8G | 2C,4H | 0 | 2C,4G | 4G | |
| VELVETLEAF | 5C,9G | 3C,7H | 4C,9H | 3C,5H | 1C | 0 | 0 | 0 | |
| GIANT FOXTAIL | 9H | 2C,3G | 3C,8G | 3G | 2C,7G | 2G | 6G | 0 | |
| BARLEY | 4C,8G | 2G | 2C,9G | 2C,5G | 4C,8H | 3G | 2C,9G | 3G | |

Test B
Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*), and teaweed (*Sida spinosa*). The second pot was planted with green foxtail (*Setaria viridis*), cocklebur (*Xanthium pensylvanicum*), morningglory (*Ipomoea hederacea*), cotton (*Gossypium hirsutum*), johnsongrass (*Sorghum halepense*), barnyardgrass (*Echinochloa crus-galli*), corn (*Zea mays*), soybean (*Glycine max*), and giant foxtail (*Setaria faberi*). The third pot was planted with wheat (*Triticum aestivum*), barley (*Hordeum vulgare*), wild buckwheat (*Polygonum convolvulus*), cheatgrass (*Bromus secalinus*) or downy brome (*Bromus tectorum*), sugarbeet (*Beta vulgaris*), wild oat (*Avena fatua*), common chickweed (*Stellaria media*) or field violet (*Viola arvensis*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice, and teaweed. The second pot was planted with green foxtail, cocklebur, morningglory, cotton, johnsongrass, barnyardgrass, corn, soybean, and giant foxtail. The third pot was planted with wheat, barley, wild buckwheat, cheatgrass or downy brome, sugarbeet, wild oat, chickweed or field violet, blackgrass, and rape. The three pans were sprayed preemergence with the chemicals dissolved in a non-phytotoxic solvent.

Treated plants and controls were maintained in the greenhouse for approximately 24 days, then all rated plants were compared to controls and visually rated for plant response.

Response ratings are based on a scale of 0 to 100 where 0=no effect, and 100=complete control. A dash (−) response means no test.

Response ratings are contained in Table B.

TABLE B

POSTEMERGENCE

| RATE = G/HA | CMPD 1 | | | | CMPD 2 | | | | CMPD 3 | | | | CMPD 4 | | | | CMPD 5 | | | | CMPD 6 | | | | CMPD 7 | |
|---|---|---|---|---|---|---|---|---|---|---|---|---|---|---|---|---|---|---|---|---|---|---|---|---|---|---|
| | 62 | 16 | 4 | 1 | 62 | 16 | 4 | 1 | 62 | 16 | 4 | 1 | 62 | 16 | 4 | 1 | 62 | 16 | 4 | 1 | 250 | 62 | 16 | 4 | 250 | 62 |
| GIANT FOXTAIL | 30 | 0 | 0 | 0 | 100 | 100 | 100 | 50 | 100 | 80 | 80 | 60 | 100 | 100 | 60 | 30 | 100 | 100 | 60 | 0 | 100 | 100 | 90 | 40 | 50 | 30 |
| VELVETLEAF | 100 | 100 | 100 | 50 | 100 | — | 90 | 60 | 100 | 100 | 80 | — | 100 | 0 | — | — | 100 | 100 | 80 | 40 | 100 | 100 | — | 100 | 100 | 100 |
| SUGARBEETS | 100 | 100 | 100 | 100 | 100 | 100 | 100 | 0 | 100 | 100 | 100 | 0 | 100 | 0 | 20 | 0 | 100 | 100 | 20 | — | 100 | 60 | 0 | 0 | 100 | 100 |
| CRABGRASS | 30 | 0 | 0 | 0 | 50 | 20 | 0 | 30 | 20 | 0 | 0 | 0 | 0 | 40 | 80 | 30 | 20 | 60 | 20 | 30 | 10 | 60 | 40 | 30 | 30 | 20 |
| TEAWEED | 90 | 70 | 50 | 30 | 90 | 70 | 30 | 70 | 100 | 50 | 40 | 40 | 40 | 0 | 20 | 50 | 100 | 100 | 80 | 0 | 90 | 90 | 60 | 0 | 90 | 90 |
| JIMSONWEED | 100 | 100 | 30 | 50 | 100 | 100 | 100 | 50 | 100 | 80 | 50 | 10 | 100 | 100 | 100 | 10 | 100 | 100 | 100 | 40 | 100 | 100 | 100 | 40 | 100 | 100 |
| RICE | 60 | 50 | 30 | 0 | 90 | 50 | 90 | 30 | 80 | 40 | 50 | 50 | 40 | 40 | 50 | 50 | 0 | 0 | 0 | 0 | 100 | 90 | 80 | 40 | 100 | 100 |
| COCKLEBUR | 100 | 100 | 80 | 40 | 100 | 90 | 60 | 50 | 100 | 100 | 80 | 0 | 80 | 100 | 50 | 0 | 80 | 80 | 60 | 40 | 100 | 90 | 80 | 0 | 90 | 40 |
| COTTON | 100 | 100 | 80 | 30 | 100 | 90 | 60 | 50 | 100 | 90 | 80 | 30 | 50 | 20 | 20 | 0 | 100 | 100 | 80 | 20 | 100 | 90 | 100 | 20 | 100 | 100 |
| SOYBEANS | 100 | 100 | 50 | 100 | 100 | 100 | 100 | 50 | 100 | 70 | 100 | 100 | 30 | 100 | 20 | 50 | 90 | 90 | 40 | 0 | 40 | 20 | 0 | 0 | 90 | 70 |
| BARNYARDGRASS | 70 | 60 | 50 | 30 | 100 | 70 | 40 | 20 | 70 | 40 | 40 | 0 | 100 | 0 | 10 | 0 | 50 | 30 | 0 | — | 10 | 30 | — | — | 50 | 40 |
| WILD OATS | 0 | 0 | 0 | 0 | 80 | 70 | 40 | 40 | 30 | 0 | 0 | 0 | 50 | 40 | 40 | 0 | 0 | 20 | 10 | — | 10 | 0 | — | — | 0 | 0 |
| MORNINGGLORY | 100 | 100 | 50 | 50 | 100 | 100 | 100 | 50 | 100 | 70 | 50 | 60 | 100 | 100 | 70 | 50 | 100 | 100 | 40 | 30 | 100 | 100 | 60 | 30 | 100 | 100 |
| WHEAT | 30 | 0 | 0 | 0 | 100 | 70 | 40 | 40 | 70 | 40 | 40 | 20 | 30 | 0 | 20 | 0 | 30 | 0 | 0 | 0 | 0 | 30 | 0 | 10 | 0 | 0 |
| SICKLEPOD | 100 | 100 | 40 | 40 | 100 | 100 | 80 | 50 | 100 | 100 | 70 | 50 | 100 | 90 | 40 | — | 100 | 100 | 60 | 40 | 50 | 100 | 60 | 40 | 100 | 100 |
| JOHNSONGRASS | 70 | 60 | 50 | 20 | 70 | 80 | 60 | 50 | 80 | 70 | 50 | 60 | 20 | 0 | 20 | 0 | 30 | 20 | 20 | 0 | 100 | 30 | — | 0 | 60 | 40 |
| NUTSEDGE | 100 | 100 | 100 | 50 | 100 | 100 | 80 | 20 | 100 | 100 | 100 | 40 | 60 | 100 | 70 | 50 | 20 | 20 | 0 | 0 | 10 | — | 0 | 0 | 0 | 0 |
| CORN | 70 | 50 | 30 | 0 | 90 | — | 60 | 50 | 90 | 70 | 40 | 30 | 100 | — | 20 | — | 40 | 40 | 40 | 0 | 100 | 100 | 80 | 30 | 90 | 80 |
| WILD BUCKWHEAT | 100 | 100 | 80 | 40 | 100 | 100 | 100 | 60 | 100 | 90 | 100 | 50 | 40 | 100 | 100 | — | 20 | 90 | 60 | 10 | 50 | 100 | 100 | 10 | 100 | 100 |
| BLACKGRASS | 90 | 80 | 70 | 30 | 80 | 80 | 50 | 30 | 80 | 70 | 70 | 60 | 40 | 40 | 20 | — | 90 | 20 | 0 | 40 | 100 | 30 | 20 | 40 | 50 | 50 |
| RAPE | 100 | 100 | 100 | 100 | 100 | 100 | 100 | 20 | 100 | 100 | 100 | 70 | 50 | 20 | 10 | 0 | 0 | 0 | 0 | 0 | 50 | — | — | 30 | 90 | 90 |
| BARLEY | 50 | 30 | 0 | 0 | 80 | 70 | 50 | 20 | 70 | 40 | 40 | 40 | 40 | 50 | 20 | 0 | 20 | 20 | 0 | 0 | 100 | 100 | 100 | 10 | 10 | 0 |
| GREEN FOXTAIL | 50 | 50 | 30 | 0 | 90 | 70 | 70 | 20 | 100 | 70 | 40 | 40 | 40 | 40 | 10 | 0 | 0 | 0 | 0 | 0 | 50 | 0 | 0 | 40 | 80 | 50 |
| CHEATGRASS | 60 | 30 | 0 | 0 | 90 | 70 | 50 | 50 | 100 | 70 | 50 | 40 | 80 | — | — | — | 60 | 60 | 60 | 60 | 0 | 100 | 90 | 0 | 0 | 0 |
| LAMBSQUARTER | 30 | 0 | 0 | 0 | 100 | 100 | 100 | 50 | 100 | 90 | 70 | 40 | 100 | 100 | 70 | 70 | 100 | 100 | 100 | 70 | 100 | — | 100 | 100 | 100 | 100 |
| CHICKWEED | 100 | 70 | 50 | 50 | 100 | 100 | 50 | 0 | 100 | 80 | 70 | 40 | 100 | 20 | — | — | 90 | 80 | 70 | 30 | — | 100 | 90 | 60 | 100 | 90 |
| DOWNY BROME | 100 | 90 | 80 | 50 | 100 | 90 | 90 | 0 | 100 | 100 | 70 | 50 | 90 | 50 | 50 | 0 | 100 | 50 | 30 | 10 | | | | | 60 | 40 |

PREEMERGENCE

| RATE = G/HA | CMPD 1 | | | CMPD 2 | | | | CMPD 3 | | | | CMPD 4 | | | | CMPD 5 | | | | CMPD 6 | | | | CMPD 7 | |
|---|---|---|---|---|---|---|---|---|---|---|---|---|---|---|---|---|---|---|---|---|---|---|---|---|---|---|
| | 250 | 62 | 16 | 250 | 62 | 16 | 4 | 250 | 62 | 16 | 4 | 250 | 62 | 16 | 4 | 250 | 62 | 16 | 4 | 250 | 62 | 16 | 4 | 250 | 62 |
| GIANT FOXTAIL | 70 | 50 | 30 | 20 | — | 90 | 40 | 70 | 50 | 20 | 20 | 90 | 80 | 60 | 30 | 90 | 40 | 10 | 0 | 60 | 20 | 10 | 0 | 70 | 40 |
| VELVETLEAF | 100 | 90 | 80 | — | 100 | 100 | 70 | 100 | 70 | 50 | 40 | 100 | 80 | 80 | 70 | 100 | 100 | 80 | 40 | 100 | 100 | 60 | 40 | 100 | 90 |
| SUGARBEETS | 100 | 100 | 100 | 40 | 100 | 100 | 90 | 100 | 100 | 100 | 100 | 100 | 60 | 40 | 100 | 100 | 100 | 100 | 100 | 100 | 100 | 100 | 80 | 100 | 100 |
| CRABGRASS | 60 | 30 | 0 | 0 | 70 | 40 | 0 | 40 | 40 | 20 | 10 | 70 | 60 | 40 | 0 | 40 | 40 | 20 | 0 | 50 | 30 | 30 | 30 | 80 | 70 |
| TEAWEED | 90 | 80 | 60 | 40 | 90 | 70 | 30 | 90 | 70 | 50 | 70 | 80 | 60 | 70 | 30 | 80 | 80 | 50 | 40 | 80 | 70 | 60 | 40 | 80 | 80 |
| JIMSONWEED | 80 | 80 | 80 | 80 | 100 | — | 80 | 100 | 100 | 70 | 70 | 100 | 100 | 80 | 70 | 90 | 90 | 40 | 40 | 90 | 80 | 40 | 30 | 80 | 80 |
| RICE | 90 | 80 | 70 | 30 | 90 | 90 | 50 | 80 | 80 | 70 | 40 | 90 | 100 | 80 | 50 | 90 | 70 | 60 | 40 | 100 | 40 | 20 | 40 | 80 | 80 |
| COCKLEBUR | 100 | 80 | 70 | 40 | 100 | 70 | 50 | 90 | 70 | 60 | 60 | 90 | 100 | 50 | 40 | 90 | 70 | 40 | 30 | 100 | 80 | 40 | 50 | 100 | 80 |
| COTTON | 90 | 60 | 30 | 30 | 70 | 70 | 30 | 80 | 50 | 50 | 50 | 90 | 80 | 60 | 40 | 90 | 70 | 20 | 40 | 80 | 40 | 20 | 20 | 100 | 80 |
| SOYBEANS | 90 | 70 | 0 | 50 | 90 | 80 | 40 | 90 | 80 | 80 | 40 | 90 | 100 | 50 | 10 | 90 | 70 | 60 | 30 | 100 | 100 | 70 | 50 | 100 | 30 |
| BARNYARDGRASS | 100 | 90 | 70 | 40 | 100 | 100 | 90 | 70 | 70 | 50 | 40 | 80 | 80 | 40 | 20 | 80 | 80 | 80 | 40 | 100 | 100 | 70 | 50 | 100 | 90 |
| WILD OATS | 90 | 60 | 60 | 0 | 50 | 50 | 30 | 40 | 60 | 60 | 60 | 40 | 30 | 20 | 0 | 40 | 10 | 40 | 30 | 10 | 10 | 40 | 20 | 80 | 40 |
| MORNINGGLORY | 80 | 80 | 70 | 80 | 100 | 100 | 80 | 100 | 70 | 50 | 70 | 70 | 70 | 20 | 20 | 100 | 100 | 90 | 40 | 100 | 90 | 90 | 50 | 70 | 40 |
| WHEAT | 80 | 50 | 30 | 10 | 60 | 30 | 10 | 50 | 30 | 30 | 10 | 50 | 30 | 20 | 0 | 40 | 10 | 10 | 0 | 10 | 10 | 0 | — | 70 | 40 |
| SICKLEPOD | 100 | 70 | 50 | — | 80 | 80 | 80 | 100 | 80 | 80 | 60 | 100 | 90 | 70 | 50 | 100 | 90 | 90 | 60 | 100 | 80 | 50 | 30 | 100 | 70 |
| JOHNSONGRASS | 80 | 50 | 30 | 80 | 100 | 100 | 30 | 70 | 100 | 100 | 80 | 90 | 90 | 90 | 80 | 90 | 80 | 80 | 30 | 50 | 50 | 30 | 20 | 50 | 50 |
| NUTSEDGE | 100 | 100 | 70 | 10 | 100 | 50 | 30 | 80 | 50 | 30 | 10 | 100 | 100 | 90 | 10 | 100 | — | 40 | 70 | 90 | 40 | 40 | 30 | 100 | 50 |
| CORN | 60 | 30 | 30 | 20 | 100 | 100 | 40 | 100 | 50 | 30 | 50 | 100 | 60 | 90 | 40 | 100 | 50 | 30 | 10 | 100 | 100 | 30 | 10 | 100 | 100 |

TABLE B-continued

POSTEMERGENCE

| | CMPD 7 | | | | CMPD 8 | | | | CMPD 9 | | | | CMPD 11 | | | | CMPD 12 | | | | CMPD 13 | | | | CMPD 20 | | | |
|---|---|---|---|---|---|---|---|---|---|---|---|---|---|---|---|---|---|---|---|---|---|---|---|---|---|---|---|---|
| RATE = G/HA | 16 | 4 | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 | | |
| WILD BUCKWHEAT | 100 | 90 | 80 | 60 | 100 | 100 | 80 | 40 | 80 | 30 | 100 | 80 | 90 | 100 | 100 | 90 | 60 | 100 | 100 | 80 | 80 | 100 | 100 | 70 | 100 | 100 | | |
| BLACKGRASS | 100 | 90 | 70 | 50 | 100 | 90 | 40 | 10 | 90 | 10 | 80 | 90 | 80 | 90 | 50 | 20 | 40 | 90 | 50 | 20 | 20 | 70 | 0 | 0 | 70 | 70 | | |
| RAPE | 100 | 90 | 80 | 50 | 100 | 100 | 70 | 30 | 100 | 30 | 100 | 100 | 100 | 100 | 100 | 100 | 90 | 100 | 10 | 100 | 100 | 30 | 90 | 90 | 90 | | | |
| BARLEY | 70 | 50 | 30 | 0 | 70 | 70 | 40 | 30 | 70 | 30 | 80 | 60 | 40 | 80 | 20 | 0 | 40 | 40 | 20 | 0 | 20 | 0 | 20 | 30 | 30 | | | |
| GREEN FOXTAIL | 90 | 60 | 30 | 0 | 100 | 80 | 40 | 10 | 80 | 40 | 70 | 40 | 70 | 70 | 100 | 80 | 60 | 100 | 100 | 60 | 60 | 0 | 30 | 30 | 90 | | | |
| CHEATGRASS | 90 | 80 | 70 | 50 | 100 | 80 | 70 | 40 | 80 | 60 | 100 | 90 | 100 | 100 | 80 | 50 | 100 | 100 | 20 | 50 | 100 | 0 | 100 | 100 | | | | |
| LAMBSQUARTER | 100 | 90 | 80 | 70 | 100 | 100 | 100 | 60 | 100 | 90 | 100 | 100 | 100 | 100 | 100 | 100 | 100 | 100 | 100 | 100 | 100 | 80 | 100 | 100 | 100 | | | |
| CHICKWEED | 100 | 95 | 90 | 80 | 100 | 90 | 80 | 20 | 100 | 80 | 100 | 80 | 70 | 100 | 90 | 20 | 100 | 100 | 90 | 60 | 80 | 60 | 90 | 90 | 90 | | | |
| DOWNY BROME | 100 | 0 | 90 | 0 | 90 | 50 | 80 | 30 | 80 | 30 | 80 | 70 | 100 | - | 80 | 60 | 90 | 100 | 40 | 0 | 0 | 60 | 30 | 60 | 60 | | | |

| | CMPD 7 | | | | CMPD 8 | | | | CMPD 9 | | | | CMPD 11 | | | | CMPD 12 | | | | CMPD 13 | | | | CMPD 20 | | | |
|---|---|---|---|---|---|---|---|---|---|---|---|---|---|---|---|---|---|---|---|---|---|---|---|---|---|---|---|---|
| RATE = G/HA | 16 | 4 | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 | | |
| GIANT FOXTAIL | 20 | 0 | 90 | 40 | 20 | 20 | 70 | 50 | 40 | 30 | 70 | 40 | 0 | 10 | 0 | 0 | 0 | 0 | 0 | 20 | 0 | 0 | 100 | 80 | 80 | 10 | | |
| VELVETLEAF | 90 | 80 | 100 | 100 | 100 | 100 | 100 | 100 | 100 | 60 | 100 | 100 | 100 | 100 | 60 | 90 | 90 | 90 | 100 | 90 | 100 | 90 | 100 | 100 | 100 | 20 | | |
| SUGARBEETS | 100 | 100 | 100 | 100 | 100 | 100 | 100 | 100 | 100 | 80 | 100 | 100 | 80 | 50 | 90 | 100 | 100 | 100 | 100 | 100 | 100 | 100 | 0 | 0 | 0 | 80 | | |
| CRABGRASS | 0 | 0 | 70 | 40 | 70 | 30 | 50 | 50 | 50 | 0 | 60 | 20 | 40 | 50 | 0 | 30 | 20 | 40 | 10 | 0 | 0 | 60 | 80 | 40 | 80 | 0 | | |
| TEAWEED | 80 | 50 | 100 | 100 | 100 | 40 | 100 | 100 | 100 | 40 | 90 | 60 | 90 | 70 | 40 | 80 | 60 | 40 | 80 | 60 | 80 | 40 | 100 | 60 | 40 | 0 | | |
| JIMSONWEED | 90 | 90 | 100 | 100 | 100 | 70 | 100 | 100 | 100 | 80 | 100 | 100 | 100 | 100 | 70 | 100 | 100 | 100 | 100 | 100 | 100 | 80 | 100 | 100 | 100 | 40 | | |
| RICE | 50 | 10 | 50 | 40 | 30 | 10 | 50 | 80 | 40 | 30 | 30 | 50 | 10 | 20 | 30 | 10 | 60 | 70 | 50 | 0 | 40 | 0 | 40 | 40 | 30 | 0 | | |
| COCKLEBUR | 20 | 0 | 100 | 100 | 100 | 90 | 90 | 100 | 90 | 100 | 100 | 80 | 100 | 100 | 90 | 50 | 100 | 100 | 40 | 80 | 100 | 80 | 100 | 100 | 100 | 10 | | |
| COTTON | 80 | 70 | 100 | 100 | 100 | 30 | 100 | 100 | 100 | 60 | 100 | 100 | 60 | 50 | 20 | 50 | 20 | 40 | 20 | 0 | 0 | 0 | 50 | 40 | 30 | 80 | | |
| SOYBEANS | 100 | 90 | 100 | 100 | 100 | 90 | 100 | 100 | 100 | 60 | 70 | 60 | 100 | 100 | 60 | 100 | 100 | 100 | 100 | 100 | 100 | 80 | 100 | 100 | 100 | 20 | | |
| BARNYARDGRASS | 50 | 10 | 100 | 100 | 100 | 30 | 100 | 100 | 100 | 50 | 100 | 60 | 50 | 20 | 40 | 20 | 40 | 20 | 0 | 10 | 0 | 0 | 50 | 50 | 50 | 0 | | |
| WILD OATS | 30 | 20 | 70 | 50 | 30 | 0 | 70 | 50 | 50 | 0 | 50 | 10 | 30 | 30 | 10 | 100 | 30 | 20 | 30 | 0 | 0 | 0 | 10 | 0 | 0 | 20 | | |
| MORNINGGLORY | 90 | 85 | 100 | 100 | 40 | 40 | 100 | 100 | 100 | 90 | 100 | 100 | 100 | 100 | 100 | 100 | 100 | 100 | 100 | 100 | 100 | 100 | 100 | 90 | 100 | 40 | | |
| WHEAT | 0 | 0 | 50 | 30 | 0 | 0 | 60 | 30 | 0 | 0 | 0 | 0 | 20 | 20 | 30 | 0 | 0 | 0 | 10 | 0 | 0 | 0 | 40 | 40 | 40 | 0 | | |
| SICKLEPOD | 100 | 80 | 100 | 100 | 90 | 80 | 90 | 100 | 90 | 50 | 90 | 80 | 50 | 70 | 20 | 80 | 70 | 70 | 100 | 60 | 80 | 0 | 90 | 90 | 90 | 10 | | |
| JOHNSONGRASS | 30 | 0 | 90 | 80 | 100 | 40 | 100 | 100 | 100 | 20 | 100 | 80 | 50 | 30 | 80 | 30 | 50 | 30 | 80 | 20 | 20 | 0 | 50 | 40 | 60 | 20 | | |
| NUTSEDGE | 0 | 0 | 100 | 100 | 30 | 0 | 100 | 100 | 100 | 0 | 100 | 100 | 20 | 30 | 0 | 100 | 80 | 0 | 90 | 0 | 90 | 60 | 60 | 50 | 50 | 20 | | |
| CORN | 80 | 40 | 50 | 40 | 100 | 90 | 100 | 100 | 100 | 60 | 100 | 70 | 100 | 100 | 40 | 100 | 100 | 50 | 100 | 20 | 100 | 0 | 100 | 50 | 70 | 30 | | |
| WILD BUCKWHEAT | 100 | 100 | 100 | 100 | 100 | 100 | 100 | 90 | 100 | 90 | 100 | 100 | 100 | 100 | 100 | 100 | 100 | 100 | 100 | 90 | 100 | 80 | 100 | 70 | 40 | 20 | | |
| BLACKGRASS | 30 | 20 | 100 | 100 | 30 | 30 | 90 | 80 | 50 | 50 | 60 | 30 | 40 | 50 | 30 | 20 | 40 | 40 | 30 | 20 | 20 | 60 | 30 | 40 | 50 | 0 | | |
| RAPE | 50 | 30 | 100 | 100 | 100 | 80 | 100 | 100 | 100 | 60 | 100 | 100 | 100 | 100 | 100 | 100 | 100 | 100 | 100 | 100 | 100 | 100 | 80 | 50 | 70 | 70 | | |
| BARLEY | 0 | 0 | 30 | 0 | 50 | 30 | 60 | 30 | 30 | 20 | 30 | 0 | 20 | 20 | 10 | 30 | 30 | 0 | 30 | 80 | 0 | 60 | 30 | 70 | 40 | 10 | | |
| GREEN FOXTAIL | 20 | 0 | 100 | 80 | 100 | 30 | 100 | 100 | 100 | 20 | 90 | 100 | 40 | 40 | 0 | 100 | 100 | 10 | 80 | 0 | 60 | 80 | 70 | 70 | 60 | 40 | | |
| CHEATGRASS | 100 | 100 | 100 | 100 | 80 | 80 | 100 | 100 | 100 | 50 | 100 | 100 | 100 | 40 | 40 | 100 | 60 | 60 | 100 | 30 | 60 | 100 | 30 | 30 | 30 | - | | |
| LAMBSQUARTER | 80 | 60 | 100 | 100 | 90 | 50 | 100 | 100 | 100 | 50 | 100 | 100 | 90 | 30 | 30 | 80 | 100 | 60 | 100 | 80 | 80 | 70 | 90 | 60 | 60 | 0 | | |
| CHICKWEED | 20 | 0 | 90 | 70 | 60 | 30 | 100 | 70 | 100 | 30 | 100 | 100 | 50 | 30 | 0 | 100 | 100 | 100 | 100 | 0 | 0 | 100 | 100 | 80 | 80 | 40 | | |
| DOWNY BROME | | | | | | | | | | | | | | | | | | | | | | | | | | | | |

PREEMERGENCE

| | CMPD 7 | | CMPD 8 | | CMPD 9 | | CMPD 11 | | CMPD 12 | | CMPD 13 | | CMPD 20 | |
|---|---|---|---|---|---|---|---|---|---|---|---|---|---|---|
| RATE = G/HA | 250 | 62 | 250 | 62 | 250 | 62 | 250 | 62 | 250 | 62 | 250 | 62 | 250 | 62 |
| GIANT FOXTAIL | 90 | 80 | 90 | 70 | 80 | 70 | 80 | 70 | 50 | 20 | 50 | 0 | 80 | 40 |
| VELVETLEAF | 90 | 70 | 100 | 100 | 90 | 70 | 70 | 50 | 100 | 90 | 100 | 90 | 100 | 100 |
| SUGARBEETS | 100 | 100 | 100 | 100 | 100 | 100 | 100 | 100 | 100 | 100 | 100 | 100 | 100 | 100 |
| CRABGRASS | 70 | 50 | 70 | 50 | 60 | 30 | 30 | 0 | 30 | 0 | 20 | 0 | 50 | 30 |
| TEAWEED | 90 | 60 | 90 | 70 | 90 | 80 | 80 | 50 | 100 | 80 | 100 | 90 | 90 | 80 |
| JIMSONWEED | 100 | 80 | 100 | 100 | 100 | 90 | 70 | 60 | 100 | 90 | 100 | 90 | 100 | 80 |
| RICE | 70 | 60 | 70 | 60 | 90 | 60 | 60 | 50 | 80 | 50 | 70 | 10 | 70 | 70 |
| COCKLEBUR | 100 | 90 | 100 | 100 | 100 | 70 | 90 | 80 | 100 | 100 | 100 | 80 | 90 | 80 |

TABLE B-continued

|  | CMPD 23 | | | CMPD 25 | | | CMPD 26 | | | CMPD 27 | | | CMPD 28 | | | CMPD 29 | | | CMPD 30 | | |
|---|---|---|---|---|---|---|---|---|---|---|---|---|---|---|---|---|---|---|---|---|---|
| RATE = G/HA | 62 | 16 | 4 | 62 | 16 | 4 | 62 | 16 | 4 | 62 | 16 | 4 | 62 | 16 | 4 | 62 | 16 | 4 | 62 | 16 | 4 |
| COTTON | 80 | | | 30 | 0 | | 0 | 0 | 40 | | | | | | | 70 | 60 | 50 | 40 | | |
| SOYBEANS | 70 | | | 60 | 30 | | 50 | 30 | 80 | | | | | | | 80 | 70 | 80 | 20 | | |
| BARNYARDGRASS | 70 | | | 50 | 0 | | 30 | 50 | 70 | | | | | | | 100 | 100 | 50 | 30 | | |
| WILD OATS | 30 | | | 30 | 30 | | 70 | 60 | 50 | | | | | | | 20 | 0 | 0 | 0 | | |
| MORNINGGLORY | 100 | | | 60 | 0 | | 30 | 0 | 80 | | | | | | | 100 | 90 | 90 | 50 | | |
| WHEAT | 0 | | | 20 | 30 | | 30 | 60 | 50 | | | | | | | 70 | 40 | 40 | 0 | | |
| SICKLEPOD | — | | | 70 | 50 | | 50 | 30 | 70 | | | | | | | 100 | 100 | 90 | 30 | | |
| JOHNSONGRASS | 30 | | | 30 | 0 | | 30 | 50 | 70 | | | | | | | 100 | 100 | 70 | 80 | | |
| NUTSEDGE | | | | 100 | 30 | | 50 | 30 | 90 | | | | | | | 90 | 70 | 70 | 60 | | |
| CORN | 60 | | | 0 | 0 | | 70 | 50 | 90 | | | | | | | 80 | 80 | 80 | 10 | | |
| WILD BUCKWHEAT | 100 | | | 60 | 70 | | 70 | 100 | 90 | | | | | | | 100 | 100 | 80 | 40 | | |
| BLACKGRASS | 40 | | | 100 | 50 | | 50 | 60 | 90 | | | | | | | 90 | 90 | 90 | 20 | | |
| RAPE | 60 | | | 20 | 90 | | 95 | 90 | 100 | | | | | | | 100 | 100 | 100 | 40 | | |
| BARLEY | 60 | | | 100 | 30 | | 20 | 30 | 40 | | | | | | | 50 | 30 | 30 | 20 | | |
| GREEN FOXTAIL | 10 | | | 60 | 30 | | 60 | 80 | 90 | | | | | | | 90 | 80 | 80 | 40 | | |
| CHEATGRASS | 40 | | | 100 | 30 | | 100 | 100 | | | | | | | | | | | | | |
| LAMBSQUARTER | 90 | | | 80 | 60 | | 80 | 60 | 90 | | | | | | | 90 | 90 | 70 | 40 | | |
| CHICKWEED | 60 | | | 90 | 30 | | 85 | 90 | 100 | | | | | | | 100 | 100 | 100 | 90 | | |
| DOWNY BROME | 30 | | | 50 | 30 | | 30 | 0 | 60 | | | | | | | 100 | 100 | 100 | 60 | | |

POSTEMERGENCE

| | CMPD 23 | | | CMPD 25 | | | CMPD 26 | | | CMPD 27 | | | CMPD 28 | | | CMPD 29 | | | CMPD 30 | | |
|---|---|---|---|---|---|---|---|---|---|---|---|---|---|---|---|---|---|---|---|---|---|
| | 62 | 16 | 4 | 62 | 16 | 4 | 62 | 16 | 4 | 62 | 16 | 4 | 62 | 16 | 4 | 62 | 16 | 4 | 62 | 16 | 4 |
| GIANT FOXTAIL | 90 | 40 | 30 | 30 | 0 | 0 | 100 | 100 | 50 | 70 | 90 | 70 | 100 | 90 | 40 | 100 | 100 | 40 | 100 | 100 | 40 |
| VELVETLEAF | 100 | 90 | 70 | 100 | 90 | 60 | 100 | 90 | 80 | 50 | 100 | — | 100 | 90 | 80 | — | — | 60 | 100 | 100 | 60 |
| SUGARBEETS | 20 | 0 | 0 | 100 | 100 | 100 | 60 | 30 | 20 | 70 | 60 | 20 | 40 | 30 | 20 | 20 | 80 | 20 | 0 | 0 | 20 |
| CRABGRASS | 10 | 0 | — | 30 | 0 | 0 | 100 | 80 | 80 | 30 | 100 | 40 | 90 | 80 | 70 | 90 | 90 | 30 | 60 | 80 | 0 |
| TEAWEED | 90 | 70 | 30 | 100 | 50 | 50 | 80 | 70 | 80 | 40 | 100 | 70 | 100 | 100 | 80 | 90 | 90 | 40 | 80 | 100 | 80 |
| JIMSONWEED | 70 | 10 | 10 | 80 | 90 | 30 | 70 | 80 | 70 | 70 | 80 | 70 | 80 | 50 | 20 | 70 | 70 | 20 | 80 | 100 | 80 |
| RICE | 40 | 80 | 20 | 60 | 60 | 50 | 40 | 40 | 40 | 50 | 90 | 40 | 40 | 100 | 30 | 100 | 100 | 80 | 100 | 100 | 10 |
| COCKLEBUR | 30 | 20 | 20 | 80 | 80 | 30 | 100 | 100 | 80 | 50 | 60 | 50 | 20 | 70 | — | 100 | 90 | 0 | 100 | 100 | 20 |
| COTTON | 90 | 90 | 20 | 100 | 100 | 50 | 100 | 80 | 50 | 100 | 80 | 100 | 70 | 50 | 30 | 100 | 100 | 80 | 100 | 100 | 80 |
| SOYBEANS | 90 | 80 | 0 | 90 | 50 | 30 | 80 | 70 | 80 | 80 | 100 | 80 | 50 | 70 | 20 | 100 | 100 | 0 | 100 | 100 | 10 |
| BARNYARDGRASS | 70 | 60 | 40 | 70 | 50 | 0 | 80 | 40 | 40 | 70 | 80 | 50 | 100 | 50 | 10 | 90 | 70 | 40 | 90 | 30 | 20 |
| WILD OATS | 100 | 70 | 30 | 50 | 100 | 40 | 100 | 70 | 30 | 100 | 100 | 60 | — | 100 | 10 | 80 | 100 | 0 | 40 | 100 | 0 |
| MORNINGGLORY | 50 | 30 | 30 | 40 | 20 | 30 | 70 | 100 | 30 | 100 | 90 | 70 | 30 | 30 | 70 | 10 | 20 | 40 | 100 | 100 | 20 |
| WHEAT | 30 | — | — | 100 | 60 | 20 | — | 100 | 80 | 40 | 90 | — | — | — | 30 | 100 | 80 | 20 | 20 | 100 | 0 |
| SICKLEPOD | 100 | 40 | 0 | 70 | 50 | 0 | 100 | 70 | 50 | 100 | 90 | 80 | 100 | 70 | 30 | 100 | 60 | 0 | 100 | 100 | 80 |
| JOHNSONGRASS | 30 | 30 | 20 | 100 | 100 | 30 | 80 | 80 | 50 | 60 | 60 | 0 | 30 | 50 | 20 | 20 | 30 | — | 40 | 30 | 10 |
| NUTSEDGE | 30 | 30 | 30 | 70 | 60 | 60 | 100 | 40 | 70 | 100 | 80 | 60 | 100 | 100 | 30 | 50 | 100 | 0 | 100 | 100 | 0 |
| CORN | 100 | 70 | 40 | 100 | 70 | 100 | 100 | — | 0 | 90 | 90 | 80 | 90 | 100 | 20 | 10 | 70 | — | 40 | 20 | 0 |
| WILD BUCKWHEAT | 80 | 60 | 0 | 70 | 80 | 0 | 70 | 100 | 70 | 80 | 90 | 80 | 40 | 30 | 40 | 10 | 0 | — | 30 | 40 | 0 |
| BLACKGRASS | 70 | 30 | 0 | 100 | 30 | 50 | 50 | 50 | 50 | 70 | 70 | 90 | 90 | 80 | 90 | 50 | 50 | 20 | 40 | 30 | 0 |
| RAPE | 100 | 90 | 40 | 100 | 100 | 100 | 90 | 90 | 60 | 100 | 100 | 80 | 100 | 100 | 0 | 100 | 70 | 20 | 100 | 100 | 90 |
| BARLEY | 40 | 30 | 10 | 50 | 30 | 0 | 80 | 70 | — | 80 | 70 | 40 | 20 | 10 | 0 | 70 | 10 | 70 | 40 | 30 | 20 |
| GREEN FOXTAIL | 20 | 0 | 0 | 90 | 20 | 30 | 90 | 80 | 50 | 90 | 90 | 50 | 40 | 80 | 0 | 50 | 50 | 0 | 100 | 100 | 0 |
| CHEATGRASS | 80 | 40 | 0 | 50 | 30 | 0 | 100 | 100 | 70 | 70 | 60 | 0 | 30 | 10 | 0 | 100 | 30 | 0 | 20 | 10 | 0 |
| LAMBSQUARTER | 100 | 100 | 0 | 90 | 80 | 60 | 90 | 80 | 50 | 90 | 100 | 70 | 100 | 100 | — | 90 | 80 | 80 | 100 | 100 | 0 |
| CHICKWEED | 70 | 60 | 0 | 100 | 90 | 50 | 90 | 50 | — | 40 | 70 | 20 | 100 | 100 | — | 100 | 100 | 30 | 100 | 100 | 100 |

| RATE = G/HA | CMPD 23 | | | CMPD 25 | | | CMPD 26 | | | CMPD 27 | | | CMPD 28 | | | CMPD 29 | | | CMPD 30 | |
|---|---|---|---|---|---|---|---|---|---|---|---|---|---|---|---|---|---|---|---|---|
| | 250 | 62 | 16 | 4 | 16 | 62 | 1 | 4 | 16 | 62 | 1 | 4 | 16 | 62 | 1 | 4 | 16 | 62 | 250 | 62 |
| PREEMERGENCE | | | | | | | | | | | | | | | | | | | | |
| GIANT FOXTAIL | 100 | 80 | 30 | 0 | 60 | 100 | 0 | 80 | 90 | 100 | 20 | 60 | 90 | 100 | 30 | 70 | 20 | 70 | 40 | 20 |
| VELVETLEAF | 100 | 80 | 60 | 40 | 60 | 100 | 0 | — | 80 | 100 | 20 | 60 | 90 | 100 | 30 | 80 | 90 | 100 | 100 | 100 |
| SUGARBEETS | 100 | 90 | 70 | 50 | 100 | 100 | 70 | 90 | 90 | 100 | 70 | 70 | 90 | 100 | 70 | 90 | 100 | 100 | 100 | 100 |
| CRABGRASS | 90 | 80 | 30 | 0 | 30 | 60 | 0 | 50 | 50 | 100 | 0 | 20 | 60 | 80 | 0 | 30 | 30 | 60 | 70 | 20 |
| TEAWEED | 50 | — | — | — | 30 | 60 | 0 | 80 | 80 | 90 | 0 | 30 | 70 | 80 | — | 50 | 20 | 80 | 80 | 100 |
| JIMSONWEED | 90 | — | 40 | 30 | 60 | 80 | 30 | 70 | 90 | 100 | 40 | 50 | 90 | 100 | 40 | 70 | 60 | 90 | 100 | 20 |
| RICE | 100 | 100 | 90 | 40 | 50 | 90 | 0 | 70 | 90 | 100 | 60 | 20 | 70 | 90 | 60 | 0 | 10 | 80 | 90 | 80 |
| COCKLEBUR | 80 | 60 | 40 | 0 | 0 | 0 | 30 | 50 | 80 | 90 | 40 | 50 | 70 | 80 | 40 | 60 | 80 | 80 | 90 | 10 |
| COTTON | 90 | 80 | 60 | 20 | 50 | 60 | 0 | 70 | 60 | 100 | 0 | 20 | 50 | 100 | 20 | 0 | 10 | 10 | 50 | 80 |
| SOYBEANS | 90 | 80 | 30 | 0 | 30 | 0 | 0 | 50 | 70 | 90 | 20 | 40 | 70 | 100 | 20 | 60 | 80 | 80 | 90 | 100 |
| BARNYARDGRASS | 100 | 50 | 20 | 0 | 20 | 60 | 0 | 50 | 50 | 80 | 20 | 40 | 70 | 100 | 20 | 60 | 70 | 70 | 100 | 80 |
| WILD OATS | 60 | 20 | 10 | 0 | 30 | 90 | 30 | 20 | 70 | 90 | 40 | 0 | 100 | 100 | 30 | 30 | 0 | 70 | 90 | 0 |
| MORNINGGLORY | 100 | 70 | 60 | 30 | 50 | 90 | 0 | 90 | 60 | 100 | 0 | 40 | 90 | 100 | 0 | 40 | 0 | 0 | 30 | 0 |
| WHEAT | 70 | 30 | 20 | 10 | 0 | 0 | 0 | 30 | 40 | 80 | 10 | 0 | 0 | 100 | — | 0 | 90 | 100 | 100 | 100 |
| SICKLEPOD | 80 | — | — | — | 30 | 40 | 30 | 20 | 50 | 100 | 10 | 60 | 100 | 100 | — | 90 | 0 | 0 | 10 | 0 |
| JOHNSONGRASS | 100 | 100 | 90 | 30 | 50 | 100 | 30 | — | 90 | 100 | 20 | 0 | 100 | 100 | — | 0 | 90 | — | 100 | 100 |
| NUTSEDGE | 80 | 70 | 70 | — | 50 | 70 | 30 | 60 | 50 | 80 | 10 | 20 | 70 | 70 | 50 | 20 | — | 40 | 70 | — |
| CORN | 50 | 30 | — | 30 | 30 | 0 | 30 | 40 | 80 | 80 | 20 | 40 | 90 | 100 | 40 | 50 | 20 | 20 | 30 | 20 |
| WILD BUCKWHEAT | 100 | 100 | 60 | 30 | 50 | 90 | 30 | 80 | 80 | 100 | 10 | 20 | 100 | 100 | 40 | 100 | 90 | 90 | 100 | 100 |
| BLACKGRASS | 100 | 100 | 20 | 0 | 50 | 90 | 30 | 30 | 70 | 90 | 10 | 10 | 50 | 100 | 40 | 80 | 70 | 70 | 100 | 40 |
| RAPE | 100 | 100 | 30 | 0 | 70 | 90 | 0 | — | 80 | 100 | 30 | 50 | 80 | — | 0 | 50 | 40 | 100 | 100 | 100 |
| BARLEY | 70 | 50 | 30 | 20 | 30 | 60 | 0 | 40 | 100 | 70 | 20 | 20 | 90 | 100 | 20 | 40 | 0 | 20 | 40 | 40 |
| GREEN FOXTAIL | 100 | 80 | 30 | 0 | 50 | 70 | 30 | 70 | 80 | 100 | 60 | 40 | 60 | 50 | 40 | 40 | 0 | 70 | 40 | 10 |
| CHEATGRASS | 50 | 50 | 10 | 0 | 30 | 0 | 0 | 20 | 80 | 90 | 20 | 20 | 50 | 40 | 20 | 0 | 30 | 60 | 40 | 10 |
| LAMBSQUARTER | 100 | 100 | 90 | 40 | 50 | 100 | 30 | 90 | 90 | 100 | 60 | 60 | 90 | 100 | 60 | 70 | 80 | 100 | 100 | 100 |
| CHICKWEED | 90 | 70 | 40 | 0 | 90 | 100 | 50 | 100 | 100 | 100 | 40 | 90 | 100 | 100 | 30 | 70 | 80 | 100 | 100 | 90 |

| RATE = G/HA | CMPD 30 | CMPD 31 | | CMPD 32 | | | CMPD 34 | | | CMPD 35 | | | CMPD 36 | | | CMPD 37 | | |
|---|---|---|---|---|---|---|---|---|---|---|---|---|---|---|---|---|---|---|
| | 4 | 1 | 62 | 16 | 62 | 16 | 1 | 62 | 16 | 4 | 1 | 62 | 16 | 4 | 62 | 16 | 4 | 16 | 4 | 1 |
| POSTEMERGENCE | | | | | | | | | | | | | | | | | | | |
| GIANT FOXTAIL | 70 | 40 | 30 | 0 | 30 | 0 | 0 | 30 | 0 | 0 | 50 | 20 | 0 | 0 | 20 | 70 | 0 | 60 | 20 |
| VELVETLEAF | 90 | 60 | 70 | 60 | 100 | 90 | 30 | 100 | 60 | 90 | 100 | 100 | 95 | 80 | 100 | 100 | 50 | 90 | 50 |
| SUGARBEETS | 0 | 0 | 100 | 70 | 90 | 30 | 90 | 100 | 80 | 80 | 100 | 90 | 100 | 80 | 100 | 100 | 70 | 100 | 90 |
| CRABGRASS | 90 | 60 | 0 | 0 | 40 | 30 | 30 | 50 | 30 | 50 | 50 | 30 | 80 | 0 | 70 | 60 | 20 | 20 | 0 |
| TEAWEED | 40 | 10 | 70 | 0 | 90 | 60 | 50 | 70 | 0 | 0 | 100 | 70 | 100 | 70 | 100 | 100 | 20 | 80 | 0 |
| JIMSONWEED | 50 | 20 | 50 | 30 | 80 | 70 | 70 | 90 | 30 | 20 | 90 | 50 | 100 | 0 | 100 | 100 | 80 | 80 | 60 |
| RICE | 0 | 0 | 90 | 60 | 90 | 50 | 50 | 70 | 50 | 0 | 80 | 30 | 90 | 70 | 80 | 100 | 40 | 70 | 40 |
| COCKLEBUR | 50 | 30 | 60 | 0 | 80 | 80 | 50 | 100 | 30 | 0 | 100 | 70 | 90 | 0 | 100 | 100 | 70 | 80 | 20 |
| COTTON | 50 | 30 | 40 | 0 | 70 | 40 | 70 | 70 | 60 | 30 | 80 | 50 | 90 | 30 | 90 | 100 | 70 | 70 | 30 |
| SOYBEANS | 100 | 80 | 80 | 50 | 80 | 40 | 100 | 100 | 30 | 30 | 100 | 100 | 100 | 80 | 100 | 100 | 80 | 100 | 20 |
| BARNYARDGRASS | 0 | 0 | 60 | 30 | 30 | 30 | 30 | 50 | 20 | 0 | 20 | 20 | 20 | 0 | 20 | 100 | 40 | 70 | 30 |
| WILD OATS | 80 | 30 | 30 | 0 | 70 | 40 | 70 | 100 | 50 | 0 | 100 | 90 | 100 | 85 | 100 | 100 | 90 | 100 | 90 |
| MORNINGGLORY | 0 | 0 | 80 | 30 | 100 | 90 | 30 | 80 | 20 | 0 | 90 | 40 | 100 | 0 | 100 | 100 | 40 | 70 | 0 |
| WHEAT | 10 | 10 | 100 | 50 | 50 | 30 | 90 | 90 | 10 | 0 | 100 | 50 | 100 | 30 | 100 | 100 | 90 | 100 | 50 |
| SICKLEPOD | — | — | 50 | 30 | 50 | 30 | 50 | 70 | 50 | 30 | 50 | 30 | 60 | 0 | 80 | 100 | 50 | 90 | 80 |
| JOHNSONGRASS | 0 | 0 | 90 | 30 | 80 | 50 | 90 | 100 | 40 | 0 | 100 | 30 | 100 | 70 | 100 | 100 | 80 | 90 | 30 |
| NUTSEDGE | 20 | 0 | 50 | 0 | 80 | 40 | 20 | 50 | 10 | 20 | 0 | 10 | 60 | 0 | 80 | 100 | 50 | 50 | 60 |
| CORN | 10 | 0 | 0 | 0 | 90 | 0 | 70 | 100 | 30 | 20 | 100 | 30 | 100 | 80 | 100 | 100 | 90 | 90 | 0 |
| WILD BUCKWHEAT | — | 50 | 100 | 100 | 90 | 80 | 40 | 100 | 80 | 80 | 100 | 100 | 100 | 0 | 100 | 100 | 80 | 90 | 80 |

-continued

|  | CMPD 30 | | CMPD 31 | | | CMPD 32 | | | CMPD 34 | | | CMPD 35 | | | CMPD 36 | | | CMPD 37 | |
|---|---|---|---|---|---|---|---|---|---|---|---|---|---|---|---|---|---|---|---|
| RATE = G/HA | 16 | 4 | 62 | 16 | 4 | 62 | 16 | 4 | 250 | 62 | 16 | 4 | 250 | 62 | 16 | 4 | 62 | 16 | 4 |
| BLACKGRASS | 0 | 0 | 90 | 100 | 50 | 100 | 80 | 40 | 70 | 50 | 30 | 0 | 70 | 50 | 30 | 20 | 70 | 40 | 50 |
| RAPE | 80 | 70 | 100 | 100 | 100 | 100 | 100 | 90 | 100 | 100 | 100 | 100 | 100 | 100 | 100 | 100 | 100 | 90 | 70 |
| BARLEY | 0 | 0 | 30 | 40 | 0 | 40 | 0 | 0 | 50 | 30 | 0 | 0 | 0 | 0 | 0 | 0 | 70 | 40 | 0 |
| GREEN FOXTAIL | 0 | 0 | 20 | 50 | 0 | 50 | 30 | 0 | 50 | 30 | 0 | 0 | 0 | 0 | 10 | 0 | 100 | 80 | 20 |
| CHEATGRASS | 0 | 0 | 30 | 100 | 0 | 70 | 50 | 40 | 70 | 80 | 60 | 30 | 90 | 70 | 100 | 40 | 90 | 80 | 50 |
| LAMBSQUARTER | 70 | 50 | 100 | 100 | 50 | 100 | 100 | 50 | 100 | 80 | 50 | 0 | 90 | 100 | 100 | 100 | 100 | 80 | 70 |
| CHICKWEED | 90 | | 100 | 100 | 50 | 100 | 100 | 100 | 80 | 50 | 30 | 0 | 100 | 100 | 100 | 0 | 90 | 80 | 30 |
| DOWNY BROME | | | 70 | 30 | 0 | 70 | 30 | 0 | 70 | 80 | 0 | 60 | 30 | 0 | 0 | 0 | 80 | 0 | 0 |

PREEMERGENCE

|  | CMPD 38 | | CMPD 39 | | | | CMPD 40 | | | CMPD 41 | | | CMPD 42 | | | CMPD 43 | | |
|---|---|---|---|---|---|---|---|---|---|---|---|---|---|---|---|---|---|---|
| RATE = G/HA | 4 | 1 | 62 | 16 | 4 | 1 | 250 | 62 | 16 | 4 | 250 | 62 | 16 | 4 | 250 | 62 | 16 | 4 |
| GIANT FOXTAIL | 70 | 0 | 30 | 0 | 0 | 0 | 50 | 30 | 0 | 0 | 50 | 30 | 40 | 0 | 100 | 100 | 20 | 20 |
| VELVETLEAF | 90 | 40 | 70 | 70 | 50 | 50 | 100 | 100 | 80 | 60 | 100 | 70 | 100 | 90 | 100 | 100 | 20 | 20 |
| SUGARBEETS | 70 | 60 | 70 | 70 | 50 | 70 | 50 | 30 | 0 | 0 | 100 | 100 | 40 | 100 | 100 | 100 | 90 | 90 |
| CRABGRASS | 70 | 0 | 70 | 0 | 0 | 0 | 50 | 30 | 0 | 0 | 90 | 30 | 20 | 0 | 100 | 100 | 40 | 0 |
| TEAWEED | 50 | 20 | 50 | 50 | 0 | 50 | 90 | 80 | 60 | 0 | 100 | 100 | 100 | 70 | 100 | 100 | 80 | 50 |
| JIMSONWEED | 80 | 60 | 100 | 100 | 50 | 80 | 50 | 70 | 20 | 0 | 80 | 100 | 90 | 30 | 100 | 100 | 60 | 20 |
| RICE | 60 | 20 | 70 | 70 | 60 | 70 | 70 | 50 | 30 | 0 | 95 | 100 | 60 | 40 | 100 | 100 | 70 | 30 |
| COCKLEBUR | 50 | 40 | 50 | 80 | 0 | 0 | 70 | 70 | 30 | 30 | 100 | 100 | 100 | 100 | 100 | 100 | 80 | 10 |
| COTTON | 70 | 50 | 70 | 60 | 50 | 60 | 90 | 90 | 20 | 30 | 50 | 40 | 100 | 30 | 90 | 100 | 30 | 0 |
| SOYBEANS | 50 | 0 | 50 | 50 | 0 | 30 | 70 | 30 | 50 | 0 | 100 | 100 | 100 | 20 | 100 | 100 | 20 | 0 |
| BARNYARDGRASS | 70 | 0 | 30 | 50 | 30 | 20 | 70 | 70 | 30 | 0 | 50 | 40 | 30 | 30 | 90 | 90 | 30 | 0 |
| WILDOATS | 50 | 0 | 30 | 70 | 0 | 50 | 90 | 90 | 0 | 0 | 100 | 80 | 100 | 20 | 80 | 80 | 20 | 0 |
| MORNINGGLORY | 90 | 60 | 100 | 80 | 60 | 30 | 60 | 80 | 80 | 0 | 80 | 100 | 0 | 100 | 100 | 90 | 90 | 20 |
| WHEAT | 30 | 0 | 70 | 0 | 0 | 30 | 30 | 0 | 0 | 0 | 0 | 0 | 0 | 0 | 30 | 90 | 0 | 0 |
| SICKLEPOD | 80 | 50 | 100 | 100 | 0 | 50 | 30 | 50 | 50 | 30 | 100 | 80 | 100 | 0 | 100 | 100 | 60 | 20 |
| JOHNSONGRASS | 70 | 50 | 90 | 70 | 60 | 60 | 70 | 50 | 0 | 30 | 50 | 30 | 40 | 0 | 100 | 100 | 0 | 30 |
| NUTSEDGE | 100 | 30 | 70 | 100 | 0 | 50 | 100 | 70 | 70 | 30 | 70 | 60 | 90 | 30 | 100 | 100 | 40 | 0 |
| CORN | 70 | 0 | 70 | 70 | 30 | 80 | 80 | 70 | 50 | 30 | 100 | 100 | 50 | 50 | 100 | 100 | 70 | 30 |
| WILD BUCKWHEAT | 90 | 70 | 100 | 100 | 60 | 100 | 30 | 50 | 50 | 30 | 80 | 100 | 100 | 70 | 80 | 80 | 90 | 30 |
| BLACKGRASS | 30 | 0 | 70 | 50 | 50 | 95 | 70 | 70 | 50 | 30 | 100 | 70 | 70 | 0 | 100 | 100 | 70 | 90 |
| RAPE | 100 | 100 | 100 | 100 | 100 | 100 | 80 | 100 | 100 | 60 | 100 | 100 | 100 | 30 | 100 | 100 | 80 | 100 |
| BARLEY | 40 | 0 | 30 | 30 | 30 | 70 | 30 | 0 | 60 | 0 | 30 | 30 | 20 | 0 | 80 | 80 | 70 | 20 |
| GREEN FOXTAIL | 60 | 0 | 60 | 90 | 0 | 60 | 30 | 0 | 90 | 0 | 100 | 40 | 40 | 0 | 90 | 90 | 20 | 0 |
| CHEATGRASS | 80 | 20 | 80 | 70 | 30 | 30 | 70 | 30 | 70 | 30 | 100 | 100 | 95 | 0 | 100 | 100 | 40 | 0 |
| LAMBSQUARTER | 100 | 80 | 90 | 100 | 70 | 100 | 80 | 80 | 30 | 70 | 100 | 100 | 100 | 90 | 100 | 100 | 70 | 40 |
| CHICKWEED | 90 | 0 | 80 | 80 | 60 | 95 | 50 | 50 | 30 | 30 | 100 | 100 | 50 | 30 | 100 | 100 | 30 | 20 |
| DOWNY BROME | 50 | | 0 | 30 | 0 | 30 | 60 | 60 | 60 | 60 | 70 | 30 | | | 90 | 90 | 80 | 80 |

POSTEMERGENCE

|  | CMPD 38 | | CMPD 39 | | CMPD 40 | | CMPD 41 | | CMPD 42 | | CMPD 43 | | CMPD 49 | |
|---|---|---|---|---|---|---|---|---|---|---|---|---|---|---|
| RATE = G/HA | 62 | 16 | 62 | 16 | 4 | 1 | 16 | 4 | 62 | 16 | 62 | 16 | 62 | 16 |
| GIANT FOXTAIL | 60 | 50 | 95 | 50 | 20 | 0 | 50 | 80 | 50 | 40 | 60 | 100 | 100 | 100 |
| VELVETLEAF | 100 | 90 | 100 | 80 | 40 | 50 | 40 | 90 | 40 | 20 | 80 | 100 | 100 | 100 |
| SUGARBEETS | 80 | 80 | 100 | 100 | 80 | 0 | 80 | 20 | 100 | 100 | 90 | 100 | 100 | 70 |
| CRABGRASS | 0 | 0 | 50 | 20 | 80 | 0 | 40 | 20 | 20 | 20 | 20 | 40 | 100 | 40 |
| TEAWEED | 70 | 50 | 90 | 70 | 20 | 40 | 0 | 80 | 80 | 80 | 70 | 80 | 90 | 80 |
| JIMSONWEED | 80 | 80 | 100 | 40 | 20 | 20 | 80 | 80 | 90 | 0 | 80 | 100 | 100 | 90 |
| RICE | 40 | 20 | 70 | 30 | 0 | 50 | 0 | 0 | 0 | 80 | 30 | 40 | 80 | 60 |
| COCKLEBUR | 0 | 0 | 70 | 20 | 20 | 0 | 80 | 30 | 30 | 0 | 50 | 30 | 100 | 100 |
| COTTON | 20 | 20 | 70 | 30 | 20 | 0 | 50 | 20 | 70 | 30 | 80 | 80 | 100 | 90 |

-continued

| | CMPD 38 | | | CMPD 39 | | | CMPD 40 | | | CMPD 41 | | | CMPD 42 | | | CMPD 43 | | | CMPD 49 | |
|---|---|---|---|---|---|---|---|---|---|---|---|---|---|---|---|---|---|---|---|---|
| RATE = G/HA | 250 | 62 | 16 | 4 | 62 | 16 | 4 | 1 | 62 | 16 | 4 | 1 | 250 | 62 | 16 | 4 | 250 | 62 | 16 | 4 | 1 | 62 | 16 | 4 | 1 | 62 | 16 |
| SOYBEANS | 90 | 80 | 70 | 50 | 100 | 90 | 80 | 30 | 80 | 80 | 20 | 20 | 100 | 70 | 60 | 0 | 100 | 100 | 100 | 0 | 30 | 100 | 90 |
| BARNYARDGRASS | 70 | 50 | 50 | 40 | 100 | 100 | 60 | 50 | 90 | 90 | 70 | 40 | 100 | 100 | 80 | 60 | 100 | 100 | 100 | 80 | 80 | 100 | 100 |
| WILD OATS | 80 | 70 | 40 | 0 | 90 | 90 | 50 | 40 | 70 | 90 | 30 | 0 | 100 | 90 | 90 | 90 | 100 | 100 | 100 | 90 | 90 | 80 | 70 |
| MORNINGGLORY | 90 | 70 | 70 | 60 | 100 | 90 | 70 | 20 | 100 | 100 | 50 | 0 | 100 | 100 | 90 | 20 | 100 | 100 | 100 | 80 | 50 | 100 | 100 |
| WHEAT | 90 | 90 | 70 | 40 | 90 | 90 | 30 | 50 | 100 | 90 | 50 | 0 | 100 | 100 | 90 | 0 | 100 | 100 | 100 | 50 | 90 | 50 | 50 |
| SICKLEPOD | 0 | 0 | 0 | 0 | 80 | 50 | 30 | 40 | 100 | 90 | 50 | 40 | 100 | 30 | 0 | 0 | 100 | 100 | 80 | 50 | 0 | 100 | 60 |
| JOHNSONGRASS | 60 | 50 | 40 | 30 | 100 | 70 | 60 | 40 | 90 | 80 | 70 | 0 | 100 | 100 | 80 | 40 | 100 | 100 | 100 | 80 | 60 | 100 | 90 |
| NUTSEDGE | 50 | 50 | 20 | 0 | 70 | 50 | 30 | 40 | 80 | 40 | 20 | 0 | 100 | 30 | 0 | 0 | 90 | 100 | 90 | 40 | 0 | 100 | 60 |
| CORN | 90 | 90 | 40 | 30 | 100 | 100 | 100 | 40 | 100 | 100 | 70 | 20 | 100 | 100 | 80 | 40 | 100 | 100 | 100 | 80 | 60 | 100 | 80 |
| WILD BUCKWHEAT | 70 | 50 | 30 | 50 | 20 | 80 | 30 | 20 | 40 | 80 | 0 | 30 | 40 | 90 | 30 | 0 | 100 | 100 | 100 | 40 | 0 | 100 | 0 |
| BLACKGRASS | 90 | 80 | 80 | 70 | 100 | 100 | 50 | 50 | 100 | 100 | 50 | 20 | 100 | 90 | 60 | 80 | 100 | 100 | 100 | 80 | 80 | 100 | 80 |
| RAPE | 50 | 40 | 30 | 0 | 80 | 80 | 70 | 70 | 100 | 90 | 100 | 30 | 90 | 100 | 50 | 70 | 100 | 100 | 100 | 90 | 50 | 100 | 70 |
| BARLEY | 100 | 40 | 30 | 40 | 90 | 70 | 70 | 20 | 80 | 50 | 40 | 20 | 100 | 50 | 40 | 30 | 100 | 100 | 90 | 70 | 50 | 70 | 70 |
| GREEN FOXTAIL | 40 | 20 | 0 | 0 | 100 | 100 | 40 | 0 | 100 | 100 | 90 | 70 | 100 | 80 | 50 | 0 | 100 | 100 | 70 | 40 | 80 | 100 | 100 |
| LAMBSQUARTER | 100 | 70 | 70 | 40 | 80 | 70 | 50 | 40 | 70 | 80 | 70 | 0 | 100 | 100 | 70 | 30 | 100 | 100 | 100 | 70 | 70 | 100 | 90 |
| CHICKWEED | 80 | 60 | 50 | 50 | 100 | 100 | 60 | 20 | 100 | 100 | 70 | 0 | 100 | 90 | 90 | 50 | 100 | 100 | 100 | 60 | 80 | 100 | 90 |
| DOWNY BROME | 80 | 60 | 50 | 0 | 90 | 90 | 40 | 20 | 70 | 90 | 0 | 0 | 100 | 100 | 80 | 40 | 100 | 100 | 100 | 90 | 40 | 100 | 90 |

PREEMERGENCE

| | CMPD 38 | | | CMPD 39 | | | CMPD 40 | | | CMPD 41 | | | CMPD 42 | | | CMPD 43 | | | CMPD 49 | |
|---|---|---|---|---|---|---|---|---|---|---|---|---|---|---|---|---|---|---|---|---|
| RATE = G/HA | 250 | 62 | 16 | 4 | 62 | 16 | 4 | 1 | 62 | 16 | 4 | 1 | 250 | 62 | 16 | 4 | 250 | 62 | 16 | 4 | 1 | 62 | 16 |
| GIANT FOXTAIL | 0 | 0 | 0 | 0 | 100 | 30 | 30 | 0 | 60 | 60 | 0 | 0 | 100 | 90 | 70 | 0 | 100 | 100 | 100 | 70 | 60 | 90 | 80 |
| VELVETLEAF | 40 | 30 | 0 | 0 | 90 | 80 | 50 | 30 | 100 | 50 | 70 | 40 | 70 | 50 | 30 | 0 | 70 | 100 | 100 | 90 | 70 | 90 | 80 |
| SUGARBEETS | 50 | 30 | 20 | 0 | 100 | 80 | 50 | 0 | 100 | 100 | 50 | 0 | 100 | 100 | 50 | 30 | 100 | 100 | 100 | 100 | 80 | 90 | 80 |
| CRABGRASS | 0 | 0 | 0 | 0 | 70 | 30 | 30 | 0 | 70 | 70 | 60 | 40 | 50 | 90 | 50 | 50 | 90 | 90 | 90 | 80 | 50 | 100 | 100 |
| TEAWEED | 40 | 40 | 0 | 0 | 60 | 40 | 0 | 0 | 70 | 70 | 30 | 30 | 100 | 90 | 50 | 0 | 50 | 100 | 90 | 80 | 50 | 100 | 90 |
| JIMSONWEED | 50 | 40 | 0 | 0 | 60 | 50 | 40 | 30 | 70 | 50 | 40 | 40 | 100 | 100 | 100 | 50 | 100 | 100 | 100 | 100 | 40 | 100 | 80 |
| RICE | 30 | 20 | 0 | 0 | 80 | 50 | 30 | 0 | 40 | 30 | 30 | 0 | 100 | 80 | 20 | 0 | 100 | 100 | 90 | 70 | 0 | 90 | 60 |
| COCKLEBUR | 50 | 50 | 0 | 0 | 90 | 100 | 30 | 0 | 100 | 100 | 60 | 40 | 80 | 70 | 70 | 0 | 100 | 100 | 100 | 50 | 90 | 100 | 80 |
| COTTON | 0 | 0 | 0 | 0 | 100 | 100 | 30 | 0 | 90 | 80 | 50 | 0 | 70 | 80 | 30 | 30 | 100 | 100 | 100 | 70 | 50 | 70 | 40 |
| SOYBEANS | 0 | 0 | 0 | 0 | 100 | 100 | 0 | 0 | 90 | 60 | 0 | 0 | 100 | 70 | 0 | 0 | 100 | 100 | 100 | 40 | 40 | 100 | 90 |
| BARNYARDGRASS | 30 | 20 | 0 | 0 | 100 | 20 | 0 | 0 | 100 | 60 | 20 | 20 | 100 | 100 | 100 | 20 | 100 | 100 | 100 | 60 | 90 | 100 | 40 |
| WILD OATS | 50 | 30 | 30 | 0 | 70 | 0 | 0 | 0 | 80 | 20 | 50 | 0 | 100 | 80 | 40 | 50 | 100 | 100 | 80 | 50 | 50 | 90 | 40 |
| MORNINGGLORY | 30 | 0 | 0 | 0 | 70 | 0 | 0 | 0 | 70 | 60 | 30 | 0 | 90 | 40 | 50 | 30 | 100 | 90 | 80 | 40 | 40 | 60 | 60 |
| WHEAT | 30 | 0 | 0 | 0 | 70 | 0 | 0 | 0 | 70 | 70 | 70 | 0 | 100 | 100 | 20 | 0 | 100 | 100 | 100 | 80 | 0 | 70 | 40 |
| SICKLEPOD | 50 | 50 | 0 | 0 | 80 | 0 | 40 | 0 | 80 | 30 | 50 | 30 | 100 | 80 | 40 | 20 | 100 | 100 | 100 | 60 | 40 | 100 | 70 |
| JOHNSONGRASS | 30 | 0 | 0 | 0 | 90 | 70 | 30 | 30 | 90 | 80 | 30 | 40 | 90 | 100 | 50 | 30 | 100 | 100 | 100 | 70 | 70 | 100 | 100 |
| NUTSEDGE | — | 0 | 0 | 50 | 100 | 100 | 50 | 0 | — | 90 | 0 | — | 50 | 40 | 20 | 0 | 100 | 100 | 100 | 80 | 70 | 100 | 90 |
| CORN | 0 | 0 | 0 | 0 | 40 | 20 | 20 | 0 | 40 | 30 | 20 | 20 | 100 | 100 | 30 | 0 | 100 | 100 | 100 | 40 | 40 | 100 | 80 |
| WILD BUCKWHEAT | 90 | 0 | 50 | 0 | 100 | 100 | 100 | 90 | 100 | 90 | 100 | 100 | 100 | 90 | 100 | 100 | 100 | 100 | 100 | 100 | 100 | 100 | 40 |
| BLACKGRASS | 30 | 20 | 20 | 0 | 70 | 30 | 0 | 0 | 90 | 50 | 40 | 20 | 90 | 70 | 50 | 40 | 80 | 90 | 80 | 50 | 50 | 90 | 60 |
| RAPE | 40 | 0 | 30 | 0 | 100 | 80 | 50 | 0 | 100 | 100 | 70 | 40 | 100 | 80 | 60 | 20 | 100 | 100 | 70 | 70 | 40 | 80 | 40 |
| BARLEY | 0 | 0 | 0 | 0 | 90 | 80 | 0 | 0 | 100 | 50 | 0 | 0 | 90 | 90 | 70 | 30 | 100 | 100 | 70 | 40 | 30 | 100 | 50 |
| GREEN FOXTAIL | 40 | 20 | 0 | 0 | 100 | 70 | 40 | 40 | 90 | 70 | 40 | 0 | 100 | 90 | 50 | 0 | 100 | 100 | 100 | 90 | 0 | 80 | 70 |
| LAMBSQUARTER | 50 | 0 | 0 | 0 | 90 | 50 | 30 | 0 | 100 | 50 | 80 | 50 | 70 | 70 | 70 | 30 | 100 | 100 | 70 | — | 30 | 100 | 30 |
| CHICKWEED | 100 | 30 | 0 | 0 | 100 | 70 | 20 | 0 | 100 | 90 | 40 | 30 | 100 | 100 | 60 | 0 | 100 | 100 | 90 | 90 | 0 | 100 | 100 |
| DOWNY BROME | 40 | 20 | 0 | 0 | 100 | 40 | 0 | 0 | 90 | 80 | 30 | 0 | 100 | 100 | 80 | 40 | 100 | 100 | 100 | 90 | 70 | 90 | 40 |

| RATE = G/HA | CMPD 49 | | CMPD 52 | | | CMPD 55 | | | CMPD 56 | | | CMPD 61 | | | CMPD 62 | | | CMPD 63 | |
|---|---|---|---|---|---|---|---|---|---|---|---|---|---|---|---|---|---|---|---|
| | 4 | 1 | 62 | 16 | 4 | 250 | 62 | 16 | 250 | 62 | 16 | 4 | 62 | 16 | 4 | 62 | 16 | 4 | 1 |
| POSTEMERGENCE | | | | | | | | | | | | | | | | | | | |
| GIANT FOXTAIL | 50 | 20 | 50 | 30 | 0 | 0 | 70 | 30 | 0 | 100 | 0 | 0 | 10 | 100 | 50 | 30 | 90 | 40 | 20 |
| VELVETLEAF | 60 | 0 | 100 | 70 | 40 | 30 | 100 | 100 | 80 | 100 | 80 | 40 | 90 | 100 | 100 | 100 | 100 | 100 | 90 |
| SUGARBEETS | 100 | 90 | 100 | 100 | 100 | 70 | 100 | 100 | 100 | 100 | 100 | 100 | 100 | 100 | 100 | 100 | 100 | 100 | 100 |
| CRABGRASS | 40 | 0 | 0 | 0 | 0 | 30 | 100 | 30 | 0 | 100 | 50 | 30 | 0 | 50 | 30 | 40 | 100 | 40 | 20 |
| TEAWEED | 80 | 10 | 80 | 40 | 30 | 40 | 100 | 70 | 0 | 100 | 90 | 50 | 40 | 100 | 100 | 100 | 100 | 100 | 80 |
| JIMSONWEED | 90 | 40 | 100 | 100 | 90 | 50 | 100 | 50 | 70 | 100 | 100 | 80 | 80 | 100 | 100 | 100 | 100 | 100 | 70 |
| RICE | 20 | 0 | 0 | 0 | 0 | 30 | 60 | 60 | 50 | 30 | 50 | 0 | 30 | 50 | 50 | 40 | 90 | 70 | 80 |
| COCKLEBUR | 70 | 50 | 80 | 70 | 60 | 60 | 100 | 50 | 0 | 100 | 100 | 80 | 70 | 100 | 70 | 70 | 100 | 90 | 40 |
| COTTON | 90 | 60 | 100 | 90 | 50 | 40 | 70 | 40 | 0 | 100 | 60 | 0 | 100 | 100 | 90 | 100 | 100 | 100 | 70 |
| SOYBEANS | 70 | 60 | 100 | 80 | 30 | 80 | 100 | 70 | 0 | 100 | 100 | 80 | 0 | 100 | 80 | 60 | 100 | 100 | 60 |
| BARNYARDGRASS | 60 | 40 | 90 | 80 | 70 | 60 | 100 | 50 | 70 | 50 | 40 | 20 | 100 | 100 | 100 | 100 | 100 | 100 | 100 |
| WILD OATS | 60 | 40 | 70 | 50 | 30 | 40 | 70 | 30 | 70 | 50 | 20 | 0 | 80 | 50 | 40 | 70 | 100 | 100 | 90 |
| MORNINGGLORY | 50 | 50 | 90 | 70 | 60 | 100 | 100 | 90 | 60 | 100 | 100 | 60 | 0 | 40 | 0 | 10 | 70 | 40 | 30 |
| WHEAT | 40 | 30 | 90 | 50 | 30 | 0 | 100 | 60 | 0 | 100 | 100 | 90 | 90 | 100 | 100 | 100 | 100 | 100 | 40 |
| SICKLEPOD | 50 | 0 | 30 | 0 | 0 | 70 | 100 | 100 | 70 | 100 | 100 | 70 | 0 | 20 | 10 | 0 | 70 | 30 | 0 |
| JOHNSONGRASS | 80 | 60 | 100 | 80 | 50 | 50 | 100 | 60 | 60 | 100 | 100 | 60 | 100 | 100 | 40 | 50 | 100 | 80 | 40 |
| NUTSEDGE | 0 | 0 | 50 | 30 | 0 | 30 | 80 | 30 | 0 | 100 | 60 | 60 | 30 | — | 0 | 70 | 100 | 90 | 70 |
| CORN | 30 | 30 | 20 | 10 | 0 | 50 | 100 | 100 | 30 | 100 | 100 | 70 | 100 | 100 | 70 | 90 | 100 | 100 | 40 |
| WILD BUCKWHEAT | 9 | 70 | 100 | 90 | 70 | 80 | 100 | 70 | 0 | 100 | 80 | 40 | 40 | 100 | 100 | 80 | 100 | 100 | 80 |
| BLACKGRASS | 60 | 50 | 100 | 100 | 50 | 70 | 100 | 80 | 100 | 100 | 100 | 70 | 100 | 100 | 60 | 30 | 100 | 70 | 20 |
| RAPE | 100 | 100 | 100 | 100 | 80 | 100 | 100 | 100 | 60 | 100 | 100 | 100 | 40 | 100 | 50 | 90 | 100 | 100 | 40 |
| BARLEY | 60 | 20 | 50 | 30 | 0 | 30 | 60 | 30 | 0 | 30 | 30 | 0 | 100 | 30 | 10 | 30 | 70 | 60 | 40 |
| GREEN FOXTAIL | 60 | 50 | 0 | 0 | 0 | 80 | 100 | 50 | 50 | 90 | 100 | 50 | 0 | 40 | 0 | 30 | 100 | 90 | 40 |
| CHEATGRASS | | | | | | | | | | | | | | | | | | | |
| LAMBSQUARTER | 90 | 60 | 100 | 100 | 70 | 50 | 100 | 100 | 30 | 100 | 100 | 90 | 70 | 100 | 80 | 80 | 100 | 70 | 60 |
| CHICKWEED | 80 | 70 | 100 | 90 | 70 | 30 | 90 | 70 | 90 | 100 | 100 | 100 | — | 100 | 100 | 100 | 100 | 100 | 90 |
| DOWNY BROME | 60 | 40 | 70 | 50 | 30 | 50 | 100 | 100 | 70 | 100 | 80 | 50 | 30 | 80 | 70 | 70 | 100 | 80 | 80 |

| RATE = G/HA | CMPD 49 | | CMPD 52 | | | CMPD 55 | | | CMPD 56 | | | CMPD 61 | | | CMPD 62 | | | CMPD 63 | |
|---|---|---|---|---|---|---|---|---|---|---|---|---|---|---|---|---|---|---|---|
| | 4 | 1 | 62 | 16 | 4 | 250 | 62 | 16 | 250 | 62 | 16 | 4 | 250 | 62 | 16 | 4 | 62 | 16 | 4 | 1 |
| PREEMERGENCE | | | | | | | | | | | | | | | | | | | |
| GIANT FOXTAIL | 80 | 70 | 70 | 50 | 30 | 30 | 100 | 30 | 0 | 40 | 30 | 0 | 40 | 30 | 0 | 20 | 60 | 40 | 0 | 0 |
| VELVETLEAF | 50 | 40 | 50 | 30 | 0 | 30 | 100 | 60 | 90 | 90 | 50 | 40 | 90 | 100 | 80 | 80 | 40 | 80 | 60 | 40 |
| SUGARBEETS | 60 | 30 | 95 | 80 | 70 | 100 | 100 | 60 | 70 | 100 | 100 | 30 | 100 | 100 | 80 | 80 | 100 | 90 | 80 | 70 |
| CRABGRASS | 90 | 50 | 90 | 90 | 70 | 0 | 70 | 30 | 0 | 50 | 0 | 0 | 90 | 90 | 70 | 70 | 100 | 90 | 80 | 30 |
| TEAWEED | 70 | 40 | 90 | 70 | 0 | 50 | 90 | 70 | 30 | 30 | 40 | 30 | 80 | 80 | 60 | 40 | 90 | 90 | 50 | 30 |
| JIMSONWEED | 40 | 20 | 70 | 60 | 0 | 40 | 100 | 80 | 50 | 30 | 30 | 0 | 80 | 70 | 50 | 20 | 80 | 80 | 40 | 20 |
| RICE | 60 | 0 | 50 | 50 | 0 | 0 | 95 | 60 | 30 | 0 | 40 | 0 | 80 | 20 | 0 | 40 | 70 | 60 | 20 | 20 |
| COCKLEBUR | 70 | 0 | 70 | 50 | 0 | 0 | 100 | 90 | 60 | 90 | 40 | 20 | 80 | 40 | 10 | 30 | 90 | 80 | 40 | 30 |
| COTTON | — | 40 | 70 | 20 | 50 | 50 | 90 | 80 | 30 | 30 | 30 | — | 60 | 90 | 30 | 20 | 80 | 60 | 40 | 20 |
| SOYBEANS | 10 | 0 | 60 | 0 | 30 | 0 | 80 | 80 | 0 | 0 | 0 | 20 | 100 | 70 | 40 | 10 | 80 | 40 | 40 | 30 |
| BARNYARDGRASS | 40 | 30 | 100 | 100 | 80 | 40 | 90 | 80 | 30 | 30 | 30 | 10 | 80 | 60 | 40 | 20 | 60 | 60 | 20 | 10 |
| WILD OATS | 40 | 40 | 40 | 30 | 0 | 20 | 90 | 70 | 30 | 0 | 50 | 0 | 90 | 90 | 60 | 20 | 100 | 50 | 40 | 10 |
| MORNINGGLORY | 40 | 40 | 80 | 50 | 50 | 50 | 80 | 50 | 0 | 0 | 0 | 0 | 70 | 20 | 0 | 30 | 60 | 90 | 50 | 20 |
| WHEAT | 0 | 0 | 80 | 30 | 20 | 30 | 70 | 30 | 30 | 0 | 0 | 0 | 100 | 10 | 0 | 0 | 100 | 70 | 70 | 30 |
| SICKLEPOD | 40 | 0 | 50 | 80 | 0 | 50 | 80 | 50 | 80 | 80 | 50 | 30 | 80 | 60 | 80 | 70 | 80 | 80 | 40 | 20 |
| JOHNSONGRASS | 40 | — | 70 | 100 | 70 | 30 | 100 | 70 | 0 | 0 | 0 | 0 | 40 | — | 30 | — | 90 | 60 | — | 40 |
| NUTSEDGE | 30 | 0 | 90 | 80 | 50 | 30 | 100 | 50 | 100 | 100 | 50 | 30 | 50 | 50 | 30 | 0 | 80 | 30 | 0 | 0 |
| CORN | 20 | 0 | 100 | 80 | 30 | 30 | 100 | 90 | 0 | 0 | 0 | 0 | 60 | 90 | 50 | 20 | 90 | 50 | 20 | 10 |

-continued

| | CMPD 64 | | | | CMPD 65 | | | | CMPD 66 | | | | CMPD 67 | | | | CMPD 68 | | | | CMPD 73 | | |
|---|---|---|---|---|---|---|---|---|---|---|---|---|---|---|---|---|---|---|---|---|---|---|---|
| WILD BUCKWHEAT | | | | 80 | | | | 80 | | | | 80 | | | | 80 | | | | 90 | | | | |
| BLACKGRASS | | | | 40 | | | | 30 | | | | 30 | | | | 30 | | | | 50 | | | | |
| RAPE | | | | 20 | | | | 0 | | | | 0 | | | | 0 | | | | 80 | | | | |
| BARLEY | | | | 20 | | | | 0 | | | | 0 | | | | 0 | | | | 80 | | | | |
| GREEN FOXTAIL | | | | 70 | | | | 60 | | | | 0 | | | | 0 | | | | 30 | | | | |
| CHEATGRASS | | | | | | | | 60 | | | | 0 | | | | 0 | | | | 0 | | | | |
| LAMBSQUARTER | | | | 100 | | | | 80 | | | | 80 | | | | 80 | | | | 100 | | | | 70 | | |
| CHICKWEED | | | | 90 | | | | 70 | | | | 90 | | | | 90 | | | | 90 | | | | 40 | | |
| DOWNY BROME | | | | 20 | | | | 0 | | | | 0 | | | | 40 | | | | 80 | | | | 60 | | |

| RATE = G/HA | 62 | 16 | 4 | 1 | 250 | 62 | 16 | 4 | 250 | 62 | 16 | 4 | 250 | 62 | 16 | 4 | 250 | 62 | 16 | 4 | 250 | 62 | 16 | 4 |

POSTEMERGENCE

| GIANT FOXTAIL | 50 | 10 | 0 | 0 | 100 | 90 | 20 | 0 | 100 | 40 | 0 | 0 | 0 | 0 | 0 | 0 | 30 | 0 | 0 | 0 | 10 | 0 | 0 | 0 |
| VELVETLEAF | 100 | 100 | 90 | 50 | 100 | 100 | 100 | 90 | 100 | 100 | 100 | 90 | 100 | 100 | 100 | 80 | 100 | 100 | 100 | 90 | 100 | 70 | 50 | 30 |
| SUGARBEETS | 100 | 100 | 100 | 90 | 100 | 100 | 100 | 100 | 100 | 100 | 100 | 80 | 100 | 80 | 80 | 100 | 100 | 100 | 100 | 100 | 100 | 70 | 50 | 30 |
| CRABGRASS | 10 | 0 | 0 | 0 | 60 | 40 | 0 | 50 | 20 | 0 | 0 | 0 | 30 | 0 | 0 | 0 | 30 | 30 | 40 | 70 | 30 | 30 | 0 | 0 |
| TEAWEED | 100 | 100 | — | 70 | 100 | 100 | 100 | 100 | 100 | 100 | 80 | 50 | 100 | 70 | 70 | 40 | 100 | 100 | 100 | 40 | 70 | 50 | 30 | 0 |
| JIMSONWEED | 100 | 100 | 100 | 90 | 100 | 100 | 100 | 100 | 100 | 100 | 100 | 80 | 100 | 80 | 80 | 70 | 100 | 100 | 100 | 70 | 70 | 30 | 30 | 30 |
| RICE | 30 | 20 | 10 | 0 | 40 | 30 | 10 | 0 | 40 | 20 | 10 | 0 | 40 | 10 | 10 | 0 | 50 | 50 | 40 | 30 | 0 | 0 | 0 | 0 |
| COCKLEBUR | 100 | 100 | 50 | 40 | 100 | 100 | 100 | 100 | 100 | 100 | 80 | 50 | 100 | 100 | 100 | 90 | 100 | 100 | 100 | 40 | 70 | 70 | 50 | 30 |
| COTTON | 90 | 90 | 70 | 50 | 100 | 100 | 90 | 70 | 100 | 100 | 90 | 40 | 100 | 80 | 80 | 40 | 100 | 70 | 70 | 30 | 60 | 60 | 30 | 0 |
| SOYBEANS | 100 | 100 | 70 | 10 | 100 | 100 | 100 | 100 | 100 | 100 | 100 | 80 | 100 | 100 | 100 | 30 | 100 | 100 | 100 | 40 | 70 | 70 | 50 | 30 |
| BARNYARDGRASS | 90 | 50 | 30 | 0 | 90 | 70 | 40 | 10 | 80 | 20 | 30 | 10 | 80 | 40 | 40 | 30 | 80 | 60 | 40 | 30 | 60 | 30 | 30 | 0 |
| WILD OATS | 100 | 100 | 0 | 60 | 30 | 10 | 0 | 0 | 10 | 10 | 0 | 0 | 30 | 0 | 0 | 60 | 30 | 50 | 50 | 70 | 80 | 70 | 70 | 50 |
| MORNINGGLORY | 100 | 100 | 60 | 0 | 100 | 100 | 100 | 100 | 100 | 100 | 100 | 100 | 100 | 100 | 70 | 30 | 100 | 100 | 100 | 20 | 80 | 70 | 30 | 0 |
| WHEAT | 20 | 0 | 0 | 0 | 10 | 10 | 10 | 0 | 0 | 10 | 0 | — | 90 | 20 | 0 | 0 | 50 | 20 | 50 | 0 | 0 | 0 | 0 | 0 |
| SICKLEPOD | 100 | 70 | 50 | 0 | 100 | 100 | 100 | 70 | 100 | 100 | 40 | 100 | 100 | 80 | 80 | 40 | 90 | 50 | 50 | 70 | 60 | 30 | 30 | 30 |
| JOHNSONGRASS | 90 | 60 | 40 | 20 | 80 | 50 | 30 | 0 | 50 | 10 | 0 | — | 30 | 30 | 0 | 100 | 50 | 100 | 20 | 30 | 80 | 60 | 30 | 30 |
| NUTSEDGE | 100 | 100 | 100 | 60 | 100 | 100 | 100 | 50 | 100 | 100 | 40 | — | 100 | 100 | 100 | 100 | 70 | 100 | 100 | 70 | 80 | 80 | 30 | 30 |
| CORN | 30 | 0 | 0 | 0 | — | — | 30 | 0 | 60 | 20 | 40 | 0 | 20 | 0 | 0 | 0 | 30 | 40 | 20 | 0 | 0 | 0 | 0 | 0 |
| WILD BUCKWHEAT | 100 | 100 | 100 | 100 | 100 | 100 | 100 | 100 | 100 | 100 | 100 | 100 | 100 | 100 | 100 | 100 | 100 | 100 | 100 | 0 | 50 | 30 | 20 | 30 |
| BLACKGRASS | 40 | 30 | 20 | 20 | 90 | 80 | 30 | 0 | 60 | 20 | 10 | — | 20 | 20 | 0 | 0 | 70 | 50 | 70 | 60 | 30 | 30 | 30 | 30 |
| RAPE | 100 | 100 | 100 | 100 | 100 | 100 | 100 | 0 | 100 | 100 | 20 | 100 | 80 | 100 | 100 | 100 | 50 | 100 | 20 | 90 | 80 | 80 | 30 | 30 |
| BARLEY | 30 | 10 | 0 | 0 | 40 | 20 | 10 | 0 | 20 | 10 | 0 | — | 10 | 0 | 0 | 0 | 30 | 10 | 30 | 30 | 0 | 0 | 0 | 0 |
| GREEN FOXTAIL | 70 | 50 | 0 | 20 | 100 | 90 | 70 | 20 | 70 | 50 | 30 | 0 | 80 | 0 | 0 | 0 | 40 | 20 | 20 | 0 | 0 | 0 | 0 | 0 |
| CHEATGRASS | | | | | | | | | | | | | | | | | | | | | | | | |
| FIELD VIOLET | | | | | | | | | | | | | | | | | | | | | | | | |
| LAMBSQUARTER | 90 | 70 | 60 | 50 | 100 | 100 | 80 | 50 | 100 | 100 | 70 | 70 | 100 | 50 | 50 | 60 | 100 | 70 | 60 | 30 | 30 | 30 | 0 | 0 |
| CHICKWEED | 100 | 100 | 90 | 90 | 100 | 100 | 100 | 100 | 100 | 100 | 100 | — | 100 | 100 | 100 | 90 | 100 | 100 | 100 | 90 | 50 | 50 | 50 | 30 |
| DOWNY BROME | 40 | 30 | 30 | 0 | 100 | 100 | 40 | 0 | 70 | 50 | 10 | 0 | 40 | 20 | 20 | 30 | 70 | 40 | 70 | 30 | 0 | 0 | 0 | 0 |

| RATE = G/HA | 250 | 62 | 16 | 4 | 250 | 62 | 16 | 4 | 250 | 62 | 16 | 4 | 250 | 62 | 16 | 4 | 250 | 62 | 16 | 4 | 250 | 62 | 16 | 4 |

PREEMERGENCE

| GIANT FOXTAIL | 40 | 0 | 0 | 0 | 90 | — | 80 | 20 | 20 | 0 | 0 | 0 | 0 | 0 | 0 | 0 | 20 | 0 | 0 | 0 | 50 | 30 | 0 | 0 |
| VELVETLEAF | 90 | 90 | 80 | 40 | 100 | 90 | 70 | 40 | 90 | 90 | 90 | 30 | 70 | 50 | — | 40 | 50 | 40 | — | 30 | 90 | 70 | 50 | 30 |
| SUGARBEETS | 100 | 90 | — | 90 | 100 | 100 | 100 | 100 | 100 | 100 | 100 | 90 | 100 | 80 | 80 | 0 | 90 | 90 | 80 | 30 | 100 | 70 | 50 | 30 |
| CRABGRASS | 100 | 80 | 0 | 40 | 90 | 90 | 60 | 30 | 80 | 80 | 30 | 0 | 40 | 0 | 0 | 30 | 40 | 20 | 30 | 40 | 60 | 30 | 0 | 0 |
| TEAWEED | 90 | 90 | 80 | 40 | 100 | 100 | 90 | 20 | 100 | 80 | 30 | 0 | 80 | 20 | 70 | 30 | 70 | 70 | 40 | 30 | 70 | 50 | 30 | 0 |
| JIMSONWEED | 100 | 90 | 80 | 50 | 100 | 100 | 100 | 40 | 80 | 80 | 40 | 0 | 70 | 40 | 60 | 30 | 80 | 40 | 30 | 0 | 80 | 50 | 30 | 0 |
| RICE | 90 | 70 | 30 | 10 | 70 | 40 | 10 | 0 | 60 | 60 | 0 | 0 | 50 | 30 | 30 | 0 | 60 | 40 | 30 | 0 | 0 | 30 | 0 | 0 |

-continued

| | | | | | | | | | | | | | | | | | |
|---|---|---|---|---|---|---|---|---|---|---|---|---|---|---|---|---|---|
| COCKLEBUR | 90 | 70 | 30 | 90 | 90 | 80 | 70 | 90 | 90 | 80 | 80 | 70 | 30 | 90 | 50 | 0 | 70 | 50 | 30 | 0 |
| COTTON | 90 | 80 | 0 | 90 | 80 | 70 | 20 | 90 | 90 | 50 | 30 | 20 | 0 | 50 | 0 | 0 | 40 | 20 | 0 | 0 |
| SOYBEANS | 50 | 30 | 10 | 100 | 90 | 50 | 0 | 90 | 90 | 20 | 10 | 10 | 10 | 20 | 10 | 0 | 50 | 30 | 0 | 0 |
| BARNYARDGRASS | 80 | 40 | 0 | 90 | 80 | 30 | 30 | 40 | 40 | 20 | 20 | 0 | 0 | 50 | 20 | 0 | 50 | 0 | 0 | 0 |
| WILD OATS | 20 | 10 | — | 50 | 30 | 30 | 90 | 30 | 30 | 20 | 10 | 10 | 20 | 60 | 50 | 40 | 50 | 0 | 30 | 0 |
| MORNINGGLORY | 100 | 90 | 80 | 100 | 90 | 90 | 0 | 100 | 100 | 90 | 70 | 30 | 0 | 80 | 70 | 40 | 70 | 50 | 0 | 0 |
| WHEAT | 30 | 20 | 0 | 10 | 0 | 0 | 80 | 10 | 0 | 0 | 0 | 0 | 0 | 40 | 10 | 0 | 0 | 0 | 30 | 0 |
| SICKLEPOD | 100 | 80 | — | 100 | 100 | 90 | 0 | 100 | 90 | 50 | 40 | 70 | 30 | 40 | — | 0 | 70 | 0 | 0 | 0 |
| JOHNSONGRASS | 60 | 50 | 20 | 30 | 20 | 10 | 80 | 20 | 20 | 0 | 0 | 20 | 0 | 40 | 0 | 0 | 30 | 0 | 0 | 0 |
| NUTSEDGE | 100 | 100 | 40 | 80 | 70 | 40 | 0 | 80 | — | 50 | 40 | 90 | 30 | 40 | 70 | 30 | 50 | 50 | 30 | 0 |
| CORN | 70 | 20 | 0 | 100 | 80 | 30 | 10 | 90 | 80 | 0 | 0 | 0 | 0 | 90 | 20 | 10 | 80 | 0 | 0 | 0 |
| WILD BUCKWHEAT | 100 | 90 | 80 | 100 | 100 | 100 | 90 | 100 | 100 | 100 | 90 | 10 | 80 | 100 | 90 | 80 | 90 | 50 | 50 | 30 |
| BLACKGRASS | 70 | 60 | 0 | 80 | 80 | 40 | — | 60 | 30 | 20 | 80 | 40 | 0 | 70 | 50 | 30 | 60 | 0 | 0 | 0 |
| RAPE | 100 | 100 | 90 | 100 | 100 | 90 | 80 | 100 | 100 | 100 | 90 | 90 | 90 | 100 | 90 | 90 | 70 | 50 | 0 | 0 |
| BARLEY | 30 | — | 10 | 60 | 40 | 20 | 0 | 30 | 10 | 20 | 0 | 40 | 0 | 60 | 30 | 20 | 30 | 30 | 50 | 0 |
| GREEN FOXTAIL | 90 | 40 | 0 | 100 | 90 | 50 | 40 | 100 | 90 | 90 | 10 | 100 | 0 | 40 | 0 | 0 | 60 | 0 | 0 | 0 |
| CHEATGRASS | | | | | | | | | | | | | | | | | | | | |
| LAMBSQUARTER | 100 | 100 | 70 | 100 | 90 | 50 | 40 | 100 | 90 | 90 | 30 | 90 | 80 | 90 | 80 | 70 | 60 | 30 | 30 | 0 |
| CHICKWEED | 100 | 100 | 90 | 100 | 100 | 100 | 80 | 100 | 100 | 100 | 90 | 100 | 80 | 100 | 90 | 90 | 60 | 30 | 50 | 30 |
| DOWNY BROME | 90 | 80 | 30 | 70 | 40 | 30 | 40 | 40 | 20 | 0 | 30 | 0 | 0 | 70 | 30 | 0 | 90 | 70 | 0 | 30 |

Test C

The Corn and Sorghum Herbicide Test included the following species in both the preemergence and postemergence evaluations:

| Category | SPECIES Common Name | Scientific Name |
|---|---|---|
| Crops | Corn | Zea mays |
| | Soybean | Glycine max |
| | Sorghum | Sorghum bicolor |
| Grasses | Green foxtail | Setaria viridis |
| | Giant foxtail | Setaria faberii |
| | Johnsongrass | Sorghum halepense |
| | Barnyardgrass | Echinochloa crus-galli |
| | Fall panicum | Panicum dichotomiflorum |
| | Crabgrass | Digitaria sanguinalis |
| | Nutsedge | Cyperus rotundus |
| Broadleaves | Cocklebur | Xanthium pensylvanicum |
| | Morningglory | Ipomoea hederacea |
| | Velvetleaf | Abutilon theophrasti |
| | Jimsonweed | Datura stramonium |
| | Lambsquarters | Chenopodium album |
| | Pigweed | Amaranthus retroflexus |
| | Smartweed | Polygonum persicaris |

Postemergence

Postemergence plantings were grown in Sassafras sandy loam soil. Corn and soybeans were grown in separate 25 cm diameter containers. Sorghum and the seven grass weed species were grown in two 18 cm diameter containers, 4 species per container. The seven broadleaf weed species were also grown in two 18 cm diameter containers, 4 species in one container, 3 species in the second container. One additional planting of corn in an 18 cm diameter container was made. The soil surface of this additional container of corn was covered with the absorbent, perlite, before spray treatment so that test chemicals would enter the plant only via the foliage. The plants were grown 10–21 days, dependent upon the species and then sprayed postemergence with the test chemicals dissolved in a nonphytotoxic solvent.

Preemergence

Preemergence plantings were grown in fertilized Tama silt loam soil. These plantings are identical to those described in the postemergence section, with the exception of the corn planting having perlite covering the soil surface. These plantings were made the day of or the day before spraying the test chemicals dissolved in a nonphytotoxic solvent.

Evaluation

Treated plants and controls were maintained in the greenhouse for 2 to 4 weeks. Visual planting response ratings were made on a percentage scale of 0 to 100 in comparison with a control where 0=no injury, and 100=death. Response ratings are contained in Table C.

TABLE C

| | CMPD 36 | | | | | | |
|---|---|---|---|---|---|---|---|
| RATE GM/HA | 125 | 64 | 32 | 16 | 8 | 4 | 2 |
| POSTEMERGENCE | | | | | | | |
| CORN | 40 | 20 | 0 | 0 | 0 | 0 | 0 |
| SOYBEANS | 100 | 100 | 100 | 100 | 95 | 75 | 55 |
| GREEN FOXTAIL | 0 | 0 | 0 | 0 | 0 | 0 | 0 |
| GIANT FOXTAIL | 0 | 0 | 0 | 0 | 0 | 0 | 0 |
| FALL PANICUM | 0 | 0 | 0 | 0 | 0 | 0 | 0 |
| LARGE CRABGRASS | 0 | 0 | 0 | 0 | 0 | 0 | 0 |
| JOHNSONGRASS | 35 | 0 | 0 | 0 | 0 | 0 | 0 |
| SORGHUM | 25 | 0 | 0 | 0 | 0 | 0 | 0 |
| PURPLE NUTSEDGE | 70 | 40 | 0 | 0 | 0 | 0 | 0 |
| VELVETLEAF | 100 | 100 | 95 | 70 | 65 | 35 | 0 |
| COCKLEBUR | 100 | 100 | 100 | 100 | 95 | 70 | 50 |
| LADY SMARTWEED | 100 | 100 | 100 | 85 | 65 | 40 | 25 |
| LAMBSQUARTER | 100 | 95 | 85 | 70 | 60 | 30 | 0 |
| REDROOT PIGWEED | 100 | 100 | 100 | 100 | 85 | 60 | 35 |
| IVY MORNINGLORY | 100 | 100 | 100 | 100 | 90 | 65 | 45 |
| JIMSONWEED | 100 | 100 | 100 | 95 | 75 | 45 | 30 |
| PERLITE CORN | 25 | 0 | 0 | 0 | 0 | 0 | 0 |
| RATE GM/HA | 250 | 125 | 64 | 32 | 16 | | |
| PREEMERGENCE | | | | | | | |
| CORN | 40 | 20 | 0 | 0 | 0 | | |
| SOYBEANS | 80 | 55 | 20 | 0 | 0 | | |
| GREEN FOXTAIL | 30 | 0 | 0 | 0 | 0 | | |
| GIANT FOXTAIL | 20 | 0 | 0 | 0 | 0 | | |
| FALL PANICUM | 20 | 0 | 0 | 0 | 0 | | |
| LARGE CRABGRASS | 20 | 0 | 0 | 0 | 0 | | |
| BARNYARDGRASS | 40 | 20 | 0 | 0 | 0 | | |
| JOHNSONGRASS | 90 | 75 | 60 | 30 | 0 | | |
| SORGHUM | 45 | 35 | 30 | 0 | 0 | | |
| PURPLE NUTSEDGE | 90 | 75 | 40 | 30 | 0 | | |
| VELVETLEAF | 100 | 70 | 55 | 30 | 0 | | |
| COCKLEBUR | 95 | 80 | 50 | 20 | 0 | | |
| LADY SMARTWEED | 100 | 100 | 80 | 50 | 25 | | |
| LAMBSQUARTER | 100 | 100 | 75 | 55 | 35 | | |
| REDROOT PIGWEED | 100 | 100 | 95 | 60 | 40 | | |
| IVY MORNINGLORY | 95 | 90 | 60 | 35 | 0 | | |
| JIMSONWEED | 100 | 80 | 50 | 25 | 0 | | |

| | CMPD 56 | | | |
|---|---|---|---|---|
| RATE GM/HA | 125 | 64 | 32 | 16 |
| POSTEMERGENCE | | | | |
| CORN | 85 | 75 | 65 | 50 |
| SOYBEANS | 100 | 100 | 100 | 100 |
| GREEN FOXTAIL | 40 | 25 | 0 | 0 |
| GIANT FOXTAIL | 40 | 25 | 0 | 0 |
| FALL PANICUM | 45 | 25 | 0 | 0 |
| LARGE CRABGRASS | 0 | 0 | 0 | 0 |
| BARNYARDGRASS | 100 | 90 | 65 | 35 |
| JOHNSONGRASS | 70 | 65 | 60 | 40 |
| SORGHUM | 90 | 85 | 70 | 50 |
| PURPLE NUTSEDGE | 100 | 100 | 70 | 35 |
| VELVETLEAF | 100 | 90 | 55 | 35 |
| COCKLEBUR | 100 | 80 | 65 | 35 |
| LADY SMARTWEED | 95 | 85 | 60 | 45 |
| LAMSQUARTER | 55 | 25 | 0 | 0 |
| REDROOT PIGWEED | 100 | 100 | 95 | 65 |
| IVY MORNINGLORY | 50 | 20 | 0 | 0 |
| JIMSONWEED | 100 | 100 | 90 | 60 |
| PERLITE CORN | 70 | 60 | 55 | 40 |
| RATE GM/HA | 250 | 125 | 64 | |
| PREEMERGENCE | | | | |
| CORN | 0 | 0 | 0 | |
| SOYBEANS | 40 | 30 | 0 | |
| GREEN FOXTAIL | 20 | 0 | 0 | |
| GIANT FOXTAIL | 20 | 0 | 0 | |
| FALL PANICUM | 0 | 0 | 0 | |
| LARGE CRABGRASS | 0 | 0 | 0 | |
| BARNYARDGRASS | 0 | 0 | 0 | |
| JOHNSONGRASS | 55 | 25 | 0 | |
| SORGHUM | 0 | 0 | 0 | |
| PURPLE NUTSEDGE | 0 | 0 | 0 | |
| VELVETLEAF | 0 | 0 | 0 | |
| COCKLEBUR | 0 | 0 | 0 | |
| LADY SMARTWEED | 35 | 20 | 0 | |
| LAMBSQUARTER | 40 | 30 | 0 | |
| REDROOT PIGWEED | 60 | 35 | 0 | |
| IVY MORNINGLORY | 0 | 0 | 0 | |
| JIMSONWEED | 30 | 0 | 0 | |

Test D

Weed species were planted 3 or 4 per 15-cm diameter pot in Sassafras sandy loam (pH 6.8; 1% OM). Cotton was planted separately in the same sized pot. Postemergence plantings were made 12–16 days prior to treating so plants were in the 2- to 3-leaf stage (5–12 cm tall). Preemergence plantings were made the day before treating. Compounds were sprayed in a suitable non-phytotoxic solvent at 374 l/ha, then after 3 weeks of growth in a greenhouse, plant responses were visually rated on a percent scale where 0=no injury and 100=plant death. The following species were included:

| Common Name | Latin Name | Planting Depth (cm) |
|---|---|---|
| Cotton (Coker 315) | Gossypium hirsutum | 2 |
| Barnyardgrass | Echinochloa crus-galli | 1 |
| Bermudagrass | Cynodon dactylon | 1 |
| Broadleaf signalgrass | Brachiaria platyphylla | 1 |
| Crabgrass | Digitaria sanguinalis | 1 |
| Fall panicum | Panicum dichotomiflorum | 1 |
| Goosegrass | Eleusin indica | 1 |
| Johnsongrass | Sorghum halepense | 1 |
| Nutsedge | Cyperus rotundus | 3 |
| Cocklebur | Xanthium pensylvanicum | 3 |
| Ivy leaf morningglory | Ipomea hederacea | 3 |
| Lambsquarters | Chenopodium album | 1 |
| Pigweed | Amaranthus retroflexus | 1 |
| Prickly sida | Sida spinosa | 1 |
| Purslane | Portulaca oleracea | 1 |
| Sicklepod | Cassia obtusifolia | 3 |
| Smartweed | Polygonum persicaria | 1 |
| Velvetleaf | Abutilon theophrasti | 3 |
| Ground cherry | Physalis heterophylla | 1 |

The results are shown in Table D.

TABLE D

| | CMPD 28 | | | | |
|---|---|---|---|---|---|
| RATE GM/HA | 125 | 64 | 32 | 16 | 8 |
| PREEMERGENCE | | | | | |
| COTTON | 90 | 90 | 80 | 50 | 20 |
| REDROOT PIGWEED | 100 | 100 | 100 | 90 | 80 |
| LAMBSQUARTER | 50 | 50 | 0 | 0 | 0 |
| VELVETLEAF | 98 | 90 | 80 | 70 | 70 |
| PRICKLY SIDA | 60 | 60 | 50 | 40 | 20 |
| SICKLEPOD | 30 | 30 | 30 | 0 | 0 |
| COCKLEBUR | 90 | 90 | 90 | 90 | 60 |
| CMN PURSLANE | 80 | 70 | 60 | 60 | 30 |
| IVY MORNINGLORY | 90 | 90 | 70 | 0 | 0 |
| GOOSEGRASS | 30 | 20 | 0 | 0 | 0 |
| BERMUDAGRASS | 30 | 20 | 0 | 0 | 0 |
| BARNYARDGRASS | 80 | 70 | 60 | 30 | 20 |
| JOHNSONGRASS | 50 | 40 | 0 | 0 | 0 |
| FALL PANICUM | 50 | 50 | 50 | 0 | 0 |
| LARGE CRABGRASS | 20 | 20 | 0 | 0 | 0 |
| BRDLF SGNLGRASS | 0 | 0 | 0 | 0 | 0 |
| PURPLE NUTSEDGE | 100 | 100 | 70 | 70 | 50 |
| LADY SMARTWEED | 90 | 90 | 80 | 80 | 80 |
| GROUND CHERRY | 70 | 60 | 60 | 50 | 30 |

Test E

Sixteen-cm-diameter Airlite plastic pots were partially filled with Tama silt loam soil and the soil saturated with water. Japonica and Indica rice seedlings at the 2.0 to 2.5 leaf stage were transplanted into ⅓ of the pots. Into another third of the pots were transplanted seedling or sprouted tubers of water plantain (*Alisma trivale*), Scripus (*Scirpus paludosus*), Cyperus (*Cyperus esculentus*), and arrowhead (Sagittaria spp.). The remaining pots were planted and barnyardgrass (*Echinochloa crus-galli*) seeds and sprouted tubers of water chestnut (Eleocharis spp.). These weeds all represent major rice weeds or genera of weeds important in rice. Three to four days after planting, the water level was raised to 3 cm (about 1200 ml/pot) and maintained at this level throughout the test. Chemical treatments were applied directly to the paddy water, within 24 hours of raising the water, after being formulated in a nonphytotoxic solvent. The pots were maintained in the greenhouse. Rates of application and plant response ratings made 21 days after treatment are summarized in Table E.

TABLE E

| | CMPD 1 | | | |
|---|---|---|---|---|
| RATE = G/HA | 16 | 8 | 4 | 2 |
| BARNYARDGRASS | 40 | 20 | 0 | 0 |
| WATERCHESTNUT | 55 | 30 | 0 | 0 |
| ARROWHEAD | 90 | 85 | 0 | 0 |
| SCIRPUS | 50 | 30 | 0 | 0 |
| WATER PLAINTAIN | 95 | 90 | 0 | 0 |
| RICE JAPONICA | 65 | 30 | 10 | 0 |
| RICE INDICA | 20 | 0 | 0 | 0 |

| | CMPD 5 | | | | |
|---|---|---|---|---|---|
| RATE = G/HA | 125 | 64 | 32 | 16 | 8 |
| BARNYARDGRASS | 20 | 0 | 0 | 0 | 0 |
| WATERCHESTNUT | 20 | 20 | 0 | 0 | 0 |
| ARROWHEAD | 90 | 80 | 65 | 0 | 0 |
| SCIRPUS | 0 | 0 | 0 | 0 | 0 |
| YELLOW NUTSEDGE | 30 | 0 | 0 | 0 | 0 |
| WATER PLAINTAIN | 85 | 70 | 65 | 0 | 0 |
| RICE JAPONICA | 20 | 0 | 0 | 0 | 0 |
| RICE INDICA | 20 | 0 | 0 | 0 | 0 |

| | CMPD 8 | | | | |
|---|---|---|---|---|---|
| RATE = G/HA | 125 | 64 | 32 | 16 | 8 |
| BARNYARDGRASS | 80 | 75 | 50 | 0 | 0 |
| WATERCHESTNUT | 95 | 90 | 90 | 80 | 70 |
| SCIRPUS | 100 | 100 | 100 | 100 | 95 |
| YELLOW NUTSEDGE | 90 | 85 | 80 | 70 | 0 |
| WATER PLAINTAIN | 100 | 100 | 98* | 95 | 90 |
| RICE JAPONICA | 75 | 60 | 50 | 40 | 30 |
| RICE INDICA | 30 | 25 | 20 | 0 | 0 |

| | CMPD 11 | | | | |
|---|---|---|---|---|---|
| RATE = G/HA | 125 | 64 | 32 | 16 | 8 |
| BARNYARDGRASS | 40 | 30 | 0 | 0 | 0 |
| WATERCHESTNUT | 90 | 90 | 85 | 75 | 70 |
| SCIRPUS | 100 | 95 | 90 | 85 | 75 |
| YELLOW NUTSEDGE | 75 | 40 | 0 | 0 | 0 |
| WATER PLAINTAIN | 98 | 95 | 95 | 80 | 0 |
| RICE JAPONICA | 60 | 50 | 40 | 20 | 0 |
| RICE INDICA | 20 | 20 | 20 | 20 | 0 |

| | CMPD 12 | | | | |
|---|---|---|---|---|---|
| RATE = G/HA | 64 | 32 | 16 | 8 | 4 |
| BARNYARDGRASS | 0 | 0 | 0 | 0 | 0 |
| WATERCHESTNUT | 60 | 60 | 30 | 0 | 0 |
| SCIRPUS | 0 | 0 | 0 | 0 | 0 |
| YELLOW NUTSEDGE | 0 | 0 | 0 | 0 | 0 |
| WATER PLAINTAIN | 0 | 0 | 0 | 0 | 0 |
| RICE JAPONICA | 0 | 0 | 0 | 0 | 0 |
| RICE INDICA | 0 | 0 | 0 | 0 | 0 |

| | CMPD 13 | | | | |
|---|---|---|---|---|---|
| RATE = G/HA | 64 | 32 | 16 | 8 | 4 |
| BARNYARDGRASS | 0 | 0 | 0 | 0 | 0 |
| WATERCHESTNUT | 70 | 0 | 0 | 0 | 0 |
| SCIRPUS | 0 | 0 | 0 | 0 | 0 |
| YELLOW NUTSEDGE | 0 | 0 | 0 | 0 | 0 |
| WATER PLAINTAIN | 0 | 0 | 0 | 0 | 0 |
| RICE JAPONICA | 0 | 0 | 0 | 0 | 0 |
| RICE INDICA | 0 | 0 | 0 | 0 | 0 |

| | CMPD 29 | | | | | | |
|---|---|---|---|---|---|---|---|
| RATE = G/HA | 250 | 125 | 64 | 32 | 16 | 8 | 4 |
| BARNYARDGRASS | 80 | 60 | 50 | 50 | 0 | 0 | 0 |
| WATERCHESTNUT | 75 | 65 | 60 | 30 | 0 | 0 | 0 |
| ARROWHEAD | — | — | 100 | 90 | 90 | 50 | 0 |
| SCIRPUS | 30 | 0 | 0 | 0 | 0 | 90 | 0 |
| YELLOW NUTSEDGE | 80 | 30 | 20 | 20 | 0 | 100 | 0 |
| WATER PLAINTAIN | 100 | 95 | 90 | 70 | 0 | 95 | 0 |
| CMN ARROWHEAD | 95 | 90 | 85 | 80 | 0 | — | — |
| RICE JAPONICA | 25 | 20 | 15 | 10 | 0 | 0 | 0 |
| RICE INDICA | 30 | 25 | 20 | 10 | 0 | 0 | 0 |

| | CMPD 30 | | | | |
|---|---|---|---|---|---|
| RATE = G/HA | 125 | 64 | 32 | 16 | 8 |
| BARNYARDGRASS | 20 | 20 | 0 | 0 | 0 |
| WATERCHESTNUT | 0 | 0 | 0 | 0 | 0 |

TABLE E-continued

| | | | | | |
|---|---|---|---|---|---|
| ARROWHEAD | 60 | 0 | 0 | 0 | 0 |
| SCIRPUS | 40 | 0 | 0 | 0 | 0 |
| YELLOW NUTSEDGE | 60 | 0 | 0 | 0 | 0 |
| WATER PLAINTAIN | 40 | 0 | 0 | 0 | 0 |
| RICE JAPONICA | 30 | 0 | 0 | 0 | 0 |
| RICE INDICA | 20 | 0 | 0 | 0 | 0 |
| | CMPD 56 | | | | |
| RATE = G/HA | 125 | 64 | 32 | 16 | 8 |
| BARNYARDGRASS | 80 | 30 | 0 | 0 | 0 |
| WATERCHESTNUT | 95 | 85 | 75 | 0 | 0 |
| ARROWHEAD | 90 | 90 | 70 | 0 | 0 |
| SCIRPUS | 100 | 98 | — | 0 | 0 |
| YELLOW NUTSEDGE | 40 | 0 | 0 | 0 | 0 |
| WATER PLAINTAIN | 100 | 90 | 100 | 80 | 40 |
| RICE JAPONICA | 60 | 20 | 10 | 0 | 0 |
| RICE INDICA | 50 | 20 | 10 | 0 | 0 |
| | CMPD 61 | | | | |
| RATE = G/HA | 64 | 32 | 16 | 8 | 4 |
| BARNYARDGRASS | 70 | 50 | 0 | 0 | 0 |
| WATERCHESTNUT | 80 | 80 | 0 | 0 | 0 |
| SCIRPUS | 100 | 100 | 80 | 40 | 0 |
| YELLOW NUTSEDGE | 100 | 90 | 80 | 75 | 70 |
| WATER PLAINTAIN | 100 | 100 | 100 | 95 | 90 |
| RICE JAPONICA | 55 | 45 | 30 | 0 | 0 |
| RICE INDICA | 20 | 10 | 10 | 0 | 0 |
| | CMPD 64 | | | | |
| RATE = G/HA | 64 | 32 | 16 | 8 | 4 |
| BARNYARDGRASS | 65 | 60 | 30 | 0 | 0 |
| WATERCHESTNUT | 90 | 90 | 70 | 70 | — |
| SCIRPUS | 100 | 100 | 85 | 70 | 0 |
| YELLOW NUTSEDGE | 95 | 90 | 50 | 40 | 0 |
| WATER PLAINTAIN | 100 | 100 | 85 | 0 | 0 |
| RICE JAPONICA | 50 | 40 | 30 | 10 | 10 |
| RICE INDICA | 25 | 20 | 10 | 10 | 10 |

Test F

For the postemergence phase of the test, crop and weed species were planted in a Sassafras sandy loam soil (approximately 1% organic matter) one to three weeks before application so that they were present as young plants at the time of treatment. Alterntively, for postemergence tests, plants were grown in a 50:50 mixture of commercially available potting mix and Sassafras soil. Plantings for the preemergence phase were made in a Tama silt loam soil (approximately 3% organic matter) the day before, or the day of treatment. Approximate planting depths were corn and soybeans—3 to 4 cm; morningglory, cocklebur, and nutsedge—2.5 to 3 cm; velvetleaf, sicklepot, and sesbania—2cm; all other species—0.5 cm.

The test chemicals were dissolved/suspended in a nonphytotoxic solvent in concentrations required to obtain the desired rate of application. The solutions or suspensions were then applied as soil/foliage sprays to the young plants (postemergence phase) and to the soil surfaces of the freshly planted containers (preemergence phase). Application was made utilizing an automatic spray machine at a spray volume of 374 liters per hectare. Immediately after treatment, the containers were transferred to a greenhouse and subsequently watered on a demand basis, taking care not to wet the foliage of the plants in the postemergence phase of the test.

The following species were included in the test:

| PLANT SPECIES | SCIENTIFIC NAME | APPROXIMATE GROWTH STAGE AT POST APPLICATION |
|---|---|---|
| Grass Weeds | | |
| Barnyardgrass | Echinochloa crus-galli | 2–3 leaves |
| Giant foxtail | Setaria faberi | 2–3 leaves |
| Green foxtail | Setaris viridis | 2–3 leaves |
| Johnsongrass | Sorghum halepense | 2–3 leaves |
| Fall panicum | Panicum dichotomiflorum | 2–3 leaves |
| Purple nutsedge | Cyperus rotundus | 5–6 leaves |
| Signalgrass | Brachiaria platyphylla | 2–3 leaves |
| Crabgrass | Digitaria sanguinalis | 2–3 leaves |
| Velvetleaf | Abutilon theophrasti | 2–3 leaves |
| Jimsonweed | Datura stramonium | 1–2 true leaves |
| Hemp sesbania | Sesbania exaltata | 1st true leaf |
| Sicklepod | Cassia obtusifolia | 1st true leaf |
| Cocklebur | Xanthium pensylvanicum | 2nd true leaf |
| Ivyleaf morningglory | Ipomoea hederacea | 1–2 true leaves |
| Ladysthumb smartweed | Polygonum persicaria | 3–4 leaves |
| Pigweed | Amaranthus retroflexus | 4–5 leaves |
| Lambsquarters | Chenopodium album | 4–5 leaves |
| Teaweed | Sida spinosa | 2–3 leaves |
| Eastern black-nightshade | Solanum ptycanthum | 2nd true leaf |
| Corn (Funk G4646) | Zea mays | 2–3 leaves |
| Soybeans (Williams) | Glycine max | 1st trifoliate |

Visual plant response ratings were made approximately two and four weeks after treatment for the post- and pre-emergence phases, respectively. The ratings were made on a percentage scale of 0 to 200, where 0=no injury, and 100=death of plants. Plant response ratings are summarized in Table F.

TABLE F

| | CMPD 28 | | | | |
|---|---|---|---|---|---|
| RATE GM/H | 250 | 125 | 64 | 32 | 16 |
| PREEMERGENCE | | | | | |
| SOYBEANS | 40 | 0 | 0 | 0 | 0 |
| CORN | 20 | 10 | 10 | 0 | 0 |
| VELVETLEAF | 60 | 50 | 40 | 20 | 0 |
| JIMSONWEED | 70 | 70 | 40 | 0 | 0 |
| SICKLEPOD | 40 | 20 | 0 | 0 | 0 |
| HEMP SESBANIA | 40 | 20 | 0 | 0 | 0 |
| COCKLEBUR | 75 | 50 | 30 | 0 | 0 |
| IVY MORNINGLORY | 50 | 50 | 30 | 0 | 0 |
| REDROOT PIGWEED | 95 | 90 | 75 | 60 | 30 |
| LAMBSQUARTER | 100 | 80 | 60 | 50 | 40 |
| PRICKLY SIDA | 40 | 20 | 0 | 0 | 0 |
| BARNYARDGRASS | 50 | 20 | 0 | 0 | 0 |
| GIANT FOXTAIL | 20 | 0 | 0 | 0 | 0 |
| GREEN FOXTAIL | 0 | 0 | 0 | 0 | 0 |
| JOHNSONGRASS | 30 | 0 | 0 | 0 | 0 |
| FALL PANICUM | 40 | 20 | 0 | 0 | 0 |
| LARGE CRABGRASS | 0 | 0 | 0 | 0 | 0 |
| BRDLF SGNLGRASS | 0 | 0 | 0 | 0 | 0 |
| PURPLE NUTSEDGE | 80 | 70 | 60 | 40 | 20 |
| LADY SMARTWEED | 85 | 75 | 60 | 40 | 20 |
| BLACK NIGHTSHAD | 75 | 50 | 30 | 0 | 0 |
| | CMPD 34 | | | | | |
| RATE GM/H | 125 | 64 | 32 | 16 | 8 | 4 |
| POSTEMERGENCE | | | | | | |
| SOYBEANS | 20 | 0 | 0 | 0 | 0 | 0 |
| CORN | 40 | 30 | 0 | 0 | 0 | 0 |
| VELVETLEAF | 80 | 70 | 50 | 40 | 30 | 20 |
| JIMSONWEED | 80 | 60 | 50 | 40 | 30 | 20 |
| SICKLEPOD | 50 | 30 | 0 | 0 | 0 | 0 |
| HEMP SESBANIA | 98 | 90 | 70 | 40 | 20 | 0 |
| COCKLEBUR | 100 | 100 | 70 | 60 | 50 | 40 |
| IVY MORNINGLORY | 100 | 100 | 100 | 100 | 70 | 50 |

TABLE F-continued

| | | | | | | |
|---|---|---|---|---|---|---|
| REDROOT PIGWEED | 98 | 90 | 80 | 70 | 40 | 20 |
| LAMBSQUARTER | 50 | 30 | 20 | 0 | 0 | 0 |
| PRICKLY SIDA | 0 | 0 | 0 | 0 | 0 | 0 |
| BARNYARDGRASS | 50 | 40 | 30 | 0 | 0 | 0 |
| GIANT FOXTAIL | 30 | 0 | 0 | 0 | 0 | 0 |
| GREEN FOXTAIL | 30 | 0 | 0 | 0 | 0 | 0 |
| JOHNSONGRASS | 50 | 30 | 0 | 0 | 0 | 0 |
| FALL PANICUM | 30 | 0 | 0 | 0 | 0 | 0 |
| LARGE CRABGRASS | 0 | 0 | 0 | 0 | 0 | 0 |
| BRDLF SGNLGRASS | 50 | 30 | 0 | 0 | 0 | 0 |
| PURPLE NUTSEDGE | 80 | 70 | 60 | 50 | 0 | 0 |
| BLACK NIGHTSHAD | 95 | 85 | 80 | 20 | 0 | 0 |

Test G

The species below were planted.

| Name | Genus Species | Size (cm) |
|---|---|---|
| Blackgrass, Stage II | Alopecurus myosuroides | 14.0 |
| Lambsquarters, Common | Chenopodium album | 4.0 |
| Catchweed Beadstraw | Galium aparine | 9.0 |
| Russian Thistle | Salsoa kali | 6.0 |
| Black Nightshade, Eastern | Solanum nigrum | 2.0 |
| Field Pennycress | Thlaspi arvense | 2.5 |
| Ivyleaf Speedwell | Veronica hederaefolia | 5.0 |
| Field Speedwell, Common | Veronica persica | 6.0 |
| Field Pansy | Viola arvensis | 1.5 |

Two days later, a second series were planted using the following species.

| Name | Genus Species | Size (cm) |
|---|---|---|
| Blackgrass, Stage I | Alopecurus myosuroides | 6.0 |
| Wild Oat Stage II | Avena fatua | 22.0 |
| Sugar Beet | Beta vulgaris | 8.0 |
| Oilseed Rape | Brassica napus | 13.0 |
| Kochia | Kochia scoparia | 5.0 |
| Mayweed, Scentless | Matricaria inodora | 4.0 |
| Annual Bluegrass | Poa annua | 7.0 |
| Wild Buckwheat | Polygonum convolvulus | 7.0 |

Seven days following the first planting, a third pot was prepared with the following species.

| Name | Genus Species | Size (cm) |
|---|---|---|
| Jointed Goatgrass | Aegilops cylindrica | 12.0 |
| Wild Oat Stage I | Avena fatua | 15.0 |
| Cheatgrass | Bromus secalinus | 8.0 |
| Winter Barley 'cv. Igri' | Hordeum vulgare | 18.0 |
| Spring Barley 'cv. Klages' | Hordeum vulgare | 24.0 |
| Annual Ryegrass | Lolium multiflorum | 11.0 |
| Green Foxtail | Setaria viridis | 6.0 |
| Winter Wheat 'cv. Centurk' | Triticum aestivum | 23.0 |
| Spring Wheat 'cv. Era' | Triticum aestivum | 16.0 |
| Downy Brome | Bromus tectorum | 8.0 |

All postemergence plantings were grown in the greenhouse until herbicide application. Preemergence treatments were prepared immediately before herbicide application in the same manner as described for the postemergence treatments. Application of the herbicide was accomplished by first diluting the technical material in a nonphytotoxic solvent and applying over the surface of the plants and soil of all six components using a belt sprayer.

After treatment, all components were removed to the greenhouse where they were maintained for 21 days at temperatures of 19° C. night and 30° C. day with a 16-hour photoperiod and a relative humidity of 45 to 80 percent. At this time, all species were rated using a visual scale of 0 representing no control and 100 representing complete control. Test results are summarized in Table G.

TABLE G

| RATE G/HA | CMPD 1 | | | | | CMPD 5 | | | | | CMPD 6 | | | | | CMPD 8 | | | | | CMPD 9 | | | | | CMPD 11 |
|---|---|---|---|---|---|---|---|---|---|---|---|---|---|---|---|---|---|---|---|---|---|---|---|---|---|---|
| | 32 | 16 | 8 | 4 | 2 | 64 | 32 | 16 | 8 | 4 | 125 | 64 | 32 | 16 | 125 | 64 | 32 | 27 | 8 | 4 | 64 | 32 | 16 | 8 | 4 | 2 | 125 |
| PREEMERGENCE | | | | | | | | | | | | | | | | | | | | | | | | | | | |
| SPRING WHEAT | 30 | 10 | 0 | 0 | 0 | 0 | 0 | 0 | 0 | 0 | 10 | 0 | 0 | 0 | 20 | 10 | 0 | 0 | 0 | 0 | 30 | 20 | 10 | 0 | 0 | 0 | 0 |
| WINTER WHEAT | 30 | 20 | 0 | 0 | 0 | 0 | 0 | 0 | 0 | 0 | 0 | 0 | 0 | 0 | 20 | 20 | 10 | 0 | 0 | 0 | 30 | 10 | 0 | 0 | 0 | 0 | 10 |
| SPRING BARLEY | 60 | 60 | 40 | 20 | 0 | 10 | 0 | 0 | 0 | 0 | 10 | 0 | 0 | 0 | 30 | 10 | 0 | 10 | 0 | 0 | 50 | 40 | 30 | 10 | 0 | 0 | 10 |
| WINTER BARLEY | 80 | 40 | 30 | 10 | 0 | 0 | 0 | 0 | 0 | 0 | 10 | 0 | 0 | 0 | 50 | 50 | 20 | 10 | 0 | 0 | 50 | 50 | 20 | 20 | 0 | 0 | 20 |
| WILD OATS | 20 | 10 | 0 | 0 | 0 | 0 | 0 | 0 | 0 | 0 | 20 | 0 | 0 | 0 | 30 | 10 | 10 | 0 | 0 | 0 | 30 | 20 | 10 | 10 | 10 | 0 | 10 |
| DOWNY BROME | 20 | 20 | 10 | 0 | 0 | 0 | 0 | 0 | 0 | 0 | 10 | 0 | 0 | 0 | 50 | 30 | 10 | 10 | 10 | 0 | 40 | 20 | 20 | 10 | 10 | 0 | 20 |
| CHEAT GRASS | 20 | 10 | 0 | 0 | 0 | 0 | 0 | 0 | 0 | 0 | 0 | 0 | 0 | 0 | 80 | 50 | 30 | 50 | 20 | 10 | 60 | 50 | 30 | 20 | 10 | 10 | 20 |
| BLACKGRASS | 80 | 60 | 60 | 30 | 10 | 30 | 10 | 0 | 0 | 0 | 40 | 10 | 0 | 0 | 80 | 80 | 70 | 50 | 40 | 40 | 90 | 90 | 80 | 70 | 70 | 40 | 80 |
| ANN. BLUEGRASS | 90 | 90 | 50 | 30 | 20 | 40 | 10 | 10 | 0 | 0 | 30 | 30 | 10 | 0 | 70 | 80 | 60 | 50 | 40 | 20 | 70 | 70 | 50 | 40 | 30 | 10 | 70 |
| ANNUAL RYEGRASS | 20 | 10 | 0 | 0 | 0 | 30 | 10 | 0 | 0 | 0 | 20 | 20 | 20 | 0 | 20 | 10 | 10 | 0 | 0 | 0 | 30 | 20 | 20 | 10 | 10 | 0 | 40 |
| JOINT GOATGRASS | 0 | 0 | 20 | 0 | 0 | 20 | 20 | 10 | 10 | 0 | 10 | 0 | 0 | 0 | 20 | 10 | 20 | 10 | 20 | 0 | 20 | 20 | 10 | 0 | 0 | 0 | 30 |
| GREEN FOXTAIL | 100 | 50 | 20 | 10 | 70 | 80 | 80 | 70 | 40 | 0 | 100 | 100 | 100 | 80 | 90 | 70 | 70 | 70 | 80 | 70 | 60 | 60 | 20 | 40 | 30 | 0 | 70 |
| RAPE | 100 | 70 | 100 | 90 | 70 | 80 | 60 | 40 | 30 | 20 | 90 | 90 | 100 | 20 | 90 | 90 | 90 | 90 | 80 | 40 | 100 | 100 | 100 | 90 | 90 | 80 | 100 |
| CTCHWD BEDSTRAW | 80 | 70 | 50 | 40 | 20 | 70 | 60 | 40 | 0 | 0 | 90 | 90 | 100 | 20 | 90 | 80 | 40 | 50 | 20 | 0 | 70 | 70 | 70 | 70 | 60 | 20 | 90 |
| WILD BUCKWHEAT | 70 | 70 | 70 | 60 | 40 | 50 | 50 | 30 | 0 | 0 | 100 | 100 | 90 | 70 | 80 | 80 | 70 | 50 | 40 | 0 | 80 | 70 | 50 | 70 | 40 | 40 | 30 |
| KOCHIA | 60 | 60 | 40 | 20 | 0 | 70 | 50 | 10 | 10 | 0 | 50 | 50 | 30 | 0 | 50 | 20 | 20 | 20 | 0 | 0 | 20 | 20 | 10 | 0 | 0 | 0 | 100 |
| SNTLS MAYWEED | 90 | 80 | 80 | 70 | 30 | 100 | 80 | 70 | 40 | 0 | 90 | 80 | 60 | 10 | 90 | 70 | 80 | 70 | 60 | 40 | 60 | 60 | 60 | 40 | 30 | 40 | 60 |
| BLACK NIGHTSHAD | 70 | 60 | 60 | 40 | 30 | 40 | 30 | 0 | 30 | 0 | 40 | 30 | 60 | 0 | 70 | 50 | 60 | 50 | 30 | 0 | 50 | 50 | 50 | 50 | 50 | 20 | 70 |
| FIELD SPEEDWELL | 50 | 80 | 40 | 30 | 10 | 30 | 50 | 30 | 0 | 10 | 100 | 100 | 80 | 30 | 50 | 50 | 40 | 40 | 40 | 60 | 40 | 40 | 30 | 30 | 30 | 10 | 100 |
| IVYLF SPEEDWELL | 100 | 100 | 100 | 60 | 30 | 100 | 100 | 100 | 90 | 60 | 100 | 100 | 100 | 70 | 90 | 80 | 90 | 80 | 80 | 60 | 100 | 90 | 90 | 90 | 80 | 70 | 100 |
| SUGARBEET | 100 | 90 | 80 | 80 | 80 | 80 | 70 | 40 | 20 | 0 | 100 | 100 | 90 | 50 | 100 | 90 | 100 | 80 | 70 | 70 | 100 | 100 | 90 | 90 | 60 | 40 | 90 |
| LAMBSQUARTER | 100 | 100 | 80 | 70 | 60 | 70 | 40 | 10 | 0 | 0 | 100 | 90 | 90 | 50 | 90 | 70 | 60 | 60 | 60 | 40 | 70 | 70 | 70 | 70 | 60 | 70 | 90 |
| FIELD PENNYCRES | 100 | 100 | 90 | 70 | 40 | 100 | 70 | 40 | 10 | 0 | 100 | 100 | 80 | 50 | 100 | 100 | 80 | 90 | 80 | 70 | 100 | 100 | 100 | 100 | 90 | 40 | 100 |
| FIELD VIOLET | 100 | 90 | 90 | 70 | 50 | 100 | 100 | 90 | 80 | 40 | 100 | 100 | 90 | 70 | 70 | 70 | 60 | 60 | 50 | 40 | 70 | 50 | 50 | 40 | 20 | 0 | 80 |
| POSTEMERGENCE | | | | | | | | | | | | | | | | | | | | | | | | | | | |
| SPRING WHEAT | 20 | – | 0 | 0 | 0 | 0 | 0 | 0 | 0 | 0 | 0 | 0 | 0 | 0 | 20 | 10 | 10 | 0 | 0 | 0 | 0 | 0 | 0 | 0 | 0 | 0 | 10 |
| WINTER WHEAT | 10 | 0 | 0 | 0 | 0 | 0 | 0 | 0 | 0 | 0 | 0 | 0 | 0 | 0 | 10 | 10 | 0 | 10 | 0 | 0 | 0 | 10 | 0 | 0 | 0 | 0 | 20 |
| SPRING BARLEY | 10 | 20 | 10 | 10 | 0 | 0 | 0 | 0 | 0 | 0 | 0 | 0 | 0 | 0 | 20 | 10 | 10 | 0 | 10 | 0 | 20 | 30 | 0 | 0 | 0 | 0 | 20 |
| WINTER BARLEY | 30 | 0 | 0 | 0 | 0 | 0 | 0 | 0 | 0 | 0 | 10 | 30 | 0 | 0 | 60 | 30 | 30 | 20 | 20 | 10 | 40 | 10 | 0 | 0 | 0 | 0 | 0 |
| WILD OATS | 0 | 0 | 0 | 0 | 0 | 0 | 0 | 0 | 0 | 0 | 0 | 0 | 0 | 0 | 10 | 10 | 10 | 0 | 10 | 10 | 20 | 0 | 0 | 0 | 0 | 0 | 0 |
| WILD OATS STG 2 | 0 | 0 | 0 | 0 | 0 | 0 | 0 | 0 | 0 | 0 | 0 | 0 | 0 | 0 | 0 | 10 | 10 | 0 | 10 | 0 | 20 | 10 | 0 | 0 | 0 | 0 | 0 |
| DOWNY BROME | 30 | 30 | 10 | 0 | 0 | 0 | 0 | 0 | 0 | 0 | 10 | 0 | 0 | 0 | 50 | 20 | 50 | 30 | 20 | 10 | 20 | 10 | 10 | 0 | 0 | 0 | 10 |
| CHEAT GRASS | 40 | 30 | 30 | 0 | 0 | 0 | 0 | 0 | 0 | 0 | 20 | 20 | 0 | 20 | 70 | 70 | 60 | 40 | 40 | 20 | 30 | 60 | 60 | 40 | 20 | 0 | 30 |
| BLACKGRASS | 50 | 40 | 20 | 20 | 0 | 0 | 0 | 0 | 0 | 0 | 50 | 30 | 0 | 0 | 80 | 70 | 60 | 50 | 30 | 20 | 60 | 50 | 50 | 10 | 10 | 0 | 20 |
| BLACKGRASS STG2 | 40 | 40 | 30 | 30 | 0 | 0 | 0 | 0 | 0 | 0 | 20 | 10 | 0 | 0 | 70 | 70 | 60 | 30 | 40 | 10 | 60 | 50 | 50 | 10 | 20 | 0 | 20 |
| ANN. BLUEGRASS | 0 | 0 | 0 | 0 | 0 | 30 | 20 | 0 | 0 | 0 | 30 | 40 | 30 | 20 | 20 | 20 | 20 | 10 | 10 | 20 | 50 | 40 | 30 | 10 | 0 | 0 | 40 |
| ANNUAL RYEGRASS | 10 | 0 | 0 | 0 | 0 | 0 | 0 | 0 | 0 | 0 | 40 | 60 | 40 | 20 | 40 | 40 | 30 | 20 | 20 | 20 | 60 | 60 | 40 | 10 | 20 | 0 | 60 |
| JOINT GOATGRASS | 0 | 0 | 0 | 0 | 0 | 30 | 0 | 0 | 0 | 0 | 20 | 60 | 40 | 40 | 70 | 50 | 50 | 30 | 30 | 20 | 50 | 50 | 30 | 10 | 0 | 0 | 70 |
| GREEN FOXTAIL | 0 | 0 | 0 | 0 | 0 | 30 | 0 | 0 | 0 | 0 | 20 | 100 | 80 | 80 | 100 | 90 | 90 | 60 | 90 | 90 | 50 | 40 | 40 | 30 | 10 | 0 | 40 |
| RAPE | 100 | 100 | 100 | 100 | 100 | 100 | 100 | 100 | 90 | 80 | 100 | 100 | 100 | 100 | 100 | 100 | 100 | 100 | 100 | 100 | 100 | 100 | 100 | 100 | 100 | 90 | 80 |
| CTCHWD BEDSTRAW | 90 | 60 | 40 | 20 | 20 | 10 | 10 | 0 | 0 | 0 | 80 | 70 | 30 | 20 | 80 | 70 | 50 | 40 | 30 | 20 | 70 | 70 | 50 | 30 | 0 | 0 | 100 |
| WILD BUCKWHEAT | 70 | 40 | 30 | 20 | 0 | 80 | 80 | 60 | 40 | 10 | 100 | 100 | 90 | 80 | 100 | 70 | 40 | 40 | 10 | 20 | 60 | 40 | 40 | 20 | 40 | 0 | 60 |
| KOCHIA | 70 | 40 | 30 | 20 | 0 | 80 | 80 | 60 | 40 | 30 | 70 | 50 | 40 | 60 | 70 | 40 | 30 | 20 | 30 | 30 | 60 | 40 | 40 | 20 | 20 | 0 | 70 |
| SNTLS MAYWEED | 90 | 80 | 70 | 60 | 30 | 100 | 100 | 70 | 50 | 30 | 100 | 100 | 80 | 60 | 100 | 100 | 100 | 100 | 90 | 90 | 50 | 50 | 40 | 20 | 20 | 70 | 30 |
| BLACK NIGHTSHAD | 90 | 50 | 0 | 0 | 0 | 40 | 20 | 10 | 0 | 0 | 80 | 70 | 60 | 40 | 80 | 50 | 50 | 30 | 30 | 20 | 60 | 50 | 40 | 20 | 10 | 0 | 80 |
| FIELD SPEEDWELL | 60 | 0 | 0 | 0 | 0 | 50 | 60 | 30 | 20 | 30 | 100 | 100 | 80 | 60 | 100 | 100 | 70 | 60 | 30 | 30 | 50 | 50 | 40 | 20 | 30 | 0 | 70 |
| IVYLF SPEEDWELL | 0 | 0 | 0 | 0 | 0 | 0 | 0 | 0 | 0 | 0 | 70 | 60 | 40 | 40 | 100 | 100 | 90 | 90 | 90 | 60 | 30 | 10 | 0 | 0 | 10 | 0 | 80 |
| SUGARBEET | 100 | 100 | 100 | 100 | 100 | 100 | 100 | 100 | 90 | 70 | 100 | 100 | 100 | 100 | 100 | 100 | 100 | 90 | 100 | 60 | 90 | 80 | 80 | 60 | 40 | 30 | 100 |

TABLE G-continued

| | CMPD 11 | | | | | CMPD 12 | | | | | CMPD 13 | | | | | CMPD 29 | | | | | CMPD 31 | | | | |
|---|---|---|---|---|---|---|---|---|---|---|---|---|---|---|---|---|---|---|---|---|---|---|---|---|---|
| LAMBSQUARTER | 20 | 10 | 0 | 0 | | 80 | 80 | 70 | 70 | 40 | 100 | 100 | 70 | 70 | 60 | 20 | 20 | 70 | 70 | 60 | 20 | 0 | 0 | 0 | 70 |
| FIELD PENNYCRES | 100 | 100 | 90 | 40 | | 100 | 90 | 60 | 70 | 20 | 80 | 100 | 100 | 100 | 100 | 100 | 100 | 100 | 100 | 100 | 100 | 100 | 100 | 100 | 100 |
| FIELD VIOLET | 60 | 40 | 20 | 0 | | 30 | 20 | 0 | 0 | 0 | 60 | 30 | 30 | 10 | 0 | 0 | 0 | 0 | 0 | 0 | 0 | 0 | 0 | 0 | 50 |
| RATE G/HA | 64 | 32 | 16 | 8 | 4 | 125 | 64 | 32 | 16 | 8 | 125 | 64 | 32 | 16 | 8 | 4 | 125 | 64 | 32 | 16 | 8 | 4 | 125 | 64 | 32 | 16 |

PREEMERGENCE

| | | | | | | | | | | | | | | | | | | | | | | | | | | |
|---|---|---|---|---|---|---|---|---|---|---|---|---|---|---|---|---|---|---|---|---|---|---|---|---|---|---|
| SPRING WHEAT | 0 | 0 | 0 | 0 | 0 | 30 | 10 | 0 | 0 | 0 | 0 | 0 | 0 | 0 | 0 | 0 | 10 | 0 | 0 | 0 | 0 | 0 | 40 | 30 | 10 | 10 |
| WINTER WHEAT | 0 | 0 | 0 | 0 | 0 | 0 | 0 | 0 | 0 | 0 | 10 | 0 | 0 | 0 | 0 | 0 | 20 | 10 | 0 | 0 | 0 | 0 | 40 | 20 | 10 | 10 |
| SPRING BARLEY | 0 | 10 | 10 | 0 | 0 | 10 | 10 | 0 | 0 | 0 | 20 | 10 | 10 | 0 | 0 | 20 | 30 | 20 | 10 | 0 | 0 | 0 | 50 | 40 | 30 | 20 |
| WINTER BARLEY | 20 | 0 | 0 | 0 | 0 | 20 | 10 | 0 | 0 | 0 | 30 | 20 | 0 | 0 | 0 | 0 | 30 | 10 | 0 | 0 | 0 | 0 | 60 | 40 | 30 | 20 |
| WILD OATS | 0 | 0 | 0 | 0 | 0 | 20 | 10 | 0 | 0 | 0 | 40 | 10 | 0 | 0 | 0 | 0 | 40 | 30 | 20 | 10 | 0 | 0 | 50 | 30 | 20 | 20 |
| DOWNY BROME | 10 | 0 | 0 | 0 | 0 | 10 | 0 | 0 | 0 | 0 | 40 | 20 | 10 | 0 | 0 | 10 | 30 | 40 | 20 | 10 | 0 | 10 | 60 | 40 | 30 | 20 |
| CHEAT GRASS | 20 | 20 | 10 | 20 | 0 | 30 | 10 | 0 | 0 | 0 | 40 | 20 | 10 | 0 | 0 | 0 | 40 | 70 | 60 | 20 | 20 | 0 | 70 | 80 | 70 | 40 |
| BLACKGRASS | 70 | 60 | 40 | 30 | 0 | 40 | 30 | 10 | 20 | 30 | 90 | 90 | 60 | 50 | 50 | 0 | 90 | 80 | 60 | 50 | 30 | 0 | 80 | 70 | 50 | 30 |
| ANN. BLUEGRASS | 60 | 50 | 50 | 30 | 20 | 50 | 50 | 30 | 0 | 20 | 80 | 80 | 80 | 90 | 80 | 20 | 80 | 80 | 50 | 40 | 20 | 10 | 70 | 60 | 40 | 20 |
| ANNUAL RYEGRASS | 20 | 10 | 0 | 0 | 0 | 40 | 10 | 10 | 10 | 30 | 40 | 40 | 30 | 20 | 10 | 20 | 50 | 40 | 20 | 10 | 10 | 0 | 40 | 30 | 30 | 20 |
| JOINT GOATGRASS | 10 | 10 | 0 | 10 | 0 | 20 | 10 | 0 | 0 | 0 | 50 | 30 | 30 | 10 | 20 | 0 | 30 | 30 | 10 | 20 | 10 | 0 | 80 | 80 | 50 | 80 |
| GREEN FOXTAIL | 70 | 50 | 30 | 0 | 0 | 30 | 20 | 10 | 20 | 0 | 90 | 70 | 60 | 40 | 50 | 0 | 100 | 80 | 80 | 50 | 20 | 10 | 100 | 100 | 70 | 50 |
| RAPE | 100 | 100 | 100 | 40 | 0 | 100 | 100 | 100 | 100 | 100 | 100 | 100 | 100 | 100 | 100 | 90 | 100 | 100 | 100 | 90 | 90 | 90 | 80 | 80 | 60 | 50 |
| CTCHWD BEDSTRAW | 70 | 70 | 50 | 10 | 0 | 70 | 60 | 50 | 50 | 30 | 90 | 90 | 60 | 50 | 50 | 30 | 90 | 90 | 60 | 40 | 30 | 30 | 70 | 100 | 70 | 40 |
| WILD BUCKWHEAT | 100 | 100 | 90 | 60 | 10 | 100 | 100 | 100 | 100 | 20 | 100 | 100 | 90 | 90 | 70 | 10 | 100 | 100 | 90 | 50 | 60 | 10 | 100 | 80 | 70 | 50 |
| KOCHIA | 20 | 20 | 0 | 0 | 0 | 80 | 60 | 50 | 30 | 70 | 50 | 60 | 60 | 40 | 20 | 0 | 50 | 60 | 50 | 40 | 30 | 30 | 70 | 50 | 40 | 20 |
| SNTLS MAYWEED | 100 | 90 | 70 | 40 | 10 | 100 | 90 | 90 | 80 | 70 | 90 | 90 | 90 | 80 | 70 | 60 | 90 | 90 | 60 | 50 | 10 | 10 | 100 | 100 | 90 | 90 |
| BLACK NIGHTSHAD | 60 | 40 | 40 | 20 | 20 | 80 | 70 | 70 | 70 | 60 | 80 | 70 | 70 | 60 | 30 | 20 | 90 | 90 | 50 | 40 | 30 | 0 | 60 | 70 | 50 | 40 |
| FIELD SPEEDWELL | 70 | 50 | 50 | 30 | 10 | 80 | 90 | 80 | 80 | 40 | 80 | 80 | 80 | 40 | 10 | 0 | 90 | 90 | 70 | 60 | 40 | 20 | 90 | 90 | 70 | 70 |
| IVYLF SPEEDWELL | 70 | 40 | 20 | 0 | 0 | 80 | 80 | 40 | 40 | 20 | 80 | 40 | 70 | 30 | 10 | 0 | 90 | 80 | 70 | 60 | 40 | 30 | 100 | 90 | 80 | 70 |
| SUGARBEET | 100 | 90 | 90 | 90 | 90 | 100 | 100 | 80 | 100 | 100 | 70 | 40 | 30 | 0 | 0 | 0 | 70 | 80 | 70 | 80 | 70 | 20 | 100 | 100 | 80 | 80 |
| LAMBSQUARTER | 90 | 80 | 70 | 70 | 50 | 100 | 90 | 80 | 80 | 80 | 90 | 100 | 90 | 90 | 70 | 60 | 100 | 90 | 80 | 70 | 50 | 20 | 100 | 100 | 80 | 80 |
| FIELD PENNYCRES | 100 | 100 | 100 | 80 | 60 | 100 | 100 | 90 | 90 | 30 | 100 | 80 | 80 | 60 | 50 | 40 | 100 | 80 | 70 | 50 | 20 | 10 | 90 | 90 | 90 | 90 |
| FIELD VIOLET | 50 | 40 | 0 | 0 | 0 | 100 | 100 | 90 | 80 | 50 | 100 | 90 | 70 | 40 | 50 | 70 | 100 | 100 | 90 | 50 | 20 | 60 | 100 | 100 | 90 | 80 |
| ALTEX RAPE | — | — | — | — | — | 70 | 70 | 40 | 40 | 20 | 70 | 90 | 50 | 40 | 30 | 10 | 100 | 100 | 70 | 50 | 20 | 60 | — | — | — | 60 |

POSTEMERGENCE

| | | | | | | | | | | | | | | | | | | | | | | | | | | |
|---|---|---|---|---|---|---|---|---|---|---|---|---|---|---|---|---|---|---|---|---|---|---|---|---|---|---|
| SPRING WHEAT | 10 | 0 | 0 | 0 | 0 | 10 | 0 | 0 | 0 | 0 | 0 | 0 | 0 | 0 | 0 | 0 | 0 | 0 | 0 | 0 | 0 | 0 | 0 | 0 | 0 | 0 |
| WINTER WHEAT | 10 | 10 | 0 | 0 | 0 | 20 | 10 | 0 | 0 | 0 | 0 | 0 | 0 | 0 | 0 | 0 | 0 | 0 | 0 | 0 | 0 | 0 | 10 | 10 | 0 | 0 |
| SPRING BARLEY | 10 | 0 | 0 | 0 | 0 | 10 | 0 | 0 | 0 | 0 | 0 | 0 | 0 | 0 | 0 | 0 | 0 | 0 | 0 | 0 | 0 | 0 | 10 | 10 | 0 | 0 |
| WINTER BARLEY | 10 | 0 | 0 | 0 | 0 | 0 | 0 | 0 | 0 | 0 | 0 | 0 | 0 | 0 | 0 | 0 | 0 | 0 | 0 | 0 | 0 | 0 | 20 | 10 | 10 | 20 |
| WILD OATS | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 20 | 20 | 10 | 0 |
| WILD OATS STG 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 20 | 30 | 20 | 0 |
| DOWNY BROME | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 30 | 30 | 20 | 20 |
| CHEAT GRASS | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 20 | 10 | 10 | 0 |
| BLACKGRASS | 20 | 20 | 20 | 10 | 0 | 30 | 20 | 10 | 10 | 0 | 0 | 0 | 0 | 0 | 0 | 0 | 0 | 0 | 0 | 0 | 0 | 0 | 30 | 30 | 20 | 10 |
| BLACKGRASS STG2 | 20 | 10 | 10 | 0 | 0 | 30 | 30 | 0 | 0 | 0 | 0 | 0 | 0 | 0 | 0 | 0 | 0 | 0 | 0 | 0 | 0 | 0 | 80 | 70 | 50 | 50 |
| ANN. BLUEGRASS | 0 | 20 | 0 | 0 | 0 | 20 | 10 | 0 | 10 | 0 | 0 | 0 | 0 | 0 | 0 | 0 | 0 | 30 | 20 | 20 | 0 | 40 | 80 | 10 | 10 | 0 |
| ANNUAL RYEGRASS | 0 | 10 | 0 | 0 | 0 | 10 | 0 | 10 | 0 | 0 | 0 | 0 | 0 | 0 | 0 | 0 | 0 | 0 | 0 | 0 | 0 | 0 | 10 | 10 | 0 | 0 |
| JOINT GOATGRASS | 10 | 0 | 0 | 0 | 0 | 20 | 10 | 0 | 0 | 0 | 0 | 0 | 0 | 0 | 0 | 0 | 0 | 0 | 0 | 0 | 0 | 0 | 30 | 10 | 0 | 0 |
| GREEN FOXTAIL | 20 | 0 | 0 | 0 | 0 | 30 | 20 | 0 | 0 | 0 | 0 | 0 | 0 | 0 | 0 | 20 | 0 | 10 | 0 | 0 | 0 | 0 | 60 | 60 | 30 | 20 |
| RAPE | 100 | 100 | 100 | 100 | 40 | 90 | 90 | 80 | 80 | 50 | 90 | 100 | 90 | 80 | 50 | 80 | 90 | 100 | 100 | 100 | 100 | 100 | 100 | 100 | 100 | 100 |
| CTCHWD BEDSTRAW | 50 | 50 | 40 | 20 | 0 | 90 | 80 | 50 | 50 | 40 | 70 | 60 | 60 | 60 | 60 | 40 | 70 | 70 | 50 | 30 | 10 | 0 | 50 | 50 | 40 | 50 |
| WILD BUCKWHEAT | 100 | 70 | 30 | 20 | 10 | 90 | 90 | 80 | 80 | 70 | 80 | 80 | 70 | 70 | 40 | 70 | 100 | 100 | 80 | 70 | 50 | 40 | 100 | 100 | 70 | 70 |
| KOCHIA | 50 | 30 | 10 | 10 | 0 | 70 | 70 | 50 | 40 | 20 | 100 | 70 | 50 | 20 | 20 | 10 | 90 | 100 | 90 | 80 | 70 | 10 | 70 | 70 | 50 | 10 |
| SNTLS MAYWEED | 80 | 70 | 40 | 20 | 20 | 80 | 70 | 50 | 40 | 20 | 80 | 60 | 40 | 40 | 40 | 30 | 100 | 100 | 90 | 80 | 60 | 30 | 100 | 80 | 80 | 60 |
| BLACK NIGHTSHAD | 70 | 60 | 50 | 40 | 20 | 70 | 70 | 60 | 40 | 20 | 60 | 70 | 50 | 40 | 30 | 20 | 80 | 80 | 60 | 30 | 20 | 10 | 50 | 30 | 10 | 20 |

TABLE G-continued

| | CMPD 31 | | | | | | CMPD 61 | | | |
|---|---|---|---|---|---|---|---|---|---|---|
| | | | | | | | 8 | 4 | 2 |
| FIELD SPEEDWELL | 30 | 30 | 20 | 10 | 0 | 0 | 20 | 10 | 0 | 0 |
| IVYLF SPEEDWELL | 70 | 20 | 10 | 0 | 0 | 0 | 0 | 0 | 0 | 0 |
| SUGARBEET | 100 | 100 | 80 | 60 | 20 | 60 | 100 | 90 | 70 | 60 |
| LAMBSQUARTER | 70 | 70 | 50 | 20 | 40 | 0 | 40 | 30 | 10 | 0 |
| FIELD PENNYCRES | 100 | 100 | 90 | 40 | 100 | 50 | 100 | 100 | 100 | 80 |
| FIELD VIOLET | 30 | 10 | 0 | 0 | 30 | 0 | 30 | 0 | 0 | 0 |
| ALTEX RAPE | | | | | | | | | | |

| | CMPD 35 | | | | | | CMPD 36 | | | | | | CMPD 55 | | | | | | CMPD 56 | | | | | CMPD 61 | | | |
|---|---|---|---|---|---|---|---|---|---|---|---|---|---|---|---|---|---|---|---|---|---|---|---|---|---|---|---|
| RATE G/HA | 8 | 125 | 64 | 32 | 16 | 8 | 4 | 125 | 64 | 32 | 16 | 8 | 4 | 125 | 64 | 32 | 16 | 8 | 4 | 125 | 64 | 32 | 32 | 16 | 8 | 4 | 2 |

PREEMERGENCE

| SPRING WHEAT | 0 | 10 | 0 | 0 | 0 | 0 | 10 | 0 | 0 | 0 | 0 | 0 | 0 | 0 | 0 | 0 | 0 | 0 | 0 | 60 | 40 | 20 | 20 | 0 | 0 | 0 | 0 |
| WINTER WHEAT | 0 | 0 | 10 | 0 | 0 | 0 | 0 | 20 | 10 | 0 | 0 | 0 | 0 | 0 | 0 | 0 | 0 | 0 | 0 | 50 | 30 | 20 | 30 | 10 | 10 | 0 | 0 |
| SPRING BARLEY | 10 | 30 | 0 | 20 | 10 | 60 | 100 | 10 | 10 | 10 | 0 | 0 | 0 | 10 | 10 | 10 | 0 | 0 | 0 | 100 | 100 | 40 | 0 | 0 | 0 | 0 | 0 |
| WINTER BARLEY | 10 | 40 | 20 | 10 | 0 | 20 | 70 | 30 | 20 | 0 | 0 | 0 | 0 | 20 | 20 | 0 | 0 | 0 | 0 | 40 | 20 | 0 | 40 | 0 | 0 | 0 | 0 |
| WILD OATS | 0 | 20 | 10 | 10 | 20 | 0 | 0 | 20 | 10 | 10 | 0 | 0 | 0 | 10 | 10 | 0 | 0 | 0 | 0 | 20 | 70 | 40 | 0 | 0 | 0 | 0 | 0 |
| DOWNY BROME | 0 | 20 | 20 | 30 | 30 | 40 | 30 | 30 | 20 | 10 | 10 | 0 | 10 | 40 | 40 | 20 | 10 | 0 | 10 | 80 | 80 | 50 | 30 | 60 | 60 | 40 | 20 |
| CHEAT GRASS | 20 | 40 | 40 | 30 | 20 | 0 | 0 | 20 | 20 | 10 | 30 | 0 | 0 | 60 | 60 | 60 | 40 | 20 | 10 | 80 | 70 | 80 | 80 | 70 | 70 | 20 | 20 |
| BLACKGRASS | 40 | 80 | 70 | 60 | 50 | 40 | 30 | 40 | 40 | 30 | 0 | 30 | 0 | 60 | 50 | 50 | 30 | 0 | 0 | 70 | 60 | 30 | 30 | 20 | 20 | 10 | 0 |
| ANN. BLUEGRASS | 20 | 60 | 60 | 70 | 70 | 20 | 50 | 50 | 40 | 10 | 20 | 0 | 10 | 70 | 60 | 50 | 40 | 20 | 20 | 20 | 0 | 30 | 30 | 30 | 30 | 30 | 0 |
| ANNUAL RYEGRASS | 10 | 40 | 40 | 30 | 20 | 0 | 30 | 40 | 40 | 40 | 40 | 0 | 0 | 70 | 60 | 50 | 30 | 0 | 20 | 70 | 40 | 30 | 70 | 100 | 100 | 100 | 100 |
| JOINT GOATGRASS | 0 | 30 | 30 | 10 | 0 | 20 | 0 | 20 | 20 | 0 | 0 | 0 | 0 | 50 | 30 | 30 | 10 | 0 | 40 | 100 | 90 | 90 | 90 | 80 | 60 | 50 | 100 |
| GREEN FOXTAIL | 20 | 50 | 50 | 30 | 10 | 10 | 30 | 30 | 20 | 10 | 0 | 10 | 10 | 30 | 10 | 30 | 20 | 0 | 10 | 60 | 50 | 30 | 60 | 60 | 50 | 30 | 0 |
| RAPE | 90 | 100 | 100 | 100 | 100 | 100 | 90 | 100 | 100 | 100 | 100 | 100 | 70 | 100 | 100 | 100 | 100 | 70 | 70 | 100 | 100 | 100 | 100 | 100 | 100 | 100 | 90 |
| CTCHWD BEDSTRAW | 30 | 80 | 70 | 70 | 70 | 50 | 50 | 70 | 80 | 70 | 50 | 50 | 10 | 50 | 50 | 40 | 50 | 40 | 10 | 60 | 50 | 60 | 40 | 60 | 50 | 50 | 40 |
| WILD BUCKWHEAT | 40 | 100 | 90 | 90 | 70 | 50 | 30 | 90 | 90 | 80 | 70 | 70 | 40 | 80 | 80 | 70 | 50 | 40 | 20 | 100 | 50 | 40 | 80 | 70 | 60 | 60 | 0 |
| KOCHIA | 0 | 80 | 80 | 50 | 40 | 20 | 0 | 70 | 60 | 50 | 50 | 20 | 20 | 70 | 70 | 50 | 70 | 30 | 10 | 80 | 30 | 20 | 40 | 50 | 60 | 30 | 0 |
| SNTLS MAYWEED | 80 | 100 | 100 | 80 | 70 | 50 | 30 | 100 | 80 | 90 | 50 | 40 | 20 | 100 | 80 | 80 | 50 | 60 | 20 | 80 | 70 | 100 | 100 | 100 | 100 | 90 | 80 |
| BLACK NIGHTSHAD | 20 | 70 | 60 | 90 | 40 | 20 | 70 | 80 | 80 | 80 | 30 | 30 | 40 | 70 | 70 | 50 | 50 | 30 | 40 | 100 | 50 | 30 | 70 | 50 | 30 | 30 | 30 |
| FIELD SPEEDWELL | 50 | 100 | 90 | 90 | 90 | 80 | 90 | 70 | 70 | 60 | 50 | 50 | 30 | 80 | 80 | 70 | 70 | 70 | 60 | 70 | 40 | 70 | 70 | 100 | 50 | 40 | 0 |
| IVYLF SPEEDWELL | 30 | 100 | 100 | 90 | 50 | 40 | 100 | 100 | 80 | 70 | 80 | 80 | 80 | 90 | 90 | 80 | 70 | 70 | 60 | 100 | 90 | 70 | 70 | 70 | 50 | 40 | 40 |
| SUGARBEET | 70 | 100 | 100 | 100 | 100 | 60 | 30 | 100 | 100 | 80 | 80 | 60 | 80 | 90 | 90 | 90 | 80 | 60 | 20 | 100 | 90 | 100 | 90 | 100 | 50 | 50 | 90 |
| LAMBSQUARTER | 60 | 100 | 100 | 80 | 90 | 80 | 50 | 100 | 100 | 90 | 90 | 80 | 60 | 90 | 90 | 80 | 60 | 70 | 20 | 90 | 70 | 70 | 70 | 50 | 50 | 60 | 80 |
| FIELD PENNYCRES | 60 | 100 | 100 | 90 | 90 | 80 | 70 | 100 | 100 | 90 | 60 | 10 | 10 | 80 | 60 | 60 | 60 | 10 | 20 | 80 | 30 | 80 | 80 | 90 | 80 | 80 | 70 |
| FIELD VIOLET | 30 | 100 | 80 | 80 | 70 | 80 | 20 | 100 | 100 | 90 | 80 | 50 | 20 | 70 | 70 | 60 | 60 | 60 | 60 | 20 | 0 | 100 | 80 | 60 | 60 | 60 | 50 |
| RUSSIAN THISTLE | | | | | | | | | | | | | | | | | | | | | | | | | | | 40 |

POSTEMERGENCE

| SPRING WHEAT | 0 | 10 | 0 | 0 | 0 | 0 | 0 | 0 | 0 | 0 | 0 | 0 | 0 | 0 | 0 | 0 | 0 | 0 | 0 | 30 | 10 | 10 | 10 | 0 | 0 | 0 | 0 |
| WINTER WHEAT | 0 | 20 | 10 | 0 | 0 | 0 | 0 | 0 | 0 | 0 | 0 | 0 | 0 | 0 | 0 | 0 | 0 | 0 | 0 | 30 | 10 | 10 | 10 | 0 | 10 | 0 | 0 |
| SPRING BARLEY | 0 | 20 | 0 | 0 | 0 | 10 | 0 | 10 | 0 | 0 | 0 | 0 | 0 | 0 | 0 | 0 | 0 | 0 | 0 | 10 | 10 | 10 | 20 | 0 | 0 | 0 | 0 |
| WINTER BARLEY | 0 | 10 | 0 | 0 | 0 | 0 | 0 | 10 | 0 | 0 | 0 | 0 | 0 | 0 | 0 | 0 | 0 | 0 | 0 | 20 | 10 | 20 | 20 | 10 | 10 | 0 | 0 |
| WILD OATS | 0 | 0 | 0 | 0 | 0 | 0 | 0 | 0 | 0 | 0 | 0 | 0 | 0 | 0 | 0 | 0 | 0 | 0 | 0 | 40 | 60 | 40 | 10 | 10 | 10 | 0 | 0 |
| WILD OATS STG 2 | 0 | 0 | 0 | 0 | 0 | 0 | 0 | 20 | 0 | 0 | 0 | 0 | 0 | 0 | 0 | 0 | 0 | 0 | 0 | 60 | 60 | 20 | 20 | 20 | 20 | 10 | 0 |
| DOWNY BROME | 0 | 0 | 0 | 0 | 0 | 0 | 0 | 0 | 0 | 0 | 0 | 0 | 0 | 0 | 0 | 0 | 10 | 0 | 0 | 90 | 70 | 40 | 60 | 40 | 20 | 20 | 10 |
| CHEAT GRASS | 30 | 70 | 60 | 40 | 10 | 0 | 0 | 100 | 60 | 60 | 10 | 0 | 0 | 60 | 70 | 60 | 30 | — | 0 | 90 | 60 | 30 | 20 | 30 | 30 | 20 | 20 |
| BLACKGRASS | 20 | 70 | 50 | 50 | 20 | 0 | 0 | 90 | 70 | 40 | 20 | 10 | 0 | 60 | 20 | 60 | 10 | 0 | 0 | 50 | 60 | 20 | 40 | 30 | 30 | 10 | 0 |
| BLACKGRASS STG2 | 0 | 20 | 10 | 0 | 0 | 0 | 0 | 60 | 20 | 40 | 30 | 0 | 0 | 20 | 60 | 0 | 0 | 0 | 0 | 20 | 0 | 10 | 60 | 90 | 80 | 80 | 20 |
| ANN. BLUEGRASS | 0 | 20 | 20 | 20 | 30 | 10 | 0 | 30 | 20 | 20 | 10 | 0 | 0 | 20 | 10 | 10 | 0 | 0 | 0 | 70 | 30 | 0 | 20 | 60 | 70 | 60 | 0 |
| ANNUAL RYEGRASS | 0 | 0 | 0 | 0 | 0 | 0 | 0 | 0 | 0 | 0 | 0 | 0 | 0 | 0 | 0 | 0 | 0 | 0 | 0 | 50 | 30 | 10 | 10 | 20 | 30 | 20 | 0 |
| JOINT GOATGRASS | 0 | 20 | 10 | 0 | 0 | 0 | 0 | 20 | 10 | 0 | 0 | 0 | 0 | 0 | 0 | 0 | 0 | 0 | 0 | 20 | 0 | 0 | 0 | 0 | 0 | 0 | 0 |
| GREEN FOXTAIL | 0 | 20 | 0 | 0 | 0 | 0 | 0 | 20 | 10 | 0 | 0 | 0 | 0 | 0 | 0 | 0 | 0 | 0 | 0 | 70 | 30 | 20 | 20 | 20 | 10 | 0 | 0 |
| RAPE | 80 | 100 | 100 | 100 | 100 | 100 | 100 | 100 | 100 | 100 | 100 | 100 | 80 | 100 | 100 | 100 | 100 | 100 | 100 | 100 | 100 | 100 | 100 | 100 | 100 | 100 | 90 |

TABLE G-continued

| | CMPD 62 | | | | | | | CMPD 64 | | | | | | | CMPD 65 | | | | | | | CMPD 66 | | | | | | |
|---|---|---|---|---|---|---|---|---|---|---|---|---|---|---|---|---|---|---|---|---|---|---|---|---|---|---|---|---|
| CTCWD BEDSTRAW | 20 | 90 | 80 | 70 | 50 | 30 | 10 | 40 | 60 | 70 | 30 | 10 | 20 | 60 | 40 | 40 | 20 | 10 | 40 | 60 | 80 | 80 | 50 | 10 | 0 | 0 |
| WILD BUCKWHEAT | 60 | 100 | 100 | 80 | 60 | 30 | 20 | 100 | 100 | 100 | 20 | 70 | 70 | 90 | 40 | 90 | 80 | 60 | 70 | 90 | 60 | 60 | 30 | 0 | 0 | 0 |
| KOCHIA | 0 | 70 | 70 | 60 | 30 | 10 | 0 | 50 | 60 | 50 | 0 | 10 | 50 | 100 | 40 | 70 | 70 | 50 | 80 | 100 | 60 | 10 | 50 | 30 | 30 |
| SNTLS MAYWEED | 40 | 100 | 100 | 90 | 80 | 70 | 50 | 80 | 90 | 100 | 70 | 60 | 60 | 80 | 90 | 80 | 90 | 80 | 100 | 100 | 30 | 10 | 10 | 0 | 70 |
| BLACK NIGHTSHAD | 10 | 40 | 30 | 10 | 0 | 0 | 0 | 0 | 40 | 30 | 0 | 0 | 0 | 0 | 0 | 90 | 30 | 10 | 60 | 30 | 30 | 10 | 0 | 0 | 0 |
| FIELD SPEEDWELL | 0 | 70 | 50 | 40 | 20 | 0 | 0 | 0 | 0 | 80 | 0 | 50 | 0 | 40 | 40 | 40 | 60 | 30 | 30 | 30 | 30 | 30 | 20 | 0 | 0 | 0 |
| IVYLF SPEEDWELL | 0 | 50 | 30 | 20 | 0 | 0 | 0 | 100 | 100 | 100 | 60 | 0 | 100 | 10 | 30 | 40 | 0 | 0 | 40 | 10 | 10 | 10 | 0 | 0 | 0 |
| SUGARBEET | 40 | 100 | 100 | 100 | 100 | 70 | 50 | 20 | 100 | 100 | 50 | 100 | 20 | 100 | 100 | 100 | 60 | 100 | 100 | 60 | 20 | 20 | 10 | 0 | 0 |
| LAMBSQUARTER | 0 | 70 | 40 | 30 | 10 | 0 | 0 | 100 | 100 | 80 | 60 | 100 | 20 | 60 | 60 | 80 | 20 | 30 | 100 | 20 | 10 | 0 | 0 | 0 | 0 |
| FIELD PENNYCRES | 60 | 100 | 100 | 100 | 80 | 60 | 40 | 100 | 100 | 100 | 50 | 100 | 90 | 100 | 100 | 50 | 40 | 100 | 100 | 100 | 100 | 100 | 60 | 40 |
| FIELD VIOLET | 0 | 60 | 50 | 40 | 20 | 0 | 0 | 0 | 10 | 0 | 0 | 0 | 0 | 20 | 0 | 0 | 0 | 0 | 0 | 20 | 0 | 0 | 0 | 0 | 0 |
| RUSSIAN THISTLE | | | | | 100 | | | | | 10 | | | | 100 | 100 | 50 | | | | | | | 10 | | | |

| | CMPD 64 | | | | | | | CMPD 65 | | | | | | | CMPD 66 | | | | | | |
|---|---|---|---|---|---|---|---|---|---|---|---|---|---|---|---|---|---|---|---|---|---|
| RATE G/HA | 125 | 64 | 32 | 16 | 8 | 4 | 2 | 1 | 125 | 64 | 32 | 16 | 8 | 4 | 2 | 1 | 125 | 64 | 32 | 16 | 8 | 4 | 2 |

PREEMERGENCE

| | | | | | | | | | | | | | | | | | | | | | | | |
|---|---|---|---|---|---|---|---|---|---|---|---|---|---|---|---|---|---|---|---|---|---|---|---|
| SPRING WHEAT | 10 | 0 | 0 | 0 | 0 | 0 | 0 | 0 | 10 | 0 | 0 | 0 | 0 | 0 | 0 | 0 | 10 | 10 | 0 | 0 | 0 | 0 | 0 |
| WINTER WHEAT | 20 | 20 | 10 | 10 | 0 | 10 | 0 | 0 | 20 | 10 | 0 | 20 | 0 | 0 | 0 | 0 | 0 | 0 | 0 | 0 | 0 | 0 | 0 |
| SPRING BARLEY | 40 | 60 | 50 | 20 | 30 | 40 | 0 | 0 | 70 | 50 | 30 | 30 | 0 | 0 | 10 | 0 | 30 | 20 | 10 | 10 | 10 | 0 | 0 |
| WINTER BARLEY | 10 | 20 | 60 | 50 | 30 | 0 | 0 | 0 | 20 | 20 | 30 | 0 | 0 | 0 | 0 | 0 | 20 | 20 | 0 | 10 | 10 | 10 | 10 |
| WILD OATS | 0 | 10 | 20 | 0 | 10 | 0 | 0 | 0 | 40 | 40 | 10 | 20 | 0 | 0 | 0 | 0 | 40 | 40 | 20 | 20 | 0 | 20 | 0 |
| DOWNY BROME | 0 | 30 | 10 | 30 | 10 | 0 | 0 | 0 | 60 | 20 | 30 | 0 | 40 | 40 | 10 | 0 | 50 | 30 | 20 | 30 | 20 | 10 | 20 |
| CHEAT GRASS | 30 | 60 | 50 | 30 | 10 | 10 | 0 | 0 | 40 | 60 | 50 | 80 | 40 | 40 | 60 | 80 | 40 | 40 | 30 | 30 | 30 | 20 | 10 |
| BLACKGRASS | 10 | 30 | 10 | 30 | 10 | 10 | 0 | 0 | 30 | 40 | 40 | 40 | 20 | 20 | 10 | 60 | 40 | 30 | 10 | 10 | 10 | 10 | 20 |
| ANN. BLUEGRASS | 30 | 60 | 40 | 30 | 10 | 10 | 0 | 0 | 60 | 60 | 40 | 30 | 30 | 10 | 10 | 80 | 30 | 30 | 30 | 30 | 20 | 10 | 10 |
| ANNUAL RYEGRASS | 30 | 40 | 50 | 30 | 10 | 0 | 0 | 0 | 50 | 40 | 50 | 30 | 20 | 10 | 10 | 70 | 70 | 70 | 70 | 70 | 70 | 70 | 60 |
| JOINT GOATGRASS | 20 | 80 | 60 | 40 | 30 | 10 | 0 | 0 | 60 | 100 | 80 | 70 | 30 | 20 | 60 | 60 | 80 | 90 | 70 | 70 | 50 | 50 | 40 |
| GREEN FOXTAIL | 40 | 100 | 100 | 100 | 30 | 0 | 0 | 0 | 100 | 100 | 100 | 100 | 90 | 70 | 60 | 60 | 100 | 90 | 90 | 80 | 60 | 50 | 30 |
| RAPE | 100 | 100 | 80 | 70 | 70 | 70 | 100 | 90 | 100 | 100 | 100 | 100 | 100 | 100 | 80 | 100 | 100 | 100 | 100 | 100 | 60 | 60 | 60 |
| CTCHWD BEDSTRAW | 20 | 20 | 70 | 80 | 70 | 40 | 40 | 0 | 80 | 80 | 90 | 80 | 70 | 70 | 60 | 80 | 70 | 90 | 100 | 70 | 70 | 70 | 70 |
| WILD BUCKWHEAT | 70 | 70 | 60 | 70 | 30 | 20 | 0 | 50 | 60 | 80 | 70 | 80 | 80 | 60 | 80 | 60 | 70 | 70 | 90 | 70 | 50 | 70 |
| KOCHIA | 60 | 20 | 70 | 70 | 60 | 10 | 0 | 20 | 30 | 40 | 30 | 30 | 30 | 20 | 30 | 40 | 50 | 30 | 30 | 10 | 30 |
| SNTLS MAYWEED | 100 | 80 | 100 | 70 | 60 | 40 | 0 | 60 | 100 | 90 | 100 | 90 | 80 | 70 | 70 | 60 | 60 | 70 | 80 | 70 | 70 | 50 |
| BLACK NIGHTSHAD | 70 | 80 | 70 | 80 | 70 | 40 | 30 | 10 | 80 | 80 | 90 | 90 | 90 | 80 | 70 | 70 | 30 | 30 | 30 | 30 | 30 | 30 | 30 |
| RUSSIAN THISTLE | 80 | 90 | 90 | 80 | 70 | 40 | 60 | 80 | 90 | 100 | 90 | 80 | 70 | 70 | 70 | 100 | 50 | 70 | 30 | 30 | 20 |
| FIELD SPEEDWELL | 70 | 80 | 80 | 60 | 50 | 30 | 0 | 40 | 60 | 60 | 60 | 60 | 60 | 60 | 60 | 60 | 80 | 50 | 70 | 70 | 50 | 30 |
| IVYLF SPEEDWELL | 70 | 80 | 80 | 70 | 60 | 50 | 0 | 30 | 90 | 70 | 60 | 50 | 50 | 60 | 40 | 70 | 70 | 70 | 50 | 50 | 40 | 20 |
| SUGARBEET | 100 | 90 | 80 | 80 | 80 | 40 | 70 | 90 | 100 | 100 | 90 | 100 | 100 | 100 | 80 | 80 | 100 | 100 | 100 | 90 | 90 | 70 |
| LAMBSQUARTER | 20 | 90 | 80 | 80 | 70 | 60 | 30 | 20 | 80 | 80 | 80 | 80 | 80 | 80 | 60 | 40 | 40 | 40 | 40 | 40 | 30 |
| FIELD PENNYCRES | 100 | 100 | 90 | 90 | 90 | 40 | 30 | 40 | 100 | 100 | 90 | 80 | 90 | 70 | 60 | 40 | 80 | 70 | 70 | 70 | 60 | 40 |
| FIELD VIOLET | 50 | 90 | 70 | 70 | 60 | 40 | 20 | 40 | 100 | 100 | 100 | 100 | 100 | 90 | 70 | 40 | 60 | 90 | 60 | 60 | 30 | 30 |

POSTEMERGENCE

| | | | | | | | | | | | | | | | | | | | | | | | |
|---|---|---|---|---|---|---|---|---|---|---|---|---|---|---|---|---|---|---|---|---|---|---|---|
| SPRING WHEAT | 40 | 30 | 10 | 0 | 0 | 0 | 0 | 0 | 10 | 0 | 0 | 0 | 0 | 0 | 0 | 0 | 0 | 0 | 0 | 0 | 0 | 0 | 0 |
| WINTER WHEAT | 30 | 10 | 0 | 0 | 0 | 0 | 0 | 0 | 0 | 0 | 0 | 0 | 0 | 0 | 0 | 0 | 0 | 0 | 0 | 0 | 0 | 0 | 0 |
| SPRING BARLEY | 40 | 20 | 0 | 0 | 0 | 0 | 0 | 0 | 10 | 10 | 0 | 0 | 0 | 0 | 0 | 0 | 20 | 20 | 10 | 10 | 10 | 10 | 0 |
| WINTER BARLEY | 30 | 10 | 0 | 0 | 0 | 0 | 0 | 0 | 20 | 0 | 0 | 0 | 0 | 0 | 0 | 0 | 10 | 10 | 10 | 10 | 0 | 0 | 0 |
| WILD OATS | 30 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| WILD OATS STG 2 | 20 | 10 | 0 | 0 | 0 | 0 | 0 | 0 | 20 | 10 | 10 | 0 | 0 | 0 | 0 | 0 | 0 | 0 | 0 | 0 | 0 | 0 | 0 |
| DOWNY BROME | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| CHEAT GRASS | 50 | 40 | 0 | 0 | 0 | 0 | 0 | 0 | 20 | 20 | 10 | 0 | 0 | 0 | 0 | 0 | 0 | 0 | 0 | 0 | 0 | 0 | 0 |
| BLACKGRASS | 40 | 10 | 10 | 0 | 0 | 0 | 0 | 0 | 40 | 10 | 10 | 0 | 0 | 0 | 0 | 0 | 0 | 0 | 0 | 0 | 10 | 10 | 0 |
| BLACKGRASS STG2 | 30 | 20 | 0 | 0 | 0 | 0 | 0 | 0 | 30 | 20 | 10 | 0 | 0 | 50 | 0 | 0 | 0 | 0 | 0 | 10 | 0 | 0 | 0 |
| ANN. BLUEGRASS | | | | | | | | | 10 | 10 | 10 | 10 | 0 | 0 | 0 | 0 | 10 | 10 | 10 | 10 | 0 | 0 | 0 |

TABLE G-continued

| | | | | | | | | | | | | | | | | | | | | |
|---|---|---|---|---|---|---|---|---|---|---|---|---|---|---|---|---|---|---|---|---|
| ANNUAL RYEGRASS | 10 | 0 | 0 | 0 | 0 | 0 | 0 | 0 | 20 | 20 | 20 | 0 | 0 | 0 | 0 | 0 | 10 | 0 | 0 | 0 |
| JOINT GOATGRASS | 20 | 20 | 0 | 0 | 40 | 10 | 0 | 0 | 0 | 0 | 0 | 0 | 0 | 0 | 0 | 0 | 20 | 10 | 0 | 0 |
| GREEN FOXTAIL | 20 | 20 | 0 | 0 | 30 | 30 | 10 | 0 | 30 | 30 | 40 | 0 | 0 | 0 | 0 | 0 | 30 | 20 | 0 | 0 |
| RAPE | 100 | 100 | 100 | 90 | 100 | 100 | 100 | 100 | 100 | 100 | 100 | 100 | 100 | 100 | 100 | 50 | 100 | 100 | 90 | 80 | 50 |
| CTCWD BEDSTRAW | 50 | 30 | 0 | 0 | 100 | 100 | 70 | 60 | 90 | 90 | 80 | 70 | 30 | 30 | 10 | 0 | 90 | 80 | 60 | 50 | 10 |
| WILD BUCKWHEAT | 60 | 30 | 20 | 10 | 100 | 100 | 60 | 70 | 80 | 100 | 60 | 80 | 60 | 30 | 10 | 0 | 60 | 60 | 40 | 20 | 10 |
| KOCHIA | 70 | 40 | 40 | 60 | 80 | 80 | 70 | 70 | 100 | 100 | 100 | 70 | 90 | 60 | 90 | 20 | 80 | 50 | 70 | 60 | 50 |
| SNTLS MAYWEED | 80 | 80 | 60 | 0 | 100 | 100 | 70 | 100 | 100 | 100 | 100 | 100 | 100 | 90 | 0 | 0 | 80 | 80 | 40 | 20 | 10 |
| BLACK NIGHTSHAD | 60 | 20 | 10 | 90 | 40 | 30 | 100 | 40 | 100 | 100 | 100 | 40 | 10 | 0 | 0 | 20 | 50 | 50 | 70 | 60 | 0 |
| FIELD SPEEDWELL | 20 | 0 | 0 | 0 | 20 | 20 | 40 | 30 | 80 | 60 | 40 | 30 | 0 | 0 | 0 | 0 | 0 | 40 | 10 | 10 | 0 |
| IVYLF SPEEDWELL | 30 | 10 | 0 | 90 | 100 | 80 | 50 | 0 | 80 | 100 | 60 | 100 | 90 | 100 | 90 | 70 | 60 | 60 | 40 | 40 | 20 |
| SUGARBEET | 100 | 100 | 90 | 0 | 100 | 100 | 100 | 100 | 100 | 100 | 100 | 10 | 0 | 0 | 0 | 0 | 100 | 100 | 90 | 90 | 50 |
| LAMBSQUARTER | 20 | 10 | 0 | 50 | 70 | 40 | 20 | 20 | 50 | 50 | 20 | 40 | 100 | 80 | 100 | 20 | 60 | 40 | 80 | 20 | 20 |
| FIELD PENNYCRES | 100 | 100 | 90 | 0 | 100 | 100 | 100 | 100 | 100 | 100 | 100 | 100 | 90 | 0 | 0 | 0 | 100 | 90 | 80 | 40 | 60 |
| FIELD VIOLET | 60 | 10 | 0 | 0 | 30 | 10 | 20 | 20 | 80 | 50 | 40 | 0 | 0 | 0 | 0 | 0 | 50 | 40 | 50 | 20 | 0 |
| RUSSIAN THISTLE | | | | | | | | | | | | | | | | | 50 | 50 | 50 | 30 | 0 |

What is claimed is:
1. A compound having the formula

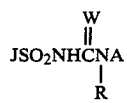

wherein
J is selected from

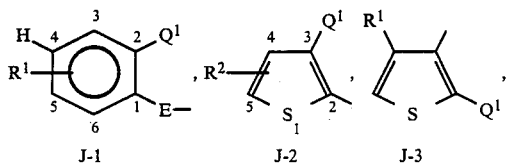

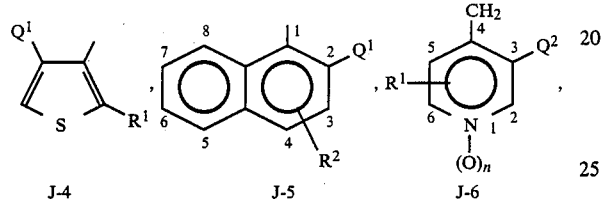

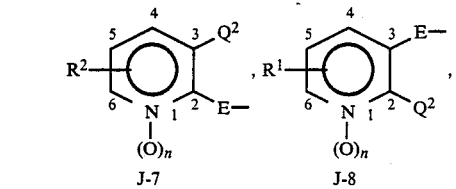

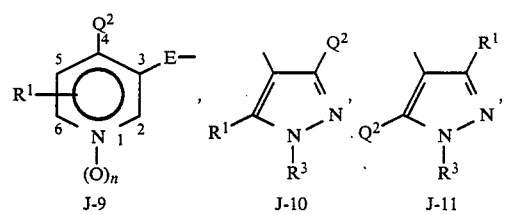

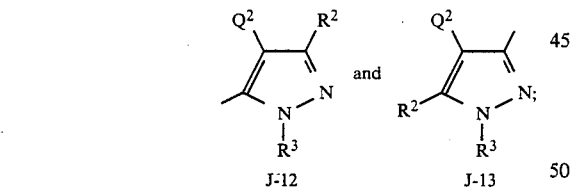

E is a single bond or —CH₂—;
$Q^1$ is —C($T^1$)=N—O—Alk;
$T^1$ is selected from CN, F, Cl, Br, SCN, N₃, C₁ to C₂ alkoxy, C₁ to C₂ thioalkyl, NH(C₁ to C₂ alkyl), N(C₁ to C₂ alkyl)₂, N(OCH₃)CH₃ and N(CH₂)₃ or 4;
Alk is selected from C₁ to C₃ alkyl, optionally substituted with CN, OCH₃, SCH₃ or halogen; and CH₂CH=CH₂;
$Q^2$ is —C($T^2$)=N—O—Alk;
$T^2$ is selected from H; C₁ to C₃ alkyl optionally substituted with CN, OCH₃, SCH₃ or halogen; cyclopropyl; F; Cl, Br; CN; SCN; N₃; C₁ to C₂ alkoxy; C₁ to C₂ thioalkyl; NH(C₁ to C₂ alkyl); N(C₁ to C₂ alkyl)₂; N(OCH₃)CH₃ and N(CH₂)₃ or 4;
$R^1$ is selected from H, C₁ to C₃ alkyl, C₁ to C₃ haloalkyl, halogen, CN, nitro, C₁ to C₃ alkoxy, C₁ to C₃ haloalkoxy, C₁ to C₃ alkylthio, C₁ to C₃ alkylsulfi-nyl, C₁ to C₃ alkylsulfonyl, SCF₂H, NH₂, NHCH₃, N(CH₃)₂ or C₁ to C₂ alkyl substituted with one C₁ to C₂ alkoxy, C₁ to C₂ haloalkoxy, SH, SCH₃, CN or OH;
$R^2$ is selected from H, F, Cl, Br, C₁ to C₂ alkyl, C₁ to C₂ haloalkyl or C₁ to C₂ alkoxy;
$R^3$ is selected from H, C₁ to C₃ alkyl, C₁ to C₂ haloalkyl, C₃ to C₄ alkenyl, C₃ to C₄ alkynyl, CH₂CN, phenyl and phenyl substituted by F, Cl, CH₃ or OCH₃;
n is 0 or 1;
R is H or CH₃;
W is O or S;
A is selected from

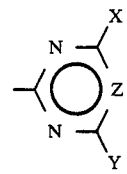 A-1

X is selected from H, C₁ to C₄ alkyl, C₁ to C₄ alkoxy, C₁ to C₄ haloalkoxy, C₁ to C₄ haloalkyl, C₁ to C₄ haloalkylthio, C₁ to C₄ alkylthio, halogen, C₂ to C₅ alkoxyalkyl, C₂ to C₅ alkoxyalkoxy, amino, C₁ to C₃ alkylamino, di(C₁ to C₃ alkyl)amino or C₃ to C₅ cycloalkyl;
Y is selected from H, C₁ to C₄ alkyl, C₁ to C₄ alkoxy, C₁ to C₄ haloalkoxy, C₁ to C₄ haloalkylthio, C₁ to C₄ alkylthio, C₂ to C₅ alkoxyalkyl, C₂ to C₅ alkoxyalkoxy, amino, C₁ to C₃ alkylamino, di(C₁ to C₃ alkyl)amino, C₃ to C₄ alkenyloxy, C₃ to C₄ alkynyloxy, C₂ to C₅ alkylthioalkyl, C₁ to C₄ haloalkyl, C₂ to C₄ alkynyl, azido, cyano, C₂ to C₅ alkylsulfinylalkyl, C₂ to C₅ alkylsulfonylalkyl,

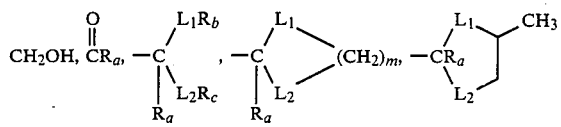

and N(OCH₃)CH₃;
m is 2 or 3;
$L_1$ and $L_2$ are independently O or S;
$R_a$ is H or C₁ to C₃ alkyl;
$R_b$ and $R_c$ are independently C₁ to C₃ alkyl; and
Z is CH provided that
  (i) when X is Cl, F, Br or I, then Y is OCH₃, OC₂H₅, N(OCH₃)CH₃, NHCH₃, N(CH₃)₂ or OCF₂H;
  (ii) when W is S, then R is H and Y is CH₃, OCH₃, OC₂H₅, CH₂OCH₃, C₂H₅, CF₃, SCH₃, OCH₂CH=CH₂, OCH₂C≡CH, OCH₂CH₂OCH₃, CH(OCH₃)₂ or 1,3-dioxolan-2-yl;
  (iii) when the total number of carbons of X and Y is greater than four, the number of carbon atoms of $Q^1$ or $Q^2$ is less than or equal to four; and
  (iv) when J is J-6, J-7, J-8 or J-9, and X and Y are haloalkoxy or haloalkylthio, then $T_2$ is F, Cl, Br, CN, SCN, N₃, C₁ to C₂ alkoxy, C₁ to C₂ thioalkyl, NH(C₁ to C₂ alkyl), N(C₁ to C₂ alkyl)₂, N(OCH₃)CH₃ or N(CH₂)₃ or 4.

2. A compound according to claim 1 wherein:
E is a single bond; and

W is O.

3. A compound according to claim 1 wherein:
E is CH$_2$ or J is J-6; and
W is O.

4. A compound according to claim 3, wherein:
R$^1$ is selected from H, F, Cl, Br, CH$_2$CN, CH$_3$, OCH$_3$, SCH$_3$ and OCF$_2$H;
R$^2$ is selected from H, F, Cl, Br or CH$_3$;
R$^3$ is selected from H, C$_1$ to C$_3$ alkyl, phenyl, CH$_2$CF$_3$ and CH$_2$CH=CH$_2$;
X is selected from C$_1$ to C$_2$ alkyl, C$_1$ to C$_2$ alkoxy, cyclopropyl, Cl, F, Br, I, OCF$_2$H, CH$_2$F, CF$_3$, OCH$_2$CH$_2$F, OCH$_2$CHF$_2$, OCH$_2$CF$_3$, CH$_2$Cl and CH$_2$Br;
Y is selected from H, C$_1$ to C$_2$ alkyl, C$_1$ to C$_2$ alkoxy, CH$_2$OCH$_3$, CH$_2$OCH$_2$CH$_3$, NHCH$_3$, N(OCH$_3$)CH$_3$, N(CH$_3$)$_2$, CF$_3$, SCH$_3$, OCH$_2$CH=CH$_2$, OCH$_2$C≡CH, OCH$_2$CH$_2$OCH$_3$, CH$_2$SCH$_3$,

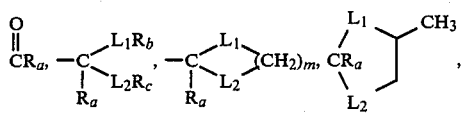

OCF$_2$H, OCF$_2$Br, SCF$_2$H, C≡CH and C≡CCH$_3$; and
R$_b$ and R$_c$ are C$_1$ to C$_2$ alkyl.

5. A compound according to claim 4 wherein:
A is A-1;
n is 0;
X is selected from cyclopropyl, CH$_3$, OCH$_3$, OCH$_2$CH$_3$, Cl and OCF$_2$H; and
Y is selected from CH$_3$, OCH$_3$, C$_2$H$_5$, CH$_2$OCH$_3$, NHCH$_3$ and CH(OCH$_3$)$_2$.

6. A compound according to claim 5 wherein:
R is H;
T$^1$ is selected from CN, Cl and C$_1$ to C$_2$ alkoxy; and
T$^2$ is selected from H, C$_1$ to C$_3$ alkyl, cyclopropyl, Cl, CN and C$_1$ to C$_2$ alkoxy.

7. A compound according to claim 6 wherein J is J-1 to J-5 and J-7 to J-13.

8. A compound according to claim 7 wherein J is J-1.

9. A compound according to claim 7 wherein J is J-2.

10. A compound according to claim 7 wherein J is J-3.

11. A compound according to claim 7 wherein J is J-4.

12. A compound according to claim 7 wherein J is J-5.

13. A compound according to claim 7 wherein J is J-7.

14. A compound according to claim 7 wherein J is J-8.

15. A compound according to claim 7 wherein J is J-9.

16. A compound according to claim 7 wherein J is J-10.

17. A compound according to claim 7 wherein J is J-11.

18. A compound according to claim 7 wherein J is J-12.

19. A compound according to claim 7 wherein J is J-13.

20. A compound according to claim 8: 2-[[[[(4-chloro-6-methoxy-2-pyrimidinyl)amino]carbonyl]amino]sulfonyl]-N-methoxybenzenecarboximidoyl chloride.

21. A compound according to claim 8: 2-[(cyano)(methoxyimino)methyl]-N-[[(4-methoxy-6-methyl-2-pyrimidinyl)amino]carbonyl]benzenesulfonamide.

22. A herbicidal composition comprising a compound according to any one of claims 1 to 21 and an agriculturally suitable carrier therefor.

23. A method for controlling weeds comprising applying to the locus of the weed, preemergence or postemergence, a herbicidally effective amount of a compound according to any one of claims 1 to 21.

* * * * *